US010913800B2

(12) United States Patent
Darimont et al.

(10) Patent No.: US 10,913,800 B2
(45) Date of Patent: Feb. 9, 2021

(54) ANTI-TRANSFERRIN RECEPTOR ANTIBODIES AND USES THEREOF

(71) Applicant: Avidity Biosciences, Inc., La Jolla, CA (US)

(72) Inventors: Beatrice Diana Darimont, San Diego, CA (US); Venkata Ramana Doppalapudi, San Diego, CA (US); Rachel Johns, La Jolla, CA (US)

(73) Assignee: AVIDITY BIOSCIENCES, INC., La Jolla, CA (US)

( * ) Notice: Subject to any disclaimer, the term of this patent is extended or adjusted under 35 U.S.C. 154(b) by 0 days.

(21) Appl. No.: 16/896,995

(22) Filed: Jun. 9, 2020

(65) Prior Publication Data

US 2020/0325237 A1   Oct. 15, 2020

Related U.S. Application Data

(63) Continuation of application No. PCT/US2019/068078, filed on Dec. 20, 2019.

(60) Provisional application No. 62/784,181, filed on Dec. 21, 2018.

(51) Int. Cl.
C07K 16/18       (2006.01)
C07K 16/28       (2006.01)
A61K 39/00       (2006.01)

(52) U.S. Cl.
CPC .... *C07K 16/2881* (2013.01); *A61K 2039/505* (2013.01); *C07K 2317/51* (2013.01); *C07K 2317/52* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 4,474,814 A | 10/1984 | Fujita et al. | |
| 4,694,778 A | 9/1987 | Learn et al. | |
| 4,866,132 A | 9/1989 | Obligin et al. | |
| 4,921,963 A | 5/1990 | Skov et al. | |
| 5,064,849 A | 11/1991 | Suzuki et al. | |
| 5,208,020 A | 5/1993 | Chari et al. | |
| 5,256,334 A | 10/1993 | Smid et al. | |
| 5,346,981 A | 9/1994 | Sarpeshkar et al. | |
| 5,416,064 A | 5/1995 | Chari et al. | |
| 5,700,825 A | 12/1997 | Hofer et al. | |
| 5,736,557 A | 4/1998 | Hofheinz et al. | |
| 5,849,738 A | 12/1998 | Lee et al. | |
| 5,872,107 A | 2/1999 | Schinazi et al. | |
| 5,939,045 A | 8/1999 | Suzuki et al. | |
| 5,945,439 A | 8/1999 | Richter et al. | |
| 6,562,806 B1 | 5/2003 | Thurston et al. | |
| 6,608,192 B1 | 8/2003 | Thurston et al. | |
| 6,716,821 B2 | 4/2004 | Zhao et al. | |
| 6,821,783 B1 | 11/2004 | Comely et al. | |
| 6,884,869 B2 | 4/2005 | Senter et al. | |
| 7,049,311 B1 | 5/2006 | Thurston et al. | |
| 7,067,511 B2 | 6/2006 | Thurston et al. | |
| 7,244,724 B2 | 7/2007 | Liu et al. | |
| 7,276,497 B2 | 10/2007 | Chari et al. | |
| 7,498,298 B2 | 3/2009 | Doronina et al. | |
| 7,528,126 B2 | 5/2009 | Howard et al. | |
| 7,612,062 B2 | 11/2009 | Gregson et al. | |
| 7,659,241 B2 | 2/2010 | Senter et al. | |
| 7,704,924 B2 | 4/2010 | Thurston et al. | |
| 7,709,226 B2 | 5/2010 | Foote | |
| 7,750,116 B1 | 7/2010 | Doronina et al. | |
| 7,850,975 B2 | 12/2010 | Mullis | |
| 7,943,762 B2 | 5/2011 | Weller et al. | |
| 7,964,566 B2 | 6/2011 | Doronina et al. | |
| 8,163,736 B2 | 4/2012 | Gauzy et al. | |
| 8,288,352 B2 | 10/2012 | Doronina et al. | |
| 8,404,678 B2 | 3/2013 | Bouchard et al. | |
| 8,426,402 B2 | 4/2013 | Li et al. | |
| 8,501,934 B2 | 8/2013 | Howard et al. | |
| 8,580,820 B2 | 11/2013 | Zanda et al. | |
| 8,591,910 B2 | 11/2013 | Mullis | |
| 8,604,184 B2 | 12/2013 | Mullis et al. | |
| 8,609,105 B2 | 12/2013 | Senter et al. | |
| 8,633,185 B2 | 1/2014 | Howard et al. | |
| 8,697,688 B2 | 4/2014 | Howard et al. | |
| 8,703,714 B2 | 4/2014 | Doronina et al. | |

(Continued)

FOREIGN PATENT DOCUMENTS

KR   20140026045 A   3/2014
WO   WO-2008036127 A2   3/2008

(Continued)

OTHER PUBLICATIONS

Almagro & Fransson, Frontiers in Bioscience 2008; 13:1619-33 (Year: 2008).*
Rudikoff et al. (Proc Natl Acad Sci USA 1982 vol. 79 p. 1979) (Year: 1979).*
MacCallum et al. J. Mol. Biol. (1996) 262, 732-745 (Year: 1996).*
Pascalis et al. (The Journal of Immunology (2002) 169, 3076-3084) (Year: 2002).*
Casset et al. (BBRC 2003, 307:198-205), (Year: 2003).*
Vajdos et al. (J. Mol. Biol. (2002) 320, 415-428), (Year: 2002).*
Chen et al. (J. Mol. Bio. (1999) 293, 865-881) (Year: 1999).*
Wu et al. (J. Mol. Biol. (1999) 294, 151-162) (Year: 1999).*
Padlan et al. (PNAS 1989, 86:5938-5942) (Year: 1989).*
Lamminmaki et al. (JBC 2001, 276:36687-36694) (Year: 2001).*
Agarwal et al. A Pictet-Spengler ligation for protein chemical modification. PNAS 110(1):46-51 (2013).

(Continued)

*Primary Examiner* — Meera Natarajan
(74) *Attorney, Agent, or Firm* — Wilson Sonsini Goodrich & Rosati

(57) ABSTRACT

Disclosed herein, in certain embodiments, are anti-transferrin receptor antibodies, anti-transferrin receptor antibody conjugates, and pharmaceutical compositions which comprise the anti-transferrin receptor antibodies or conjugates. In some embodiments, also disclosed herein are methods of delivering a payload utilizing an anti-transferrin receptor antibody described herein, and methods of treatment with use of an anti-transferrin receptor antibody described herein.

27 Claims, 20 Drawing Sheets

Specification includes a Sequence Listing.

(56) References Cited

U.S. PATENT DOCUMENTS

| | | | |
|---|---|---|---|
| 8,802,667 B2 | 8/2014 | Li et al. |
| 8,809,320 B2 | 8/2014 | Li et al. |
| 8,871,720 B2 | 10/2014 | Doronina et al. |
| 8,936,910 B2 | 1/2015 | Mitsch et al. |
| 8,980,833 B2 | 3/2015 | Richter |
| 9,089,614 B2 | 7/2015 | Lin et al. |
| 9,242,013 B2 | 1/2016 | Howard et al. |
| 9,605,019 B2 | 3/2017 | Verdine et al. |
| 9,695,211 B2 | 7/2017 | Wada et al. |
| 9,982,257 B2 | 5/2018 | Butler et al. |
| 2012/0065169 A1 | 3/2012 | Hanson et al. |
| 2013/0028919 A1 | 1/2013 | Howard et al. |
| 2013/0029900 A1 | 1/2013 | Widdison |
| 2013/0217638 A1 | 8/2013 | Wessjohann |
| 2013/0224228 A1 | 8/2013 | Jackson et al. |
| 2013/0309256 A1 | 11/2013 | Lyon et al. |
| 2013/0323268 A1 | 12/2013 | Chari et al. |
| 2014/0127239 A1 | 5/2014 | Howard |
| 2014/0194610 A1 | 7/2014 | Verdine et al. |
| 2014/0286970 A1 | 9/2014 | Jeffrey et al. |
| 2014/0294851 A1 | 10/2014 | Nguyen |
| 2014/0294868 A1 | 10/2014 | Howard et al. |
| 2014/0296321 A1 | 10/2014 | Iversen |
| 2014/0363454 A1 | 12/2014 | Jackson et al. |
| 2015/0037360 A1 | 2/2015 | Smith |
| 2015/0105539 A1 | 4/2015 | Miao et al. |
| 2015/0105540 A1 | 4/2015 | Miao et al. |
| 2015/0211006 A1 | 7/2015 | Butler et al. |

FOREIGN PATENT DOCUMENTS

| | | | |
|---|---|---|---|
| WO | WO-2009126933 A2 | 10/2009 |
| WO | WO-2011150408 A2 | 12/2011 |
| WO | WO-2013166155 A1 | 11/2013 |
| WO | WO-2014080251 A1 | 5/2014 |
| WO | WO-2014140317 A2 | 9/2014 |
| WO | WO-2014145090 A1 | 9/2014 |
| WO | WO-2014177042 A1 | 11/2014 |
| WO | WO-2014189973 A2 | 11/2014 |
| WO | WO-2014197854 A1 | 12/2014 |
| WO | WO-2015038426 A1 | 3/2015 |
| WO | WO-2015057699 A2 | 4/2015 |
| WO | WO-2015069587 A2 | 5/2015 |
| WO | WO-2015107425 A2 | 7/2015 |
| WO | WO-2016081643 A1 | 5/2016 |
| WO | WO-2020132584 A1 | 6/2020 |

OTHER PUBLICATIONS

Albarran et al. Efficient intracellular delivery of a pro-apoptotic peptide with a pH-responsive carrier. React Funct Polym 71:261-265 (2011).
Alegre et al. Effect of a Single Amino Acid Mutation on the Activating and Immunosuppressive Properties of a "Humanized" OKT3 Monoclonal Antibody J Immunol 148:3461-3468 (1992).
Al-Lazikani et al. Standard conformations for the canonical structures of immunoglobulins. J. Mol Biology 273(4):927-948 (1997).
Axup et al. Synthesis of site-specific antibody-drug conjugates using unnatural amino acids. PNAS 109(40):16101-16106 (2012).
Ballangrud et al. Response of LNCaP Spheroids After Treatment With an Alpha-Particle Emitter (213Bi)-labeled Anti-Prostate-Specific Membrane Antigen Antibody (J591) Cancer Res. 61:2008-2014 (2001).
Bird et al. Single-chain antigen-binding proteins. Science 242:423-442 (1988).
Borchardt et al. Targeted actinium-225 in Vivo Generators for Therapy of Ovarian Cancer Cancer Res. 63:5084-50 (2003).
Brinkmann et al. The making of bispecific antibodies. MABS 9(2):182-212 (2017).
Bulmus et al. A new pH-responsive and glutathione-reactive, endosomal membrane-disruptive polymeric carrier for intracellular delivery of biomolecular drugs. J Controlled Release 93:105-120 (2003).

Casi et al. Site-specific traceless coupling of potent cytotoxic drugs to recombinant antibodies for pharmacodelivery. J Am Chem Soc 134(13):5887-5892 (2012).
Chotha et al. Structural repertoire of the human VH segments. J.Mol.Biol. 227:799-817 (1992).
Chothia et al. Canonical structures for the hypervariable regions of immunoglobulins. J Mol Biol. 196(4):901-917 (1987).
Clackson et al. Making antibody fragments using phage display libraries. Nature 352(6336):624-628 (1991).
Colberre-Garapin et al. A new dominant hybrid selective marker for higher eukaryotic cells. J Mol Biol 150:1-14 (1981).
Cole et al. The EBV-hybridoma technique and its application to human lung cancer. In, Monoclonal Antibodies and Cancer Therapy (vol. 27, UCLA Symposia on Molecular and Cellular Biology, New Series) (eds. R.A. Reisfeld and S.Sell), New York: Alan R. Liss, Inc. pp. 77-96 (1985).
Crouse et al. Expression and amplification of engineered mouse dihydrofolate reductase minigenes. Mol Cell Biol 3(2):257-266 (1983).
Dawson et al. Modulation of Reactivity in Native Chemical Ligation through the Use of Thiol Additives. J. Am. Chem. Soc. 119:4325-4329 (1997).
Dawson et al. Synthesis of proteins by native chemical ligation. Science 266(5186):776-779 (1994).
Dimasi et al. Development of a trispecific antibody designed to simultaneously and efficiently target three different antigens on tumor cells. Mol Pharm 12(9):3490-3501 (2015).
Duncan et al. A polymer-Triton X-100 conjugate capable of pH-dependent red blood cell lysis: a model system illustrating the possibility of drug delivery within acidic intracellular compartments. J Drug Target 2:341-347 (1994).
El-Sayed et al. Rational design of composition and activity correlations for pH-responsive and glutathione-reactive polymer therapeutics. J Control Release 104:417-427 (2005).
Flanary et al. Antigen delivery with poly(propylacrylic acid) conjugation enhanced MHC-1 presentation and T-cell activation. Bioconjugate Chem. 20:241-248 (2009).
Goldspiel et al. Human gene therapy. Clin Pharm 12:488-505 (1993).
Hackeng et al. Protein synthesis by native chemical ligation: Expanded scope by using straightforward methodology. PNAS USA 96:10068-10073 (1999).
Hanes et al. In vitro selection and evolution of functional proteins by using ribosome display. PNAS USA 94:4937-4942 (1997).
Hejesen et al. A traceless aryl-triazene linker for DNA-directed chemistry. Org Biomol Chem 11(15):2493-2497 (2013).
Henry et al. pH-responsive poly(styrene-alt-maleic anhydride) alkylamide copolymers for intracellular drug delivery. Biomacromolecules 7:2407-2414 (2006).
Huse et al. Generation of a large combinatorial library of the immunoglobulin repertoire in phage lambda. Science 246(4935):1275-1281 (1989).
Huston et al. Protein engineering of antibody binding sites: recovery of specific activity in an anti-digoxin single-chain Fv analogue produced in *Escherichia coli*. PNAS USA 85(16):5879-5883 (1988).
Idusogie, et al. Mapping of the C1q binding site on rituxan, a chimeric antibody with a human IgG1 Fc. J Immunol. Apr. 15, 2000;164(8):4178-84.
Jones et al. Poly(2-alkylacrylic acid) polymers deliver molecules to the cytosol by pH-sensitive disruption of endosomal vesicles. Biochem J 372:65-75 (2003).
Kabat et al. Attempts to Locate Complementarity-Determining Residues in the Variable Positions of Light and Heavy Chains. Ann. NY Acad. Sci. 190:382-391 (1971).
Kabat et al. Sequences of proteins of immunological interest. NIH Publ. No. 91-3242 1:647-669 (1991).
Kaneko et al. Optimizing Therapeutic Antibody Function: Progress With Fc Domain Engineering. Biodrugs 25(1):1-11 (2011).
Khormaee et al. Edosomolytic anionic polymer for the cytoplasmic delivery of siRNAs in localized in vivo applications. Adv Funct Mater 23:565-574 (2013).
Kohler et al. Continuous cultures of fused cells secreting antibody of predefined specificity. Nature 256:495-497 (1975).

(56) References Cited

OTHER PUBLICATIONS

Kozbor et al. The production of monoclonal antibodies from human lymphocytes. Immunology Today 4:72-79 (1983).
Kutmeier et al. Assembly of humanized antibody genes from synthetic oligonucleotides using a single-round PCR. BioTechniques 17:242 (1994).
Lazar et al. Engineered antibody Fc variants with enhanced effector function. PNAS USA 103(11):4005-10 (2006).
Lefranc et al. IMGT, the International ImMunoGeneTics Database. Nucleic Acids Res. 27:209-212 (1999).
Lefranc. The IMGT Unique Numbering for Immunoglobulins, T-Cell Receptors, and Ig-Like Domains. The Immunologist 7:132-136 (1999).
Loakes. Survey and summary: The applications of universal DNA base analogues. Nucleic Acids Research 29:2437-2447 (2001).
Lowy et al., Isolation of transforming DNA: Cloning the hamster aprt gene. Cell 22:817-823 (1980).
Lyon et al. Self-hydrolyzing maleimides improve the stability and pharmacological properties of antibody-drug conjugates. Nat. Biotechnol. 32(10):1059-1062 (2014).
MacCallum et al. Antibody-antigen interactions: contact analysis and binding site topography. J Mol Biol. 262(5):732-745 (1996).
Martin. Chapter 3. Protein Sequence and Structure Analysis of Antibody Variable Domains. in Antibody Engineering, Kontermann and Dübel, eds., pp. 422-439, Springer-Verlag, Berlin (2001).
Martinez et al. Single-stranded antisense siRNAs guide target RNA cleavage in RNAi. Cell 110(5):563-574 (2002).
McDevitt et al. Tumor Therapy With Targeted Atomic Nanogenerators. Science 294:1537-1540 (2001).
Moore et al. Engineered Fc variant antibodies with enhanced ability to recruit complement and mediate effector functions. mAbs 2(2):181-189 (2010).
Morgan et al. Human gene therapy. Ann Rev Biochem 62:191-217 (1993).
Morrison et al. Chimeric human antibody molecules: mouse antigen-binding domains with human constant region domains. PNAS USA 81(21):6851-6855 (1984).
Mulligan et al. Selection for animal cells that express the *Escherichia coli* gene coding for xanthine-guanine phosphoribosyltransferase. PNAS USA 78(4):2072-2076 (1981).
Mulligan. The basic science of gene therapy. Science 260(5110):926-932 (1993).
Naisbitt et al. Disposition of amodiaquine and related antimalarial agents in human neutrophils: implications for drug design. J Pharmacol Exp Ther 280:884-893 (1997).
Natsume et al. Engineered Antibodies of IgG1/IgG3 Mixed Isotype With Enhanced Cytotoxic Activities. Cancer Res 68(10):3863-72 (2008).
Neuberger et al. Recombinant antibodies possessing novel effector functions. Nature 312(5995):604-608 (1984).
O'Hare et al. Transformation of mouse fibroblasts to methotrexate resistance by a recombinant plasmid expressing a prokaryotic dihydrofolate reductase. PNAS USA 78:1527-1531 (1981).
PCT/US2019/068078 International Search Report and Written Opinion dated Apr. 24, 2020.
Pizzamiglio et al. Expression of iron-related proteins differentiate non-cancerous and cancerous breast tumors. Int J Mol Sci. 18(2):410 (2017).
Rangasamy et. al. New mechanism for release of endosomal contents: osmotic lysis via nigeri-cin-mediated K+/H+ exchange. Bioconjugate Chem. 29:1047-1059 (2018).
Rosager et al., Transferrin receptor-1 and ferritin heavy and light chains in astrocytic brain tu-mors: Expression and prognostic value. PLoS One 12:e0182954 (2017).
Rychtarcikova et al. Tumorinitiating cells of breast and prostate origin show alterations in the expression of genes related to iron metabolism. Oncotarget. 8:6376-6398 (2017).
Santerre et al. Expression of prokaryotic genes for hygromycin B and G418 resistance as dominant-selection markers in mouse L cells. Gene 30(1-3):147-156 (1984).
Schwarz et al. Evidence that siRNAs function as guides, not primers, in the *Drosophila* and human RNAi pathways. Molecular Cell 10:537-548 (2002).
Shields et al. High Resolution Mapping of the Binding Site on Human IgG1 for FcγRl, FcγRll, FcγRlll, and FcRn and Design of IgG1 Variants with Improved Binding to the FcγR. J Biol Chem 276(9):6591-6604 (2001).
Skerra et al. Assembly of a functional Immunoglobulin Fv fragment in *Escherichia coli*. Science 240(4855):1038-1041 (1988).
Stavenhagen et al. Enhancing the potency of therapeutic monoclonal antibodies via Fc optimization. Adv Enzyme Regul. 48:152-64 (2008).
Stavenhagen et al. Fc Optimization of Therapeutic Antibodies Enhances Their Ability to Kill Tumor Cells In vitro and Controls Tumor Expansion In vivo via Low-Affinity Activating Fcγ Receptors. Cancer Res 67(18):8882-91 (2007).
Strop et al. Location matters: site of conjugation modulates stability and pharmacokinetics of antibody drug conjugates. Chem Biol 20(2):161-167 (2013).
Szybalska et al. Genetics of human cell line. IV. DNA-mediated heritable transformation of a biochemical trait. PNAS USA 48:2026-2034 (1962).
Takeda et al. Construction of chimaeric processed immunoglobulin genes containing mouse variable and human constant region sequences. Nature 314(6010):452-454 (1985).
Tolstoshev. Gene Therapy, Concepts, Current Trials and Future Directions. Ann. Rev. Pharmacol. Toxicol. 32:573-596 (1993).
Tramontano et al. Framework Residue 71 is a Major Determinant of the Position and Conformation of the Second Hypervariable Region in the VH Domains of Immunoglobulins. J. Mol. Biol. 215(1):175-82 (1990).
Ward et al. Binding activities of a repertoire of single immunoglobulin variable domains secreted from *Escherichia coli*. Nature 341(6242):544-546 (1989).
Wigler et al. Transfer of purified herpes virus thymidine kinase gene to cultured mouse cells. Cell 11:223-232 (1977).
Wigler et al. Transformation of mammalian cells with an amplifiable dominant-acting gene. PNAS USA 77:3567-3570 (1980).
Wu et al. Building complex glycopeptides: Development of a cysteine-free native chemical ligation protocol. Angew. Chem. Int. Ed. 45:4116-4125 (2006).
Wu et al. Delivery systems for gene therapy. Biotherapy 3:87-95 (1991).
Wu et al. Site-specific chemical modification of recombinant proteins produced in mammalian cells by using the genetically encoded aldehyde tag. PNAS USA 106(9):3000-3005 (2009).
Zapata et al. Engineering linear F(ab')2 fragments for efficient production in *Escherichia coli* and enhanced antiproliferative activity. Protein Eng. 8(10):1057-1062 (1995).

\* cited by examiner

| | hTfR1.IgG2 mAb-SSB DAR1 | hTfR1.IgG2 mAb |
|---|---|---|
| Specific binding with Hill slope | | |
| Best-fit values | | |
| Bmax | 2.339 | 2.371 |
| h | 1.794 | 1.717 |
| Kd | 3.179 | 3.224 |

| | hTfR1.IgG2 mAb-SSB DAR1 | hTfR1.IgG2 mAb |
|---|---|---|
| Specific binding with Hill slope | | |
| Best-fit values | | |
| Bmax | 2.283 | 2.273 |
| h | 1.959 | 1.86 |
| Kd | 4.994 | 4.872 |

|  | IgG1 TfR WT | blocking AF2474 | hIgG1TfR-v2i | hIgG1TfR-v2ii | hIgG1TfR-v2iii | hIgG1TfR-v9i |
|---|---|---|---|---|---|---|
| Bmax | 3.452 | 4.258 | 3.477 | 3.533 | 3.474 | 3.528 |
| h | 1.575 | 1.117 | 1.487 | 1.447 | 1.614 | 1.451 |
| Kd | 51.79 | 2181 | 67.76 | 57.8 | 52.17 | 55.95 |
| Kd(Tf+TfR)/Kd(TfR) | 3.1 | 51.8 | 2.8 | 2.5 | 2.1 | 2.2 |
|  | hIgG1TfR-v9ii | hIgGTfR-v9iii | hIgG1TfR-v15i | hIgG1TfR-v15ii | hIgG1TfR-v15iii |  |
| Bmax | 3.509 | 3.527 | 3.473 | 3.523 | 3.5 |  |
| h | 1.481 | 1.491 | 1.562 | 1.456 | 1.516 |  |
| Kd | 56.99 | 54.62 | 61.87 | 84.94 | 60.39 |  |
| Kd(Tf+TfR)/Kd(TfR) | 2.6 | 2.5 | 2.9 | 2.5 | 2.4 |  |

| HFE+TfR | IgG1 TfR WT | blocking AF2474 | hIgG1TfR-v2i | hIgG1TfR-v2ii | hIgG1TfR-v2iii | hIgG1TfR-v9i |
|---|---|---|---|---|---|---|
| Bmax | 2.875 | 5.703 | 2.999 | 3.155 | 2.658 | 2.789 |
| h | 1.544 | 0.8004 | 1.627 | 1.642 | 1.261 | 1.368 |
| Kd | 286.4 | 28940 | 273.2 | 227 | 289.2 | 340.9 |
| Kd(HFE+TfR)/Kd(TfR) | 16.9 | 687.7 | 11.1 | 9.9 | 11.9 | 13.6 |
|  | hIgG1TfR-v9ii | hIgGTfR-v9iii | hIgG1TfR-v15i | hIgG1TfR-v15ii | hIgG1TfR-v15iii |  |
| Bmax | 2.996 | 3.136 | 2.699 | 2.79 | 1.811 |  |
| h | 1.357 | 1.38 | 1.653 | 1.285 | 1.452 |  |
| Kd | 229.2 | 248.2 | 182.3 | 346.4 | 213.5 |  |
| Kd(HFE+TfR)/Kd(TfR) | 10.4 | 11.4 | 8.5 | 10.2 | 8.5 |  |

| | hIgG1 TfR-Var2i-SSB | hIgG1 TfR-Var2ii-SSB | hIgG1 TfR-Var2iii-SSB | hIgG1 TfR-Var9i-SSB | hIgG1 TfR-Var9ii-SSB |
|---|---|---|---|---|---|
| Bottom | 97.38 | 107.3 | 102.3 | 99.1 | 103.2 |
| Top | 44.58 | 46.89 | 50.43 | 53.83 | 54.82 |
| LogEC50 | -0.4851 | -0.6479 | -0.5046 | -0.5777 | -0.8734 |
| EC50 (nM) | 0.3273 | 0.225 | 0.3129 | 0.2644 | 0.1338 |
| Span | -52.8 | -60.46 | -51.83 | -45.26 | -48.37 |
| Emax (%KD) | 55.42 | 53.11 | 49.57 | 46.17 | 45.18 |

| | hIgG1 TfR-Var9iii-SSB | hIgG1 TfR-Var15i-SSB | hIgG1 TfR-Var15ii-SSB | hIgG1 TfR-Var15iii-SSB | hIgG1 TfR-WT Chim-SSB |
|---|---|---|---|---|---|
| Bottom | 98.01 | 103 | 99.32 | 104 | 108.4 |
| Top | 50.34 | 50.4 | 53.94 | 54.36 | 61.06 |
| LogEC50 | -0.5671 | -0.4047 | -0.2551 | -0.289 | -0.4791 |
| EC50 (nM) | 0.2709 | 0.3938 | 0.5557 | 0.514 | 0.3318 |
| Span | -47.67 | -52.59 | -45.37 | -49.62 | -47.38 |
| Emax (%KD) | 49.66 | 49.6 | 46.06 | 45.64 | 38.94 |

US 10,913,800 B2

ANTI-TRANSFERRIN RECEPTOR ANTIBODIES AND USES THEREOF

CROSS-REFERENCE

This application is a continuation of the International Application No. PCT/US2019/068078, filed Dec. 20, 2019, which claims the benefit of U.S. Provisional Application No. 62/784,181, filed Dec. 21, 2018, both of which are incorporated herein by reference in their entireties.

SEQUENCE LISTING

The instant application contains a Sequence Listing which has been submitted electronically in ASCII format and is hereby incorporated by reference in its entirety. The ASCII copy, created on Oct. 29, 2020 is named 45532-731_301_SL.txt, and is 135,245 bytes in size.

BACKGROUND OF THE DISCLOSURE

The present invention is in the fields of pharmaceutical agents and specially relates to antibody. This invention provides anti-transferrin receptor antibodies and methods of preparing and using the anti-transferrin receptor antibodies.

In addition to known uses in diagnostics, antibodies have been shown to be useful as therapeutic agents. For example, immunotherapy, or the use of antibodies for therapeutic purposes has been used in recent years to treat cancer and other disorders. The transferrin receptor is one of the mostly widely targeted receptors for development of targeted cancer diagnostics and therapeutics. This type II transmembrane glycoprotein is responsible for cellular iron transport and is found at low levels on the surface of many normal cell types. There is a need for developing improved anti-transferrin receptor antibody for pharmaceutical uses.

SUMMARY OF THE DISCLOSURE

Disclosed herein, in certain embodiments, are anti-transferrin receptor antibodies, anti-transferrin receptor antibody conjugates, and pharmaceutical compositions which comprise the anti-transferrin receptor antibodies or conjugates. In some embodiments, also disclosed herein are methods of delivering a payload utilizing an anti-transferrin receptor antibody described herein, and methods of treatment with use of an anti-transferrin receptor antibody described herein.

Disclosed herein, in certain embodiments, is an anti-transferrin receptor antibody comprising a variable heavy chain (VH) region and a variable light chain (VL) region, wherein the VH region comprises HCDR1 sequence comprising SEQ ID NO: 1; HCDR2 sequence EINPIX$_1$GRSNYAX$_2$KFQG (SEQ ID NO:88), wherein X$_1$ is selected from N or Q and X$_2$ is selected from Q or E; and HCDR3 sequence comprising SEQ ID NO: 3. In some embodiments, the VH region comprises HCDR1 sequence comprising SEQ ID NO: 1, HCDR2 sequence comprising SEQ ID NO: 2, and HCDR3 sequence comprising SEQ ID NO: 3. In some embodiments, the VH region comprises HCDR1 sequence comprising SEQ ID NO: 1, HCDR2 sequence comprising SEQ ID NO: 4, and HCDR3 sequence comprising SEQ ID NO: 3. In some embodiments, the VH region comprises HCDR1 sequence comprising SEQ ID NO: 1, HCDR2 sequence comprising SEQ ID NO: 5, and HCDR3 sequence comprising SEQ ID NO: 3. In some embodiments, the VL region comprises LCDR1 sequence RTSENIYX$_3$NLA (SEQ ID NO: 89), LCDR2 sequence AX$_4$TNLAX$_5$ (SEQ ID NO: 90), and LCDR3 sequence QHFWGTPLTX6 (SEQ ID NO: 91), wherein X$_3$ is selected from N or S, X$_4$ is selected from A or G, X$_5$ is selected from D or E, and X$_6$ is present or absence, and if present, is F. In some embodiments, the VL region comprises LCDR1 sequence comprising SEQ ID NO: 6, LCDR2 sequence AATNLAX$_5$ (SEQ ID NO: 92), and LCDR3 sequence QHFWGTPLTX$_6$ (SEQ ID NO: 91), wherein X$_5$ is selected from D or E and X$_6$ is present or absence, and if present, is F. In some embodiments, the VL region comprises LCDR1 sequence comprising SEQ ID NO: 6, LCDR2 sequence comprising SEQ ID NO: 7, and LCDR3 sequence comprising SEQ ID NO: 8. In some embodiments, the VL region comprises LCDR1 sequence comprising SEQ ID NO: 6, LCDR2 sequence comprising SEQ ID NO: 9, and LCDR3 sequence comprising SEQ ID NO: 10. In some embodiments, the VL region comprises LCDR1 sequence comprising SEQ ID NO: 11, LCDR2 sequence comprising SEQ ID NO: 12, and LCDR3 sequence comprising SEQ ID NO: 10. In some embodiments, the VH region comprises HCDR1 sequence comprising SEQ ID NO: 1, HCDR2 sequence comprising SEQ ID NO: 2, and HCDR3 sequence comprising SEQ ID NO: 3; and the VL region comprises LCDR1 sequence comprising SEQ ID NO: 6, LCDR2 sequence comprising SEQ ID NO: 7, and LCDR3 sequence comprising SEQ ID NO: 8. In some embodiments, the VH region comprises HCDR1 sequence comprising SEQ ID NO: 1, HCDR2 sequence comprising SEQ ID NO: 4, and HCDR3 sequence comprising SEQ ID NO: 3; and the VL region comprises LCDR1 sequence comprising SEQ ID NO: 6, LCDR2 sequence comprising SEQ ID NO: 7, and LCDR3 sequence comprising SEQ ID NO: 8. In some embodiments, the VH region comprises HCDR1 sequence comprising SEQ ID NO: 1, HCDR2 sequence comprising SEQ ID NO: 5, and HCDR3 sequence comprising SEQ ID NO: 3; and the VL region comprises LCDR1 sequence comprising SEQ ID NO: 6, LCDR2 sequence comprising SEQ ID NO: 9, and LCDR3 sequence comprising SEQ ID NO: 10. In some embodiments, the VH region comprises HCDR1 sequence comprising SEQ ID NO: 1, HCDR2 sequence comprising SEQ ID NO: 4, and HCDR3 sequence comprising SEQ ID NO: 3; and the VL region comprises LCDR1 sequence comprising SEQ ID NO: 11, LCDR2 sequence comprising SEQ ID NO: 12, and LCDR3 sequence comprising SEQ ID NO: 10. In some embodiments, the VH region comprises at least 80%, 85%, 90%, 95%, 99%, or 100% sequence identity to a sequence selected from SEQ ID NOs: 13-16. In some embodiments, the VL region comprises at least 80%, 85%, 90%, 95%, 99%, or 100% sequence identity to a sequence selected from SEQ ID NOs: 18-21. In some embodiments, the anti-transferrin receptor antibody comprises a humanized antibody or binding fragment thereof or a chimeric antibody or binding fragment thereof. In some embodiments, the anti-transferrin receptor antibody comprises a multi-specific antibody or binding fragment thereof. In some embodiments, the anti-transferrin receptor antibody comprises a bispecific antibody or binding fragment thereof. In some embodiments, the anti-transferrin receptor antibody comprises an IgG-scFv, nanobody, BiTE, diabody, DART, TandAb, scDiabody, scDiabody-CH3, triple body, miniantibody, minibody, TriBi minibody, scFv-CH3 KIH, Fab-scFv-Fc KIH, Fab-scFv, scFv-CH-CL-scFv, F(ab')2, F(ab')2-scFv2, scFv-KIH, Fab-scFv-Fc, tetravalent HCAb, scDiabody-Fc, diabody-Fc, tandem scFv-Fc, or intrabody. In some embodiments, the anti-transferrin receptor antibody comprises an IgG1 framework. In some embodiments, the anti-transferrin receptor antibody comprises an IgG2 framework. In some embodiments, the IgG2 framework is IgG2b framework. In some embodiments, the anti-transferrin receptor antibody comprises IgG4 framework. In some embodiments, the anti-transferrin receptor antibody further comprises at least one mutation in the Fc region. In some embodiments, the at least one mutation modulates effector function. In some embodiments, the at least one mutation attenuates or eliminates Fc-γ receptor binding. In some embodiments, the at least one mutation is at residue position D265, N297, K322, L328, or P329, wherein the residue position is in reference to IgG1. In some embodiments, the Fc region comprises two or more, three or more, or four or more mutations. In some embodiments, the Fc region comprises mutations at L233 and L234, wherein the residues correspond to position 233 and 234 of SEQ ID NO: 23. In some embodiments, the Fc region comprises mutations at D265 and N297. In some embodiments, the anti-transferrin receptor antibody comprises a heavy chain (HC) sequence selected from SEQ ID NOs: 23-46 and a light chain (LC) sequence selected from SEQ ID NOs: 47-50. In some embodiments, the anti-transferrin receptor antibody specifically binds to human transferrin receptor (TfR).

Disclosed herein, in certain embodiments, is an anti-transferrin receptor antibody conjugate comprising an anti-transferrin receptor antibody described herein and a payload. In some embodiments, the payload comprises a small molecule, a peptide, a protein, or a polynucleic acid molecule. In some embodiments, the payload comprises a polynucleic acid molecule. In some embodiments, the polynucleic acid molecule comprises short interfering nucleic acid (siNA), short interfering RNA (siRNA), double-stranded RNA (dsRNA), micro-RNA (miRNA), short hairpin RNA (shRNA), antisense oligonucleotide (ASO), a PMO, or mRNA. In some embodiments, the payload comprises a dsRNA. In some embodiments, the payload comprises an antisense oligonucleotide (ASO). In some embodiments, the payload comprises a small molecule, a peptide, or a protein. In some embodiments, the payload comprises a microtubule disrupting agent, a DNA modifying agent, or an Akt inhibitor. In some embodiments, the payload comprises an auristatin or a derivative thereof, a dolastatin or a derivative or analog thereof, a maytansinoid, or a pyrrolobenzodiazepine or a derivative thereof. In some embodiments, the auristatin or derivative thereof is monomethyl auristatin E (MMAE) or monomethyl auristatin F (MMAF). In some embodiments, the maytansinoid is DM1 or DM4. In some embodiments, pyrrolobenzodiazepine is a pyrrolobenzodiazepine dimer. In some embodiments, the payload comprises an immunomodulatory agent or an immune modulator. In some embodiments, the immune modulator comprises a cytokine. In some embodiments, the payload comprises a protein or peptide toxin or fragment thereof. In some embodiments, the payload is conjugated to the anti-transferrin receptor antibody through a linker. In some embodiments, the anti-transferrin receptor antibody is further conjugated to two or more payloads. In some embodiments, a ratio of the payloads to the anti-transferrin receptor antibody is about 1:1, 2:1, 3:1, 4:1, 5:1, 6:1, 7:1, 8:1, 9:1, 10:1, 11:1, or 12:1. In some embodiments, the anti-transferrin conjugate comprises A-$(X^1$-$B)_n$ Formula (I)), wherein A comprises the anti-transferrin receptor antibody; B comprises the payload; $X^1$ consists of a bond or linker; and n is an averaged value selected from 1-12. In some embodiments, the payload is a polynucleic acid molecule. In some embodiments, the polynucleic acid molecule comprises a passenger strand and a guide strand. In some embodiments, the guide strand comprises at least one modified internucleotide linkage, at least one inverted abasic moiety, at least one 5'-vinylphosphonate modified non-natural nucleotide, or a combination thereof. In some embodiments, the at least one 5'-vinylphosphonate modified non-natural nucleotide is located about 1, 2, 3, 4, or 5 bases away from the 5' terminus of the guide strand. In some embodiments, the polynucleic acid molecule further comprises a modification of a sugar moiety at the 2' position. In some embodiments, the modification at the 2'-position is selected from 2'-O-methyl, 2'-O-methoxyethyl (2'-O-MOE), 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified nucleotide. In some embodiments, the passenger strand comprises at least 6, 7, 8, 9, 10, 11, 12, 13, 14, 15, 16, 17, 18, 19, 20, or more phosphorodiamidate morpholino oligomer-modified non-natural nucleotides. In some embodiments, the passenger strand is shorter in length than the guide strand, thereby generating a 5' overhang, a 3' overhang, a blunt end at one terminus, or a combination thereof. In some embodiments, the passenger strand is equal in length to the guide strand, thereby generating a blunt end at each terminus of the polynucleic acid molecule. In some embodiments, the passenger strand is conjugated to A-$X^1$. In some embodiments, A-$X^1$ is conjugated to the 5' end of the passenger strand. In some embodiments, A-$X^1$ is conjugated to the 3' end of the passenger strand. In some embodiments, the anti-transferrin conjugate comprises: A-$X^1$-$(B$-$X^2$-$C)_n$ (Formula (II)), wherein A comprises the anti-transferrin receptor antibody; B comprises the polynucleic acid molecule; C consists of a polymer; $X^1$ consists a bond or first linker; $X^2$ consists of a bond or second linker; and n is an averaged value selected from 1-12. In some embodiments, C is polyethylene glycol. In some embodiments, the polynucleic acid molecule comprises a passenger strand and a guide strand. In some embodiments, the passenger strand is conjugated to A-$X^1$ and $X^2$-C. In some embodiments, A-$X^1$ is conjugated to the 5' end of the passenger strand and $X^2$-C is conjugated to the 3' end of the passenger strand. In some embodiments, $X^2$-C is conjugated to the 5' end of the passenger strand and A-$X^1$ is conjugated to the 3' end of the passenger strand. In some embodiments, $X^1$ and $X^2$ are each independently a non-polymeric linker. In some embodiments, the anti-transferrin receptor antibody conjugate further comprises D. In some embodiments, D is an endosomolytic moiety.

Disclosed herein, in certain embodiments, is a nucleic acid polymer encoding an anti-transferrin receptor antibody described herein.

Disclosed herein, in certain embodiments, is a vector comprising a nucleic acid polymer encoding an anti-transferrin receptor antibody described herein.

Disclosed herein, in certain embodiments, is a pharmaceutical composition comprising: an anti-transferrin receptor antibody described herein or an anti-transferrin receptor antibody conjugate described herein; and a pharmaceutically acceptable excipient. In some embodiments, the pharmaceutical composition is formulated for systemic administration. In some embodiments, the pharmaceutical composition is formulated for parenteral administration.

Disclosed herein, in certain embodiments, is a method of delivering a payload to a target site of interest in a subject, comprising: administering to the subject an anti-transferrin receptor antibody conjugate described herein or a pharmaceutical composition described herein to deliver the payload to the target site of interest. In some embodiments, the target site of interest is a cell comprising an overexpressed causative protein. In some embodiments, the target site of interest is a tumor site. In some embodiments, the target site of interest is a site located with the brain.

Disclosed herein, in certain embodiments, is a method of treating a cancer in a subject in need thereof, comprising: administering to the subject an anti-transferrin receptor antibody conjugate described herein or a pharmaceutical composition described herein to treat the cancer in the subject. In some embodiments, the cancer is a solid cancer. In some embodiments, the cancer is a hematologic malignancy. In some embodiments, the cancer is bladder cancer, lung cancer, brain cancer, melanoma, breast cancer, Non-Hodgkin lymphoma, cervical cancer, ovarian cancer, colorectal cancer, pancreatic cancer, esophageal cancer, prostate cancer, kidney cancer, skin cancer, leukemia, thyroid cancer, liver cancer, or uterine cancer. In some embodiments, the cancer is a metastatic cancer. In some embodiments, the cancer is a relapsed or refractory cancer.

Disclosed herein, in certain embodiments, is a method of treating a muscle atrophy or myotonic dystrophy in a subject in need thereof, comprising: administering to the subject an anti-transferrin receptor antibody conjugate described herein or a pharmaceutical composition described herein, wherein the polynucleic acid molecule hybridizes to a target sequence of an atrogene, and wherein the polynucleic acid molecule mediates RNA interference against the atrogene, thereby threatening muscle atrophy in the subject. In some embodiments, the muscle atrophy is a diabetes-associated muscle atrophy or a cancer cachexia-associated muscle atrophy. In some embodiments, the muscle atrophy is associated with insulin deficiency, chronic renal failure, congestive heart failure, chronic respiratory disease, a chronic infection, fasting, denervation, sarcopenia, or myotonic dystrophy type 1 (DM1). In some embodiments, the reticulocyte levels in the subject are not reduced following the administration of anti-transferrin receptor antibody. In some embodiments, the administration of anti-transferrin receptor antibody conjugate downregulates SSB siRNA or SSB mRNA levels in the subject. In some embodiments, the downregulation of SSB siRNA or SSB mRNA is in muscle. In some embodiments, the muscle is skeletal muscle. In some embodiments, the muscle is cardiac muscle.

In some embodiments, the myotonic dystrophy is DM1. In some embodiments, the atrogene comprises an upregulated gene within the IGF1-Akt-FoxO pathway, the glucocorticoids-GR pathway, the PGC1α-FoxO pathway, the TNFα-NF$_\kappa$B pathway, or the myostatin-ActRIIb-Smad2/3 pathway. In some embodiments, the atrogene encodes an E3 ligase. In some embodiments, the atrogene encodes a Forkhead box transcription factor. In some embodiments, the atrogene comprises atrogin-1 gene (FBXO32), MuRF1 gene (TRIM63), FOXO1, FOXO3, or MSTN. In some embodiments, the atrogene comprises DMPK. In some embodiments, the subject is a human.

Disclosed herein, in certain embodiments, is a method of treating a muscular dystrophy in a subject in need thereof, comprising: administering to the subject an anti-transferrin receptor antibody conjugate described herein or a pharmaceutical composition described herein, thereby treating the muscular dystrophy in the subject. In some embodiments, the muscular dystrophy is Duchenne muscular dystrophy, Becker muscular dystrophy, faciscapulohumeral muscular dystrophy, congenital muscular dystrophy, or myotonic dystrophy. In some embodiments, the muscular dystrophy is Duchenne muscular dystrophy. In some embodiments, the subject is a human.

Disclosed herein, in certain embodiments, is a kit comprising an anti-transferrin receptor antibody described herein, an anti-transferrin receptor antibody conjugate described herein, a nucleic acid polymer described herein, a vector described herein, or a pharmaceutical composition described herein.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings below. The patent application file contains at least one drawing executed in color. Copies of this patent application publication with color drawing(s) will be provided by the Office upon request and payment of the necessary fee.

DETAILED DESCRIPTION OF THE DISCLOSURE

Figure 1:
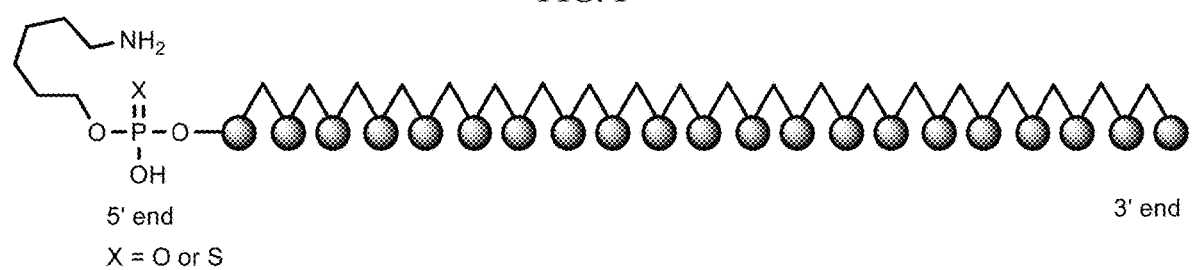
FIG. 1 illustrates the structure of an exemplary SSB passenger strand.

Transferrin receptors (TfRs) comprise a family of membrane glycoproteins and are encoded by the gene TFRC. TfRs are involved in iron metabolism by interacting with the iron-transferrin complex to facilitate iron into cells. There are two subtypes of TfRs, transferrin receptor 1 (TfR1 or CD71) and transferrin receptor 2 (TfR2). TfR1 is ubiquitously expressed in different cell types while TfR2 is specifically expressed in liver cells.

In some instances, abnormal expression of TfR1 has been noted in various cancers. Indeed, one study has shown that the expression level of TfR1 is elevated in breast cancer cells (Pizzamiglio, et al., "Expression of iron-related proteins differentiate non-cancerous and cancerous breast tumors," *Int J Mol Sci.* 2017; 18). In a separate study, TFR1 has also been shown to be overexpressed in brain cancer (Rosager, et al., "Transferrin receptor-1 and ferritin heavy and light chains in astrocytic brain tumors: Expression and prognostic value," *PLoS One* 12:e0182954 (2017)). A further study has noted that iron uptake is elevated in tumor-initiating cells (Rychtarcikova, et al., "Tumorinitiating cells of breast and prostate origin show alterations in the expression of genes related to iron metabolism," *Oncotarget.* 8:6376-6398 (2017)).

In some embodiments, disclosed herein is an anti-transferrin receptor antibody, an anti-transferrin receptor antibody conjugate, and pharmaceutical compositions comprising the same. In additional embodiments, disclosed herein is a method of utilizing the anti-transferrin receptor antibody for delivery of a payload, and method of treating a disease or condition by utilizing the presence of transferrin receptors for targeted delivery.

Anti-Transferrin Receptor Antibodies

In certain embodiments, disclosed herein is an anti-transferrin receptor antibody. In some instances, the anti-transferrin receptor antibody specifically binds to a transferrin receptor (TfR). In some instances, the anti-transferrin receptor antibody specifically binds to a human transferrin receptor (TfR). In some cases, the anti-transferrin receptor antibody specifically binds to transferrin receptor 1 (TfR1) (or CD71). In some cases, the anti-transferrin receptor antibody specifically binds to human transferrin receptor 1 (TfR1) (or human CD71).

In some instances, the anti-transferrin receptor antibody comprises a variable heavy chain (VH) region and a variable light chain (VL) region, wherein the VH region comprises HCDR1 sequence comprising SEQ ID NO: 1; HCDR2 sequence EINPIX$_1$GRSNYAX$_2$KFQG EINPIX1GRSNYAX2KFQG (SEQ ID NO: 88), wherein X$_1$ is selected from N or Q and X$_2$ is selected from Q or E; and HCDR3 sequence comprising SEQ ID NO: 3.

In some embodiments, the VH region of the anti-transferrin receptor antibody comprises HCDR1, HCDR2, and HCDR3 sequences selected from Table 1.

TABLE 1

| Name | HCDR1 | SEQ ID NO: | HCDR2 | SEQ ID NO: | HCDR3 | SEQ ID NO: |
|---|---|---|---|---|---|---|
| 13E4_VH1 | YTFTN YWMH | 1 | EINPINGRS NYAQKFQG | 2 | GTRA MHY | 3 |
| 13E4_VH2* | YTFTN YWMH | 1 | EINPINGRS NYWAEKFQG | 4 | GTRA MHY | 3 |
| 13E4_VH3 | YTFTN YWMH | 1 | EINPIQGRS NYAEKFQG | 5 | GTRA MHY | 3 |

*13E4_VH2 shares the same HCDR1, HCDR2, and HCDR3 sequences with anti-transferrin receptor antibody 13E4_VH4

In some embodiments, the VH region comprises HCDR1 sequence comprising SEQ ID NO: 1; HCDR2 sequence comprising SEQ ID NO: 2, 4, or 5; and HCDR3 sequence comprising SEQ ID NO: 3. In some instances, the VH region comprises HCDR1 sequence comprising SEQ ID NO: 1, HCDR2 sequence comprising SEQ ID NO: 2, and HCDR3 sequence comprising SEQ ID NO: 3. In some instances, the VH region comprises HCDR1 sequence comprising SEQ ID NO: 1, HCDR2 sequence comprising SEQ ID NO: 4, and HCDR3 sequence comprising SEQ ID NO: 3. In some instances, the VH region comprises HCDR1 sequence comprising SEQ ID NO: 1, HCDR2 sequence comprising SEQ ID NO: 5, and HCDR3 sequence comprising SEQ ID NO: 3.

In some embodiments, the VL region of the anti-transferrin receptor antibody comprises LCDR1 sequence RTSENIYX$_3$NLA (SEQ ID NO: 89), LCDR2 sequence AX$_4$TNLAX$_5$ (SEQ ID NO: 90), and LCDR3 sequence QHFWGTPLTX$_6$ (SEQ ID NO: 91), wherein X$_3$ is selected from N or S, X$_4$ is selected from A or G, X$_5$ is selected from D or E, and X$_6$ is present or absence, and if present, is F.

In some embodiments, the VL region of the anti-transferrin receptor antibody comprises LCDR1, LCDR2, and LCDR3 sequences selected from Table 2.

TABLE 2

| Name | LCDR1 | SEQ ID NO: | LCDR2 | SEQ ID NO: | LCDR3 | SEQ ID NO: |
|---|---|---|---|---|---|---|
| 13E4_VL1* | RTSENI YNNLA | 6 | AATN LAD | 7 | QHFWG TPLT | 8 |
| 13E4_VL3 | RTSENI YNNLA | 6 | AATN LAE | 9 | QHFWG TPLTF | 10 |

TABLE 2-continued

| Name | LCDR1 | SEQ ID NO: | LCDR2 | SEQ ID NO: | LCDR3 | SEQ ID NO: |
|---|---|---|---|---|---|---|
| 13E4_VL4 | RTSENI YSNLA | 11 | AGTN LAD | 12 | QHFWG TPLTF | 10 |

*13E4_VL1 shares the same LCDR1, LCDR2, and LCDR3 sequences with anti-transferrin receptor antibody 13E4_VL2

In some instances, the VL region comprises LCDR1 sequence RTSENIYX$_3$NLA (SEQ ID NO: 89), LCDR2 sequence comprising SEQ ID NO: 7, 9, or 12, and LCDR3 sequence comprising SEQ ID NO: 8 or 10, wherein X$_3$ is selected from N or S.

In some instances, the VL region comprises LCDR1 sequence comprising SEQ ID NO: 6 or 11, LCDR2 sequence AX$_4$TNLAX$_5$ (SEQ ID NO: 90), and LCDR3 sequence comprising SEQ ID NO: 8 or 10, wherein X$_4$ is selected from A or G, and X$_5$ is selected from D or E.

In some instances, the VL region comprises LCDR1 sequence comprising SEQ ID NO: 6 or 11, LCDR2 sequence SEQ ID NO: 7, 9, or 12, and LCDR3 sequence QHFWGTPLTX$_6$ (SEQ ID NO: 91), wherein X$_6$ is present or absence, and if present, is F.

In some instances, the VL region comprises LCDR1 sequence comprising SEQ ID NO: 6, LCDR2 sequence AATNLAX$_5$ (SEQ ID NO: 92), and LCDR3 sequence QHFWGTPLTX$_6$ (SEQ ID NO: 91), wherein X$_5$ is selected from D or E and X$_6$ is present or absence, and if present, is F.

In some instances, the VL region comprises LCDR1 sequence comprising SEQ ID NO: 6, LCDR2 sequence comprising SEQ ID NO: 7, and LCDR3 sequence comprising SEQ ID NO: 8.

In some instances, the VL region comprises LCDR1 sequence comprising SEQ ID NO: 6, LCDR2 sequence comprising SEQ ID NO: 9, and LCDR3 sequence comprising SEQ ID NO: 10.

In some instances, the VL region comprises LCDR1 sequence comprising SEQ ID NO: 11, LCDR2 sequence comprising SEQ ID NO: 12, and LCDR3 sequence comprising SEQ ID NO: 10.

In some embodiments, the anti-transferrin receptor antibody comprises a VH region and a VL region, wherein the VH region comprises HCDR1 sequence comprising SEQ ID NO: 1; HCDR2 sequence EINPIX$_1$GRSNYAX$_2$KFQG (SEQ ID NO: 88), wherein X$_1$ is selected from N or Q and X$_2$ is selected from Q or E; and HCDR3 sequence comprising SEQ ID NO: 3; and the VL region comprises LCDR1 sequence RTSENIYX$_3$NLA (SEQ ID NO: 89), LCDR2 sequence AX$_4$TNLAX$_5$ (SEQ ID NO: 90), and LCDR3 sequence QHFWGTPLTX$_6$ (SEQ ID NO: 91), wherein X$_3$ is selected from N or S, X$_4$ is selected from A or G, X$_5$ is selected from D or E, and X$_6$ is present or absence, and if present, is F.

In some instances, the anti-transferrin receptor antibody comprises a VH region and a VL region, wherein the VH region comprises HCDR1 sequence comprising SEQ ID NO: 1; HCDR2 sequence EINPIX$_1$GRSNYAX$_2$KFQG (SEQ ID NO: 88), wherein X$_1$ is selected from N or Q and X$_2$ is selected from Q or E; and HCDR3 sequence comprising SEQ ID NO: 3; and the VL region comprises LCDR1 sequence RTSENIYX$_3$NLA (SEQ ID NO: 89), LCDR2 sequence comprising SEQ ID NO: 7, 9, or 12, and LCDR3 sequence comprising SEQ ID NO: 8 or 10, wherein X$_3$ is selected from N or S.

In some instances, the anti-transferrin receptor antibody comprises a VH region and a VL region, wherein the VH region comprises HCDR1 sequence comprising SEQ ID NO: 1; HCDR2 sequence EINPIX$_1$GRSNYAX$_2$KFQG (SEQ ID NO: 88), wherein X$_1$ is selected from N or Q and X$_2$ is selected from Q or E; and HCDR3 sequence comprising SEQ ID NO: 3; and the VL region comprises LCDR1 sequence comprising SEQ ID NO: 6 or 11, LCDR2 sequence AX$_4$TNLAX$_5$, and LCDR3 sequence comprising SEQ ID NO: 8 or 10, wherein X$_4$ is selected from A or G, and X$_5$ is selected from D or E.

In some instances, the anti-transferrin receptor antibody comprises a VH region and a VL region, wherein the VH region comprises HCDR1 sequence comprising SEQ ID NO: 1; HCDR2 sequence EINPIX$_1$GRSNYAX$_2$KFQG (SEQ ID NO: 88), wherein X$_1$ is selected from N or Q and X$_2$ is selected from Q or E; and HCDR3 sequence comprising SEQ ID NO: 3; and the VL region comprises LCDR1 sequence comprising SEQ ID NO: 6 or 11, LCDR2 sequence SEQ ID NO: 7, 9, or 12, and LCDR3 sequence QHFWGTPLTX$_6$ (SEQ ID NO: 91), wherein X$_6$ is present or absence, and if present, is F.

In some instances, the anti-transferrin receptor antibody comprises a VH region and a VL region, wherein the VH region comprises HCDR1 sequence comprising SEQ ID NO: 1; HCDR2 sequence EINPIX$_1$GRSNYAX$_2$KFQG (SEQ ID NO: 88), wherein X$_1$ is selected from N or Q and X$_2$ is selected from Q or E; and HCDR3 sequence comprising SEQ ID NO: 3; and the VL region comprises LCDR1 sequence comprising SEQ ID NO: 6, LCDR2 sequence AATNLAX$_5$ (SEQ ID NO: 92), and LCDR3 sequence QHFWGTPLTX$_6$ (SEQ ID NO: 91), wherein X$_5$ is selected from D or E and X$_6$ is present or absence, and if present, is F.

In some instances, the anti-transferrin receptor antibody comprises a VH region and a VL region, wherein the VH region comprises HCDR1 sequence comprising SEQ ID NO: 1; HCDR2 sequence EINPIX$_1$GRSNYAX$_2$KFQG (SEQ ID NO: 88), wherein X$_1$ is selected from N or Q and X$_2$ is selected from Q or E; and HCDR3 sequence comprising SEQ ID NO: 3; and the VL region comprises LCDR1 sequence comprising SEQ ID NO: 6, LCDR2 sequence comprising SEQ ID NO: 7, and LCDR3 sequence comprising SEQ ID NO: 8.

In some instances, the anti-transferrin receptor antibody comprises a VH region and a VL region, wherein the VH region comprises HCDR1 sequence comprising SEQ ID NO: 1; HCDR2 sequence EINPIX$_1$GRSNYAX$_2$KFQG (SEQ ID NO: 88), wherein X$_1$ is selected from N or Q and X$_2$ is selected from Q or E; and HCDR3 sequence comprising SEQ ID NO: 3; and the VL region comprises LCDR1 sequence comprising SEQ ID NO: 6, LCDR2 sequence comprising SEQ ID NO: 9, and LCDR3 sequence comprising SEQ ID NO: 10.

In some instances, the anti-transferrin receptor antibody comprises a VH region and a VL region, wherein the VH region comprises HCDR1 sequence comprising SEQ ID NO: 1; HCDR2 sequence EINPIX$_1$GRSNYAX$_2$KFQG (SEQ ID NO: 88), wherein X$_1$ is selected from N or Q and X$_2$ is selected from Q or E; and HCDR3 sequence comprising SEQ ID NO: 3; and the VL region comprises LCDR1 sequence comprising SEQ ID NO: 11, LCDR2 sequence comprising SEQ ID NO: 12, and LCDR3 sequence comprising SEQ ID NO: 10.

In some instances, the anti-transferrin receptor antibody comprises a VH region and a VL region, in which the VH region comprises HCDR1 sequence comprising SEQ ID NO: 1, HCDR2 sequence comprising SEQ ID NO: 2, and HCDR3 sequence comprising SEQ ID NO: 3; and the VL region comprises LCDR1 sequence RTSENIYX$_3$NLA (SEQ ID NO: 89), LCDR2 sequence comprising SEQ ID NO: 7, 9, or 12, and LCDR3 sequence comprising SEQ ID NO: 8 or 10, wherein X$_3$ is selected from N or S.

In some instances, the anti-transferrin receptor antibody comprises a VH region and a VL region, in which the VH region comprises HCDR1 sequence comprising SEQ ID NO: 1, HCDR2 sequence comprising SEQ ID NO: 2, and HCDR3 sequence comprising SEQ ID NO: 3; and the VL region comprises LCDR1 sequence comprising SEQ ID NO: 6 or 11, LCDR2 sequence AX$_4$TNLAX$_5$ (SEQ ID NO: 90), and LCDR3 sequence comprising SEQ ID NO: 8 or 10, wherein X$_4$ is selected from A or G, and X$_5$ is selected from D or E.

In some instances, the anti-transferrin receptor antibody comprises a VH region and a VL region, in which the VH region comprises HCDR1 sequence comprising SEQ ID NO: 1, HCDR2 sequence comprising SEQ ID NO: 2, and HCDR3 sequence comprising SEQ ID NO: 3; and the VL region comprises LCDR1 sequence comprising SEQ ID NO: 6 or 11, LCDR2 sequence SEQ ID NO: 7, 9, or 12, and LCDR3 sequence QHFWGTPLTX$_6$ (SEQ ID NO: 91), wherein X$_6$ is present or absence, and if present, is F.

In some instances, the anti-transferrin receptor antibody comprises a VH region and a VL region, in which the VH region comprises HCDR1 sequence comprising SEQ ID NO: 1, HCDR2 sequence comprising SEQ ID NO: 2, and HCDR3 sequence comprising SEQ ID NO: 3; and the VL region comprises LCDR1 sequence comprising SEQ ID NO: 6, LCDR2 sequence AATNLAX$_5$ (SEQ ID NO: 92), and LCDR3 sequence QHFWGTPLTX$_6$ (SEQ ID NO: 91), wherein X$_5$ is selected from D or E and X$_6$ is present or absence, and if present, is F.

In some instances, the anti-transferrin receptor antibody comprises a VH region and a VL region, in which the VH region comprises HCDR1 sequence comprising SEQ ID NO: 1, HCDR2 sequence comprising SEQ ID NO: 2, and HCDR3 sequence comprising SEQ ID NO: 3; and the VL region comprises LCDR1 sequence comprising SEQ ID NO: 6, LCDR2 sequence comprising SEQ ID NO: 7, and LCDR3 sequence comprising SEQ ID NO: 8.

In some instances, the anti-transferrin receptor antibody comprises a VH region and a VL region, in which the VH region comprises HCDR1 sequence comprising SEQ ID NO: 1, HCDR2 sequence comprising SEQ ID NO: 2, and HCDR3 sequence comprising SEQ ID NO: 3; and the VL region comprises LCDR1 sequence comprising SEQ ID NO: 6, LCDR2 sequence comprising SEQ ID NO: 9, and LCDR3 sequence comprising SEQ ID NO: 10.

In some instances, the anti-transferrin receptor antibody comprises a VH region and a VL region, in which the VH region comprises HCDR1 sequence comprising SEQ ID NO: 1, HCDR2 sequence comprising SEQ ID NO: 2, and HCDR3 sequence comprising SEQ ID NO: 3; and the VL region comprises LCDR1 sequence comprising SEQ ID NO: 11, LCDR2 sequence comprising SEQ ID NO: 12, and LCDR3 sequence comprising SEQ ID NO: 10.

In some instances, the anti-transferrin receptor antibody comprises a VH region and a VL region, in which the VH region comprises HCDR1 sequence comprising SEQ ID NO: 1, HCDR2 sequence comprising SEQ ID NO: 4, and HCDR3 sequence comprising SEQ ID NO: 3; and the VL region comprises LCDR1 sequence RTSENIYX$_3$NLA (SEQ ID NO: 89), LCDR2 sequence comprising SEQ ID NO: 7, 9, or 12, and LCDR3 sequence comprising SEQ ID NO: 8 or 10, wherein X$_3$ is selected from N or S.

In some instances, the anti-transferrin receptor antibody comprises a VH region and a VL region, in which the VH region comprises HCDR1 sequence comprising SEQ ID NO: 1, HCDR2 sequence comprising SEQ ID NO: 4, and HCDR3 sequence comprising SEQ ID NO: 3; and the VL region comprises LCDR1 sequence comprising SEQ ID NO: 6 or 11, LCDR2 sequence AX$_4$TNLAX$_5$ (SEQ ID NO: 90), and LCDR3 sequence comprising SEQ ID NO: 8 or 10, wherein X$_4$ is selected from A or G, and X$_5$ is selected from D or E.

In some instances, the anti-transferrin receptor antibody comprises a VH region and a VL region, in which the VH region comprises HCDR1 sequence comprising SEQ ID NO: 1, HCDR2 sequence comprising SEQ ID NO: 4, and HCDR3 sequence comprising SEQ ID NO: 3; and the VL region comprises LCDR1 sequence comprising SEQ ID NO: 6 or 11, LCDR2 sequence SEQ ID NO: 7, 9, or 12, and LCDR3 sequence QHFWGTPLTX$_6$ (SEQ ID NO: 91), wherein X$_6$ is present or absence, and if present, is F.

In some instances, the anti-transferrin receptor antibody comprises a VH region and a VL region, in which the VH region comprises HCDR1 sequence comprising SEQ ID NO: 1, HCDR2 sequence comprising SEQ ID NO: 4, and HCDR3 sequence comprising SEQ ID NO: 3; and the VL region comprises LCDR1 sequence comprising SEQ ID NO: 6, LCDR2 sequence AATNLAX$_5$ (SEQ ID NO: 92), and LCDR3 sequence QHFWGTPLTX$_6$ (SEQ ID NO: 91), wherein X$_5$ is selected from D or E and X$_6$ is present or absence, and if present, is F.

In some instances, the anti-transferrin receptor antibody comprises a VH region and a VL region, in which the VH region comprises HCDR1 sequence comprising SEQ ID NO: 1, HCDR2 sequence comprising SEQ ID NO: 4, and HCDR3 sequence comprising SEQ ID NO: 3; and the VL region comprises LCDR1 sequence comprising SEQ ID NO: 6, LCDR2 sequence comprising SEQ ID NO: 7, and LCDR3 sequence comprising SEQ ID NO: 8.

In some instances, the anti-transferrin receptor antibody comprises a VH region and a VL region, in which the VH region comprises HCDR1 sequence comprising SEQ ID NO: 1, HCDR2 sequence comprising SEQ ID NO: 4, and HCDR3 sequence comprising SEQ ID NO: 3; and the VL region comprises LCDR1 sequence comprising SEQ ID NO: 6, LCDR2 sequence comprising SEQ ID NO: 9, and LCDR3 sequence comprising SEQ ID NO: 10.

In some instances, the anti-transferrin receptor antibody comprises a VH region and a VL region, in which the VH region comprises HCDR1 sequence comprising SEQ ID NO: 1, HCDR2 sequence comprising SEQ ID NO: 4, and HCDR3 sequence comprising SEQ ID NO: 3; and the VL region comprises LCDR1 sequence comprising SEQ ID NO: 11, LCDR2 sequence comprising SEQ ID NO: 12, and LCDR3 sequence comprising SEQ ID NO: 10.

In some instances, the anti-transferrin receptor antibody comprises a VH region and a VL region, in which the VH region comprises HCDR1 sequence comprising SEQ ID NO: 1, HCDR2 sequence comprising SEQ ID NO: 5, and HCDR3 sequence comprising SEQ ID NO: 3; and the VL region comprises LCDR1 sequence RTSENIYX$_3$NLA (SEQ ID NO: 89), LCDR2 sequence comprising SEQ ID NO: 7, 9, or 12, and LCDR3 sequence comprising SEQ ID NO: 8 or 10, wherein X$_3$ is selected from N or S.

In some instances, the anti-transferrin receptor antibody comprises a VH region and a VL region, in which the VH region comprises HCDR1 sequence comprising SEQ ID NO: 1, HCDR2 sequence comprising SEQ ID NO: 5, and HCDR3 sequence comprising SEQ ID NO: 3; and the VL region comprises LCDR1 sequence comprising SEQ ID NO: 6 or 11, LCDR2 sequence $AX_4TNLAX_5$ (SEQ ID NO: 90), and LCDR3 sequence comprising SEQ ID NO: 8 or 10, wherein $X_4$ is selected from A or G, and $X_5$ is selected from D or E.

In some instances, the anti-transferrin receptor antibody comprises a VH region and a VL region, in which the VH region comprises HCDR1 sequence comprising SEQ ID NO: 1, HCDR2 sequence comprising SEQ ID NO: 5, and HCDR3 sequence comprising SEQ ID NO: 3; and the VL region comprises LCDR1 sequence comprising SEQ ID NO: 6 or 11, LCDR2 sequence SEQ ID NO: 7, 9, or 12, and LCDR3 sequence $QHFWGTPLTX_6$ (SEQ ID NO: 91), wherein $X_6$ is present or absence, and if present, is F.

In some instances, the anti-transferrin receptor antibody comprises a VH region and a VL region, in which the VH region comprises HCDR1 sequence comprising SEQ ID NO: 1, HCDR2 sequence comprising SEQ ID NO: 5, and HCDR3 sequence comprising SEQ ID NO: 3 and the VL region comprises LCDR1 sequence comprising SEQ ID NO: 6, LCDR2 sequence $AATNLAX_5$ (SEQ ID NO: 92), and LCDR3 sequence $QHFWGTPLTX_6$ (SEQ ID NO: 91), wherein $X_5$ is selected from D or E and $X_6$ is present or absence, and if present, is F.

In some instances, the anti-transferrin receptor antibody comprises a VH region and a VL region, in which the VH region comprises HCDR1 sequence comprising SEQ ID NO: 1, HCDR2 sequence comprising SEQ ID NO: 5, and HCDR3 sequence comprising SEQ ID NO: 3; and the VL region comprises LCDR1 sequence comprising SEQ ID NO: 6, LCDR2 sequence comprising SEQ ID NO: 7, and LCDR3 sequence comprising SEQ ID NO: 8.

In some instances, the anti-transferrin receptor antibody comprises a VH region and a VL region, in which the VH region comprises HCDR1 sequence comprising SEQ ID NO: 1, HCDR2 sequence comprising SEQ ID NO: 5, and HCDR3 sequence comprising SEQ ID NO: 3; and the VL region comprises LCDR1 sequence comprising SEQ ID NO: 6, LCDR2 sequence comprising SEQ ID NO: 9, and LCDR3 sequence comprising SEQ ID NO: 10.

In some instances, the anti-transferrin receptor antibody comprises a VH region and a VL region, in which the VH region comprises HCDR1 sequence comprising SEQ ID NO: 1, HCDR2 sequence comprising SEQ ID NO: 5, and HCDR3 sequence comprising SEQ ID NO: 3; and the VL region comprises LCDR1 sequence comprising SEQ ID NO: 11, LCDR2 sequence comprising SEQ ID NO: 12, and LCDR3 sequence comprising SEQ ID NO: 10.

In some embodiments, the anti-transferrin receptor antibody comprises a VH region and a VL region in which the sequence of the VH region comprises about 80%, 85%, 90%, 95%, 96% 97%, 98%, 99%, or 100% sequence identity to SEQ ID NOs: 13-16 and the sequence of the VL region comprises about 80%, 85%, 90%, 95%, 96% 97%, 98%, 99%, or 100% sequence identity to SEQ ID NOs: 18-21.

In some embodiments, the VH region comprises a sequence selected from SEQ ID NOs: 13-16 (Table 3) and the VL region comprises a sequence selected from SEQ ID NOs: 18-21 (Table 4). The underlined regions in Table 3 and Table 4 denote the respective CDR1, CDR2, or CDR3 sequence.

TABLE 3

| NAME | VH SEQUENCE | SEQ ID NO: |
|---|---|---|
| 13E4_VH1 | QVQLVQSGAEVKKPGASVKVSCKASG<u>YTFTNYWMH</u>WV RQAPGQGLEWMG<u>EINPINGRSNYAQKFQ</u>GRVTLTVDT SISTAYMELSRLRSDDTAVYYCAR<u>GTRAMHY</u>WGQGTL VTVSS | 13 |
| 13E4_VH2 | QVQLVQSGAEVKKPGASVKVSCKASG<u>YTFTNYWMH</u>WV RQAPGQGLEWIG<u>EINPINGRSNYAEKFQ</u>GRVTLTVDT SSSTAYMELSRLRSDDTAVYYCAR<u>GTRAMHY</u>WGQGTL VTVSS | 14 |
| 13E4_VH3 | QVQLVQSGAEVKKPGASVKVSCKASG<u>YTFTNYWMH</u>WV RQAPGQGLEWMG<u>EINPIQGRSNYAEKFQ</u>GRVTLTVDT SSSTAYMELSSLRSEDTATYYCAR<u>GTRAMHY</u>WGQGTL VTVSS | 15 |
| 13E4_VH4 | QVQLVQSGAEVKKPGASVKVSCKASG<u>YTFTNYWMH</u>WV RQAPGQGLEWMG<u>EINPINGRSNYAEKFQ</u>GRVTLTVDT SSSTAYMELSSLRSEDTATYYCAR<u>GTRAMHY</u>WGQGTL VTVSS | 16 |
| 13E_VH | QVQLQQPGAELVKPGASVKLSCKASG<u>YTFTNYWMH</u>WV KQRPGQGLEWIG<u>EINPINGRSNYGERFKT</u>KATLTVDK SSSTAYMQLSSLTSEDSAVYYCAR<u>GTRAMHY</u>WGQGTS VTVSS | 17 |

TABLE 4

| NAME | VL SEQUENCE | SEQ ID NO: |
|---|---|---|
| 13E4_VL1 | DIQMTQSPSSLSASVGDRVTITC<u>RTSENIYNNLA</u>WYQ QKPGKSPKLLIY<u>AATNLAD</u>GVPSRFSGSGSGTDYTLT ISSLQPEDFATYYC<u>QHFWGTPLTF</u>GGGTKVEIK | 18 |
| 13E4_VL2 | DIQMTQSPSSLSASVGDRVTITC<u>RTSENIYNNLA</u>WYQ QKPGKAPKLLIY<u>AATNLAD</u>GVPSRFSGSGSGTDYTLT ISSLQPEDFATYYC<u>QHFWGTPLTF</u>GGGTKVEIK | 19 |
| 13E4_VL3 | DIQMTQSPSSLSASVGDRVTITC<u>RTSENIYNNLA</u>WYQ QKPGKAPKLLIY<u>AATNLAE</u>GVPSRFSGSGSGTDYTLT ISSLQPEDFATYYC<u>QHFWGTPLTF</u>GGGTKVEIK | 20 |
| 13E4_VL4 | DIQMTQSPSSLSASVGDRVTITC<u>RTSENIYSNLA</u>WYQ QKPGKAPKLLIY<u>AGTNLAD</u>GVPSRFSGSGSGTDYTLT ISSLQPEDFANYYC<u>QHFWGTPLTF</u>GGGTKVEIK | 21 |
| 13E4_VL | DIQMTQSPASLSVSVGETVTITC<u>RTSENIYNNLA</u>WYQ QKQGKSPQLLVY<u>AATNLAD</u>GVPSRFSGSGSGTQYSLK INSLQSEDFGNYYC<u>QHFWGTPLTF</u>GAGTKLELK | 22 |

In some embodiments, the anti-transferrin receptor antibody comprises a VH region and a VL region as illustrated in Table 5.

TABLE 5

| | 13E4_VH1 (SEQ ID NO: 13) | 13E4_VH2 (SEQ ID NO: 14) | 13E4_VH3 (SEQ ID NO: 15) | 13E4_VH4 (SEQ ID NO: 16) |
|---|---|---|---|---|
| 13E4_VL1 (SEQ ID NO: 18) | SEQ ID NO: 13 + SEQ ID NO: 18 | SEQ ID NO: 14 + SEQ ID NO: 18 | SEQ ID NO: 15 + SEQ ID NO: 18 | SEQ ID NO: 16 + SEQ ID NO: 18 |
| 13E4_VL2 (SEQ ID NO: 19) | SEQ ID NO: 13 + SEQ ID NO: 19 | SEQ ID NO: 14 + SEQ ID NO: 19 | SEQ ID NO: 15 + SEQ ID NO: 19 | SEQ ID NO: 16 + SEQ ID NO: 19 |

TABLE 5-continued

| | 13E4_VH1<br>(SEQ ID NO: 13) | 13E4_VH2<br>(SEQ ID NO: 14) | 13E4_VH3<br>(SEQ ID NO: 15) | 13E4_VH4<br>(SEQ ID NO: 16) |
|---|---|---|---|---|
| 13E4_VL3<br>(SEQ ID NO: 20) | SEQ ID NO: 13 +<br>SEQ ID NO: 20 | SEQ ID NO: 14 +<br>SEQ ID NO: 20 | SEQ ID NO: 15 +<br>SEQ ID NO: 20 | SEQ ID NO: 16 +<br>SEQ ID NO: 20 |
| 13E4_VL4<br>(SEQ ID NO: 21) | SEQ ID NO: 13 +<br>SEQ ID NO: 21 | SEQ ID NO: 14 +<br>SEQ ID NO: 21 | SEQ ID NO: 15 +<br>SEQ ID NO: 21 | SEQ ID NO: 16 +<br>SEQ ID NO: 21 |

In some embodiments, an anti-transferrin receptor antibody described supra is a full-length antibody. In other embodiments, the anti-transferrin receptor antibody is a binding fragment thereof. In some cases, the anti-transferrin receptor antibody is a humanized antibody or binding fragment thereof, a chimeric antibody or binding fragment thereof, a monoclonal antibody or binding fragment thereof, a multi-specific antibody or binding fragment thereof, or a bispecific antibody or binding fragment thereof. In some cases, the anti-transferrin receptor antibody is monovalent Fab', divalent $Fab_2$, $F(ab)'_3$ fragments, single-chain variable fragment (scFv), bis-scFv, $(scFv)_2$, diabody, minibody, nanobody, triabody, tetrabody, disulfide stabilized Fv protein ("dsFv"), single-domain antibody (sdAb), Ig NAR, camelid antibody or binding fragment thereof, or a chemically modified derivative thereof.

In some embodiments, the anti-transferrin receptor antibody is a multi-specific antibody. In some cases, the multi-specific antibody comprises two or more target binding moieties in which each of the two or more target binding moieties binds specifically to an antigen, and the two or more antigens are different. In some cases, the multi-specific antibody comprises target binding moieties that specifically bind to three or more different antigens, four or more different antigens, or five or more different antigens.

In some embodiments, the anti-transferrin receptor antibody is a bispecific antibody. In some cases, the bispecific antibody or binding fragment includes a Knobs-into-Holes (KiH), Asymmetric Re-engineering Technology-immunoglobulin (ART-Ig), Triomab quadroma, bispecific monoclonal antibody (BiMAb, BsmAb, BsAb, bsMab, BS-Mab, or Bi-MAb), FcAAdp, XmAb, Azymetric, Bispecific Engagement by Antibodies based on the T-cell receptor (BEAT), Bispecific T-cell Engager (BiTE), Biclonics, Fab-scFv-Fc, Two-in-one/Dual Action Fab (DAF), FinomAb, scFv-Fc-(Fab)-fusion, Dock-aNd-Lock (DNL), Adaptir (previously SCORPION), Tandem diAbody (TandAb), Dual-affinity-ReTargeting (DART), or nanobody.

In some instances, the bispecific antibody is a trifunctional antibody or a bispecific mini-antibody. In some cases, the bispecific antibody is a trifunctional antibody. In some instances, the trifunctional antibody is a full length monoclonal antibody comprising binding sites for two different antigens.

In some cases, the bispecific antibody is a bispecific mini-antibody. In some instances, the bispecific mini-antibody comprises divalent $Fab_2$, $F(ab)'_3$ fragments, bis-scFv, $(scFv)_2$, diabody, minibody, triabody, tetrabody or a bi-specific T-cell engager (BiTE). In some embodiments, the bi-specific T-cell engager is a fusion protein that contains two single-chain variable fragments (scFvs) in which the two scFvs target epitopes of two different antigens.

In some instances, the anti-transferrin receptor antibody is a trispecific antibody. In some instances, the trispecific antibody comprises $F(ab)'_3$ fragments or a triabody. In some embodiments, the anti-transferrin receptor antibody is a trispecific antibody as described in Dimas, et al., "Development of a trispecific antibody designed to simultaneously and efficiently target three different antigens on tumor cells, "*Mol. Pharmaceutics,* 12(9): 3490-3501 (2015).

Figure 2:
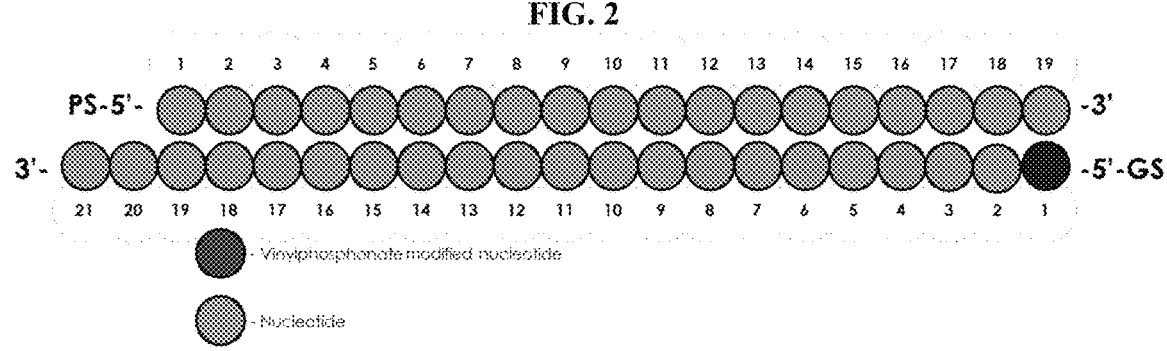
FIG. 2 illustrates the structure of an exemplary blunt ended duplex with 19 bases of complementarity and one 3' dinucleotide overhang. Purified single strands were duplexed to get the double stranded siRNA.

In some instances, the anti-transferrin receptor antibody comprises an antibody format illustrated in FIG. 2 of Brinkmann and Kontermann, "The making of bispecific antibodies," *MABS* 9(2): 182-212 (2017).

In some embodiments, an anti-transferrin receptor antibody described herein comprises an IgG framework, an IgA framework, an IgE framework, or an IgM framework. In some instances, the anti-transferrin receptor antibody comprises an IgG framework (e.g., IgG1, IgG2, IgG3, or IgG4). In some cases, the anti-transferrin receptor antibody comprises an IgG1 framework. In some cases, the anti-transferrin receptor antibody comprises an IgG2 (e.g., an IgG2a or IgG2b) framework. In some cases, the anti-transferrin receptor antibody comprises an IgG2a framework. In some cases, the anti-transferrin receptor antibody comprises an IgG2b framework. In some cases, the anti-transferrin receptor antibody comprises an IgG3 framework. In some cases, the anti-transferrin receptor antibody comprises an IgG4 framework.

In some cases, an anti-transferrin receptor antibody comprises one or more mutations in a framework region, e.g., in the CH1 domain, CH2 domain, CH3 domain, hinge region, or a combination thereof. In some instances, the one or more mutations are to stabilize the antibody and/or to increase half-life. In some instances, the one or more mutations are to modulate Fc receptor interactions, to reduce or eliminate Fc effector functions such as FcγR, antibody-dependent cell-mediated cytotoxicity (ADCC), or complement-dependent cytotoxicity (CDC). In additional instances, the one or more mutations are to modulate glycosylation.

In some embodiments, the one or more mutations are located in the Fc region. In some instances, the Fc region comprises a mutation at residue position L234, L235, or a combination thereof. In some instances, the mutations comprise L234 and L235. In some instances, the mutations comprise L234A and L235A. In some cases, the residue positions are in reference to IgG1.

In some instances, the Fc region comprises a mutation at residue position L234, L235, D265, N297, K322, L328, or P329, or a combination thereof. In some instances, the mutations comprise L234 and L235 in combination with a mutation at residue position K322, L328, or P329. In some cases, the Fc region comprises mutations at L234, L235, and K322. In some cases, the Fc region comprises mutations at L234, L235, and L328. In some cases, the Fc region comprises mutations at L234, L235, and P329. In some cases, the Fc region comprises mutations at D265 and N297. In some cases, the residue position is in reference to IgG1.

In some instances, the Fc region comprises L234A, L235A, D265A, N297G, K322G, L328R, or P329G, or a combination thereof. In some instances, the Fc region comprises L234A and L235A in combination with K322G, L328R, or P329G. In some cases, the Fc region comprises L234A, L235A, and K322G. In some cases, the Fc region comprises L234A, L235A, and L328R. In some cases, the Fc region comprises L234A, L235A, and P329G. In some cases, the Fc region comprises D265A and N297G. In some cases, the residue position is in reference to IgG1.

In some instances, the Fc region comprises a mutation at residue position L235, L236, D265, N297, K322, L328, or P329, or a combination of the mutations. In some instances, the Fc region comprises mutations at L235 and L236. In some instances, the Fc region comprises mutations at L235 and L236 in combination with a mutation at residue position K322, L328, or P329. In some cases, the Fc region comprises mutations at L235, L236, and K322. In some cases, the Fc region comprises mutations at L235, L236, and L328. In some cases, the Fc region comprises mutations at L235, L236, and P329. In some cases, the Fc region comprises mutations at D265 and N297. In some cases, the residue position is in reference to IgG2b.

In some embodiments, the Fc region comprises L235A, L236A, D265A, N297G, K322G, L328R, or P329G, or a combination thereof. In some instances, the Fc region comprises L235A and L236A. In some instances, the Fc region comprises L235A and L236A in combination with K322G, L328R, or P329G. In some cases, the Fc region comprises L235A, L236A, and K322G. In some cases, the Fc region comprises L235A, L236A, and L328R. In some cases, the Fc region comprises L235A, L236A, and P329G. In some cases, the Fc region comprises D265A and N297G. In some cases, the residue position is in reference to IgG2b.

In some embodiments, the Fc region comprises a mutation at residue position L233, L234, D264, N296, K321, L327, or P328, wherein the residues correspond to positions 233, 234, 264, 296, 321, 327, and 328 of SEQ ID NO: 23. In some instances, the Fc region comprises mutations at L233 and L234. In some instances, the Fc region comprises mutations at L233 and L234 in combination with a mutation at residue position K321, L327, or P328. In some cases, the Fc region comprises mutations at L233, L234, and K321. In some cases, the Fc region comprises mutations at L233, L234, and L327. In some cases, the Fc region comprises mutations at L233, L234, and K321. In some cases, the Fc region comprises mutations at L233, L234, and P328. In some instances, the Fc region comprises mutations at D264 and N296. In some cases, equivalent positions to residue L233, L234, D264, N296, K321, L327, or P328 in an IgG1, IgG2, IgG3, or IgG4 framework are contemplated. In some cases, mutations to a residue that corresponds to residue L233, L234, D264, N296, K321, L327, or P328 of SEQ ID NO: 23 in an IgG1, IgG2, or IgG4 framework are also contemplated.

In some embodiments, the Fc region comprises L233A, L234A, D264A, N296G, K321G, L327R, or P328G, wherein the residues correspond to positions 233, 234, 264, 296, 321, 327, and 328 of SEQ ID NO: 23. In some instances, the Fc region comprises L233A and L234A. In some instances, the Fc region comprises L233A and L234A in combination with K321G, L327R, or P328G. In some cases, the Fc region comprises L233A, L234A, and K321G. In some cases, the Fc region comprises L233A, L234A, and L327R. In some cases, the Fc region comprises L233A, L234A, and K321G. In some cases, the Fc region comprises L233A, L234A, and P328G. In some instances, the Fc region comprises D264A and N296G.

In some embodiments, the human IgG constant region is modified to alter antibody-dependent cellular cytotoxicity (ADCC) and/or complement-dependent cytotoxicity (CDC), e.g., with an amino acid modification described in Natsume et al., 2008 Cancer Res, 68(10): 3863-72; Idusogie et al., 2001 J Immunol, 166(4): 2571-5; Moore et al., 2010 mAbs, 2(2): 181-189; Lazar et al., 2006 PNAS, 103(11): 4005-4010, Shields et al., 2001 JBC, 276(9): 6591-6604; Stavenhagen et al., 2007 Cancer Res, 67(18): 8882-8890; Stavenhagen et al., 2008 Advan. Enzyme Regul., 48: 152-164; Alegre et al, 1992 J Immunol, 148: 3461-3468; Reviewed in Kaneko and Niwa, 2011 Biodrugs, 25(1): 1-11.

In some embodiments, an anti-transferrin receptor antibody described herein is a full-length antibody, comprising a heavy chain (HC) and a light chain (LC). In some cases, the heavy chain (HC) comprises a sequence selected from Table 6. In some cases, the light chain (LC) comprises a sequence selected from Table 7. The underlined region denotes the respective CDRs.

TABLE 6

| NAME | HC SEQUENCE | SEQ ID NO: |
|---|---|---|
| 13E4_VH1 | QVQLVQSGAEVKKPGASVKVSCKASG<u>YTFTNYWMH</u>WVRQ APGQGLEWMG<u>EINPINGRSNYAQKFQG</u>RVTLTVDTSISTAY MELSRLRSDDTAVYYCAR<u>GTRAMHY</u>WGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTHTCPPCPAPELLGGPSVFLFPP KPKDTLMISRTPEVTCVVVDVSHEDPEVKFNWYVDGVEVH NAKTKPREEQYNSTYRVVSVLTVLHQDWLNGKEYKCKVS NKALPAPIEKTISKAKGQPREPQVYTLPPSREEMTKNQVSLT CLVKGFYPSDIAVEWESNGQPENNYKTTPPVLDSDGSFFLY SKLTVDKSRWQQGNVFSCSVMHEALHNHYTQKSLSLSPG | 23 |
| 13E4_VH1_a | QVQLVQSGAEVKKPGASVKVSCKASG<u>YTFTNYWMH</u>WVRQ APGQGLEWMG<u>EINPINGRSNYAQKFQG</u>RVTLTVDTSISTAY MELSRLRSDDTAVYYCAR<u>GTRAMHY</u>WGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTHTCPPCPAPEAAGGPSVFLFPP KPKDTLMISRTPEVTCVVVDVSHEDPEVKFNWYVDGVEVH NAKTKPREEQYNSTYRVVSVLTVLHQDWLNGKEYKCKVS NKALPAPIEKTISKAKGQPREPQVYTLPPSREEMTKNQVSLT CLVKGFYPSDIAVEWESNGQPENNYKTTPPVLDSDGSFFLY SKLTVDKSRWQQGNVFSCSVMHEALHNHYTQKSLSLSPG | 24 |
| 13E4_VH1_b | QVQLVQSGAEVKKPGASVKVSCKASG<u>YTFTNYWMH</u>WVRQ APGQGLEWMG<u>EINPINGRSNYAQKFQG</u>RVTLTVDTSISTAY MELSRLRSDDTAVYYCAR<u>GTRAMHY</u>WGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTHTCPPCPAPEAAGGPSVFLFPP KPKDTLMISRTPEVTCVVVDVSHEDPEVKFNWYVDGVEVH NAKTKPREEQYNSTYRVVSVLTVLHQDWLNGKEYKCGVS NKALPAPIEKTISKAKGQPREPQVYTLPPSREEMTKNQVSLT CLVKGFYPSDIAVEWESNGQPENNYKTTPPVLDSDGSFFLY SKLTVDKSRWQQGNVFSCSVMHEALHNHYTQKSLSLSPG | 25 |
| 13E4_VH1_c | QVQLVQSGAEVKKPGASVKVSCKASG<u>YTFTNYWMH</u>WVRQ APGQGLEWMG<u>EINPINGRSNYAQKFQG</u>RVTLTVDTSISTAY MELSRLRSDDTAVYYCAR<u>GTRAMHY</u>WGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTHTCPPCPAPEAAGGPSVFLFPP KPKDTLMISRTPEVTCVVVDVSHEDPEVKFNWYVDGVEVH NAKTKPREEQYNSTYRVVSVLTVLHQDWLNGKEYKCKVS NKARPAPIEKTISKAKGQPREPQVYTLPPSREEMTKNQVSLT CLVKGFYPSDIAVEWESNGQPENNYKTTPPVLDSDGSFFLY SKLTVDKSRWQQGNVFSCSVMHEALHNHYTQKSLSLSPG | 26 |
| 13E4_VH1_d | QVQLVQSGAEVKKPGASVKVSCKASG<u>YTFTNYWMH</u>WVRQ APGQGLEWMG<u>EINPINGRSNYAQKFQG</u>RVTLTVDTSISTAY MELSRLRSDDTAVYYCAR<u>GTRAMHY</u>WGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTHTCPPCPAPEAAGGPSVFLFPP KPKDTLMISRTPEVTCVVVDVSHEDPEVKFNWYVDGVEVH NAKTKPREEQYNSTYRVVSVLTVLHQDWLNGKEYKCKVS NKALGAPIEKTISKAKGQPREPQVYTLPPSREEMTKNQVSLT | 27 |

TABLE 6-continued

| NAME | HC SEQUENCE | SEQ ID NO: |
|---|---|---|
| | CLVKGFYPSDIAVEWESNGQPENNYKTTPPVLDSDGSFFLY SKLTVDKSRWQQGNVFSCSVMHEALHNHYTQKSLSLSPG | |
| 13E4_VH1_e | QVQLVQSGAEVKKPGASVKVSCKASG<u>YTFTNYWMH</u>WVRQ APGQGLEWMG<u>EINPINGRSNYAQKFQ</u>GRVTLTVDTSISTAY MELSRLSDDTAVYYCA<u>RGTRAMHY</u>WGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTHTCPPCPAPELLGGPSVFLFPP KPKDTLMISRTPEVTCVVVAVSHEDPEVKFNWYVDGVEVH NAKTKPREEQYGSTYRVVSVLTVLHQDWLNGKEYKCKVS NKALPAPIEKTISKAKGQPREPQVYTLPPSREEMTKNQVSLT CLVKGFYPSDIAVEWESNGQPENNYKTTPPVLDSDGSFFLY SKLTVDKSRWQQGNVFSCSVMHEALHNHYTQKSLSLSPG | 28 |
| 13E4_VH2 | QVQLVQSGAEVKKPGASVKVSCKASG<u>YTFTNYWMH</u>WVRQ APGQGLEWIG<u>EINPINGRSNYAEKFQ</u>GRVTLTVDTSSSTAY MELSRLSDDTAVYYCA<u>RGTRAMHY</u>WGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTHTCPPCPAPELLGGPSVFLFPP KPKDTLMISRTPEVTCVVVDVSHEDPEVKFNWYVDGVEVH NAKTKPREEQYNSTYRVVSVLTVLHQDWLNGKEYKCKVS NKALPAPIEKTISKAKGQPREPQVYTLPPSREEMTKNQVSLT CLVKGFYPSDIAVEWESNGQPENNYKTTPPVLDSDGSFFLY SKLTVDKSRWQQGNVFSCSVMHEALHNHYTQKSLSLSPG | 29 |
| 13E4_VH2_a | QVQLVQSGAEVKKPGASVKVSCKASG<u>YTFTNYWMH</u>WVRQ APGQGLEWIG<u>EINPINGRSNYAEKFQ</u>GRVTLTVDTSSSTAY MELSRLSDDTAVYYCA<u>RGTRAMHY</u>WGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTHTCPPCPAPEAAGGPSVFLFPP KPKDTLMISRTPEVTCVVVDVSHEDPEVKFNWYVDGVEVH NAKTKPREEQYNSTYRVVSVLTVLHQDWLNGKEYKCKVS NKALPAPIEKTISKAKGQPREPQVYTLPPSREEMTKNQVSLT CLVKGFYPSDIAVEWESNGQPENNYKTTPPVLDSDGSFFLY SKLTVDKSRWQQGNVFSCSVMHEALHNHYTQKSLSLSPG | 30 |
| 13E4_VH2_b | QVQLVQSGAEVKKPGASVKVSCKASG<u>YTFTNYWMH</u>WVRQ APGQGLEWIG<u>EINPINGRSNYAEKFQ</u>GRVTLTVDTSSSTAY MELSRLSDDTAVYYCA<u>RGTRAMHY</u>WGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTHTCPPCPAPEAAGGPSVFLFPP KPKDTLMISRTPEVTCVVVDVSHEDPEVKFNWYVDGVEVH NAKTKPREEQYNSTYRVVSVLTVLHQDWLNGKEYKCGVS NKALPAPIEKTISKAKGQPREPQVYTLPPSREEMTKNQVSLT CLVKGFYPSDIAVEWESNGQPENNYKTTPPVLDSDGSFFLY SKLTVDKSRWQQGNVFSCSVMHEALHNHYTQKSLSLSPG | 31 |
| 13E4_VH2_c | QVQLVQSGAEVKKPGASVKVSCKASG<u>YTFTNYWMH</u>WVRQ APGQGLEWIG<u>EINPINGRSNYAEKFQ</u>GRVTLTVDTSSSTAY MELSRLSDDTAVYYCA<u>RGTRAMHY</u>WGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTHTCPPCPAPEAAGGPSVFLFPP KPKDTLMISRTPEVTCVVVDVSHEDPEVKFNWYVDGVEVH NAKTKPREEQYNSTYRVVSVLTVLHQDWLNGKEYKCKVS NKARPAPIEKTISKAKGQPREPQVYTLPPSREEMTKNQVSLT CLVKGFYPSDIAVEWESNGQPENNYKTTPPVLDSDGSFFLY SKLTVDKSRWQQGNVFSCSVMHEALHNHYTQKSLSLSPG | 32 |
| 13E4_VH2_d | QVQLVQSGAEVKKPGASVKVSCKASG<u>YTFTNYWMH</u>WVRQ APGQGLEWIG<u>EINPINGRSNYAEKFQ</u>GRVTLTVDTSSSTAY MELSRLSDDTAVYYCA<u>RGTRAMHY</u>WGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTHTCPPCPAPEAAGGPSVFLFPP KPKDTLMISRTPEVTCVVVDVSHEDPEVKFNWYVDGVEVH NAKTKPREEQYNSTYRVVSVLTVLHQDWLNGKEYKCKVS NKALGAPIEKTISKAKGQPREPQVYTLPPSREEMTKNQVSLT CLVKGFYPSDIAVEWESNGQPENNYKTTPPVLDSDGSFFLY SKLTVDKSRWQQGNVFSCSVMHEALHNHYTQKSLSLSPG | 33 |
| 13E4_VH2_e | QVQLVQSGAEVKKPGASVKVSCKASG<u>YTFTNYWMH</u>WVRQ APGQGLEWIG<u>EINPINGRSNYAEKFQ</u>GRVTLTVDTSSSTAY MELSRLSDDTAVYYCA<u>RGTRAMHY</u>WGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTHTCPPCPAPELLGGPSVFLFPP KPKDTLMISRTPEVTCVVVAVSHEDPEVKFNWYVDGVEVH NAKTKPREEQYGSTYRVVSVLTVLHQDWLNGKEYKCKVS NKALPAPIEKTISKAKGQPREPQVYTLPPSREEMTKNQVSLT CLVKGFYPSDIAVEWESNGQPENNYKTTPPVLDSDGSFFLY SKLTVDKSRWQQGNVFSCSVMHEALHNHYTQKSLSLSPG | 34 |
| 13E4_VH3 | QVQLVQSGAEVKKPGASVKVSCKASG<u>YTFTNYWMH</u>WVRQ APGQGLEWMG<u>EINPIQRSNYAEKFQ</u>GRVTLTVDTSSSTAY MELSSLRSEDTATYYCA<u>RGTRAMHY</u>WGQGTLVTVSSASTK GPSVFPLAPSSKSTSGGTAALGCLVKDYFPEPVTVSWNSGA LTSGVHTFPAVLQSSGLYSLSSVVTVPSSSLGTQTYICNVNH KPSNTKVDKRVEPKSCDKTHTCPPCPAPELLGGPSVFLFPPK PKDTLMISRTPEVTCVVVDVSHEDPEVKFNWYVDGVEVHN AKTKPREEQYNSTYRVVSVLTVLHQDWLNGKEYKCKVSN KALPAPIEKTISKAKGQPREPQVYTLPPSREEMTKNQVSLTC LVKGFYPSDIAVEWESNGQPENNYKTTPPVLDSDGSFFLYS KLTVDKSRWQQGNVFSCSVMHEALHNHYTQKSLSLSPG | 35 |
| 13E4_VH3_a | QVQLVQSGAEVKKPGASVKVSCKASG<u>YTFTNYWMH</u>WVRQ APGQGLEWMG<u>EINPIQRSNYAEKFQ</u>GRVTLTVDTSSSTAY MELSSLRSEDTATYYCA<u>RGTRAMHY</u>WGQGTLVTVSSASTK GPSVFPLAPSSKSTSGGTAALGCLVKDYFPEPVTVSWNSGA LTSGVHTFPAVLQSSGLYSLSSVVTVPSSSLGTQTYICNVNH KPSNTKVDKRVEPKSCDKTHTCPPCPAPEAAGGPSVFLFPPK PKDTLMISRTPEVTCVVVDVSHEDPEVKFNWYVDGVEVHN AKTKPREEQYNSTYRVVSVLTVLHQDWLNGKEYKCKVSN KALPAPIEKTISKAKGQPREPQVYTLPPSREEMTKNQVSLTC LVKGFYPSDIAVEWESNGQPENNYKTTPPVLDSDGSFFLYS KLTVDKSRWQQGNVFSCSVMHEALHNHYTQKSLSLSPG | 36 |
| 13E4_VH3_b | QVQLVQSGAEVKKPGASVKVSCKASG<u>YTFTNYWMH</u>WVRQ APGQGLEWMG<u>EINPIQRSNYAEKFQ</u>GRVTLTVDTSSSTAY MELSSLRSEDTATYYCA<u>RGTRAMHY</u>WGQGTLVTVSSASTK GPSVFPLAPSSKSTSGGTAALGCLVKDYFPEPVTVSWNSGA LTSGVHTFPAVLQSSGLYSLSSVVTVPSSSLGTQTYICNVNH KPSNTKVDKRVEPKSCDKTHTCPPCPAPEAAGGPSVFLFPPK PKDTLMISRTPEVTCVVVDVSHEDPEVKFNWYVDGVEVHN AKTKPREEQYNSTYRVVSVLTVLHQDWLNGKEYKCGVSN KALPAPIEKTISKAKGQPREPQVYTLPPSREEMTKNQVSLTC LVKGFYPSDIAVEWESNGQPENNYKTTPPVLDSDGSFFLYS KLTVDKSRWQQGNVFSCSVMHEALHNHYTQKSLSLSPG | 37 |
| 13E4_VH3_c | QVQLVQSGAEVKKPGASVKVSCKASG<u>YTFTNYWMH</u>WVRQ APGQGLEWMG<u>EINPIQRSNYAEKFQ</u>GRVTLTVDTSSSTAY MELSSLRSEDTATYYCA<u>RGTRAMHY</u>WGQGTLVTVSSASTK GPSVFPLAPSSKSTSGGTAALGCLVKDYFPEPVTVSWNSGA LTSGVHTFPAVLQSSGLYSLSSVVTVPSSSLGTQTYICNVNH KPSNTKVDKRVEPKSCDKTHTCPPCPAPEAAGGPSVFLFPPK PKDTLMISRTPEVTCVVVDVSHEDPEVKFNWYVDGVEVHN AKTKPREEQYNSTYRVVSVLTVLHQDWLNGKEYKCKVSN KARPAPIEKTISKAKGQPREPQVYTLPPSREEMTKNQVSLTC LVKGFYPSDIAVEWESNGQPENNYKTTPPVLDSDGSFFLYS KLTVDKSRWQQGNVFSCSVMHEALHNHYTQKSLSLSPG | 38 |
| 13E4_VH3_d | QVQLVQSGAEVKKPGASVKVSCKASG<u>YTFTNYWMH</u>WVRQ APGQGLEWMG<u>EINPIQRSNYAEKFQ</u>GRVTLTVDTSSSTAY MELSSLRSEDTATYYCA<u>RGTRAMHY</u>WGQGTLVTVSSASTK GPSVFPLAPSSKSTSGGTAALGCLVKDYFPEPVTVSWNSGA LTSGVHTFPAVLQSSGLYSLSSVVTVPSSSLGTQTYICNVNH KPSNTKVDKRVEPKSCDKTHTCPPCPAPEAAGGPSVFLFPPK PKDTLMISRTPEVTCVVVDVSHEDPEVKFNWYVDGVEVHN AKTKPREEQYNSTYRVVSVLTVLHQDWLNGKEYKCKVSN KALGAPIEKTISKAKGQPREPQVYTLPPSREEMTKNQVSLTC LVKGFYPSDIAVEWESNGQPENNYKTTPPVLDSDGSFFLYS KLTVDKSRWQQGNVFSCSVMHEALHNHYTQKSLSLSPG | 39 |
| 13E4_VH3_e | QVQLVQSGAEVKKPGASVKVSCKASG<u>YTFTNYWMH</u>WVRQ APGQGLEWMG<u>EINPIQRSNYAEKFQ</u>GRVTLTVDTSSSTAY MELSSLRSEDTATYYCA<u>RGTRAMHY</u>WGQGTLVTVSSASTK | 40 |

TABLE 6-continued

| NAME | HC SEQUENCE | SEQ ID NO: |
|---|---|---|
|  | GPSVFPLAPSSKSTSGGTAALGCLVKDYFPEPVTVSWNSGA LTSGVHTFPAVLQSSGLYSLSSVVTVPSSSLGTQTYICNVNH KPSNTKVDKRVEPKSCDKTHTCPPCPAPELLGGPSVFLFPPK PKDTLMISRTPEVTCVVVAVSHEDPEVKFNWYVDGVEVHN AKTKPREEQYGSTYRVVSVLTVLHQDWLNGKEYKCKVSN KALPAPIEKTISKAKGQPREPQVYTLPPSREEMTKNQVSLTC LVKGFYPSDIAVEWESNGQPENNYKTTPPVLDSDGSFFLYS KLTVDKSRWQQGNVFSCSVMHEALHNHYTQKSLSLSPG |  |
| 13E4_VH4 | QVQLVQSGAEVKKPGASVKVSCKASGYTFTNYWMHWVRQ APGQGLEWMGEINPINGRSNYAEKFQGRVTLTVDTSSSTAY MELSSLRSEDTATYYCARGTRAMHYWGQGTLVTVSSASTK GPSVFPLAPSSKSTSGGTAALGCLVKDYFPEPVTVSWNSGA LTSGVHTFPAVLQSSGLYSLSSVVTVPSSSLGTQTYICNVNH KPSNTKVDKRVEPKSCDKTHTCPPCPAPELLGGPSVFLFPPK PKDTLMISRTPEVTCVVVDVSHEDPEVKFNWYVDGVEVHN AKTKPREEQYNSTYRVVSVLTVLHQDWLNGKEYKCKVSN KALPAPIEKTISKAKGQPREPQVYTLPPSREEMTKNQVSLTC LVKGFYPSDIAVEWESNGQPENNYKTTPPVLDSDGSFFLYS KLTVDKSRWQQGNVFSCSVMHEALHNHYTQKSLSLSPG | 41 |
| 13E4_VH4_a | QVQLVQSGAEVKKPGASVKVSCKASGYTFTNYWMHWVRQ APGQGLEWMGEINPINGRSNYAEKFQGRVTLTVDTSSSTAY MELSSLRSEDTATYYCARGTRAMHYWGQGTLVTVSSASTK GPSVFPLAPSSKSTSGGTAALGCLVKDYFPEPVTVSWNSGA LTSGVHTFPAVLQSSGLYSLSSVVTVPSSSLGTQTYICNVNH KPSNTKVDKRVEPKSCDKTHTCPPCPAPEAAGGPSVFLFPPK PKDTLMISRTPEVTCVVVDVSHEDPEVKFNWYVDGVEVHN AKTKPREEQYNSTYRVVSVLTVLHQDWLNGKEYKCKVSN KALPAPIEKTISKAKGQPREPQVYTLPPSREEMTKNQVSLTC LVKGFYPSDIAVEWESNGQPENNYKTTPPVLDSDGSFFLYS KLTVDKSRWQQGNVFSCSVMHEALHNHYTQKSLSLSPG | 42 |
| 13E4_VH4_b | QVQLVQSGAEVKKPGASVKVSCKASGYTFTNYWMHWVRQ APGQGLEWMGEINPINGRSNYAEKFQGRVTLTVDTSSSTAY MELSSLRSEDTATYYCARGTRAMHYWGQGTLVTVSSASTK GPSVFPLAPSSKSTSGGTAALGCLVKDYFPEPVTVSWNSGA LTSGVHTFPAVLQSSGLYSLSSVVTVPSSSLGTQTYICNVNH KPSNTKVDKRVEPKSCDKTHTCPPCPAPEAAGGPSVFLFPPK PKDTLMISRTPEVTCVVVDVSHEDPEVKFNWYVDGVEVHN AKTKPREEQYNSTYRVVSVLTVLHQDWLNGKEYKCGVSN KALPAPIEKTISKAKGQPREPQVYTLPPSREEMTKNQVSLTC LVKGFYPSDIAVEWESNGQPENNYKTTPPVLDSDGSFFLYS KLTVDKSRWQQGNVFSCSVMHEALHNHYTQKSLSLSPG | 43 |
| 13E4_VH4_c | QVQLVQSGAEVKKPGASVKVSCKASGYTFTNYWMHWVRQ APGQGLEWMGEINPINGRSNYAEKFQGRVTLTVDTSSSTAY MELSSLRSEDTATYYCARGTRAMHYWGQGTLVTVSSASTK GPSVFPLAPSSKSTSGGTAALGCLVKDYFPEPVTVSWNSGA LTSGVHTFPAVLQSSGLYSLSSVVTVPSSSLGTQTYICNVNH KPSNTKVDKRVEPKSCDKTHTCPPCPAPEAAGGPSVFLFPPK PKDTLMISRTPEVTCVVVDVSHEDPEVKFNWYVDGVEVHN AKTKPREEQYNSTYRVVSVLTVLHQDWLNGKEYKCKVSN KARPAPIEKTISKAKGQPREPQVYTLPPSREEMTKNQVSLTC LVKGFYPSDIAVEWESNGQPENNYKTTPPVLDSDGSFFLYS KLTVDKSRWQQGNVFSCSVMHEALHNHYTQKSLSLSPG | 44 |
| 13E4_VH4_d | QVQLVQSGAEVKKPGASVKVSCKASGYTFTNYWMHWVRQ APGQGLEWMGEINPINGRSNYAEKFQGRVTLTVDTSSSTAY MELSSLRSEDTATYYCARGTRAMHYWGQGTLVTVSSASTK GPSVFPLAPSSKSTSGGTAALGCLVKDYFPEPVTVSWNSGA LTSGVHTFPAVLQSSGLYSLSSVVTVPSSSLGTQTYICNVNH KPSNTKVDKRVEPKSCDKTHTCPPCPAPEAAGGPSVFLFPPK PKDTLMISRTPEVTCVVVDVSHEDPEVKFNWYVDGVEVHN AKTKPREEQYNSTYRVVSVLTVLHQDWLNGKEYKCKVSN KALGAPIEKTISKAKGQPREPQVYTLPPSREEMTKNQVSLTC LVKGFYPSDIAVEWESNGQPENNYKTTPPVLDSDGSFFLYS KLTVDKSRWQQGNVFSCSVMHEALHNHYTQKSLSLSPG | 45 |
| 13E4_VH4_e | QVQLVQSGAEVKKPGASVKVSCKASGYTFTNYWMHWVRQ APGQGLEWMGEINPINGRSNYAEKFQGRVTLTVDTSSSTAY MELSSLRSEDTATYYCARGTRAMHYWGQGTLVTVSSASTK GPSVFPLAPSSKSTSGGTAALGCLVKDYFPEPVTVSWNSGA LTSGVHTFPAVLQSSGLYSLSSVVTVPSSSLGTQTYICNVNH KPSNTKVDKRVEPKSCDKTHTCPPCPAPELLGGPSVFLFPPK PKDTLMISRTPEVTCVVVAVSHEDPEVKFNWYVDGVEVHN AKTKPREEQYGSTYRVVSVLTVLHQDWLNGKEYKCKVSN KALPAPIEKTISKAKGQPREPQVYTLPPSREEMTKNQVSLTC LVKGFYPSDIAVEWESNGQPENNYKTTPPVLDSDGSFFLYS KLTVDKSRWQQGNVFSCSVMHEALHNHYTQKSLSLSPG | 46 |

TABLE 7

| NAME | LC SEQUENCE | SEQ ID NO: |
|---|---|---|
| 13E4_VL1 | DIQMTQSPSSLSASVGDRVTITCRTSENIYNNLAWYQQK PGKSPKLLIYAATNLADGVPSRFSGSGSGTDYTLTISSL QPEDFFATYYCQHFWGTPLTFGGGTKVEIKRTVAAPSVF IFPPSDEQLKSGTASVVCLLNNFYPREAKVQWKVDNALQ SGNSQESVTEQDSKDSTYSLSSTLTLSKADYEKHKVYAC EVTHQGLSSPVTKSFNRGEC | 47 |
| 13E4_VL2 | DIQMTQSPSSLSASVGDRVTITCRTSENIYNNLAWYQQK PGKAPKLLIYAATNLADGVPSRFSGSGSGTDYTLTISSL QPEDFATYYCQHFWGTPLTFGGGTKVEIKRTVAAPSVFI FPPSDEQLKSGTASVVCLLNNFYPREAKVQWKVDNALQS GNSQESVTEQDSKDSTYSLSSTLTLSKADYEKHKVYACE VTHQGLSSPVTKSFNRGEC | 48 |
| 13E4_VL3 | DIQMTQSPSSLSASVGDRVTITCRTSENIYNNLAWYQQK PGKAPKLLIYAATNLAEGVPSRFSGSGSGTDYTLTISSL QPEDFATYYCQHFWGTPLTFGGGTKVEIKRTVAAPSVFI FPPSDEQLKSGTASVVCLLNNFYPREAKVQWKVDNALQS GNSQESVTEQDSKDSTYSLSSTLTLSKADYEKHKVYACE VTHQGLSSPVTKSFNRGEC | 49 |
| 13E4_VL4 | DIQMTQPSSLSASVGDRVTITCRTSENIYSNLAWYQQKP GKAPKLLIYAGTNLADGVPSRFSGSGSGTDYTLTISSLQ PEDFANYYCQHFWGTPLTFGGGTKVEIKRTVAAPSVFIF PPSDEQLKSGTASVVCLLNNFYPREAKVQWKVDNALQSG NSQESVTEQDSKDSTYSLSSTLTLSKADYEKHKVYACEV THQGLSSPVTKSFNRGEC | 50 |

In some embodiments, an anti-transferrin receptor antibody described herein has an improved serum half-life compared to a reference anti-transferrin receptor antibody. In some instances, the improved serum half-life is at least 30 minutes, 1 hour, 1.5 hour, 2 hours, 3 hours, 4 hours, 5 hours, 6 hours, 7 hours, 8 hours, 9 hours, 10 hours, 12 hours, 18 hours, 24 hours, 2 days, 3 days, 4 days, 5 days, 6 days, 7 days, 14 days, 30 days, or longer than reference anti-transferrin receptor antibody.

Production of Antibodies or Binding Fragments Thereof

In some embodiments, polypeptides described herein (e.g., antibodies and its binding fragments) are produced using any method known in the art to be useful for the synthesis of polypeptides (e.g., antibodies), in particular, by chemical synthesis or by recombinant expression, and are preferably produced by recombinant expression techniques.

In some instances, an antibody or its binding fragment thereof is expressed recombinantly, and the nucleic acid encoding the antibody or its binding fragment is assembled from chemically synthesized oligonucleotides (e.g., as described in Kutmeier et al., 1994, *BioTechniques* 17:242), which involves the synthesis of overlapping oligonucleotides containing portions of the sequence encoding the antibody, annealing and ligation of those oligonucleotides, and then amplification of the ligated oligonucleotides by PCR.

Alternatively, a nucleic acid molecule encoding an antibody is optionally generated from a suitable source (e.g., an antibody cDNA library, or cDNA library generated from any tissue or cells expressing the immunoglobulin) by PCR amplification using synthetic primers hybridizable to the 3' and 5' ends of the sequence or by cloning using an oligonucleotide probe specific for the particular gene sequence.

In some instances, an antibody or its binding is optionally generated by immunizing an animal, such as a rabbit, to generate polyclonal antibodies or, more preferably, by generating monoclonal antibodies, e.g., as described by Kohler and Milstein (1975, Nature 256:495-497) or, as described by Kozbor et al. (1983, Immunology Today 4:72) or Cole et al. (1985 in Monoclonal Antibodies and Cancer Therapy, Alan R. Liss, Inc., pp. 77-96). Alternatively, a clone encoding at least the Fab portion of the antibody is optionally obtained by screening Fab expression libraries (e.g., as described in Huse et al., 1989, Science 246:1275-1281) for clones of Fab fragments that bind the specific antigen or by screening antibody libraries (See, e.g., Clackson et al., 1991, Nature 352:624; Hane et al., 1997 Proc. Natl. Acad. Sci. USA 94:4937).

In some embodiments, techniques developed for the production of "chimeric antibodies" (Morrison et al., 1984, Proc. Natl. Acad. Sci. 81:851-855; Neuberger et al., 1984, Nature 312:604-608; Takeda et al., 1985, Nature 314:452-454) by splicing genes from a mouse antibody molecule of appropriate antigen specificity together with genes from a human antibody molecule of appropriate biological activity are used. A chimeric antibody is a molecule in which different portions are derived from different animal species, such as those having a variable region derived from a murine monoclonal antibody and a human immunoglobulin constant region, e.g., humanized antibodies.

In some embodiments, techniques described for the production of single chain antibodies (U.S. Pat. No. 4,694,778; Bird, 1988, Science 242:423-42; Huston et al., 1988, Proc. Natl. Acad. Sci. USA 85:5879-5883; and Ward et al., 1989, Nature 334:544-54) are adapted to produce single chain antibodies. Single chain antibodies are formed by linking the heavy and light chain fragments of the Fv region via an amino acid bridge, resulting in a single chain polypeptide. Techniques for the assembly of functional Fv fragments in E. coli are also optionally used (Skerra et al., 1988, Science 242:1038-1041).

In some embodiments, an expression vector comprising the nucleotide sequence of an antibody or the nucleotide sequence of an antibody is transferred to a host cell by conventional techniques (e.g., electroporation, liposomal transfection, and calcium phosphate precipitation), and the transfected cells are then cultured by conventional techniques to produce the antibody. In specific embodiments, the expression of the antibody is regulated by a constitutive, an inducible or a tissue, specific promoter.

In some embodiments, a variety of host-expression vector systems is utilized to express an antibody or its binding fragment described herein. Such host-expression systems represent vehicles by which the coding sequences of the antibody is produced and subsequently purified, but also represent cells that are, when transformed or transfected with the appropriate nucleotide coding sequences, express an antibody or its binding fragment in situ. These include, but are not limited to, microorganisms such as bacteria (e.g., E. coli and B. subtilis) transformed with recombinant bacteriophage DNA, plasmid DNA or cosmid DNA expression vectors containing an antibody or its binding fragment coding sequences; yeast (e.g., Saccharomyces Pichia) transformed with recombinant yeast expression vectors containing an antibody or its binding fragment coding sequences; insect cell systems infected with recombinant virus expression vectors (e.g., baculovirus) containing an antibody or its binding fragment coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing an antibody or its binding fragment coding sequences; or mammalian cell systems (e.g., COS, CHO, BH, 293, 293T, 3T3 cells) harboring recombinant expression constructs containing promoters derived from the genome of mammalian cells (e.g., metallothionein promoter) or from mammalian viruses (e.g. the adenovirus late promoter; the vaccinia virus 7.5K promoter).

For long-term, high-yield production of recombinant proteins, stable expression is preferred. In some instances, cell lines that stably express an antibody are optionally engineered. Rather than using expression vectors that contain viral origins of replication, host cells are transformed with DNA controlled by appropriate expression control elements (e.g., promoter, enhancer, sequences, transcription terminators, polyadenylation sites, etc.), and a selectable marker. Following the introduction of the foreign DNA, engineered cells are then allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn are cloned and expanded into cell lines. This method can advantageously be used to engineer cell lines which express the antibody or its binding fragments.

In some instances, a number of selection systems are used, including but not limited to the herpes simplex virus thymidine kinase (Wigler et al., 1977, Cell 11:223), hypoxanthine-guanine phosphoribosyltransferase (Szybalska & Szybalski, 192, Proc. Natl. Acad. Sci. USA 48:202), and adenine phosphoribosyltransferase (Lowy et al., 1980, Cell 22:817) genes are employed in tk–, hgprt– or aprt– cells, respectively. Also, antimetabolite resistance are used as the basis of selection for the following genes: dhfr, which confers resistance to methotrexate (Wigler et al., 1980, Proc. Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIB TECH 11(5):155-215) and hygro, which confers resistance to hygromycin (Santerre et al., 1984, Gene 30:147). Methods commonly known in the art of recombinant DNA technology which can be used are described in Ausubel et al. (eds., 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds), 1994, Current Protocols in Human Genetics, John Wiley & Sons, NY; Colberre-Garapin et al., 1981, J Mol. Biol. 150:1).

In some instances, the expression levels of an antibody are increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing an antibody is amplifiable, an increase in the level of inhibitor present in culture of host cell will increase the number of copies of the marker gene. Since the amplified region is associated with the nucleotide sequence of the antibody, production of the antibody will also increase (Crouse et al., 1983, *Mol. Cell Biol.* 3:257).

In some instances, any method known in the art for purification or analysis of an antibody or antibody conjugates is used, for example, by chromatography (e.g., ion exchange, affinity, particularly by affinity for the specific antigen after Protein A, and sizing column chromatography), centrifugation, differential solubility, or by any other standard technique for the purification of proteins. Exemplary chromatography methods included, but are not limited to, strong anion exchange chromatography, hydrophobic interaction chromatography, size exclusion chromatography, and fast protein liquid chromatography.

Anti-Transferrin Receptor Antibody Conjugate

In some embodiments, an anti-transferrin receptor antibody described above is further conjugated to a payload. In some instances, the payload comprises a small molecule. In other instances, the payload comprises a protein or a peptide. In additional instances, the payload comprises a polynucleic acid molecule.

In some instances, a ratio of the payload to the anti-transferrin receptor antibody (drug-to-antibody ratio or DAR ratio) is about 1:1, 2:1, 3:1, 4:1, 5:1, 6:1, 7:1, 8:1, 9:1, 10:1, 11:1, 12:1, 13:1, 14:1, 15:1, or 16:1.

In some cases, an anti-transferrin receptor antibody conjugate comprises $$A\text{-}(X^1\text{-}B)_n \qquad \text{Formula (I)}$$

wherein,

A comprises the anti-transferrin receptor antibody;
B comprises the payload;
$X^1$ consists of a bond or linker; and
n is an averaged value selected from 1-12.

In some instances, the DAR ratio of B to A (the anti-transferrin receptor antibody) is about 1, 2, 3, 4, 5, 6, 7, 8, 9, 10, 11, 12, 13, 14, 15, or 16. In some cases, the DAR ratio of B to A is about 1. In some cases, the DAR ratio of B to A is about 2. In some cases, the DAR ratio of B to A is about 3. In some cases, the DAR ratio of B to A is about 4. In some cases, the DAR ratio of B to A is about 6. In some cases, the DAR ratio of B to A is about 8. In some cases, the DAR ratio of B to A is about 10. In some cases, the DAR ratio of B to A is about 12. In some cases, the DAR ratio of B to A is about 16.

In some instances, the DAR ratio of the polynucleic acid molecule (B) to anti-transferrin receptor antibody A is about 1, 2, 3, 4, 5, 6, 7, 8, 9, 10, 11, 12, 13, 14, 15, or 16. In some instances, the DAR ratio of the polynucleic acid molecule (B) to anti-transferrin receptor antibody A is about 1. In some instances, the DAR ratio of the polynucleic acid molecule (B) to anti-transferrin receptor antibody A is about 2. In some instances, the DAR ratio of the polynucleic acid molecule (B) to anti-transferrin receptor antibody A is about 3. In some instances, the DAR ratio of the polynucleic acid molecule (B) to anti-transferrin receptor antibody A is about 4. In some instances, the DAR ratio of the polynucleic acid molecule (B) to anti-transferrin receptor antibody A is about 5. In some instances, the DAR ratio of the polynucleic acid molecule (B) to anti-transferrin receptor antibody A is about 6. In some instances, the DAR ratio of the polynucleic acid molecule (B) to anti-transferrin receptor antibody A is about 7. In some instances, the DAR ratio of the polynucleic acid molecule (B) to anti-transferrin receptor antibody A is about 8. In some instances, the DAR ratio of the polynucleic acid molecule (B) to anti-transferrin receptor antibody A is about 9. In some instances, the DAR ratio of the polynucleic acid molecule (B) to anti-transferrin receptor antibody A is about 10. In some instances, the DAR ratio of the polynucleic acid molecule (B) to anti-transferrin receptor antibody A is about 11. In some instances, the DAR ratio of the polynucleic acid molecule (B) to anti-transferrin receptor antibody A is about 12. In some instances, the DAR ratio of the polynucleic acid molecule (B) to anti-transferrin receptor antibody A is about 13. In some instances, the DAR ratio of the polynucleic acid molecule (B) to anti-transferrin receptor antibody A is about 14. In some instances, the DAR ratio of the polynucleic acid molecule (B) to anti-transferrin receptor antibody A is about 15. In some instances, the DAR ratio of the polynucleic acid molecule (B) to anti-transferrin receptor antibody A is about 16.

In some embodiments, B comprises a small molecule, a peptide, or a protein.

In some embodiments, B comprises a polynucleic acid molecule. In some cases, the polynucleic acid molecule comprises a passenger strand and a guide strand. In some cases, the passenger strand is conjugated to $A\text{-}X^1$. In some cases, $A\text{-}X^1$ is conjugated to the 5' end of the passenger strand. In some cases, $A\text{-}X^1$ is conjugated to the 3' end of the passenger strand.

In some cases, an anti-transferrin receptor antibody conjugate comprises $$A\text{-}X^1\text{-}(B\text{-}X^2\text{-}C)_n \qquad \text{Formula (II)}$$

wherein,

A comprises the anti-transferrin receptor antibody;
B comprises the payload;
C consists of a polymer;
$X^1$ consists a bond or first linker;
$X^2$ consists of a bond or second linker; and
n is an averaged value selected from 1-12.

In some cases, C is a polyethylene glycol.

In some instances, B is a polynucleic acid molecule. In some cases, the polynucleic acid molecule comprises a passenger strand and a guide strand. In some cases, the passenger strand is conjugated to $A\text{-}X^1$ and $X^2\text{-}C$. In some cases, $A\text{-}X^1$ is conjugated to the 5' end of the passenger strand and $X^2\text{-}C$ is conjugated to the 3' end of the passenger strand. In some cases, $X^2\text{-}C$ is conjugated to the 5' end of the passenger strand and $A\text{-}X^1$ is conjugated to the 3' end of the passenger strand.

In some cases, $X^1$ and $X^2$ are each independently a non-polymeric linker.

In some cases, the conjugate of Formula (II) $A\text{-}X^1\text{-}(B\text{-}X^2\text{-}C)_n$ further comprises D, an endosomolytic moiety.

Conjugation Chemistry

In some embodiments, B is conjugated to A by a chemical ligation process. In some instances, B is conjugated to A by a native ligation. In some instances, the conjugation is as described in: Dawson, et al. "Synthesis of proteins by native chemical ligation," *Science* 1994, 266, 776-779; Dawson, et al. "Modulation of Reactivity in Native Chemical Ligation through the Use of Thiol Additives," *J. Am. Chem. Soc.* 1997, 119, 4325-4329; Hackeng, et al. "Protein synthesis by native chemical ligation: Expanded scope by using straightforward methodology," *Proc. Natl. Acad. Sci. USA* 1999, 96, 10068-10073; or Wu, et al. "Building complex glycopeptides: Development of a cysteine-free native chemical ligation protocol,"*Angew. Chem. Int. Ed.* 2006, 45, 4116-4125. In some instances, the conjugation is as described in U.S. Pat. No. 8,936,910. In some embodiments, the polynucleic acid molecule is conjugated to the binding moiety either site-specifically or non-specifically via native ligation chemistry.

In some instances, B is conjugated to A by a site-directed method utilizing a "traceless" coupling technology (Philochem). In some instances, the "traceless" coupling technology utilizes an N-terminal 1,2-aminothiol group on the binding moiety which is then conjugate with a polynucleic acid molecule containing an aldehyde group. (see Casi et al., "Site-specific traceless coupling of potent cytotoxic drugs to recombinant antibodies for pharmacodelivery," JACS 134(13): 5887-5892 (2012))

In some instances, B is conjugated to A by a site-directed method utilizing an unnatural amino acid incorporated into the binding moiety. In some instances, the unnatural amino acid comprises p-acetylphenylalanine (pAcPhe). In some instances, the keto group of pAcPhe is selectively coupled to an alkoxy-amine derivatived conjugating moiety to form an oxime bond. (see Axup et al., "Synthesis of site-specific antibody-drug conjugates using unnatural amino acids," PNAS 109(40): 16101-16106 (2012)).

In some instances, B is conjugated to A by a site-directed method utilizing an enzyme-catalyzed process. In some instances, the site-directed method utilizes SMARTag™ technology (Redwood). In some instances, the SMARTag™ technology comprises generation of a formylglycine (FGly) residue from cysteine by formylglycine-generating enzyme (FGE) through an oxidation process under the presence of an aldehyde tag and the subsequent conjugation of FGly to an alkylhydraine-functionalized polynucleic acid molecule via hydrazino-Pictet-Spengler (HIPS) ligation. (see Wu et al., "Site-specific chemical modification of recombinant proteins produced in mammalian cells by using the genetically encoded aldehyde tag," PNAS 106(9): 3000-3005 (2009); Agarwal, et al., "A Pictet-Spengler ligation for protein chemical modification," PNAS 110(1): 46-51 (2013))

In some instances, the enzyme-catalyzed process comprises microbial transglutaminase (mTG). In some cases, B is conjugated to A utilizing a microbial transglutaminze catalyzed process. In some instances, mTG catalyzes the formation of a covalent bond between the amide side chain of a glutamine within the recognition sequence and a primary amine of a functionalized polynucleic acid molecule. In some instances, mTG is produced from *Streptomyces mobarensis*. (see Strop et al., "Location matters: site of conjugation modulates stability and pharmacokinetics of antibody drug conjugates," Chemistry and Biology 20(2) 161-167 (2013))

In some instances, B is conjugated to A by a method as described in PCT Publication No. WO2014/140317, which utilizes a sequence-specific transpeptidase.

In some instances, B is conjugated to A by a method as described in U.S. Patent Publication Nos. 2015/0105539 and 2015/0105540.

Payloads
Polynucleic Acid Molecules

In some embodiments, the payload is a polynucleic acid molecule. In some instances, the polynucleic acid molecule is involved in gene therapy, such as in RNA interference (RNAi) or gene silencing (e.g., antisense oligonucleotide) therapies. In some instances, the polynucleic acid molecule modulates the splicing of an mRNA, and thereby modulates subsequently production of the encoded protein.

In some embodiments, the polynucleic acid molecule comprises a short interfering nucleic acid (siNA), a short interfering RNA (siRNA), a double-stranded RNA (dsRNA), a micro-RNA (miRNA), or a short hairpin RNA (shRNA).

In other embodiments, the polynucleic acid molecule comprises an antisense oligonucleotide.

In other embodiments, the polynucleic acid molecule comprises a PMO.

In additional embodiments, the polynucleic acid molecule comprises an mRNA.

In some instances, the polynucleic acid molecule hybridizes to a target sequence of an atrophy-related gene (also referred to as an atrogene). Atrogenes, or atrophy-related genes, are genes that are upregulated or downregulated in atrophying muscle. In some instances, upregulated atrogenes include genes that encode ubiquitin ligases, Forkhead box transcription factors, growth factors, deubiquitinating enzymes, or proteins that are involved in glucocorticoid-induced atrophy. In some instances, a polynucleic acid molecule described herein hybridizes to a target sequence of an ubiquitin ligase (e.g., an E3 ubiquitin ligase or a mitochondrial ubiquitin ligase). In some instances, a polynucleic acid molecule described herein hybridizes to a target sequence of a Forkhead box transcription factor. In some instances, a polynucleic acid molecule described herein hybridizes to a target sequence of a growth factor. In some instances, a polynucleic acid molecule described herein hybridizes to a target sequence of a deubiquitinating enzyme.

In some embodiments, a polynucleic acid molecule described herein hybridizes to a target sequence of FBXO32, TRIM63, TRAF6, FBXO30, FBXO40, NEDD4, TRIM32, MUL1, STUB1, FOXO1, FOXO3, MSTN, USP14, USP19, DDIT4, CTSL2, TGIF, MYOG, HDAC2, HDAC3, MT1L, MT1B, or DMPK. In some cases, a polynucleic acid molecule described herein hybridizes to a target sequence of FBXO32, TRIM63, FOXO1, FOXO3, or MSTN. In some cases, a polynucleic acid molecule described herein hybridizes to a target sequence of FBXO32. In some cases, a polynucleic acid molecule described herein hybridizes to a target sequence of TRIM63. In some cases, a polynucleic acid molecule described herein hybridizes to a target sequence of TRAF6. In some cases, a polynucleic acid molecule described herein hybridizes to a target sequence of FBXO30. In some cases, a polynucleic acid molecule described herein hybridizes to a target sequence of FBXO40. In some cases, a polynucleic acid molecule described herein hybridizes to a target sequence of NEDD4. In some cases, a polynucleic acid molecule described herein hybridizes to a target sequence of TRIM32. In some cases, a polynucleic acid molecule described herein hybridizes to a target sequence of MUL1. In some cases, a polynucleic acid molecule described herein hybridizes to a target sequence of STUB1. In some cases, a polynucleic acid molecule described herein hybridizes to a target sequence of FOXO1. In some cases, a polynucleic acid molecule described herein hybridizes to a target sequence of FOXO3. In some cases, a polynucleic acid molecule described herein hybridizes to a target sequence of MSTN. In some cases, a polynucleic acid molecule described herein hybridizes to a target sequence of USP14. In some cases, a polynucleic acid molecule described herein hybridizes to a target sequence of USP19. In some cases, a polynucleic acid molecule described herein hybridizes to a target sequence of DDIT4. In some cases, a polynucleic acid molecule described herein hybridizes to a target sequence of CTSL2. In some cases, a polynucleic acid molecule described herein hybridizes to a target sequence of TGIF. In some cases, a polynucleic acid molecule described herein hybridizes to a target sequence of MYOG. In some cases, a polynucleic acid molecule described herein hybridizes to a target sequence of HDAC2. In some cases, a polynucleic acid molecule described herein hybridizes to a target sequence of HDAC3. In some cases, a polynucleic acid molecule described herein hybridizes to a target sequence of MT1L. In some cases, a polynucleic acid molecule described herein hybridizes to a target sequence of MT1B. In some cases, a polynucleic acid molecule described herein hybridizes to a target sequence of DMPK.

In some instances, the polynucleic acid molecule hybridizes to a target region of an incorrectly spliced mRNA which results in a disease or disorder not limited to a neuromuscular disease, a genetic disease, cancer, a hereditary disease, or a cardiovascular disease. In some cases, a neuromuscular disease or disorder is Duchenne muscular dystrophy, Becker muscular dystrophy, facioscapulohumeral muscular dystrophy, congenital muscular dystrophy, or myotonic dystrophy.

In some instances, the polynucleic acid molecule targets an exon that is mutated in the DMD gene that causes Duchenne muscular dystrophy. Exemplary exons that are mutated in the DMD gene that causes Duchenne muscular dystrophy include, but not limited to, exon 2, 3, 4, 5, 6, 7, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, and 78.

In some instances, the polynucleic acid molecule hybridizes to a target region of an oncogene. Exemplary oncogenes include, but are not limited to, Abl, AKT-2, ALK, AML1 (or RUNX1), AR, AXE BCL-2, 3, 6, BRAF, c-MYC, EGFR, ErbB-2 (Her2, Neu), Fms, FOS, GLI1, HPRT1, IL-3, INTS2, JUN, KIT, KS3, K-sam, LBC (AKAP13), LCK, LMO1, LMO2, LYL1, MAS1, MDM2, MET, MLL (KMT2A), MOS, MYB, MYH11/CBFB, NOTCH1 (TAN1), NTRK1 (TRK), OST (SLC51B), PAX5, PIM1, PRAD-1, RAF, RAR/PML, HRAS, KRAS, NRAS, REL/NRG, RET, ROS, SKI, SRC, TIAMI, or TSC2. In some cases, the polynucleic acid molecule hybridizes to a target region of KRAS, EGFR, AR, HPRT1, CNNTB1 (β-catenin), or β-catenin associated genes.

In some embodiments, the polynucleic acid molecule comprises an mRNA. In some cases, the mRNA encodes a cytotoxic protein or peptide. Exemplary cytotoxic proteins or peptides include a bacterial cytotoxin such as an alpha-pore forming toxin (e.g., cytolysin A from *E. coli*), a beta-pore-forming toxin (e.g., α-Hemolysin, PVL—panton Valentine leukocidin, aerolysin, clostridial Epsilon-toxin, *Clostridium perfringens* enterotoxin), binary toxins (anthrax toxin, edema toxin, *C. botulinum* C2 toxin, *C spirofome* toxin, *C. perfringens* iota toxin, *C. difficile* cyto-lethal toxins (A and B)), prion, parasporin, a cholesterol-dependent cytolysins (e.g., pneumolysin), a small pore-forming toxin (e.g., Gramicidin A), a cyanotoxin (e.g., microcystins, nodularins), a hemotoxin, a neurotoxin (e.g., botulinum neurotoxin), a cytotoxin, cholera toxin, diphtheria toxin, *Pseudomonas* exotoxin A, tetanus toxin, or an immunotoxin (idarubicin, ricin A, CRM9, Pokeweed antiviral protein, DT).

In some instances, the mRNA encodes a cytotoxic peptide or peptide related to the immune system such as a cytotoxic T cell or B cell epitope to stimulate a specific immune response via presentation of such epitope with an MHC I complex, an membrane attack complex protein (MAC) of the complement system, perforin, a granzyme and a granulysin.

In some cases, the mRNA encodes an apoptotic triggering protein or peptide such as an apoptotic protease activating factor-1 (Apaf-1), cytochrome-c, caspase initiator proteins (CASP2, CASP8, CASP9, CASP10), apoptosis inducing factor (AIF), p53, p73, p63, Bcl-2, Bax, granzyme B, poly-ADP ribose polymerase (PARP), and P 21-activated kinase 2 (PAK2).

In some embodiments, the polynucleic acid molecule is a nucleic acid decoy. In some instances, the nucleic acid decoy is a mimic of protein-binding nucleic acids such as RNA-based protein-binding mimics. Exemplary nucleic acid decoys include transactivating region (TAR) decoy and Rev response element (RRE) decoy.

In some instances, the payload is an aptamer. Aptamers are small oligonucleotide or peptide molecules that bind to specific target molecules. Exemplary nucleic acid aptamers include DNA aptamers, RNA aptamers, or XNA aptamers which are RNA and/or DNA aptamers comprising one or more unnatural nucleotides. Exemplary nucleic acid aptamers include ARC19499 (Archemix Corp.), REG1 (Regado Biosciences), and ARC1905 (Ophthotech).

In some embodiments, the polynucleic acid molecule comprises natural or synthetic or artificial nucleotide analogues or bases. In some cases, the polynucleic acid molecule comprises combinations of DNA, RNA and/or nucleotide analogues. In some instances, the synthetic or artificial nucleotide analogues or bases comprise modifications at one or more of ribose moiety, phosphate moiety, nucleoside moiety, or a combination thereof.

In some embodiments, nucleotide analogues or artificial nucleotide base comprise a nucleic acid with a modification at a 2' hydroxyl group of the ribose moiety. In some instances, the modification includes an H, OR, R, halo, SH, SR, NH2, NHR, NR2, or CN, wherein R is an alkyl moiety. Exemplary alkyl moiety includes, but is not limited to, halogens, sulfurs, thiols, thioethers, thioesters, amines (primary, secondary, or tertiary), amides, ethers, esters, alcohols and oxygen. In some instances, the alkyl moiety further comprises a modification. In some instances, the modification comprises an azo group, a keto group, an aldehyde group, a carboxyl group, a nitro group, a nitroso, group, a nitrile group, a heterocycle (e.g., imidazole, hydrazino or hydroxylamino) group, an isocyanate or cyanate group, or a sulfur containing group (e.g., sulfoxide, sulfone, sulfide, or disulfide). In some instances, the alkyl moiety further comprises a hetero substitution. In some instances, the carbon of the heterocyclic group is substituted by a nitrogen, oxygen or sulfur. In some instances, the heterocyclic substitution includes but is not limited to, morpholino, imidazole, and pyrrolidino.

In some instances, the modification at the 2' hydroxyl group is a 2'-O-methyl modification or a 2'-O-methoxyethyl (2'-O-MOE) modification. In some cases, the 2'-O-methyl modification adds a methyl group to the 2' hydroxyl group of the ribose moiety whereas the 2'O-methoxyethyl modification adds a methoxyethyl group to the 2' hydroxyl group of the ribose moiety. Exemplary chemical structures of a 2'-O-methyl modification of an adenosine molecule and 2'O-methoxyethyl modification of an uridine are illustrated below.

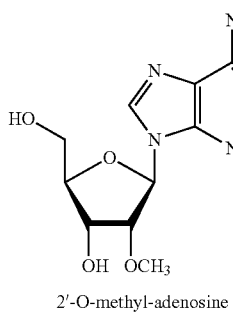

2'-O-methyl-adenosine

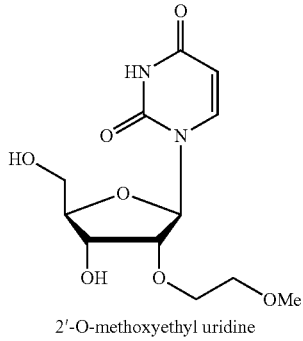

2'-O-methoxyethyl uridine

In some instances, the modification at the 2' hydroxyl group is a 2'-O-aminopropyl modification in which an extended amine group comprising a propyl linker binds the amine group to the 2' oxygen. In some instances, this modification neutralizes the phosphate derived overall negative charge of the oligonucleotide molecule by introducing one positive charge from the amine group per sugar and thereby improves cellular uptake properties due to its zwitterionic properties. An exemplary chemical structure of a 2'-O-aminopropyl nucleoside phosphoramidite is illustrated below.

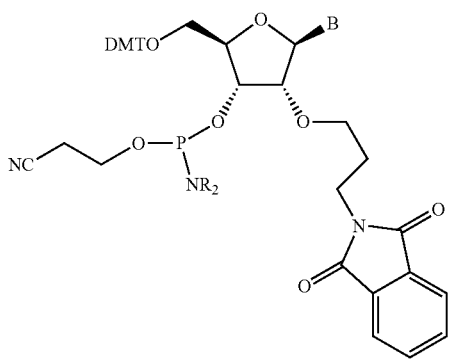

2'-O-aminopropyl nucleoside phosphoramidite

In some instances, the modification at the 2' hydroxyl group is a locked or bridged ribose modification (e.g., locked nucleic acid or LNA) in which the oxygen molecule bound at the 2' carbon is linked to the 4' carbon by a methylene group, thus forming a 2'-C,4'-C-oxy-methylene-linked bicyclic ribonucleotide monomer. Exemplary representations of the chemical structure of LNA are illustrated below. The representation shown to the left highlights the chemical connectivities of an LNA monomer. The representation shown to the right highlights the locked 3'-endo ($^3$E) conformation of the furanose ring of an LNA monomer.

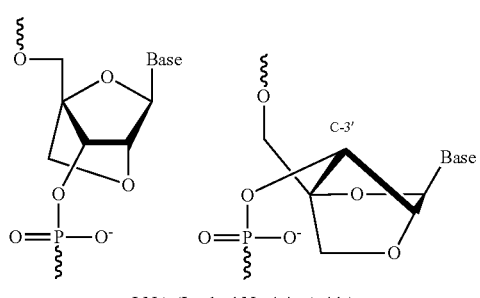

LNA (Locked Nucleic Acids)

In some instances, the modification at the 2' hydroxyl group comprises ethylene nucleic acids (ENA) such as for example 2'-4'-ethylene-bridged nucleic acid, which locks the sugar conformation into a $C_3$'-endo sugar puckering conformation. ENA are part of the bridged nucleic acids class of modified nucleic acids that also comprises LNA. Exemplary chemical structures of the ENA and bridged nucleic acids are illustrated below.

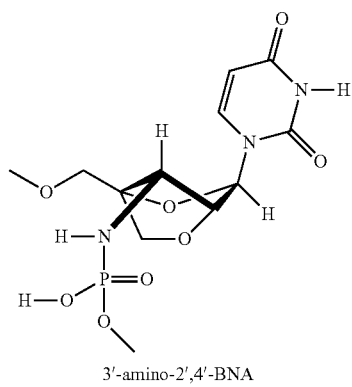

3'-amino-2',4'-BNA

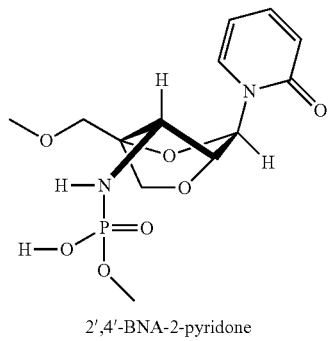

2',4'-BNA-2-pyridone

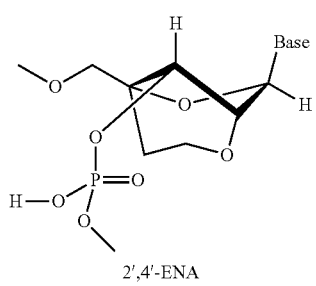

2',4'-ENA

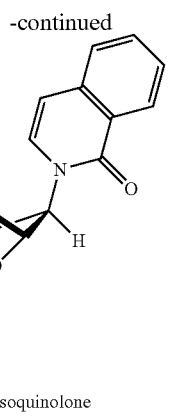

2',4'-BNA-1-isoquinolone

In some embodiments, additional modifications at the 2' hydroxyl group include 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA).

In some embodiments, nucleotide analogues comprise modified bases such as, but not limited to, 5-propynyluridine, 5-propynylcytidine, 6-methyladenine, 6-methylguanine, N, N-dimethyladenine, 2-propyladenine, 2propylguanine, 2-aminoadenine, 1-methylinosine, 3-methyluridine, 5-methylcytidine, 5-methyluridine and other nucleotides having a modification at the 5 position, 5-(2-amino) propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2, 2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4, 6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyi nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties, in some cases are or be based on, mannoses, arabinoses, glucopyranoses, galactopyranoses, 4'-thioribose, and other sugars, heterocycles, or carbocycles. The term nucleotide also includes what are known in the art as universal bases. By way of example, universal bases include but are not limited to 3-nitropyrrole, 5-nitroindole, or nebularine.

In some embodiments, nucleotide analogues further comprise morpholinos, peptide nucleic acids (PNAs), methylphosphonate nucleotides, thiolphosphonate nucleotides, 2'-fluoro N3-P5'-phosphoramidites, 5'-anhydrohexitol nucleic acids (HNAs), or a combination thereof. Morpholino or phosphorodiamidate morpholino oligo (PMO) comprises synthetic molecules whose structure mimics natural nucleic acid structure by deviates from the normal sugar and phosphate structures. In some instances, the five member ribose ring is substituted with a six member morpholino ring containing four carbons, one nitrogen and one oxygen. In some cases, the ribose monomers are linked by a phosphordiamidate group instead of a phosphate group. In such cases, the backbone alterations remove all positive and negative charges making morpholinos neutral molecules capable of crossing cellular membranes without the aid of cellular delivery agents such as those used by charged oligonucleotides.

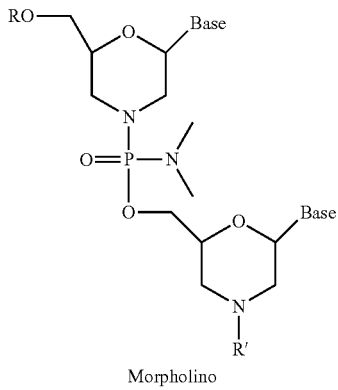

Morpholino

In some embodiments, peptide nucleic acid (PNA) does not contain sugar ring or phosphate linkage and the bases are attached and appropriately spaced by oligoglycine-like molecules, therefore, eliminating a backbone charge.

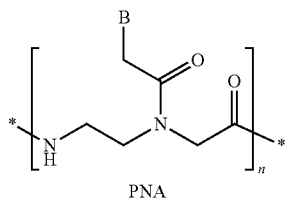

PNA

In some embodiments, one or more modifications optionally occur at the internucleotide linkage. In some instances, modified internucleotide linkage include, but is not limited to, phosphorothioates, phosphorodithioates, methylphosphonates, 5'-alkylenephosphonates, 5'-methylphosphonate, 3'-alkylene phosphonates, borontrifluoridates, borano phosphate esters and selenophosphates of 3'-5'linkage or 2'-5'linkage, phosphotriesters, thionoalkylphosphotriesters, hydrogen phosphonate linkages, alkyl phosphonates, alkylphosphonothioates, arylphosphonothioates, phosphoroselenoates, phosphorodiselenoates, phosphinates, phosphoramidates, 3'-alkylphosphoramidates, aminoalkylphosphoramidates, thionophosphoramidates, phosphoropiperazidates, phosphoroanilothioates, phosphoroanilidates, ketones, sulfones, sulfonamides, carbonates, carbamates, methylenehydrazos, methylenedimethylhydrazos, formacetals, thioformacetals, oximes, methyleneiminos, methylenemethyliminos, thioamidates, linkages with riboacetyl groups, aminoethyl glycine, silyl or siloxane linkages, alkyl or cycloalkyl linkages with or without heteroatoms of, for example, 1 to 10 carbons that are saturated or unsaturated and/or substituted and/or contain heteroatoms, linkages with morpholino structures, amides, polyamides wherein the bases are attached to the aza nitrogens of the backbone directly or indirectly, and combinations thereof. Phosphorothioate antisene oligonucleotides (PS ASO) are antisense oligonucleotides comprising a phosphorothioate linkage. An exemplary PS ASO is illustrated below.

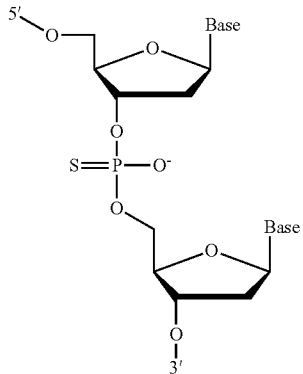

In some instances, the modification is a methyl or thiol modification such as methylphosphonate or thiolphosphonate modification. Exemplary thiolphosphonate nucleotide (left) and methylphosphonate nucleotide (right) are illustrated below.

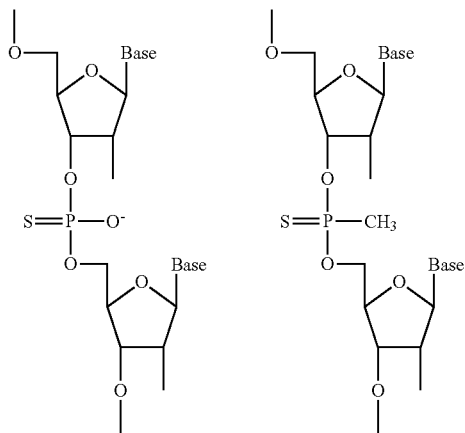

In some instances, a modified nucleotide includes, but is not limited to, 2'-fluoro N3-P5'-phosphoramidites illustrated as:

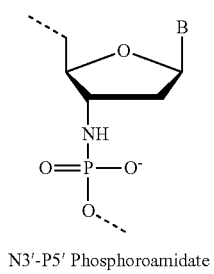

N3'-P5' Phosphoroamidate

In some instances, a modified nucleotide includes, but is not limited to, hexitol nucleic acid (or 1', 5'-anhydrohexitol nucleic acids (HNA)) illustrated as:

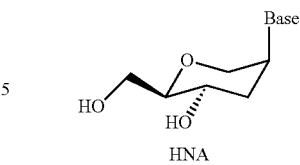

HNA

In some embodiments, a nucleotide analogue or artificial nucleotide base described above comprises a 5'-vinylphosphonate modified nucleotide nucleic acid with a modification at a 5' hydroxyl group of the ribose moiety. In some embodiments, the 5'-vinylphosphonate modified nucleotide is selected from the nucleotide provided below, wherein X is O or S; and B is a heterocyclic base moiety.

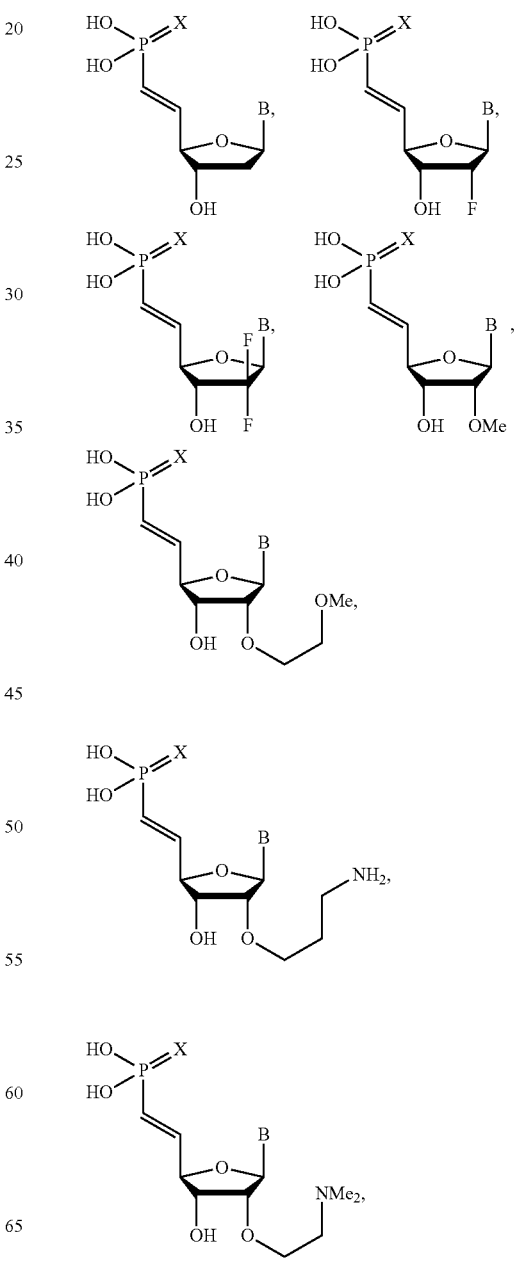

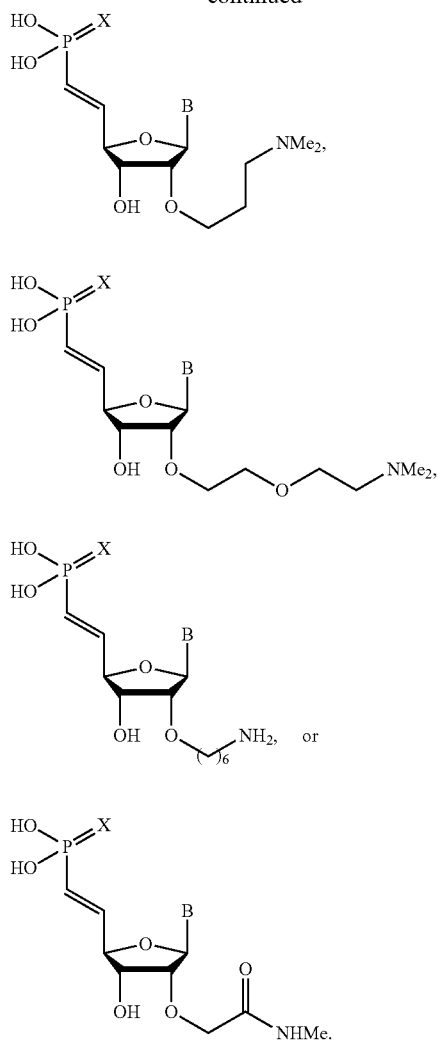

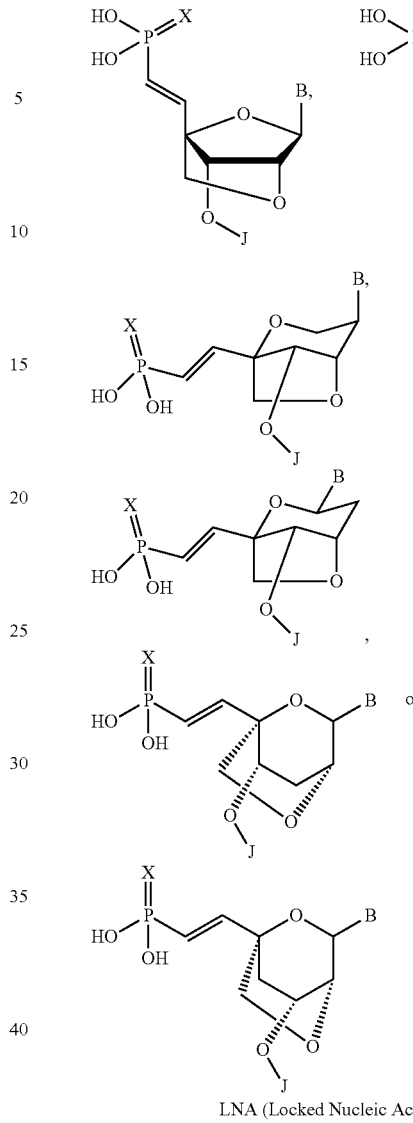

LNA (Locked Nucleic Acids)

In some instances, the modification at the 2' hydroxyl group is a 2'-O-aminopropyl modification in which an extended amine group comprising a propyl linker binds the amine group to the 2' oxygen. In some instances, this modification neutralizes the phosphate-derived overall negative charge of the oligonucleotide molecule by introducing one positive charge from the amine group per sugar and thereby improves cellular uptake properties due to its zwitterionic properties.

In some instances, the 5'-vinylphosphonate modified nucleotide is further modified at the 2' hydroxyl group in a locked or bridged ribose modification (e.g., locked nucleic acid or LNA) in which the oxygen molecule bound at the 2' carbon is linked to the 4' carbon by a methylene group, thus forming a 2'-C,4'-C-oxy-methylene-linked bicyclic ribonucleotide monomer. Exemplary representations of the chemical structure of 5'-vinylphosphonate modified LNA are illustrated below, wherein X is O or S; B is a heterocyclic base moiety; and J is an internucleotide linking group linking to the adjacent nucleotide of the polynucleotide.

In some embodiments, additional modifications at the 2' hydroxyl group include 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA).

In some embodiments, a nucleotide analogue comprises a modified base such as, but not limited to, 5-propynyluridine, 5-propynylcytidine, 6-methyladenine, 6-methylguanine, N, N-dimethyladenine, 2-propyladenine, 2propylguanine, 2-aminoadenine, 1-methylinosine, 3-methyluridine, 5-methylcytidine, 5-methyluridine and other nucleotides having a modification at the 5 position, 5-(2-amino) propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2, 2-dimethylguanosine, 5-methylaminoethyluridine, 5-methyloxyuridine, deazanucleotides (such as 7-deaza-adenosine, 6-azouridine, 6-azocytidine, or 6-azothymidine), 5-methyl-2-thiouridine, other thio bases (such as 2-thiouridine, 4-thiouridine, and 2-thiocytidine), dihydrouridine, pseudouridine, queuosine, archaeosine, naphthyl and substituted naphthyl groups, any O- and N-alkylated purines and pyrimidines (such as N6-methyladenosine, 5-methylcarbonylmethyluridine, uridine 5-oxyacetic acid, pyridine-4-one, or pyridine-2-one), phenyl and modified phenyl groups such as aminophenol or 2,4, 6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyi nucleotides, and alkylcarbonylalkylated nucleotides. 5'-Vinylphosphonate modified nucleotides also include those nucleotides that are modified with respect to the sugar moiety, as well as 5'-vinylphosphonate modified nucleotides having sugars or analogs thereof that are not ribosyl. For example, the sugar moieties, in some cases are or are based on, mannoses, arabinoses, glucopyranoses, galactopyranoses, 4'-thioribose, and other sugars, heterocycles, or carbocycles. The term nucleotide also includes what are known in the art as universal bases. By way of example, universal bases include but are not limited to 3-nitropyrrole, 5-nitroindole, or nebularine.

In some embodiments, a 5'-vinylphosphonate modified nucleotide analogue further comprises a morpholino, a peptide nucleic acid (PNA), a methylphosphonate nucleotide, a thiolphosphonate nucleotide, a 2'-fluoro N3-P5'-phosphoramidite, or a 1', 5'-anhydrohexitol nucleic acid (HNA). Morpholino or phosphorodiamidate morpholino oligo (PMO) comprises synthetic molecules whose structure mimics natural nucleic acid structure but deviates from the normal sugar and phosphate structures. In some instances, the five member ribose ring is substituted with a six member morpholino ring containing four carbons, one nitrogen, and one oxygen. In some cases, the ribose monomers are linked by a phosphordiamidate group instead of a phosphate group. In such cases, the backbone alterations remove all positive and negative charges making morpholinos neutral molecules capable of crossing cellular membranes without the aid of cellular delivery agents such as those used by charged oligonucleotides. A non-limiting example of a 5'-vinylphosphonate modified morpholino oligonucleotide is illustrated below, wherein X is O or S; and B is a heterocyclic base moiety.

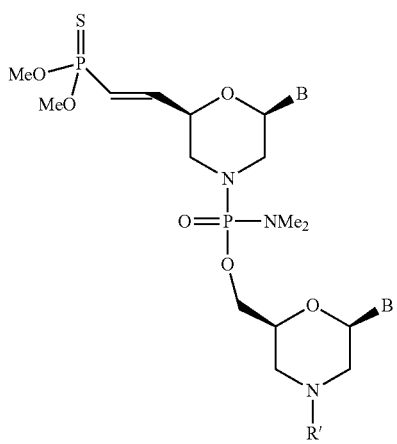

In some embodiments, a 5'-vinylphosphonate modified morpholino or PMO described above is a PMO comprising a positive or cationic charge. In some instances, the PMO is PMOplus (Sarepta). PMOplus refers to phosphorodiamidate morpholino oligomers comprising any number of (1-piperazino)phosphinylideneoxy, (1-(4-(omega-guanidino-alkanoyl))-piperazino)phosphinylideneoxy linkages (e.g., as such those described in PCT Publication No. WO2008/036127. In some cases, the PMO is a PMO described in U.S. Pat. No. 7,943,762.

In some embodiments, a morpholino or PMO described above is a PMO-X (Sarepta). In some cases, PMO-X refers to phosphorodiamidate morpholino oligomers comprising at least one linkage or at least one of the disclosed terminal modifications, such as those disclosed in PCT Publication No. WO2011/150408 and U.S. Publication No. 2012/0065169.

In some embodiments, a morpholino or PMO described above is a PMO as described in Table 5 of U.S. Publication No. 2014/0296321.

Exemplary representations of the chemical structure of 5'-vinylphosphonate modified nucleic acids are illustrated below, wherein X is O or S; B is a heterocyclic base moiety; and J is an internucleotide linkage.

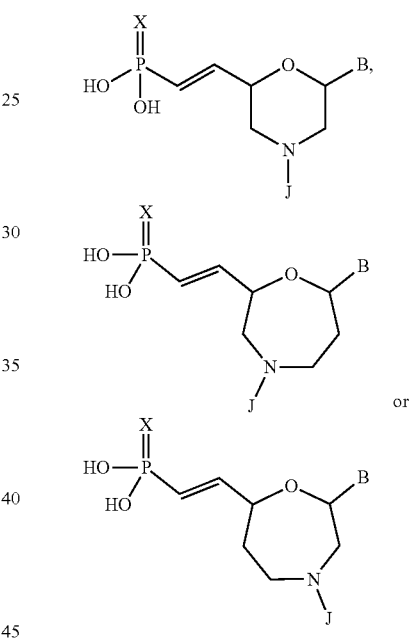

In some embodiments, peptide nucleic acid (PNA) does not contain sugar ring or phosphate linkage and the bases are attached and appropriately spaced by oligoglycine-like molecules, therefore, eliminating a backbone charge.

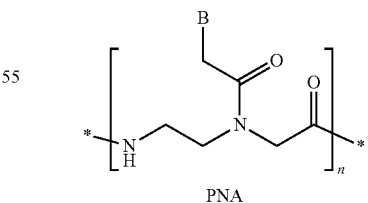

PNA

In some embodiments, one or more modifications of the 5'-vinylphosphonate modified oligonucleotide optionally occur at the internucleotide linkage. In some instances, modified internucleotide linkage includes, but is not limited to, phosphorothioates; phosphorodithioates; methylphosphonates; 5'-alkylenephosphonates; 5'-methylphosphonate;

3'-alkylene phosphonates; borontrifluoridates; borano phosphate esters and selenophosphates of 3'-5'linkage or 2'-5'linkage; phosphotriesters; thionoalkylphosphotriesters; hydrogen phosphonate linkages; alkyl phosphonates; alkylphosphonothioates; arylphosphonothioates; phosphoroselenoates; phosphorodiselenoates; phosphinates; phosphoramidates; 3'-alkylphosphoramidates; aminoalkylphosphoramidates; thionophosphoramidates; phosphoropiperazidates; phosphoroanilothioates; phosphoroanilidates; ketones; sulfones; sulfonamides; carbonates; carbamates; methylenehydrazos; methylenedimethylhydrazos; formacetals; thioformacetals; oximes; methyleneiminos; methylenemethyliminos; thioamidates; linkages with riboacetyl groups; aminoethyl glycine; silyl or siloxane linkages; alkyl or cycloalkyl linkages with or without heteroatoms of, for example, 1 to 10 carbons that are saturated or unsaturated and/or substituted and/or contain heteroatoms; linkages with morpholino structures, amides, or polyamides wherein the bases are attached to the aza nitrogens of the backbone directly or indirectly; and combinations thereof.

In some instances, the modification is a methyl or thiol modification such as methylphosphonate or thiolphosphonate modification. Exemplary thiolphosphonate nucleotide (left), phosphorodithioates (center) and methylphosphonate nucleotide (right) are illustrated below.

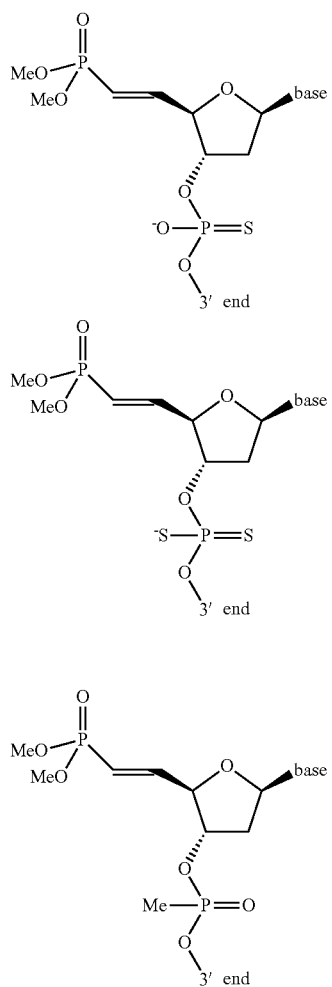

In some instances, a 5'-vinylphosphonate modified nucleotide includes, but is not limited to, phosphoramidites illustrated as:

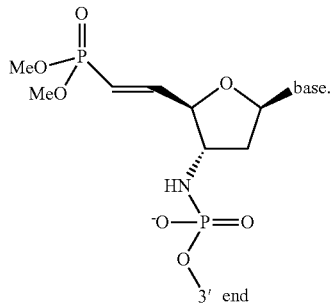

In some instances, the modified internucleotide linkage is a phosphorodiamidate linkage. A non-limiting example of a phosphorodiamidate linkage with a morpholino system is shown below.

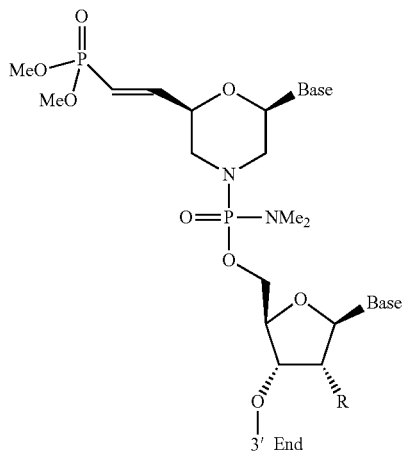

In some instances, the modified internucleotide linkage is a methylphosphonate linkage. A non-limiting example of a methylphosphonate linkage is shown below.

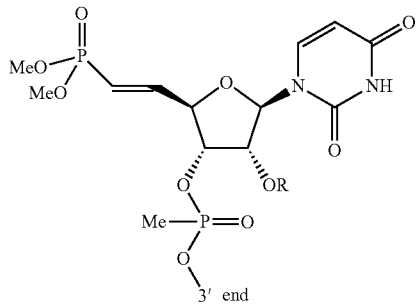

In some instances, the modified internucleotide linkage is a amide linkage. A non-limiting example of an amide linkage is shown below.

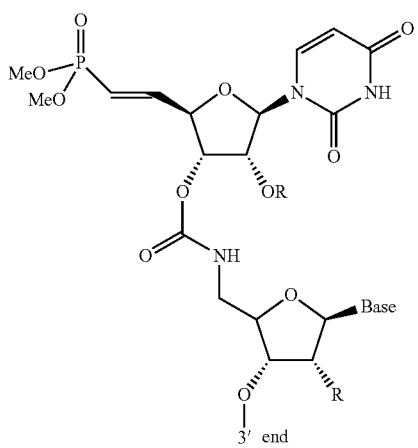

In some instances, a 5'-vinylphosphonate modified nucleotide includes, but is not limited to, the modified nucleic acid illustrated below.

In some embodiments, one or more modifications comprise a modified phosphate backbone in which the modification generates a neutral or uncharged backbone. In some instances, the phosphate backbone is modified by alkylation to generate an uncharged or neutral phosphate backbone. As used herein, alkylation includes methylation, ethylation, and propylation. In some cases, an alkyl group, as used herein in the context of alkylation, refers to a linear or branched saturated hydrocarbon group containing from 1 to 6 carbon atoms. In some instances, exemplary alkyl groups include, but are not limited to, methyl, ethyl, n-propyl, isopropyl, n-butyl, isobutyl, sec-butyl, tert-butyl, n-pentyl, isopentyl, neopentyl, hexyl, isohexyl, 1, 1-dimethylbutyl, 2,2-dimethylbutyl, 3.3-dimethylbutyl, and 2-ethylbutyl groups. In some cases, a modified phosphate is a phosphate group as described in U.S. Pat. No. 9,481,905.

In some embodiments, additional modified phosphate backbones comprise methylphosphonate, ethylphosphonate, methylthiophosphonate, or methoxyphosphonate. In some cases, the modified phosphate is methylphosphonate. In some cases, the modified phosphate is ethylphosphonate. In some cases, the modified phosphate is methylthiophosphonate. In some cases, the modified phosphate is methoxyphosphonate.

In some embodiments, one or more modifications further optionally include modifications of the ribose moiety, phosphate backbone and the nucleoside, or modifications of the nucleotide analogues at the 3' or the 5' terminus. For example, the 3' terminus optionally include a 3' cationic group, or by inverting the nucleoside at the 3'-terminus with a 3'-3' linkage. In another alternative, the 3'-terminus is optionally conjugated with an aminoalkyl group, e.g., a 3' C5-aminoalkyl dT. In an additional alternative, the 3'-terminus is optionally conjugated with an abasic site, e.g., with an apurinic or apyrimidinic site. In some instances, the 5'-terminus is conjugated with an aminoalkyl group, e.g., a 5'-O-alkylamino substituent. In some cases, the 5'-terminus is conjugated with an abasic site, e.g., with an apurinic or apyrimidinic site.

In some embodiments, the polynucleic acid molecule comprises one or more of the artificial nucleotide analogues described herein. In some instances, the polynucleic acid molecule comprises 1, 2, 3, 4, 5, 6, 7, 8, 9, 10, 11, 12, 13, 14, 15, 16, 17, 18, 20, 25, or more of the artificial nucleotide analogues described herein. In some embodiments, the artificial nucleotide analogues include 2'-O-methyl, 2'-O-methoxyethyl(2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or a combination thereof. In some instances, the polynucleic acid molecule comprises 1, 2, 3, 4, 5, 6, 7, 8, 9, 10, 11, 12, 13, 14, 15, 16, 17, 18, 20, 25, or more of the artificial nucleotide analogues selected from 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or a combination thereof. In some instances, the polynucleic acid molecule comprises 1, 2, 3, 4, 5, 6, 7, 8, 9, 10, 11, 12, 13, 14, 15, 16, 17, 18, 20, 25, or more of 2'-O-methyl modified nucleotides. In some instances, the polynucleic acid molecule comprises 1, 2, 3, 4, 5, 6, 7, 8, 9, 10, 11, 12, 13, 14, 15, 16, 17, 18, 20, 25, or more of 2'-O-methoxyethyl (2'-O-MOE) modified nucleotides. In some instances, the polynucleic acid molecule comprises 1, 2, 3, 4, 5, 6, 7, 8, 9, 10, 11, 12, 13, 14, 15, 16, 17, 18, 20, 25, or more of thiolphosphonate nucleotides.

In some embodiments, the polynucleic acid molecule comprises a plurality of phosphorodiamidate morpholino oligomers or a plurality of peptide nucleic acid-modified non-natural nucleotides, and optionally comprises at least one inverted abasic moiety. In some instances, the polynucleic acid molecule comprises at least 6, 7, 8, 9, 10, 11, 12, 13, 14, 15, 16, 17, 18, 19, 20, or more phosphorodiamidate morpholino oligomer-modified non-natural nucleotides. In some instances, the polynucleic acid molecule comprises 100% phosphorodiamidate morpholino oligomer-modified non-natural nucleotides.

In some instances, the polynucleic acid molecule comprises at least 6, 7, 8, 9, 10, 11, 12, 13, 14, 15, 16, 17, 18, 19, 20, or more peptide nucleic acid-modified non-natural nucleotides. In some instances, the polynucleic acid molecule comprises 100% peptide nucleic acid-modified non-natural nucleotides.

In some embodiments, the polynucleic acid molecule comprises one or more nucleotide analogs in which each nucleotide analog is in a stereochemically isomeric form. In such instance, the polynucleic acid molecule is a chiral molecule. In some cases, the nucleotide analog comprises a backbone stereochemistry. In additional cases, the nucleotide analog comprises a chiral analog as described in U.S. Pat. Nos. 9,982,257, 9,695,211, or 9,605,019.

In some instances, the polynucleic acid molecule comprises at least one of: from about 5% to about 100% modification, from about 10% to about 100% modification, from about 20% to about 100% modification, from about 30% to about 100% modification, from about 40% to about 100% modification, from about 50% to about 100% modification, from about 60% to about 100% modification, from about 70% to about 100% modification, from about 80% to about 100% modification, and from about 90% to about 100% modification.

In some cases, the polynucleic acid molecule comprises at least one of: from about 10% to about 90% modification, from about 20% to about 90% modification, from about 30% to about 90% modification, from about 40% to about 90% modification, from about 50% to about 90% modification, from about 60% to about 90% modification, from about 70% to about 90% modification, and from about 80% to about 100% modification.

In some cases, the polynucleic acid molecule comprises at least one of: from about 10% to about 80% modification, from about 20% to about 80% modification, from about 30% to about 80% modification, from about 40% to about 80% modification, from about 50% to about 80% modification, from about 60% to about 80% modification, and from about 70% to about 80% modification.

In some instances, the polynucleic acid molecule comprises at least one of: from about 10% to about 70% modification, from about 20% to about 70% modification, from about 30% to about 70% modification, from about 40% to about 70% modification, from about 50% to about 70% modification, and from about 60% to about 70% modification.

In some instances, the polynucleic acid molecule comprises at least one of: from about 10% to about 60% modification, from about 20% to about 60% modification, from about 30% to about 60% modification, from about 40% to about 60% modification, and from about 50% to about 60% modification.

In some cases, the polynucleic acid molecule comprises at least one of: from about 10% to about 50% modification, from about 20% to about 50% modification, from about 30% to about 50% modification, and from about 40% to about 50% modification.

In some cases, the polynucleic acid molecule comprises at least one of: from about 10% to about 40% modification, from about 20% to about 40% modification, and from about 30% to about 40% modification.

In some cases, the polynucleic acid molecule comprises at least one of: from about 10% to about 30% modification, and from about 20% to about 30% modification.

In some cases, the polynucleic acid molecule comprises from about 10% to about 20% modification.

In some cases, the polynucleic acid molecule comprises from about 15% to about 90%, from about 20% to about 80%, from about 30% to about 70%, or from about 40% to about 60% modifications.

In additional cases, the polynucleic acid molecule comprises at least about 15%, 20%, 30%, 40%, 50%, 60%, 70%, 80%, 90%, 95%, or 99% modification.

In some embodiments, the polynucleic acid molecule comprises at least about 1, about 2, about 3, about 4, about 5, about 6, about 7, about 8, about 9, about 10, about 11, about 12, about 13, about 14, about 15, about 16, about 17, about 18, about 19, about 20, about 21, about 22 or more modifications.

In some instances, the polynucleic acid molecule comprises at least about 1, about 2, about 3, about 4, about 5, about 6, about 7, about 8, about 9, about 10, about 11, about 12, about 13, about 14, about 15, about 16, about 17, about 18, about 19, about 20, about 21, about 22 or more modified nucleotides.

In some instances, from about 5 to about 100% of the polynucleic acid molecule comprise the artificial nucleotide analogues described herein. In some instances, about 5%, 10%, 15%, 20%, 25%, 30%, 35%, 40%, 45%, 50%, 55%, 60%, 65%, 70%, 75%, 80%, 85%, 90%, 95% or 100% of the polynucleic acid molecule comprise the artificial nucleotide analogues described herein. In some instances, about 5% of a polynucleic acid molecule comprises the artificial nucleotide analogues described herein. In some instances, about 10% of a polynucleic acid molecule comprises the artificial nucleotide analogues described herein. In some instances, about 15% of a polynucleic acid molecule comprises the artificial nucleotide analogues described herein. In some instances, about 20% of a polynucleic acid molecule comprises the artificial nucleotide analogues described herein. In some instances, about 25% of a polynucleic acid molecule comprises the artificial nucleotide analogues described herein. In some instances, about 30% of a polynucleic acid molecule comprises the artificial nucleotide analogues described herein. In some instances, about 35% of a polynucleic acid molecule comprises the artificial nucleotide analogues described herein. In some instances, about 40% of a polynucleic acid molecule comprises the artificial nucleotide analogues described herein. In some instances, about 45% of a polynucleic acid molecule comprises the artificial nucleotide analogues described herein. In some instances, about 50% of a polynucleic acid molecule comprises the artificial nucleotide analogues described herein. In some instances, about 55% of a polynucleic acid molecule comprises the artificial nucleotide analogues described herein. In some instances, about 60% of a polynucleic acid molecule comprises the artificial nucleotide analogues described herein. In some instances, about 65% of a polynucleic acid molecule comprises the artificial nucleotide analogues described herein. In some instances, about 70% of a polynucleic acid molecule comprises the artificial nucleotide analogues described herein. In some instances, about 75% of a polynucleic acid molecule comprises the artificial nucleotide analogues described herein. In some instances, about 80% of a polynucleic acid molecule comprises the artificial nucleotide analogues described herein. In some instances, about 85% of a polynucleic acid molecule comprises the artificial nucleotide analogues described herein. In some instances, about 90% of a polynucleic acid molecule comprises the artificial nucleotide analogues described herein. In some instances, about 95% of a polynucleic acid molecule comprises the artificial nucleotide analogues described herein. In some instances, about 96% of a polynucleic acid molecule comprises the artificial nucleotide analogues described herein. In some instances, about 97% of a polynucleic acid molecule comprises the artificial nucleotide analogues described herein. In some instances, about 98% of a polynucleic acid molecule comprises the artificial nucleotide analogues described herein. In some instances, about 99% of a polynucleic acid molecule comprises the artificial nucleotide analogues described herein. In some instances, about 100% of a polynucleic acid molecule comprises the artificial nucleotide analogues described herein. In some embodiments, the artificial nucleotide analogues include 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or a combination thereof.

In some embodiments, the polynucleic acid molecule comprises from about 1 to about 25 modifications in which the modification comprises an artificial nucleotide analogues described herein. In some embodiments, a polynucleic acid molecule comprises about 1 modification in which the modification comprises an artificial nucleotide analogue described herein. In some embodiments, a polynucleic acid molecule comprises about 2 modifications in which the modifications comprise an artificial nucleotide analogue described herein. In some embodiments, a polynucleic acid molecule comprises about 3 modifications in which the modifications comprise an artificial nucleotide analogue described herein. In some embodiments, a polynucleic acid molecule comprises about 4 modifications in which the modifications comprise an artificial nucleotide analogue described herein. In some embodiments, a polynucleic acid molecule comprises about 5 modifications in which the modifications comprise an artificial nucleotide analogue described herein. In some embodiments, a polynucleic acid molecule comprises about 6 modifications in which the modifications comprise an artificial nucleotide analogue described herein. In some embodiments, a polynucleic acid molecule comprises about 7 modifications in which the modifications comprise an artificial nucleotide analogue described herein. In some embodiments, a polynucleic acid molecule comprises about 8 modifications in which the modifications comprise an artificial nucleotide analogue described herein. In some embodiments, a polynucleic acid molecule comprises about 9 modifications in which the modifications comprise an artificial nucleotide analogue described herein. In some embodiments, a polynucleic acid molecule comprises about 10 modifications in which the modifications comprise an artificial nucleotide analogue described herein. In some embodiments, a polynucleic acid molecule comprises about 11 modifications in which the modifications comprise an artificial nucleotide analogue described herein. In some embodiments, a polynucleic acid molecule comprises about 12 modifications in which the modifications comprise an artificial nucleotide analogue described herein. In some embodiments, a polynucleic acid molecule comprises about 13 modifications in which the modifications comprise an artificial nucleotide analogue described herein. In some embodiments, a polynucleic acid molecule comprises about 14 modifications in which the modifications comprise an artificial nucleotide analogue described herein. In some embodiments, a polynucleic acid molecule comprises about 15 modifications in which the modifications comprise an artificial nucleotide analogue described herein. In some embodiments, a polynucleic acid molecule comprises about 16 modifications in which the modifications comprise an artificial nucleotide analogue described herein. In some embodiments, a polynucleic acid molecule comprises about 17 modifications in which the modifications comprise an artificial nucleotide analogue described herein. In some embodiments, a polynucleic acid molecule comprises about 18 modifications in which the modifications comprise an artificial nucleotide analogue described herein. In some embodiments, a polynucleic acid molecule comprises about 19 modifications in which the modifications comprise an artificial nucleotide analogue described herein. In some embodiments, a polynucleic acid molecule comprises about 20 modifications in which the modifications comprise an artificial nucleotide analogue described herein. In some embodiments, a polynucleic acid molecule comprises about 21 modifications in which the modifications comprise an artificial nucleotide analogue described herein. In some embodiments, a polynucleic acid molecule comprises about 22 modifications in which the modifications comprise an artificial nucleotide analogue described herein. In some embodiments, a polynucleic acid molecule comprises about 23 modifications in which the modifications comprise an artificial nucleotide analogue described herein. In some embodiments, a polynucleic acid molecule comprises about 24 modifications in which the modifications comprise an artificial nucleotide analogue described herein. In some embodiments, a polynucleic acid molecule comprises about 25 modifications in which the modifications comprise an artificial nucleotide analogue described herein.

In some embodiments, a polynucleic acid molecule is assembled from two separate polynucleotides wherein one polynucleotide comprises the sense strand and the second polynucleotide comprises the antisense strand of the polynucleic acid molecule. In other embodiments, the sense strand is connected to the antisense strand via a linker molecule, which in some instances is a polynucleotide linker or a non-nucleotide linker.

In some embodiments, a polynucleic acid molecule comprises a sense strand and antisense strand, wherein pyrimidine nucleotides in the sense strand comprises 2'-O-methylpyrimidine nucleotides and purine nucleotides in the sense strand comprise 2'-deoxy purine nucleotides. In some embodiments, a polynucleic acid molecule comprises a sense strand and antisense strand, wherein pyrimidine nucleotides present in the sense strand comprise 2'-deoxy-2'-fluoro pyrimidine nucleotides and wherein purine nucleotides present in the sense strand comprise 2'-deoxy purine nucleotides.

In some embodiments, a polynucleic acid molecule comprises a sense strand and antisense strand, wherein the pyrimidine nucleotides when present in said antisense strand are 2'-deoxy-2'-fluoro pyrimidine nucleotides and the purine nucleotides when present in said antisense strand are 2'-O-methyl purine nucleotides.

In some embodiments, a polynucleic acid molecule comprises a sense strand and antisense strand, wherein the pyrimidine nucleotides when present in said antisense strand are 2'-deoxy-2'-fluoro pyrimidine nucleotides and wherein the purine nucleotides when present in said antisense strand comprise 2'-deoxy-purine nucleotides.

In some embodiments, a polynucleic acid molecule comprises a sense strand and antisense strand, wherein the sense strand includes a terminal cap moiety at the 5'-end, the 3'-end, or both of the 5' and 3' ends of the sense strand. In other embodiments, the terminal cap moiety is an inverted deoxy abasic moiety.

In some embodiments, a polynucleic acid molecule comprises a sense strand and an antisense strand, wherein the antisense strand comprises a phosphate backbone modification at the 3' end of the antisense strand. In some instances, the phosphate backbone modification is a phosphorothioate. In some cases, the passenger strand comprises more phosphorothioate modifications than the guide strand. In other cases, the guide strand comprises more phosphorothioate modifications than the passenger strand. In additional cases, the passenger strand comprises about 2, 3, 4, 5, 6, 7, 8, 9, 10, or more phosphorothioate modifications. In additional cases, the guide strand comprises about 2, 3, 4, 5, 6, 7, 8, 9, 10, or more phosphorothioate modifications.

In some embodiments, a polynucleic acid molecule comprises a sense strand and an antisense strand, wherein the antisense strand comprises a glyceryl modification at the 3' end of the antisense strand.

In some embodiments, a polynucleic acid molecule comprises a sense strand and an antisense strand, in which the sense strand comprises one or more, for example, about 1, 2, 3, 4, 5, 6, 7, 8, 9, 10, 11, 12, 13, 14, 15, 16, 17, 18, 19, 20, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or about one or more (e.g., about 1, 2, 3, 4, 5, 6, 7, 8, 9, 10 or more)

universal base modified nucleotides, and optionally a terminal cap molecule at the 3'-end, the 5'-end, or both of the 3'- and 5'-ends of the sense strand; and in which the antisense strand comprises about 1 to about 10 or more, specifically about 1, 2, 3, 4, 5, 6, 7, 8, 9, 10, 11, 12, 13, 14, 15, 16, 17, 18, 19, 20, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In other embodiments, one or more, for example about 1, 2, 3, 4, 5, 6, 7, 8, 9, 10, or more, pyrimidine nucleotides of the sense and/or antisense strand are chemically-modified with 2'-deoxy, 2'-O-methyl and/or 2'-deoxy-2'-fluoro nucleotides, with or without one or more, for example about 1, 2, 3, 4, 5, 6, 7, 8, 9, 10, or more, phosphorothioate internucleotide linkages and/or a terminal cap molecule at the 3'-end, the 5'-end, or both of the 3'- and 5'-ends, being present in the same or different strand.

In some embodiments, a polynucleic acid molecule comprises a sense strand and an antisense strand, in which the sense strand comprises about 1 to about 25, for example, about 1, 2, 3, 4, 5, 6, 7, 8, 9, 10, 11, 12, 13, 14, 15, 16, 17, 18, 19, 20, or more phosphorothioate internucleotide linkages, and/or one or more (e.g., about 1, 2, 3, 4, 5, 6, 7, 8, 9, 10, or more) 2'-deoxy, 2'-O-methyl, 2'-deoxy-2'-fluoro, and/or one or more (e.g., about 1, 2, 3, 4, 5, 6, 7, 8, 9, 10, or more) universal base modified nucleotides, and optionally a terminal cap molecule at the 3-end, the 5'-end, or both of the 3'- and 5'-ends of the sense strand; and in which the antisense strand comprises about 1 to about 25 or more, for example about 1, 2, 3, 4, 5, 6, 7, 8, 9, 10, 11, 12, 13, 14, 15, 16, 17, 18, 19, 20, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In other embodiments, one or more, for example about 1, 2, 3, 4, 5, 6, 7, 8, 9, 10, or more, pyrimidine nucleotides of the sense and/or antisense strand are chemically-modified with 2'-deoxy, 2'-O-methyl and/or 2'-deoxy-2'-fluoro nucleotides, with or without about 1 to about 25 or more, for example about 1, 2, 3, 4, 5, 6, 7, 8, 9, 10, 11, 12, 13, 14, 15, 16, 17, 18, 19, 20, or more phosphorothioate internucleotide linkages and/or a terminal cap molecule at the 3'-end, the 5'-end, or both of the 3'- and 5'-ends, being present in the same or different strand.

In some embodiments, a polynucleic acid molecule comprises a sense strand and an antisense strand, in which the antisense strand comprises one or more, for example, about 1, 2, 3, 4, 5, 6, 7, 8, 9, 10, 11, 12, 13, 14, 15, 16, 17, 18, 19, 20, or more phosphorothioate internucleotide linkages, and/or about one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the sense strand; and wherein the antisense strand comprises about 1 to about 10 or more, specifically about 1, 2, 3, 4, 5, 6, 7, 8, 9, 10 or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In other embodiments, one or more, for example about 1, 2, 3, 4, 5, 6, 7, 8, 9, 10, 11, 12, 13, 14, 15, 16, 17, 18, 19, 20, or more pyrimidine nucleotides of the sense and/or antisense strand are chemically-modified with 2'-deoxy, 2'-O-methyl and/or 2'-deoxy-2'-fluoro nucleotides, with or without one or more, for example, about 1, 2, 3, 4, 5, 6, 7, 8, 9, 10 or more phosphorothioate internucleotide linkages and/or a terminal cap molecule at the 3'-end, the 5'-end, or both of the 3' and 5'-ends, being present in the same or different strand.

In some embodiments, a polynucleic acid molecule comprises a sense strand and an antisense strand, in which the antisense strand comprises about 1 to about 25 or more, for example, about 1, 2, 3, 4, 5, 6, 7, 8, 9, 10, 11, 12, 13, 14, 15, 16, 17, 18, 19, 20, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the sense strand; and wherein the antisense strand comprises about 1 to about 25 or more, for example about 1, 2, 3, 4, 5, 6, 7, 8, 9, 10, 11, 12, 13, 14, 15, 16, 17, 18, 19, 20, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In other embodiments, one or more, for example about 1, 2, 3, 4, 5, 6, 7, 8, 9, 10 or more pyrimidine nucleotides of the sense and/or antisense strand are chemically-modified with 2'-deoxy, 2'-O-methyl and/or 2'-deoxy-2'-fluoro nucleotides, with or without about 1 to about 5, for example about 1, 2, 3, 4, 5 or more phosphorothioate internucleotide linkages and/or a terminal cap molecule at the 3'-end, the 5'-end, or both of the 3'- and 5'-ends, being present in the same or different strand.

In some embodiments, a polynucleic acid molecule is a duplex polynucleic acid molecule with one or more of the following properties: a greater hepatocyte stability, reduced overall charge, reduced hepatocyte uptake, or extended pharmacokinetics. In some embodiments, the duplex polynucleic acid molecule comprises a passenger strand (e.g., a sense strand) and a guide strand (e.g., an antisense strand) comprising a plurality of modifications.

In some embodiments, the duplex polynucleic acid molecule comprises a guide strand (e.g., an antisense strand) with one or more of the modification described above, and a passenger strand (e.g., a sense strand) with a plurality of phosphorodiamidate morpholino oligomers or a plurality of peptide nucleic acid-modified non-natural nucleotides.

In some embodiments, a polynucleic acid molecule described herein is a chemically-modified short interfering nucleic acid molecule having about 1 to about 25, for example, about 1, 2, 3, 4, 5, 6, 7, 8, 9, 10, 11, 12, 13, 14, 15, 16, 17, 18, 19, 20 or more phosphorothioate internucleotide linkages in each strand of the polynucleic acid molecule.

In another embodiment, a polynucleic acid molecule described herein comprises 2'-5' internucleotide linkages. In some instances, the 2'-5' internucleotide linkage(s) is at the 3'-end, the 5'-end, or both of the 3'- and 5'-ends of one or both sequence strands. In addition instances, the 2'-5' internucleotide linkage(s) is present at various other positions within one or both sequence strands, for example, about 1, 2, 3, 4, 5, 6, 7, 8, 9, 10, or more including every internucleotide linkage of a pyrimidine nucleotide in one or both strands of the polynucleic acid molecule comprise a 2'-5' internucleotide linkage, or about 1, 2, 3, 4, 5, 6, 7, 8, 9, 10, or more including every internucleotide linkage of a purine nucleotide in one or both strands of the polynucleic acid molecule comprise a 2'-5' internucleotide linkage.

In some cases, the polynucleic acid molecule is a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. In other cases, the polynucleic acid molecule is a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide is processed either in vivo or in vitro to generate an active polynucleic acid molecule capable of mediating RNAi. In additional cases, the polynucleic acid molecule also comprises a single stranded polynucleotide having nucleotide sequence complementary to nucleotide sequence in a target nucleic acid molecule or a portion thereof (for example, where such polynucleic acid molecule does not require the presence within the polynucleic acid molecule of nucleotide sequence corresponding to the target nucleic acid sequence or a portion thereof), wherein the single stranded polynucleotide further comprises a terminal phosphate group, such as a 5'-phosphate (see for example Martinez et al., 2002, *Cell.*, 110, 563-574 and Schwarz et al., 2002, *Molecular Cell*, 10, 537-568), or 5',3'-diphosphate.

In some embodiments, a polynucleic acid molecule is a single stranded polynucleic acid molecule that mediates RNAi activity in a cell or reconstituted in vitro system, wherein the polynucleic acid molecule comprises a single stranded polynucleotide having complementarity to a target nucleic acid sequence, and wherein one or more pyrimidine nucleotides present in the polynucleic acid are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any purine nucleotides present in the polynucleic acid are 2'-deoxy purine nucleotides (e.g., wherein all purine nucleotides are 2'-deoxy purine nucleotides or alternately a plurality of purine nucleotides are 2'-deoxy purine nucleotides), and a terminal cap modification, that is optionally present at the 3'-end, the 5'-end, or both of the 3' and 5'-ends of the antisense sequence, the polynucleic acid molecule optionally further comprising about 1 to about 4 (e.g., about 1, 2, 3, or 4) terminal 2'-deoxynucleotides at the 3'-end of the polynucleic acid molecule, wherein the terminal nucleotides further comprise one or more (e.g., 1, 2, 3, or 4) phosphorothioate internucleotide linkages, and wherein the polynucleic acid molecule optionally further comprises a terminal phosphate group, such as a 5'-terminal phosphate group.

In some instances, an asymmetric duplex is a linear polynucleic acid molecule comprising an antisense region, a loop portion that comprises nucleotides or non-nucleotides, and a sense region that comprises fewer nucleotides than the antisense region to the extent that the sense region has enough complimentary nucleotides to base pair with the antisense region and form a duplex with loop. For example, an asymmetric hairpin polynucleic acid molecule comprises an antisense region having length sufficient to mediate RNAi in a cell or in vitro system (e.g. about 19 to about 22 nucleotides) and a loop region comprising about 4 to about 8 nucleotides, and a sense region having about 3 to about 18 nucleotides that are complementary to the antisense region. In some cases, the asymmetric hairpin polynucleic acid molecule also comprises a 5'-terminal phosphate group that is chemically modified. In additional cases, the loop portion of the asymmetric hairpin polynucleic acid molecule comprises nucleotides, non-nucleotides, linker molecules, or conjugate molecules.

In some embodiments, an asymmetric duplex is a polynucleic acid molecule having two separate strands comprising a sense region and an antisense region, wherein the sense region comprises fewer nucleotides than the antisense region to the extent that the sense region has enough complimentary nucleotides to base pair with the antisense region and form a duplex. For example, an asymmetric duplex polynucleic acid molecule comprises an antisense region having length sufficient to mediate RNAi in a cell or in vitro system (e.g. about 19 to about 22 nucleotides) and a sense region having about 3 to about 18 nucleotides that are complementary to the antisense region.

In some cases, one or more of the artificial nucleotide analogues described herein are resistant toward nucleases such as for example ribonuclease such as RNase H, deoxyribunuclease such as DNase, or exonuclease such as 5'-3' exonuclease and 3'-5' exonuclease when compared to natural polynucleic acid molecules. In some instances, artificial nucleotide analogues comprising 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or combinations thereof are resistant toward nucleases such as for example ribonuclease such as RNase H, deoxyribunuclease such as DNase, or exonuclease such as 5'-3' exonuclease and 3'-5' exonuclease. In some instances, 2'-O-methyl modified polynucleic acid molecule is nuclease resistance (e.g., RNase H, DNase, 5'-3' exonuclease or 3'-5' exonuclease resistance). In some instances, 2'O-methoxyethyl (2'-O-MOE) modified polynucleic acid molecule is nuclease resistance (e.g., RNase H, DNase, 5'-3' exonuclease or 3'-5' exonuclease resistance). In some instances, 2'-O-aminopropyl modified polynucleic acid molecule is nuclease resistance (e.g., RNase H, DNase, 5'-3' exonuclease or 3'-5' exonuclease resistance). In some instances, 2'-deoxy modified polynucleic acid molecule is nuclease resistance (e.g., RNase H, DNase, 5'-3' exonuclease or 3'-5' exonuclease resistance). In some instances, 2'-deoxy-2'-fluoro modified polynucleic acid molecule is nuclease resistance (e.g., RNase H, DNase, 5'-3' exonuclease or 3'-5' exonuclease resistance). In some instances, 2'-O-aminopropyl (2'-O-AP) modified polynucleic acid molecule is nuclease resistance (e.g., RNase H, DNase, 5'-3' exonuclease or 3'-5' exonuclease resistance). In some instances, 2'-O-dimethylaminoethyl (2'-O-DMAOE) modified polynucleic acid molecule is nuclease resistance (e.g., RNase H, DNase, 5'-3' exonuclease or 3'-5' exonuclease resistance). In some instances, 2'-O-dimethylaminopropyl (2'-O-DMAP) modified polynucleic acid molecule is nuclease resistance (e.g., RNase H, DNase, 5'-3' exonuclease or 3'-5' exonuclease resistance). In some instances, 2'-O-dimethylaminoethyloxyethyl (2'-O-DMAEOE) modified polynucleic acid molecule is nuclease resistance (e.g., RNase H, DNase, 5'-3' exonuclease or 3'-5' exonuclease resistance). In some instances, 2'-O—N-methylacetamido (2'-O-NMA) modified polynucleic acid molecule is nuclease resistance (e.g., RNase H, DNase, 5'-3' exonuclease or 3'-5' exonuclease resistance). In some instances, LNA modified polynucleic acid molecule is nuclease resistance (e.g., RNase H, DNase, 5'-3' exonuclease or 3'-5' exonuclease resistance). In some instances, ENA modified polynucleic acid molecule is nuclease resistance (e.g., RNase H, DNase, 5'-3' exonuclease or 3'-5' exonuclease resistance). In some instances, HNA modified polynucleic acid molecule is nuclease resistance (e.g., RNase H, DNase, 5'-3' exonuclease or 3'-5' exonuclease resistance). In some instances, morpholinos is nuclease resistance (e.g., RNase H, DNase, 5'-3' exonuclease or 3'-5' exonuclease resistance). In some instances, PNA modified polynucleic acid molecule is resistant to nucleases (e.g., RNase H, DNase, 5'-3' exonuclease or 3'-5' exonuclease resistance). In some instances, methylphosphonate nucleotides modified polynucleic acid molecule is nuclease resistance (e.g., RNase H, DNase, 5'-3' exonuclease or 3'-5' exonuclease resistance). In some instances, thiolphosphonate nucleotides modified polynucleic acid molecule is nuclease resistance (e.g., RNase H, DNase, 5'-3' exonuclease or 3'-5' exonuclease resistance). In some instances, polynucleic acid molecule comprising 2'-fluoro N3-P5'-phosphoramidites is nuclease resistance (e.g., RNase H, DNase, 5'-3' exonuclease or 3'-5' exonuclease resistance). In some instances, the 5' conjugates described herein inhibit 5'-3' exonucleolytic cleavage. In some instances, the 3' conjugates described herein inhibit 3'-5" exonucleolytic cleavage.

In some embodiments, one or more of the artificial nucleotide analogues described herein have increased binding affinity toward their mRNA target relative to an equivalent natural polynucleic acid molecule. The one or more of the artificial nucleotide analogues comprising 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, or 2'-fluoro N3-P5'-phosphoramidites have increased binding affinity toward their mRNA target relative to an equivalent natural polynucleic acid molecule. In some instances, 2'-O-methyl modified polynucleic acid molecule has increased binding affinity toward their mRNA target relative to an equivalent natural polynucleic acid molecule. In some instances, 2'-O-methoxyethyl (2'-O-MOE) modified polynucleic acid molecule has increased binding affinity toward their mRNA target relative to an equivalent natural polynucleic acid molecule. In some instances, 2'-O-aminopropyl modified polynucleic acid molecule has increased binding affinity toward their mRNA target relative to an equivalent natural polynucleic acid molecule. In some instances, 2'-deoxy modified polynucleic acid molecule has increased binding affinity toward their mRNA target relative to an equivalent natural polynucleic acid molecule. In some instances, 2'deoxy-2'-fluoro modified polynucleic acid molecule has increased binding affinity toward their mRNA target relative to an equivalent natural polynucleic acid molecule. In some instances, 2'-O-aminopropyl (2'-O-AP) modified polynucleic acid molecule has increased binding affinity toward their mRNA target relative to an equivalent natural polynucleic acid molecule. In some instances, 2'-O-dimethylaminoethyl (2'-O-DMAOE) modified polynucleic acid molecule has increased binding affinity toward their mRNA target relative to an equivalent natural polynucleic acid molecule. In some instances, 2'-O-dimethylaminopropyl (2'-O-DMAP) modified polynucleic acid molecule has increased binding affinity toward their mRNA target relative to an equivalent natural polynucleic acid molecule. In some instances, 2'-O-dimethylaminoethyloxyethyl (2'-O-DMAEOE) modified polynucleic acid molecule has increased binding affinity toward their mRNA target relative to an equivalent natural polynucleic acid molecule. In some instances, 2'-O—N-methylacetamido (2'-O-NMA) modified polynucleic acid molecule has increased binding affinity toward their mRNA target relative to an equivalent natural polynucleic acid molecule. In some instances, LNA modified polynucleic acid molecule has increased binding affinity toward their mRNA target relative to an equivalent natural polynucleic acid molecule. In some instances, ENA modified polynucleic acid molecule has increased binding affinity toward their mRNA target relative to an equivalent natural polynucleic acid molecule. In some instances, PNA modified polynucleic acid molecule has increased binding affinity toward their mRNA target relative to an equivalent natural polynucleic acid molecule. In some instances, HNA modified polynucleic acid molecule has increased binding affinity toward their mRNA target relative to an equivalent natural polynucleic acid molecule. In some instances, morpholino modified polynucleic acid molecule has increased binding affinity toward their mRNA target relative to an equivalent natural polynucleic acid molecule. In some instances, methylphosphonate nucleotides modified polynucleic acid molecule has increased binding affinity toward their mRNA target relative to an equivalent natural polynucleic acid molecule. In some instances, thiolphosphonate nucleotides modified polynucleic acid molecule has increased binding affinity toward their mRNA target relative to an equivalent natural polynucleic acid molecule. In some instances, polynucleic acid molecule comprising 2'-fluoro N3-P5'-phosphoramidites has increased binding affinity toward their mRNA target relative to an equivalent natural polynucleic acid molecule. In some cases, the increased affinity is illustrated with a lower Kd, a higher melt temperature (Tm), or a combination thereof.

In some embodiments, a polynucleic acid molecule described herein is a chirally pure (or stereo pure) polynucleic acid molecule, or a polynucleic acid molecule comprising a single enantiomer. In some instances, the polynucleic acid molecule comprises L-nucleotide. In some instances, the polynucleic acid molecule comprises D-nucleotides. In some instance, a polynucleic acid molecule composition comprises less than 30%, 25%, 20%, 15%, 10%, 5%, 4%, 3%, 2%, 1%, or less of its mirror enantiomer. In some cases, a polynucleic acid molecule composition comprises less than 30%, 25%, 20%, 15%, 10%, 5%, 4%, 3%, 2%, 1%, or less of a racemic mixture. In some instances, the polynucleic acid molecule is a polynucleic acid molecule described in: U.S. Patent Publication Nos: 2014/194610 and 2015/211006; and PCT Publication No.: WO2015107425.

In some embodiments, a polynucleic acid molecule described herein is further modified to include an aptamer conjugating moiety. In some instances, the aptamer conjugating moiety is a DNA aptamer conjugating moiety. In some instances, the aptamer conjugating moiety is Alphamer (Centauri Therapeutics), which comprises an aptamer portion that recognizes a specific cell-surface target and a portion that presents a specific epitopes for attaching to circulating antibodies. In some instance, a polynucleic acid molecule described herein is further modified to include an aptamer conjugating moiety as described in: U.S. Pat. Nos. 8,604,184, 8,591,910, and 7,850,975.

In additional embodiments, a polynucleic acid molecule described herein is modified to increase its stability. In some embodiment, the polynucleic acid molecule is RNA (e.g., siRNA). In some instances, the polynucleic acid molecule is modified by one or more of the modifications described above to increase its stability. In some cases, the polynucleic acid molecule is modified at the 2' hydroxyl position, such as by 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-0-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modification or by a locked or bridged ribose conformation (e.g., LNA or ENA). In some cases, the polynucleic acid molecule is modified by 2'-O-methyl and/or 2'-O-methoxyethyl ribose. In some cases, the polynucleic acid molecule also includes morpholinos, PNAs, HNA, methylphosphonate nucleotides, thiolphosphonate nucleotides, and/or 2'-fluoro N3-P5'-phosphoramidites to increase its stability. In some instances, the polynucleic acid molecule is a chirally pure (or stereo pure) polynucleic acid molecule. In some instances, the chirally pure (or stereo pure) polynucleic acid molecule is modified to increase its stability. Suitable modifications to the RNA to increase stability for delivery will be apparent to the skilled person.

In some cases, a universal base refers to nucleotide base analogs that form base pairs with each of the natural DNA/RNA bases with little discrimination between them. Non-limiting examples of universal bases include C-phenyl, C-naphthyl and other aromatic derivatives, inosine, azole carboxamides, and nitroazole derivatives such as 3-nitropyrrole, 4-nitroindole, 5-nitroindole, and 6-nitroindole as known in the art (see for example Loakes, 2001, *Nucleic Acids Research*, 29, 2437-2447).

Small Molecules, Proteins, and Peptides

In some embodiment, the payload is a small molecule. In some instances, the small molecule is a cytotoxic payload. Exemplary cytotoxic payloads include, but are not limited to, microtubule disrupting agents, DNA modifying agents, or Akt inhibitors.

In some embodiments, the payload comprises a microtubule disrupting agent. Exemplary microtubule disrupting agents include, but are not limited to, 2-methoxyestradiol, auristatin, chalcones, colchicine, combretastatin, cryptophycin, dictyostatin, discodermolide, dolastain, eleutherobin, epothilone, halichondrin, laulimalide, maytansine, noscapinoid, paclitaxel, peloruside, phomopsin, podophyllotoxin, rhizoxin, spongistatin, taxane, tubulysin, vinca alkaloid, vinorelbine, or derivatives or analogs thereof.

In some embodiments, the tubulysin is a tubulysin analog or derivative such as described in U.S. Pat. Nos. 8,580,820 and 8,980,833 and in U.S. Publication Nos. 20130217638, 20130224228, and 201400363454.

In some embodiments, the maytansine is a maytansinoid. In some embodiments, the maytansinoid is DM1, DM4, or ansamitocin. In some embodiments, the maytansinoid is DM1. In some embodiments, the maytansinoid is DM4. In some embodiments, the maytansinoid is ansamitocin. In some embodiments, the maytansinoid is a maytansinoid derivative or analog such as described in U.S. Pat. Nos. 5,208,020, 5,416,064, 7,276,497, and 6,716,821 or U.S. Publication Nos. 2013029900 and US20130323268.

In some embodiments, the payload is a dolastatin, or a derivative or analog thereof. In some embodiments, the dolastatin is dolastatin 10 or dolastatin 15, or derivatives or analogs thereof. In some embodiments, the dolastatin 10 analog is auristatin, soblidotin, symplostatin 1, or symplostatin 3. In some embodiments, the dolastatin 15 analog is cemadotin or tasidotin.

In some embodiments, the dolastatin 10 analog is auristatin or an auristatin derivative. In some embodiments, the auristatin or auristatin derivative is auristatin E (AE), auristatin F (AF), auristatin E5-benzoylvaleric acid ester (AEVB), monomethyl auristatin E (MMAE), monomethyl auristatin F (MMAF), or monomethyl auristatin D (MMAD), auristatin PE, or auristatin PYE. In some embodiments, the auristatin derivative is monomethyl auristatin E (MMAE). In some embodiments, the auristatin derivative is monomethyl auristatin F (MMAF). In some embodiments, the auristatin is an auristatin derivative or analog such as described in U.S. Pat. Nos. 6,884,869, 7,659,241, 7,498,298, 7,964,566, 7,750,116, 8,288,352, 8,703,714 and 8,871,720.

In some embodiments, the payload comprises a DNA modifying agent. In some embodiments, the DNA modifying agent comprises DNA cleavers, DNA intercalators, DNA transcription inhibitors, or DNA cross-linkers. In some instances, the DNA cleaver comprises bleomycine A2, calicheamicin, or derivatives or analogs thereof. In some instances, the DNA intercalator comprises doxorubicin, epirubicin, PNU-159682, duocarmycin, pyrrolobenzodiazepine, oligomycin C, daunorubicin, valrubicin, topotecan, or derivatives or analogs thereof. In some instances, the DNA transcription inhibitor comprises dactinomycin. In some instances, the DNA cross-linker comprises mitomycin C.

In some embodiments, the DNA modifying agent comprises amsacrine, anthracycline, camptothecin, doxorubicin, duocarmycin, enediyne, etoposide, indolinobenzodiazepine, netropsin, teniposide, or derivatives or analogs thereof.

In some embodiments, the anthracycline is doxorubicin, daunorubicin, epirubicin, idarubicin, mitomycin-C, dactinomycin, mithramycin, nemorubicin, pixantrone, sabarubicin, or valrubicin.

In some embodiments, the analog of camptothecin is topotecan, irinotecan, silatecan, cositecan, exatecan, lurtotecan, gimatecan, belotecan, rubitecan, or SN-38.

In some embodiments, the duocarmycin is duocarmycin A, duocarmycin B1, duocarmycin B2, duocarmycin C1, duocarmycin C2, duocarmycin D, duocarmycin SA, or CC-1065. In some embodiments, the enediyne is a calicheamicin, esperamicin, or dynemicin A.

In some embodiments, the pyrrolobenzodiazepine is anthramycin, abbeymycin, chicamycin, DC-81, mazethramycin, neothramycins A, neothramycin B, porothramycin, prothracarcin, sibanomicin (DC-102), sibiromycin, or tomaymycin. In some embodiments, the pyrrolobenzodiazepine is a tomaymycin derivative, such as described in U.S. Pat. Nos. 8,404,678 and 8,163,736. In some embodiments, the pyrrolobenzodiazepine is such as described in U.S. Pat. Nos. 8,426,402, 8,802,667, 8,809,320, 6,562,806, 6,608,192, 7,704,924, 7,067,511, 7,612,062, 7,244,724, 7,528,126, 7,049,311, 8,633,185, 8,501,934, and 8,697,688 and U.S. Publication No. US20140294868.

In some embodiments, the pyrrolobenzodiazepine is a pyrrolobenzodiazepine dimer. In some embodiments, the PBD dimer is a symmetric dimer. Examples of symmetric PBD dimers include, but are not limited to, SJG-136 (SG- 2000), ZC-423 (SG2285), SJG-720, SJG-738, ZC-207 (SG2202), and DSB-120 (Table 2). In some embodiments, the PBD dimer is an unsymmetrical dimer. Examples of unsymmetrical PBD dimers include, but are not limited to, SJG-136 derivatives such as described in U.S. Pat. Nos. 8,697,688 and 9,242,013 and U.S. Publication No. 20140286970.

In some embodiments, the payload comprises an Akt inhibitor. In some cases, the Akt inhibitor comprises ipatasertib (GDC-0068) or derivatives thereof.

In some embodiments, the payload comprises a polymerase inhibitor, including, but not limited to polymerase II inhibitors such as a-amanitin, and poly(ADP-ribose) polymerase (PARP) inhibitors. Exemplary PARP inhibitors include, but are not limited to Iniparib (BSI 201), Talazoparib (BMN-673), Olaparib (AZD-2281), Olaparib, Rucaparib (AG014699, PF-01367338), Veliparib (ABT-888), CEP 9722, MK 4827, BGB-290, or 3-aminobenzamide.

In some embodiments, the payload is an imaging agent. In some instances, the payload comprises a "radio-opaque" label, e.g. a label visualized using x-rays. Radio-opaque materials are well known to those of skill in the art. Exemplary radio-opaque materials include iodide, bromide or barium salts. Additional radiopaque materials include, but are not limited to, organic bismuth derivatives {see, e.g., U.S. Pat. No. 5,939,045), radio-opaque polyurethanes (see, e.g., U.S. Pat. No. 5,346,981), organobismuth composites (see, e.g., U.S. Pat. No. 5,256,334), radio-opaque barium polymer complexes (see, e.g., U.S. Pat. No. 4,866,132), and the like.

In some instances, the payload comprises a detectable label, for example, for use in immunoconjugates include any composition detectable by spectroscopic, photochemical, biochemical, immunochemical, electrical, optical or chemical means. Useful labels in the include magnetic beads (e.g., DYNABEADS™), fluorescent dyes (e.g., fluorescein isothiocyanate, texas red, rhodamine, green fluorescent protein, and the like), radiolabels (e.g., $^{3}$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads, nanoparticles, quantum dots, and the like.

In some embodiments, suitable radiolabels include, but are not limited to, $^{99}$Tc, $^{203}$Pb, $^{67}$Ga, $^{68}$Ga, $^{72}$As, $^{111}$In, $^{113m}$In, $^{97}$Ru, $^{62}$Cu, $^{64}$Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, and $^{111}$Ag.

In some instances, the payload comprises a radiosensitizer that enhances the cytotoxic effect of ionizing radiation (e.g., such as might be produced by $^{60}$Co or an x-ray source) on a cell. Numerous radiosensitizing agents are known and include, but are not limited to benzoporphyrin derivative compounds (see, e.g., U.S. Pat. No. 5,945,439), 1,2,4-benzotriazine oxides (see, e.g., U.S. Pat. No. 5,849,738), compounds containing certain diamines (see, e.g., U.S. Pat. No. 5,700,825), BCNT (see, e.g., U.S. Pat. No. 5,872,107), radiosensitizing nitrobenzoic acid amide derivatives (see, e.g., U.S. Pat. No. 4,474,814), various heterocyclic derivatives (see, e.g., U.S. Pat. No. 5,064,849), platinum complexes (see, e.g., U.S. Pat. No. 4,921,963), and the like.

In some instances, the payload comprises an alpha emitter, i.e. a radioactive isotope that emits alpha particles. Alpha-emitters have recently been shown to be effective in the treatment of cancer (see, e.g., McDevitt et al. (2001) Science 294: 1537-1540; Ballangrud et al. (2001) Cancer Res. 61: 2008-2014; Borchardt et al. (2003) Cancer Res. 63: 5084-50). Suitable alpha emitters include, but are not limited to $^{213}$Bi, $^{211}$At, and the like.

In some instances, the payload comprises an immunomodulatory agent. Useful immunomodulatory agents include anti-hormones that block hormone action on tumors and immunosuppressive agents that suppress cytokine production, down-regulate self-antigen expression, or mask MHC antigens. Representative anti-hormones include anti-estrogens including, for example, tamoxifen, raloxifene, aromatase inhibiting 4(5)-imidazoles, 4-hydroxytamoxifen, trioxifene, keoxifene, LY 117018, onapnstone, and toremifene; and anti-androgens such as flutamide, nilutamide, bicalutamide, leuprolide, and goserelin; and anti-adrenal agents. Illustrative immunosuppressive agents include, but are not limited to 2-amino-6-aryl-5-substituted pyrimidines, azathioprine, cyclophosphamide, bromocryptine, danazol, dapsone, glutaraldehyde, anti-idiotypic antibodies for MHC antigens and MHC fragments, cyclosporin A, steroids such as glucocorticosteroids, streptokinase, or rapamycin.

In some embodiments, the payload comprises a protein or peptide toxin or fragment thereof. Exemplary enzymatically active toxins and fragments thereof include, but are not limited to, diphtheria toxin A fragment, nonbinding active fragments of diphtheria toxin, exotoxin A (from *Pseudomonas aeruginosa*), ricin A chain, abrin A chain, modeccin A chain, a-sacrin, certain A leurites fordii proteins, certain Dianthin proteins, *Phytolacca americana* proteins (PAP, PAPII and PAP-S), Morodica charantia inhibitor, curcin, crotin, *Saponaria officinalis* inhibitor, gelonin, mitogillin, restrictocin, phenomycin, enomycin, and tricothecenes. In some instances, the payload is an immune modulator. Exemplary immune modulators include, but are not limited to, gancyclovier, etanercept, tacrolimus, sirolimus, voclosporin, cyclosporine, rapamycin, cyclophosphamide, azathioprine, mycophenolgate mofetil, methotrextrate, glucocorticoid and its analogs, xanthines, stem cell growth factors, lymphotoxins, hematopoietic factors, tumor necrosis factor (TNF) (e.g., TNFα), interleukins (e.g., interleukin-1 (IL-1), IL-2, IL-3, IL-6, IL-10, IL-12, IL-18, and IL-21), colony stimulating factors (e.g., granulocyte-colony stimulating factor (G-CSF) and granulocyte macrophage-colony stimulating factor (GM-CSF)), interferons (e.g., interferons-alpha, interferon-beta, interferon-gamma), the stem cell growth factor designated "Si factor," erythropoietin and thrombopoietin, or a combination thereof.

In some instances, the payload comprises a cytokine. In some embodiments, the cytokine comprises IL-2, IL-2, IL-3, IL-6, IL-10, IL-12, IL-18, IL-21, interferon (e.g., IFNα, IFNβ), or TNFα.

Polymers

In some embodiments, an anti-transferrin receptor antibody conjugate described herein further comprises a polymer (polymer moiety C). In some instances, the polymer is a natural or synthetic polymer, consisting of long chains of branched or unbranched monomers, and/or cross-linked network of monomers in two or three dimensions. In some instances, the polymer includes a polysaccharide, lignin, rubber, or polyalkylen oxide (e.g., polyethylene glycol). In some instances, the at least one polymer includes, but is not limited to, alpha-, omega-dihydroxylpolyethyleneglycol, biodegradable lactone-based polymer, e.g. polyacrylic acid, polylactide acid (PLA), poly(glycolic acid) (PGA), polypropylene, polystyrene, polyolefin, polyamide, polycyanoacrylate, polyimide, polyethylenterephthalat (PET, PETG), polyethylene terephthalate (PETE), polytetramethylene glycol (PTG), or polyurethane as well as mixtures thereof. As used herein, a mixture refers to the use of different polymers within the same compound as well as in reference to block copolymers. In some cases, block copolymers are polymers wherein at least one section of a polymer is build up from monomers of another polymer. In some instances, the polymer comprises polyalkylene oxide. In some instances, the polymer comprises PEG. In some instances, the polymer comprises polyethylene imide (PEI) or hydroxy ethyl starch (HES).

In some instances, C is a PEG moiety. In some instances, the PEG moiety is conjugated at the 5' terminus of the polynucleic acid molecule while the binding moiety is conjugated at the 3' terminus of the polynucleic acid molecule. In some instances, the PEG moiety is conjugated at the 3' terminus of the polynucleic acid molecule while the binding moiety is conjugated at the 5' terminus of the polynucleic acid molecule. In some instances, the PEG moiety is conjugated to an internal site of the polynucleic acid molecule. In some instances, the PEG moiety, the binding moiety, or a combination thereof, are conjugated to an internal site of the polynucleic acid molecule. In some instances, the conjugation is a direct conjugation. In some instances, the conjugation is via native ligation.

In some embodiments, the polyalkylene oxide (e.g., PEG) is a polydispers or monodispers compound. In some instances, polydispers material comprises disperse distribution of different molecular weight of the material, characterized by mean weight (weight average) size and dispersity. In some instances, the monodisperse PEG comprises one size of molecules. In some embodiments, C is poly- or monodispersed polyalkylene oxide (e.g., PEG) and the indicated molecular weight represents an average of the molecular weight of the polyalkylene oxide, e.g., PEG, molecules.

In some embodiments, the molecular weight of the polyalkylene oxide (e.g., PEG) is about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da.

In some embodiments, C is polyalkylene oxide (e.g., PEG) and has a molecular weight of about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da. In some embodiments, C is PEG and has a molecular weight of about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da. In some instances, the molecular weight of C is about 200 Da. In some instances, the molecular weight of C is about 300 Da. In some instances, the molecular weight of C is about 400 Da. In some instances, the molecular weight of C is about 500 Da. In some instances, the molecular weight of C is about 600 Da. In some instances, the molecular weight of C is about 700 Da. In some instances, the molecular weight of C is about 800 Da. In some instances, the molecular weight of C is about 900 Da. In some instances, the molecular weight of C is about 1000 Da. In some instances, the molecular weight of C is about 1100 Da. In some instances, the molecular weight of C is about 1200 Da. In some instances, the molecular weight of C is about 1300 Da. In some instances, the molecular weight of C is about 1400 Da. In some instances, the molecular weight of C is about 1450 Da. In some instances, the molecular weight of C is about 1500 Da. In some instances, the molecular weight of C is about 1600 Da. In some instances, the molecular weight of C is about 1700 Da. In some instances, the molecular weight of C is about 1800 Da. In some instances, the molecular weight of C is about 1900 Da. In some instances, the molecular weight of C is about 2000 Da. In some instances, the molecular weight of C is about 2100 Da. In some instances, the molecular weight of C is about 2200 Da. In some instances, the molecular weight of C is about 2300 Da. In some instances, the molecular weight of C is about 2400 Da. In some instances, the molecular weight of C is about 2500 Da. In some instances, the molecular weight of C is about 2600 Da. In some instances, the molecular weight of C is about 2700 Da. In some instances, the molecular weight of C is about 2800 Da. In some instances, the molecular weight of C is about 2900 Da. In some instances, the molecular weight of C is about 3000 Da. In some instances, the molecular weight of C is about 3250 Da. In some instances, the molecular weight of C is about 3350 Da. In some instances, the molecular weight of C is about 3500 Da. In some instances, the molecular weight of C is about 3750 Da. In some instances, the molecular weight of C is about 4000 Da. In some instances, the molecular weight of C is about 4250 Da. In some instances, the molecular weight of C is about 4500 Da. In some instances, the molecular weight of C is about 4600 Da. In some instances, the molecular weight of C is about 4750 Da. In some instances, the molecular weight of C is about 5000 Da. In some instances, the molecular weight of C is about 5500 Da. In some instances, the molecular weight of C is about 6000 Da. In some instances, the molecular weight of C is about 6500 Da. In some instances, the molecular weight of C is about 7000 Da. In some instances, the molecular weight of C is about 7500 Da. In some instances, the molecular weight of C is about 8000 Da. In some instances, the molecular weight of C is about 10,000 Da. In some instances, the molecular weight of C is about 12,000 Da. In some instances, the molecular weight of C is about 20,000 Da. In some instances, the molecular weight of C is about 35,000 Da. In some instances, the molecular weight of C is about 40,000 Da. In some instances, the molecular weight of C is about 50,000 Da. In some instances, the molecular weight of C is about 60,000 Da. In some instances, the molecular weight of C is about 100,000 Da.

In some embodiments, the polyalkylene oxide (e.g., PEG) is a discrete PEG, in which the discrete PEG is a polymeric PEG comprising more than one repeating ethylene oxide units. In some instances, a discrete PEG (dPEG) comprises from 2 to 60, from 2 to 50, or from 2 to 48 repeating ethylene oxide units. In some instances, a dPEG comprises about 2, 3, 4, 5, 6, 7, 8, 9, 10, 11, 12, 13, 14, 15, 16, 17, 18, 19, 20, 22, 24, 26, 28, 30, 35, 40, 42, 48, 50 or more repeating ethylene oxide units. In some instances, a dPEG comprises about 2 or more repeating ethylene oxide units. In some instances, a dPEG comprises about 3 or more repeating ethylene oxide units. In some instances, a dPEG comprises about 4 or more repeating ethylene oxide units. In some instances, a dPEG comprises about 5 or more repeating ethylene oxide units. In some instances, a dPEG comprises about 6 or more repeating ethylene oxide units. In some instances, a dPEG comprises about 7 or more repeating ethylene oxide units. In some instances, a dPEG comprises about 8 or more repeating ethylene oxide units. In some instances, a dPEG comprises about 9 or more repeating ethylene oxide units. In some instances, a dPEG comprises about 10 or more repeating ethylene oxide units. In some instances, a dPEG comprises about 11 or more repeating ethylene oxide units. In some instances, a dPEG comprises about 12 or more repeating ethylene oxide units. In some instances, a dPEG comprises about 13 or more repeating ethylene oxide units. In some instances, a dPEG comprises about 14 or more repeating ethylene oxide units. In some instances, a dPEG comprises about 15 or more repeating ethylene oxide units. In some instances, a dPEG comprises about 16 or more repeating ethylene oxide units. In some instances, a dPEG comprises about 17 or more repeating ethylene oxide units. In some instances, a dPEG comprises about 18 or more repeating ethylene oxide units. In some instances, a dPEG comprises about 19 or more repeating ethylene oxide units. In some instances, a dPEG comprises about 20 or more repeating ethylene oxide units. In some instances, a dPEG comprises about 22 or more repeating ethylene oxide units. In some instances, a dPEG comprises about 24 or more repeating ethylene oxide units. In some instances, a dPEG comprises about 26 or more repeating ethylene oxide units. In some instances, a dPEG comprises about 28 or more repeating ethylene oxide units. In some instances, a dPEG comprises about 30 or more repeating ethylene oxide units. In some instances, a dPEG comprises about 35 or more repeating ethylene oxide units. In some instances, a dPEG comprises about 40 or more repeating ethylene oxide units. In some instances, a dPEG comprises about 42 or more repeating ethylene oxide units. In some instances, a dPEG comprises about 48 or more repeating ethylene oxide units. In some instances, a dPEG comprises about 50 or more repeating ethylene oxide units. In some cases, a dPEG is synthesized as a single molecular weight compound from pure (e.g., about 95%, 98%, 99%, or 99.5%) staring material in a step-wise fashion. In some cases, a dPEG has a specific molecular weight, rather than an average molecular weight. In some cases, a dPEG described herein is a dPEG from Quanta Biodesign, LMD.

In some embodiments, the polymer moiety C comprises a cationic mucic acid-based polymer (cMAP). In some instances, cMAP comprises one or more subunit of at least one repeating subunit, and the subunit structure is represented as Formula (III):

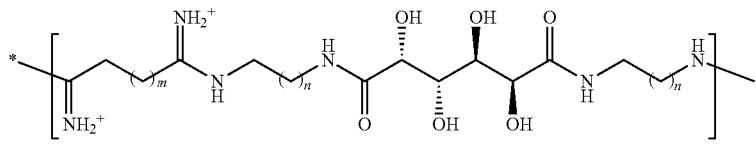

Formula III wherein m is independently at each occurrence 1, 2, 3, 4, 5, 6, 7, 8, 9, or 10, preferably 4-6 or 5; and n is independently at each occurrence 1, 2, 3, 4, or 5. In some embodiments, m and n are, for example, about 10.

In some instances, cMAP is further conjugated to a PEG moiety, generating a cMAP-PEG copolymer, an mPEG-cMAP-PEGm triblock polymer, or a cMAP-PEG-cMAP triblock polymer. In some instances, the PEG moiety is in a range of from about 500 Da to about 50,000 Da. In some instances, the PEG moiety is in a range of from about 500 Da to about 1000 Da, greater than 1000 Da to about 5000 Da, greater than 5000 Da to about 10,000 Da, greater than 10,000 to about 25,000 Da, greater than 25,000 Da to about 50,000 Da, or any combination of two or more of these ranges.

In some instances, C is cMAP-PEG copolymer, an mPEG-cMAP-PEGm triblock polymer, or a cMAP-PEG-cMAP triblock polymer. In some cases, C is cMAP-PEG copolymer. In other cases, C is an mPEG-cMAP-PEGm triblock polymer. In additional cases, C is a cMAP-PEG-cMAP triblock polymer.

Endosomolytic Moiety

In some embodiments, an anti-transferrin receptor antibody conjugate further comprises an additional conjugating moiety. In some instances, the additional conjugating moiety is an endosomolytic moiety. In some cases, the endosomolytic moiety is a cellular compartmental release component, such as a compound capable of releasing from any of the cellular compartments known in the art, such as the endosome, lysosome, endoplasmic reticulum (ER), golgi apparatus, microtubule, peroxisome, or other vesicular bodies with the cell. In some cases, the endosomolytic moiety comprises an endosomolytic polypeptide, an endosomolytic polymer, an endosomolytic lipid, or an endosomolytic small molecule. In some cases, the endosomolytic moiety comprises an endosomolytic polypeptide. In other cases, the endosomolytic moiety comprises an endosomolytic polymer.

Endosomolytic Polypeptides

In some embodiments, the anti-transferrin receptor antibody conjugate is further conjugated with an endosomolytic polypeptide. In some embodiments, a conjugate of Formula (I): A-$(X^1$-B$)_n$ or Formula (II): A-$X^1$-(B-$X^2$-C$)_n$ is further conjugated with an endosomolytic polypeptide. In some cases, the endosomolytic polypeptide is a pH-dependent membrane active peptide. In some cases, the endosomolytic polypeptide is an amphipathic polypeptide. In additional cases, the endosomolytic polypeptide is a peptidomimetic. In some instances, the endosomolytic polypeptide comprises INF, melittin, meucin, or their respective derivatives thereof. In some instances, the endosomolytic polypeptide comprises INF or its derivatives thereof. In other cases, the endosomolytic polypeptide comprises melittin or its derivatives thereof. In additional cases, the endosomolytic polypeptide comprises meucin or its derivatives thereof.

In some instances, INF7 is a 24 residue polypeptide those sequence comprises CGIFGEIEELIEEGLENLIDWGNA (SEQ ID NO: 51), or GLFEAIEGFIENGWEG-MIDGWYGC (SEQ ID NO: 52). In some instances, INF7 or its derivatives comprise a sequence of: GLFEAIEGFIEN-GWEGMIWDYGSGSCG (SEQ ID NO: 53), GLFEAIEG-FIENGWEGMIDG WYG-(PEG)6-NH2 (SEQ ID NO: 54), or GLFEAIEGFIENGWEGMIWDYG-SGSC-K(GalNAc)2 (SEQ ID NO: 55).

In some cases, melittin is a 26 residue polypeptide those sequence comprises CLIGAILKVLATGLPTLISWIKNK-RKQ (SEQ ID NO: 56), or GIGAVLKVLITGLPAL- ISWIKRKRQQ (SEQ ID NO: 57). In some instances, melittin comprises a polypeptide sequence as described in U.S. Pat. No. 8,501,930.

In some instances, meucin is an antimicrobial peptide (AMP) derived from the venom gland of the scorpion *Mesobuthus eupeus*. In some instances, meucin comprises of meucin-13 those sequence comprises IFGAIAGLLKNIF-NH2 (SEQ ID NO: 58) and meucin-18 those sequence comprises FFGHLFKLATKIIPSLFQ (SEQ ID NO: 59).

In some instances, the endosomolytic polypeptide comprises a polypeptide in which its sequence is at least 50%, 60%, 70%, 80%, 90%, 95%, or 99% sequence identity to INF7 or its derivatives thereof, melittin or its derivatives thereof, or meucin or its derivatives thereof. In some instances, the endosomolytic moiety comprises INF7 or its derivatives thereof, melittin or its derivatives thereof, or meucin or its derivatives thereof.

In some instances, the endosomolytic moiety comprises a sequence as illustrated in Table 8.

TABLE 8

| Name | Origin | Amino Acid Sequence | SEQ ID NO: | Type |
| --- | --- | --- | --- | --- |
| Pep-1 | NLS from Simian Virus 40 large antigen and Reverse transcriptase of HIV | KETWWETWWT EWSQPKKKRK V | 60 | Primary amphipathic |
| pVEC | VE-cadherin | LLIILRRRRI RKQAHAHSK | 61 | Primary amphipathic |
| VT5 | Synthetic peptide | DPKGDPKGVT VTVTVTVTG KGDPKPD | 62 | β-sheet amphipathic |
| C105Y | 1-antitrypsin | CSIPPEVKFN KPFVYLI | 63 | — |
| Transportan | Galanin and mastoparan | GWTLNSAGYL LGKINLKALA ALAKKIL | 64 | Primary amphipathic |
| TP10 | Galanin and mastoparan | AGYLLGKINL KALAALAKKI L | 65 | Primary amphipathic |
| MPG | A hydrofobic domain from the fusion sequence of HIV gp41 and NLS of SV40 T antigen | GALFLGFLGA AGSTMGA | 66 | β-sheet amphipathic |
| gH625 | Glycoprotein gH of HSV type I | HGLASTLTRW AHYNALIRAF | 67 | Secondary amphipathic α-helical |
| CADY | PPTG1 peptide | GLWRALWRLL RSLWRLLWRA | 68 | Secondary amphipathic α-helical |
| GALA | Synthetic peptide | WEAALAEALA EALAEHLAEA LAEALEALAA | 69 | Secondary amphipathic α-helical |
| INF | Influenza HA2 fusion peptide | GLFEAIEGFI ENGWEGMID GWYGC | 70 | Secondary amphipathic α-helical/pH-dependent membrane active peptide |

TABLE 8-continued

| Name | Origin | Amino Acid Sequence | SEQ ID NO: | Type |
| --- | --- | --- | --- | --- |
| HA2E5-TAT | Influenza HA2 subunit of influenza virus X31 strain fusion peptide | GLFGAIAGFI ENGWEGMID GWYG | 71 | Secondary amphipathic α-helical/pH-dependent membrane active peptide |
| HA2-penetratin | Influenza HA2 subunit of influenza virus X31 strain fusion peptide | GLFGAIAGFI ENGWEGMIDG RQIKIWFQNR RMKWKK-amide | 72 | pH-dependent membrane active peptide |
| HA-K4 | Influenza HA2 subunit of influenza virus X31 strain fusion peptide | GLFGAIAGFI ENGWEGMID G-SSKKKK | 73 | pH-dependent membrane active peptide |
| HA2E4 | Influenza HA2 subunit of influenza virus X31 strain fusion peptide | GLFEAIAGFI ENGWEGMIDG GGYC | 74 | pH-dependent membrane active peptide |
| H5WYG | HA2 analogue | GLFHAIAHFI HGGWHGLIHG WYG | 75 | pH-dependent membrane active peptide |
| GALA-INF3-(PEG)6-NH | INF3 fusion peptide | GLFEAIEGFI ENGWEGLAEA LAEALEALA A-(PEG)6-NH2 | 76 | pH-dependent membrane active peptide |
| CM18-TAT11 | Cecropin-A-Melittin$_{2-12}$ (CM$_{18}$) fusion peptide | KWKLFKKIGA VLKVLTTG-Y GRKKRRQRRR | 77 | pH-dependent membrane active peptide |

In some cases, the endosomolytic moiety comprises a Bak BH3 polypeptide which induces apoptosis through antagonization of suppressor targets such as Bcl-2 and/or Bcl-$_{XL}$. In some instances, the endosomolytic moiety comprises a Bak BH3 polypeptide described in Albarran, et al., "Efficient intracellular delivery of a pro-apoptotic peptide with a pH-responsive carrier," *Reactive & Functional Polymers* 71: 261-265 (2011).

In some instances, the endosomolytic moiety comprises a polypeptide (e.g., a cell-penetrating polypeptide) as described in PCT Publication Nos. WO2013/166155 or WO2015/069587.

Endosomolytic Polymers

In some embodiments, a conjugate of Formula (I): A-(X$_1$-B)$_n$ or Formula (II): A-X$^1$-(B-X$^2$-C)$_n$ is further conjugated with an endosomolytic polymer. As used herein, an endosomolytic polymer comprises a linear, a branched network, a star, a comb, or a ladder type of polymer. In some instances, an endosomolytic polymer is a homopolymer or a copolymer comprising two or more different types of monomers. In some cases, an endosomolytic polymer is a polycation polymer. In other cases, an endosomolytic polymer is a polyanion polymer.

In some instances, a polycation polymer comprises monomer units that are charge positive, charge neutral, or charge negative, with a net charge being positive. In other cases, a polycation polymer comprises a non-polymeric molecule that contains two or more positive charges. Exemplary cationic polymers include, but are not limited to, poly(L-lysine) (PLL), poly(L-arginine) (PLA), polyethyleneimine (PEI), poly[α-(4-aminobutyl)-L-glycolic acid] (PAGA), 2-(dimethylamino)ethyl methacrylate (DMAEMA), or N,N-Diethylaminoethyl Methacrylate (DEAEMA).

In some cases, a polyanion polymer comprises monomer units that are charge positive, charge neutral, or charge negative, with a net charge being negative. In other cases, a polyanion polymer comprises a non-polymeric molecule that contains two or more negative charges. Exemplary anionic polymers include p(alkylacrylates) (e.g., poly(propyl acrylic acid) (PPAA)) or poly(N-isopropylacrylamide) (NIPAM). Additional examples include PP75, a L-phenylalanine-poly(L-lysine isophthalamide) polymer described in Khormaee, et al., "Edosomolytic anionic polymer for the cytoplasmic delivery of siRNAs in localized in vivo applications," Advanced Functional Materials 23: 565-574 (2013).

In some embodiments, an endosomolytic polymer described herein is a pH-responsive endosomolytic polymer. A pH-responsive polymer comprises a polymer that increases in size (swell) or collapses depending on the pH of the environment. Polyacrylic acid and chitosan are examples of pH-responsive polymers.

In some instances, an endosomolytic moiety described herein is a membrane-disruptive polymer. In some cases, the membrane-disruptive polymer comprises a cationic polymer, a neutral or hydrophobic polymer, or an anionic polymer. In some instances, the membrane-disruptive polymer is a hydrophilic polymer.

In some instances, an endosomolytic moiety described herein is a pH-responsive membrane-disruptive polymer. Exemplary pH-responsive membrane-disruptive polymers include p(alkylacrylic acids), poly(N-isopropylacrylamide) (NIPAM) copolymers, succinylated p(glycidols), and p(β-malic acid) polymers.

In some instances, p(alkylacrylic acids) include poly (propylacrylic acid) (polyPAA), poly(methacrylic acid) (PMAA), poly(ethylacrylic acid) (PEAA), and poly(propyl acrylic acid) (PPAA). In some instances, a p(alkylacrylic acid) include a p(alkylacrylic acid) described in Jones, et al., Biochemistry Journal 372: 65-75 (2003).

In some embodiments, a pH-responsive membrane-disruptive polymer comprises p(butyl acrylate-co-methacrylic acid). (see Bulmus, et al., Journal of Controlled Release 93: 105-120 (2003); and Yessine, et al., Biochimica et Biophysica Acta 1613: 28-38 (2003))

In some embodiments, a pH-responsive membrane-disruptive polymer comprises p(styrene-alt-maleic anhydride). (see Henry, et al., Biomacromolecules 7: 2407-2414 (2006))

In some embodiments, a pH-responsive membrane-disruptive polymer comprises pyridyldisulfide acrylate (PDSA) polymers such as poly(MAA-co-PDSA), poly(EAA-co-PDSA), poly(PAA-co-PDSA), poly(MAA-co-BA-co-PDSA), poly(EAA-co-BA-co-PDSA), or poly(PAA-co-BA-co-PDSA) polymers. (see El-Sayed, et al., "Rational design of composition and activity correlations for pH-responsive and glutathione-reactive polymer therapeutics," Journal of Controlled Release 104: 417-427 (2005); or Flanary et al., "Antigen delivery with poly(propylacrylic acid) conjugation enhanced MHC-1 presentation and T-cell activation," Bioconjugate Chem. 20: 241-248 (2009))

In some embodiments, a pH-responsive membrane-disruptive polymer comprises a lytic polymer comprising the base structure of:

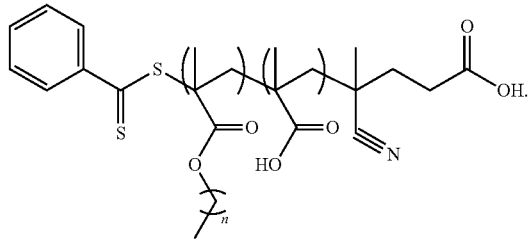

n = 3, 5, 7

In some instances, an endosomolytic moiety described herein is further conjugated to an additional conjugate, e.g., a polymer (e.g., PEG), or a modified polymer (e.g., cholesterol-modified polymer).

In some instances, the additional conjugate comprises a detergent (e.g., Triton X-100). In some instances, an endosomolytic moiety described herein comprises a polymer (e.g., a poly(amidoamine)) conjugated with a detergent (e.g., Triton X-100). In some instances, an endosomolytic moiety described herein comprises poly(amidoamine)-Triton X-100 conjugate (Duncan, et al., "A polymer-Triton X-100 conjugate capable of pH-dependent red blood cell lysis: a model system illustrating the possibility of drug delivery within acidic intracellular compartments," Journal of Drug Targeting 2: 341-347 (1994)).

Endosomolytic Lipids

In some embodiments, the endosomolytic moiety is a lipid (e.g., a fusogenic lipid). In some embodiments, a conjugate of Formula (I): A-(X$_1$-B)$_n$ or Formula (II): A-X$^1$-(B-X$^2$-C)$_n$ is further conjugated with an endosomolytic lipid (e.g., fusogenic lipid). Exemplary fusogenic lipids include 1,2-dileoyl-sn-3-phosphoethanolamine (DOPE), phosphatidylethanolamine (POPE), palmitoyloleoylphosphatidylcholine (POPC), (6Z,9Z,28Z,31Z)-heptatriaconta-6,9,28,31-tetraen-19-ol (Di-Lin), N-methyl(2,2-di((9Z,12Z)-octadeca-9,12-dienyl)-1,3-dioxolan-4-yl)methanamine (DLin-k-DMA) and N-methyl-2-(2,2-di((9Z,12Z)-octadeca-9,12-dienyl)-1,3-dioxolan-4-yl)ethanamine (XTC).

In some instances, an endosomolytic moiety is a lipid (e.g., a fusogenic lipid) described in PCT Publication No. WO09/126,933.

Endosomolytic Small Molecules

In some embodiments, the endosomolytic moiety is a small molecule. In some embodiments, a molecule of Formula (I): A-(X$_1$-B)$_n$ or Formula (II): A-X$^1$-(B-X$^2$-C)$_n$ is further conjugated with an endosomolytic small molecule. Exemplary small molecules suitable as endosomolytic moieties include, but are not limited to, quinine, chloroquine, hydroxychloroquines, amodiaquins (carnoquines), amopyroquines, primaquines, mefloquines, nivaquines, halofantrines, quinone imines, or a combination thereof. In some instances, quinoline endosomolytic moieties include, but are not limited to, 7-chloro-4-(4-diethylamino-1-methylbutyl-amino)quinoline (chloroquine); 7-chloro-4-(4-ethyl-(2-hydroxyethyl)-amino-1-methylbutyl-amino)quinoline (hydroxychloroquine); 7-fluoro-4-(4-diethylamino-1-methylbutyl-amino)quinoline; 4-(4-diethylamino-1-methylbutylamino) quinoline; 7-hydroxy-4-(4-diethyl-amino-1-methylbutylamino)quinoline; 7-chloro-4-(4-diethylamino-1-butylamino)quinoline (desmethylchloroquine); 7-fluoro-4-(4-diethylamino-1-butylamino)quinoline); 4-(4-diethyl-amino-1-butylamino) quinoline; 7-hydroxy-4-(4-diethylamino-1-butylamino)quinoline; 7-chloro-4-(1-carboxy-4-diethylamino-1-butylamino)quinoline; 7-fluoro-4-(1-carboxy-4-diethyl-amino-1-butylamino)quinoline; 4-(1-carboxy-4-diethylamino-1-butylamino) quinoline; 7-hydroxy-4-(1-carboxy-4-diethylamino-1-butylamino)quinoline; 7-chloro-4-(1-carboxy-4-diethylamino-1-methylbutylamino) quinoline; 7-fluoro-4-(1-carboxy-4-diethyl-amino-1-methylbutylamino)quinoline; 4-(1-carboxy-4-diethylamino-1-methylbutylamino)quinoline; 7-hydroxy-4-(1-carboxy-4-diethylamino-1-methylbutylamino)quinoline; 7-fluoro-4-(4-ethyl-(2-hydroxyethyl)-amino-1-methylbutylamino) quinoline; 4-(4-ethyl-(2-hydroxy-ethyl)-amino-1-methylbutylamino-)quinoline; 7-hydroxy-4-(4-ethyl-(2-hydroxyethyl)-amino-1-methylbutylamino)quinoline; hydroxychloroquine phosphate; 7-chloro-4-(4-ethyl-(2-hydroxyethyl-1)-amino-1-butylamino)quinoline (desmethylhydroxychloroquine); 7-fluoro-4-(4-ethyl-(2-hydroxy-ethyl)-amino-1-butylamino)quinoline; 4-(4-ethyl-(2-hydroxyethyl)-amino-1-butylamino)quinoline; 7-hydroxy-4-(4-ethyl-(2-hydroxyethyl)-amino-1-butylamino) quinoline; 7-chloro-4-(1-carboxy-4-ethyl-(2-hydroxyethyl)-amino-1-butylamino)quinoline; 7-fluoro-4-(1-carboxy-4-ethyl-(2-hydroxyethyl)-amino-1-butylamino)quinoline; 4-(1-carboxy-4-ethyl-(2-hydroxyethyl)-amino-1-butylamino)quinoline; 7-hydroxy-4-(1-carboxy-4-ethyl-(2-hydroxyethyl)-amino-1-butylamino)quinoline; 7-chloro-4-(1-carboxy-4-ethyl-(2-hydroxyethyl)-amino-1-methylbutylamino)quinoline; 7-fluoro-4-(1-carboxy-4-ethyl-(2-hydroxyethyl)-amino-1-methylbutylamino) quinoline; 4-(1-carboxy-4-ethyl-(2-hydroxyethyl)-amino-1-methylbutylamino)quinoline; 7-hydroxy-4-(1-carboxy-4-ethyl-(2-hydroxyethyl)-amino-1-methylbutylamino) quinoline; 8-[(4-aminopentyl)amino-6-methoxydihydrochloride quinoline; 1-acetyl-1,2,3,4-tetrahydroquinoline; 8-[(4-aminopentyl)amino]-6-methoxyquinoline dihydrochloride; 1-butyryl-1,2,3,4-tetrahydroquinoline; 3-chloro-4-(4-hydroxy-alpha,alpha'-bis(2-methyl-1-pyrrolidinyl)-2,5-xylidinoquinoline, 4-[(4-diethyl-amino)-1-methylbutyl-amino]-6-methoxyquinoline; 3-fluoro-4-(4-hydroxy-alpha,alpha'-bis(2-methyl-1-pyrrolidinyl)-2,5-xylidinoquinoline, 4-[(4-diethylamino)-1-methylbutyl-amino]-6-methoxyquinoline; 4-(4-hydroxy-alpha,alpha'-bis(2-methyl-1-pyrrolidinyl)-2,5-xylidinoquinoline; 4-[(4-diethylamino)-1-methylbutyl-amino]-6-methoxyquinoline; 3,4-dihydro-1-(2H)-quinolinecarboxyaldehyde; 1,1'-pentamethylene diquinoleinium diiodide; 8-quinolinol sulfate and amino, aldehyde, carboxylic, hydroxyl, halogen, keto, sulfhydryl and vinyl derivatives or analogs thereof. In some instances, an endosomolytic moiety is a small molecule described in Naisbitt et al (1997, J Pharmacol Exp Therapy 280:884-893) and in U.S. Pat. No. 5,736,557.

In some embodiments, the endosomolytic moiety is nigericin or a conjugate thereof, e.g., such as a folate-nigericin ester conjugate, a folate-nigericin amide conjugate, or a folate-nigericin carbamate conjugate. In some instances, the endosomolytic moiety is nigericin described in Rangasamy, et. al., "New mechanism for release of endosomal contents: osmotic lysis via nigericin-mediated K+/H+ exchange," *Bioconjugate Chem.* 29:1047-1059 (2018).

Linkers

In some embodiments, a linker described herein is a cleavable linker or a non-cleavable linker. In some instances, the linker is a cleavable linker. In other instances, the linker is a non-cleavable linker.

In some cases, the linker is a non-polymeric linker. A non-polymeric linker refers to a linker that does not contain a repeating unit of monomers generated by a polymerization process. Exemplary non-polymeric linkers include, but are not limited to, $C_1$-$C_6$ alkyl group (e.g., a $C_5$, $C_4$, $C_3$, $C_2$, or $C_1$ alkyl group), homobifunctional cross linkers, heterobifunctional cross linkers, peptide linkers, traceless linkers, self-immolative linkers, maleimide-based linkers, or combinations thereof. In some cases, the non-polymeric linker comprises a $C_1$-$C_6$ alkyl group (e.g., a $C_5$, $C_4$, $C_3$, $C_2$, or $C_1$ alkyl group), a homobifunctional cross linker, a heterobifunctional cross linker, a peptide linker, a traceless linker, a self-immolative linker, a maleimide-based linker, or a combination thereof. In additional cases, the non-polymeric linker does not comprise more than two of the same type of linkers, e.g., more than two homobifunctional cross linkers, or more than two peptide linkers. In further cases, the non-polymeric linker optionally comprises one or more reactive functional groups.

In some instances, the non-polymeric linker does not encompass a polymer that is described above. In some instances, the non-polymeric linker does not encompass a polymer encompassed by the polymer moiety C. In some cases, the non-polymeric linker does not encompass a polyalkylene oxide (e.g., PEG). In some cases, the non-polymeric linker does not encompass a PEG.

In some instances, the linker comprises a homobifunctional linker. Exemplary homobifunctional linkers include, but are not limited to, Lomant's reagent dithiobis (succinimidylpropionate) DSP, 3'3'-dithiobis(sulfosuccinimidyl proprionate (DTSSP), disuccinimidyl suberate (DSS), bis (sulfosuccinimidyl)suberate (BS), disuccinimidyl tartrate (DST), disulfosuccinimidyl tartrate (sulfo DST), ethylene glycobis(succinimidylsuccinate) (EGS), disuccinimidyl glutarate (DSG), N,N'-disuccinimidyl carbonate (DSC), dimethyl adipimidate (DMA), dimethyl pimelimidate (DMP), dimethyl suberimidate (DMS), dimethyl-3,3'-dithiobispropionimidate (DTBP), 1,4-di-3'-(2'-pyridyldithio)propionamido)butane (DPDPB), bismaleimidohexane (BMH), aryl halide-containing compound (DFDNB), such as e.g. 1,5-difluoro-2,4-dinitrobenzene or 1,3-difluoro-4,6-dinitrobenzene, 4,4'-difluoro-3,3'-dinitrophenylsulfone (DFDNPS), bis-[β-(4-azidosalicylamido)ethyl]disulfide (BASED), formaldehyde, glutaraldehyde, 1,4-butanediol diglycidyl ether, adipic acid dihydrazide, carbohydrazide, o-toluidine, 3,3'-dimethylbenzidine, benzidine, α,α'-p-diaminodiphenyl, diiodo-p-xylene sulfonic acid, N,N'-ethylene-bis(iodoacetamide), or N,N'-hexamethylene-bis(iodoacetamide).

In some embodiments, the linker comprises a heterobifunctional linker. Exemplary heterobifunctional linker include, but are not limited to, amine-reactive and sulfhydryl cross-linkers such as N-succinimidyl 3-(2-pyridyldithio) propionate (sPDP), long-chain N-succinimidyl 3-(2-pyridyldithio)propionate (LC-sPDP), water-soluble-long-chain N-succinimidyl 3-(2-pyridyldithio) propionate (sulfo-LC-sPDP), succinimidyloxycarbonyl-α-methyl-α-(2-pyridyldithio)toluene (sMPT), sulfosuccinimidyl-6-[α-methyl-α-(2-pyridyldithio)toluamido]hexanoate (sulfo-LC-sMPT), succinimidyl-4-(N-maleimidomethyl)cyclohexane-1-carboxylate (sMCC), sulfosuccinimidyl-4-(N-maleimidomethyl)cyclohexane-1-carboxylate (sulfo-sMCC), m-maleimidobenzoyl-N-hydroxysuccinimide ester (MBs), m-maleimidobenzoyl-N-hydroxysulfosuccinimide ester (sulfo-MBs), N-succinimidyl(4-iodoacteyl)aminobenzoate (sIAB), sulfosuccinimidyl(4-iodoactyl)aminobenzoate (sulfo-sIAB), succinimidyl-4-(p-maleimidophenyl)butyrate (sMPB), sulfosuccinimidyl-4-(p-maleimidophenyl)butyrate (sulfo-sMPB), N-(γ-maleimidobutyryloxy)succinimide ester (GMBs), N-(γ-maleimidobutyryloxy)sulfosuccinimide ester (sulfo-GMBs), succinimidyl 6-((iodoacetyl)amino)hexanoate (sIAX), succinimidyl 6-[6-(((iodoacetyl)amino) hexanoyl)amino]hexanoate (sIAXX), succinimidyl 4-(((iodoacetyl)amino)methyl)cyclohexane-1-carboxylate (sIAC), succinimidyl 6-((((4-iodoacetyl)amino)methyl)cyclohexane-1-carbonyl)amino) hexanoate (sIACX), p-nitrophenyl iodoacetate (NPIA), carbonyl-reactive and sulfhydryl-reactive cross-linkers such as 4-(4-N-maleimidophenyl) butyric acid hydrazide (MPBH), 4-(N-maleimidomethyl) cyclohexane-1-carboxyl-hydrazide-8 ($M_2C_2H$), 3-(2-pyridyldithio)propionyl hydrazide (PDPH), amine-reactive and photoreactive cross-linkers such as N-hydroxysuccinimidyl-4-azidosalicylic acid (NHs-AsA), N-hydroxysulfosuccinimidyl-4-azidosalicylic acid (sulfo-NHs-AsA), sulfosuccinimidyl-(4-azidosalicylamido)hexanoate (sulfo-NHs-LC-AsA), sulfosuccinimidyl-2-(ρ-azidosalicylamido)ethyl-1,3'-dithiopropionate (sAsD), N-hydroxysuccinimidyl-4-azidobenzoate (HsAB), N-hydroxysulfosuccinimidyl-4-azidobenzoate (sulfo-HsAB), N-succinimidyl-6-(4'-azido-2'-nitrophenylamino)hexanoate (sANPAH), sulfosuccinimidyl-6-(4'-azido-2'-nitrophenylamino)hexanoate (sulfo-sANPAH), N-5-azido-2-nitrobenzoyloxysuccinimide (ANB-NOs), sulfosuccinimidyl-2-(m-azido-o-nitrobenzamido)-ethyl-1,3'-dithiopropionate (sAND), N-succinimidyl-4(4-azidophenyl)1,3'-dithiopropionate (sADP), N-sulfosuccinimidyl(4-azidophenyl)-1,3'-dithiopropionate (sulfo-sADP), sulfosuccinimidyl 4-(ρ-azidophenyl)butyrate (sulfo-sAPB), sulfosuccinimidyl 2-(7-azido-4-methylcoumarin-3-acetamide)ethyl-1,3'-dithiopropionate (sAED), sulfosuccinimidyl 7-azido-4-methylcoumain-3-acetate (sulfo-sAMCA), ρ-nitrophenyl diazopyruvate (ρNPDP), ρ-nitrophenyl-2-diazo-3,3,3-trifluoropropionate (PNP-DTP), sulfhydryl-reactive and photoreactive cross-linkers such as 1-(ρ-Azidosalicylamido)-4-(iodoacetamido) butane (AsIB), N-[4-(ρ-azidosalicylamido)butyl]-3'-(2'-pyridyldithio)propionamide (APDP), benzophenone-4-iodoacetamide, benzophenone-4-maleimide carbonyl-reactive and photoreactive cross-linkers such as ρ-azidobenzoyl hydrazide (ABH), carboxylate-reactive and photoreactive cross-linkers such as 4-(ρ-azidosalicylamido) butylamine (AsBA), and arginine-reactive and photoreactive cross-linkers such as ρ-azidophenyl glyoxal (APG).

In some instances, the linker comprises a reactive functional group. In some cases, the reactive functional group comprises a nucleophilic group that is reactive to an electrophilic group present on a binding moiety. Exemplary electrophilic groups include carbonyl groups—such as aldehyde, ketone, carboxylic acid, ester, amide, enone, acyl halide or acid anhydride. In some embodiments, the reactive functional group is aldehyde. Exemplary nucleophilic groups include hydrazide, oxime, amino, hydrazine, thiosemicarbazone, hydrazine carboxylate, and arylhydrazide.

In some embodiments, the linker comprises a maleimide group. In some instances, the maleimide group is also referred to as a maleimide spacer. In some instances, the maleimide group further encompasses a caproic acid, forming maleimidocaproyl (mc). In some cases, the linker comprises maleimidocaproyl (mc). In some cases, the linker is maleimidocaproyl (mc). In other instances, the maleimide group comprises a maleimidomethyl group, such as succinimidyl-4-(N-maleimidomethyl)cyclohexane-1-carboxylate (sMCC) or sulfosuccinimidyl-4-(N-maleimidomethyl)cyclohexane-1-carboxylate (sulfo-sMCC) described above.

In some embodiments, the maleimide group is a self-stablizing maleimide. In some instances, the self-stabilizing maleimide utilizes diaminopropionic acid (DPR) to incorporate a basic amino group adjacent to the maleimide to provide intramolecular catalysis of tiosuccinimide ring hydrolysis, thereby eliminating maleimide from undergoing an elimination reaction through a retro-Michael reaction. In some instances, the self-stabilizing maleimide is a maleimide group described in Lyon, et al., "Self-hydrolyzing maleimides improve the stability and pharmacological properties of antibody-drug conjugates," Nat. Biotechnol. 32(10): 1059-1062 (2014). In some instances, the linker comprises a self-stablizing maleimide. In some instances, the linker is a self-stablizing maleimide.

In some embodiments, the linker comprises a peptide moiety. In some instances, the peptide moiety comprises at least 2, 3, 4, 5, or 6 more amino acid residues. In some instances, the peptide moiety comprises at most 2, 3, 4, 5, 6, 7, or 8 amino acid residues. In some instances, the peptide moiety comprises about 2, about 3, about 4, about 5, or about 6 amino acid residues. In some instances, the peptide moiety is a cleavable peptide moiety (e.g., either enzymatically or chemically). In some instances, the peptide moiety is a non-cleavable peptide moiety. In some instances, the peptide moiety comprises Val-Cit (valine-citrulline), Gly-Gly-Phe-Gly (SEQ ID NO: 78), Phe-Lys, Val-Lys, Gly-Phe-Lys, Phe-Phe-Lys, Ala-Lys, Val-Arg, Phe-Cit, Phe-Arg, Leu-Cit, Ile-Cit, Trp-Cit, Phe-Ala, Ala-Leu-Ala-Leu (SEQ ID NO: 79), or Gly-Phe-Leu-Gly (SEQ ID NO: 80). In some instances, the linker comprises a peptide moiety such as: Val-Cit (valine-citrulline), Gly-Gly-Phe-Gly (SEQ ID NO: 78), Phe-Lys, Val-Lys, Gly-Phe-Lys, Phe-Phe-Lys, Ala-Lys, Val-Arg, Phe-Cit, Phe-Arg, Leu-Cit, Ile-Cit, Trp-Cit, Phe-Ala, Ala-Leu-Ala-Leu (SEQ ID NO: 79), or Gly-Phe-Leu-Gly (SEQ ID NO: 80). In some cases, the linker comprises Val-Cit. In some cases, the linker is Val-Cit.

In some embodiments, the linker comprises a benzoic acid group, or its derivatives thereof. In some instances, the benzoic acid group or its derivatives thereof comprise paraaminobenzoic acid (PABA). In some instances, the benzoic acid group or its derivatives thereof comprise gamma-aminobutyric acid (GABA).

In some embodiments, the linker comprises one or more of a maleimide group, a peptide moiety, and/or a benzoic acid group, in any combination. In some embodiments, the linker comprises a combination of a maleimide group, a peptide moiety, and/or a benzoic acid group. In some instances, the maleimide group is maleimidocaproyl (mc). In some instances, the peptide group is val-cit. In some instances, the benzoic acid group is PABA. In some instances, the linker comprises a mc-val-cit group. In some cases, the linker comprises a val-cit-PABA group. In additional cases, the linker comprises a mc-val-cit-PABA group.

In some embodiments, the linker is a self-immolative linker or a self-elimination linker. In some cases, the linker is a self-immolative linker. In other cases, the linker is a self-elimination linker (e.g., a cyclization self-elimination linker). In some instances, the linker comprises a linker described in U.S. Pat. No. 9,089,614 or PCT Publication No. WO2015038426.

In some embodiments, the linker is a dendritic type linker. In some instances, the dendritic type linker comprises a branching, multifunctional linker moiety. In some instances, the dendritic type linker is used to increase the molar ratio of polynucleotide B to the binding moiety A. In some instances, the dendritic type linker comprises PAMAM dendrimers.

In some embodiments, the linker is a traceless linker or a linker in which after cleavage does not leave behind a linker moiety (e.g., an atom or a linker group) to a binding moiety A, a polynucleotide B, a polymer C, or an endosomolytic moiety D. Exemplary traceless linkers include, but are not limited to, germanium linkers, silicium linkers, sulfur linkers, selenium linkers, nitrogen linkers, phosphorus linkers, boron linkers, chromium linkers, or phenylhydrazide linker. In some cases, the linker is a traceless aryl-triazene linker as described in Hejesen, et al., "A traceless aryl-triazene linker for DNA-directed chemistry," *Org Biomol Chem* 11(15): 2493-2497 (2013). In some instances, the linker is a traceless linker described in Blaney, et al., "Traceless solid-phase organic synthesis," *Chem. Rev.* 102: 2607-2024 (2002). In some instances, a linker is a traceless linker as described in U.S. Pat. No. 6,821,783.

In some instances, the linker is a linker described in U.S. Pat. Nos. 6,884,869; 7,498,298; 8,288,352; 8,609,105; or 8,697,688; U.S. Patent Publication Nos. 2014/0127239; 2013/028919; 2014/286970; 2013/0309256; 2015/037360; or 2014/0294851; or PCT Publication Nos. WO2015057699; WO2014080251; WO2014197854; WO2014145090; or WO2014177042.

In some embodiments, $X^1$ and $X^2$ are each independently a bond or a non-polymeric linker. In some instances, $X^1$ and $X^2$ are each independently a bond. In some cases, $X^1$ and $X^2$ are each independently a non-polymeric linker.

In some instances, $X^1$ is a bond or a non-polymeric linker. In some instances, $X^1$ is a bond. In some instances, $X^1$ is a non-polymeric linker. In some instances, the linker is a $C_1$-$C_6$ alkyl group. In some cases, $X^1$ is a $C_1$-$C_6$ alkyl group, such as for example, a $C_5$, $C_4$, $C_3$, $C_2$, or $C_1$ alkyl group. In some cases, the $C_1$-$C_6$ alkyl group is an unsubstituted $C_1$-$C_6$ alkyl group. As used in the context of a linker, and in particular in the context of X', alkyl means a saturated straight or branched hydrocarbon radical containing up to six carbon atoms. In some instances, $X^1$ includes a homobifunctional linker or a heterobifunctional linker described supra. In some cases, $X^1$ includes a heterobifunctional linker. In some cases, $X^1$ includes sMCC. In other instances, $X^1$ includes a heterobifunctional linker optionally conjugated to a $C_1$-$C_6$ alkyl group. In other instances, $X^1$ includes sMCC optionally conjugated to a $C_1$-$C_6$ alkyl group. In additional instances, $X_1$ does not include a homobifunctional linker or a heterobifunctional linker described supra.

In some instances, $X^2$ is a bond or a linker. In some instances, $X^2$ is a bond. In other cases, $X^2$ is a linker. In additional cases, $X^2$ is a non-polymeric linker. In some embodiments, $X^2$ is a $C_1$-$C_6$ alkyl group. In some instances, $X^2$ is a homobifunctional linker or a heterobifunctional linker described supra. In some instances, $X^2$ is a homobifunctional linker described supra. In some instances, $X^2$ is a heterobifunctional linker described supra. In some instances, $X^2$ comprises a maleimide group, such as maleimidocaproyl (mc) or a self-stabilizing maleimide group described above. In some instances, $X^2$ comprises a peptide moiety, such as Val-Cit. In some instances, $X^2$ comprises a benzoic acid group, such as PABA. In additional instances, $X^2$ comprises a combination of a maleimide group, a peptide moiety, and/or a benzoic acid group. In additional instances, $X^2$ comprises a mc group. In additional instances, $X^2$ comprises a mc-val-cit group. In additional instances, $X^2$ comprises a val-cit-PABA group. In additional instances, $X^2$ comprises a mc-val-cit-PABA group.

Methods of Use

In some embodiments, described herein are methods delivering a payload to a target site of interest with use of an anti-transferrin receptor antibody described herein. In some instances, the target site of interest is a cell that overexpresses a causative protein that is associated with a disease or condition. In some instances, the target site of interest is a cell that comprises an incorrectly processed mRNA, which encodes a non-functional protein or a reduced expression of a protein leading to a disease or condition. In some instances, the target site of interest is a tumor site. In additional instances, the target site of interest is a site located with the brain.

In some embodiments, described herein is a method of treating a disease or disorder characterized with an overexpressed protein. In some instances, the disease or disorder is a muscle atrophy. In some instances, the disease or disorder is myotonic dystrophy.

In one embodiment, muscle atrophy refers to a significant loss in muscle strength. By significant loss in muscle strength is meant a reduction of strength in diseased, injured, or unused muscle tissue in a subject relative to the same muscle tissue in a control subject. In an embodiment, a significant loss in muscle strength is a reduction in strength of at least 10%, at least 15%, at least 20%, at least 25%, at least 30%, at least 35%, at least 40%, at least 45%, at least 50%, or more relative to the same muscle tissue in a control subject. In another embodiment, by significant loss in muscle strength is meant a reduction of strength in unused muscle tissue relative to the muscle strength of the same muscle tissue in the same subject prior to a period of nonuse. In an embodiment, a significant loss in muscle strength is a reduction of at least 10%, at least 15%, at least 20%, at least 25%, at least 30%, at least 35%, at least 40%, at least 45%, at least 50%, or more relative to the muscle strength of the same muscle tissue in the same subject prior to a period of nonuse.

In another embodiment, muscle atrophy refers to a significant loss in muscle mass. By significant loss in muscle mass is meant a reduction of muscle volume in diseased, injured, or unused muscle tissue in a subject relative to the same muscle tissue in a control subject. In an embodiment, a significant loss of muscle volume is at least 10%, at least 15%, at least 20%, at least 25%, at least 30%, at least 35%, at least 40%, at least 45%, at least 50%, or more relative to the same muscle tissue in a control subject. In another embodiment, by significant loss in muscle mass is meant a reduction of muscle volume in unused muscle tissue relative to the muscle volume of the same muscle tissue in the same subject prior to a period of nonuse. In an embodiment, a significant loss in muscle tissue is at least 10%, at least 15%, at least 20%, at least 25%, at least 30%, at least 35%, at least 40%, at least 45%, at least 50%, or more relative to the muscle volume of the same muscle tissue in the same subject prior to a period of nonuse. Muscle volume is optionally measured by evaluating the cross-section area of a muscle such as by Magnetic Resonance Imaging (e.g., by a muscle volume/cross-section area (CSA) MRI method).

In some embodiments, the muscle atrophy comprises or is associated with cachexia, denervation, myopathy, motor neuron diseases, diabetes, chronic obstructive pulmonary disease, liver disease, congestive heart failure, chronic renal failure, chronic infection, sepsis, fasting, sarcopenia, glucocorticoid-associated muscle atrophy, or disuse-associated muscle atrophy.

Cachexia is an acquired, accelerated loss of muscle caused by an underlying disease. In some instances, cachexia refers to a loss of body mass that cannot be reversed nutritionally, and is generally associated with an underlying disease, such as cancer, COPD, AIDS, heart failure, and the like. When cachexia is seen in a patient with end-stage cancer, it is called "cancer cachexia". Cancer cachexia affects the majority of patients with advanced cancer and is associated with a reduction in treatment tolerance, response to therapy, quality of life and duration of survival. It some instances, cancer cachexia is defined as a multifactorial syndrome characterized by an ongoing loss of skeletal muscle mass, with or without loss of fat mass, which cannot be fully reversed by conventional nutritional support and leads to progressive functional impairment. In some cases, skeletal muscle loss appears to be the most significant event in cancer cachexia. In addition, the classification of cancer cachexia suggests that the diagnostic criteria takes into account not only that weight loss is a signal event of the cachectic process but that the initial reserve of the patient should also be considered, such as low BMI or low level of muscularity.

Denervation is an injury to the peripheral motoneurons with a partial or complete interruption of the nerve fibers between an organ and the central nervous system, resulting in an interruption of nerve conduction and motoneuron firing which, in turn, prevents the contractability of skeletal muscles. This loss of nerve function is either localized or generalized due to the loss of an entire motor neuron unit. The resulting inability of skeletal muscles to contract leads to muscle atrophy. In some instances, denervation is associated with or as a result of degenerative, metabolic, or inflammatory neuropathy (e.g., Guillain-Barre syndrome, peripheral neuropathy, or exposure to environmental toxins or drugs). In additional instances, denervation is associated with a physical injury, e.g., a surgical procedure.

Myopathy is an umbrella term that describes a disease of the muscle. In some instances, myopathy includes myotonia; congenital myopathy such as nemaline myopathy, multi/minicore myopathy and myotubular (centronuclear) myopathy; mitochondrial myopathy; familial periodic paralysis; inflammatory myopathy; metabolic myopathy, for example, caused by a glycogen or lipid storage disease; dermatomyositis; polymyositis; inclusion body myositis; myositis ossificans; rhabdomyolysis; and myoglobinurias. In some instances, myopathy is caused by a muscular dystrophy syndrome, such as Duchenne, Becker, myotonic, fascioscapulohumeral, Emery-Dreifuss, oculopharyngeal, scapulohumeral, limb girdle, Fukuyama, a congenital muscular dystrophy, or hereditary distal myopathy. In some instances, myopathy is caused by myotonic dystrophy (e.g., myotonic dystrophy type 1 or DM1). In some instances, myopathy is caused by DM1.

Motor neuron disease (MND) encompasses a neurological disorder that affects motor neurons, cells that control voluntary muscles of the body. Exemplary motor neuron diseases include, but are not limited to, adult motor neuron diseases, infantile spinal muscular atrophy, amyotrophic lateral sclerosis, juvenile spinal muscular atrophy, autoimmune motor neuropathy with multifocal conductor block, paralysis due to stroke or spinal cord injury, or skeletal immobilization due to trauma.

Diabetes (diabetes mellitus, DM) comprises type 1 diabetes, type 2 diabetes, type 3 diabetes, type 4 diabetes, double diabetes, latent autoimmune diabetes (LAD), gestational diabetes, neonatal diabetes mellitus (NDM), maturity onset diabetes of the young (MODY), Wolfram syndrome, Alstrom syndrome, prediabetes, or diabetes insipidus. Type 2 diabetes, also called non-insulin dependent diabetes, is the most common type of diabetes accounting for 95% of all diabetes cases. In some instances, type 2 diabetes is caused by a combination of factors, including insulin resistance due to pancreatic beta cell dysfunction, which in turn leads to high blood glucose levels. In some cases, increased glucagon levels stimulate the liver to produce an abnormal amount of unneeded glucose, which contributes to high blood glucose levels. Type 1 diabetes, also called insulin-dependent diabetes, comprises about 5% to 10% of all diabetes cases. Type 1 diabetes is an autoimmune disease where T cells attack and destroy insulin-producing beta cells in the pancreas. In some embodiments, Type 1 diabetes is caused by genetic and environmental factors. Type 4 diabetes is a type of diabetes affecting about 20% of diabetic patients age 65 and over. In some embodiments, type 4 diabetes is characterized by age-associated insulin resistance. Type 3 diabetes is used as a term for Alzheimer's disease resulting in insulin resistance in the brain.

Chronic obstructive pulmonary disease (COPD) is a type of obstructive lung disease characterized by long-term breathing problems and poor airflow. Chronic bronchitis and emphysema are two different types of COPD.

Liver disease (or hepatic disease) comprises fibrosis, cirrhosis, hepatitis, alcoholic liver disease, hepatic steatosis, a hereditary disease, or primary liver cancer.

Congestive heart failure is a condition in which the heart is unable to pump enough blood and oxygen to the body's tissues.

Chronic renal failure or chronic kidney disease is a condition characterized by a gradual loss of kidney function over time.

In some embodiments, chronic infection such as AIDS further leads to muscle atrophy.

Sepsis is an immune response to an infection leading to tissue damage, organ failure, and/or death.

Fasting is a willing abstinence or reduction from some or all food, drinks, or both, for a period of time.

Sarcopenia is the continuous process of muscle atrophy in the course of regular aging that is characterized by a gradual loss of muscle mass and muscle strength over a span of months and years. A regular aging process means herein an aging process that is not influenced or accelerated by the presence of disorders and diseases which promote skeletomuscular neurodegeneration.

In some instances, treatment with a glucocorticoid further results in muscle atrophy. Exemplary glucocorticoids include, but are not limited to, cortisol, dexamethasone, betamethasone, prednisone, methylprednisolone, and prednisolone.

Disuse-associated muscle atrophy results when a limb is immobilized (e.g., due to a limb or joint fracture or an orthopedic surgery such as a hip or knee replacement surgery). As used herein, "immobilization" or "immobilized" refers to the partial or complete restriction of movement of limbs, muscles, bones, tendons, joints, or any other body parts for an extended period of time (e.g., for 2 days, 3 days, 4 days, 5 days, 6 days, a week, two weeks, or more). In some instances, a period of immobilization includes short periods or instances of unrestrained movement, such as to bathe, to replace an external device, or to adjust an external device. Limb immobilization is optionally carried out by any variety of external devices including, but are not limited to, braces, slings, casts, bandages, and splints (any of which is optionally composed of hard or soft material including but not limited to cloth, gauze, fiberglass, plastic, plaster, or metal), as well as any variety of internal devices including surgically implanted splints, plates, braces, and the like. In the context of limb immobilization, the restriction of movement involves a single joint or multiple joints (e.g., simple joints such as the shoulder joint or hip joint, compound joints such as the radiocarpal joint, and complex joints such as the knee joint, including but not limited to one or more of the following: articulations of the hand, shoulder joints, elbow joints, wrist joints, auxiliary articulations, sternoclavicular joints, vertebral articulations, temporomandibular joints, sacroiliac joints, hip joints, knee joints, and articulations of the foot), a single tendon or ligament or multiple tendons or ligaments (e.g., including but not limited to one or more of the following: the anterior cruciate ligament, the posterior cruciate ligament, rotator cuff tendons, medial collateral ligaments of the elbow and knee, flexor tendons of the hand, lateral ligaments of the ankle, and tendons and ligaments of the jaw or temporomandibular joint), a single bone or multiple bones (e.g., including but not limited to one or more of the Wowing: the skull, mandible, clavicle, ribs, radius, ulna, humorous, pelvis, sacrum, femur, patella, phalanges, carpals, metacarpals, tarsals, metatarsals, fibula, tibia, scapula, and vertebrae), a single muscle or multiple muscles (e.g., including but not limited to one or more of the following: latissimus dorsi, trapezius, deltoid, pectorals, biceps, triceps, external obliques, abdominals, gluteus maximus, hamstrings, quadriceps, gastrocnemius, and diaphragm); a single limb or multiple limbs one or more of the arms and legs), or the entire skeletal muscle system or portions thereof (e.g., in the case of a full body cast or spica cast).

Myotonic dystrophy is a multisystemic neuromuscular disease comprising two main types: myotonic dystrophy type 1 (DM1) and myotonic dystrophy type 2 (DM2). DM1 is caused by a dominantly inherited "CTG" repeat expansion in the gene DM protein kinase (DMPK), which when transcribed into mRNA, forms hairpins that bind with high affinity to the Muscleblind-like (MBNL) family of proteins. MBNL proteins are involved in post-transcriptional splicing and polyadenylatin site regulation and loss of the MBNL protein functions lead to downstream accumulation of nuclear foci and increase in mis-splicing events and subsequently to myotonia and other clinical symptoms.

In some embodiments, described herein is a method of treating a disease or disorder characterized with an incorrectly spliced mRNA. In some embodiments, an anti-transferrin receptor antibody described herein delivers a polynucleic acid molecule to the site of the incorrectly spliced mRNA transcript to induce exon skipping or exon inclusion.

In some instances, a disease or disorder resulting from improperly spliced or partially spliced mRNA includes, but not limited to, a neuromuscular disease, a genetic disease, cancer, a hereditary disease, or a cardiovascular disease.

In some instances, genetic diseases or disorders include an autosomal dominant disorder, an autosomal recessive disorder, X-linked dominant disorder, X-linked recessive disorder, P-linked disorder, mitochondrial disease, or multifactorial or polygenic disorder.

In some instances, cardiovascular disease such as hypercholesterolemia results from improperly spliced or partially spliced mRNA. In hypercholesterolemia, it has been shown that a single nucleotide polymorphism in exon 12 of the low density lipoprotein receptor (LDLR) promotes exon skipping.

In some instances, improperly spliced or partially spliced mRNA results in cancer. For example, improperly spliced or partially spliced mRNA affects cellular processes involved in cancer including, but not limited to, proliferation, motility, and drug response. In some instances is a solid cancer or a hematologic cancer. In some instances, the cancer is bladder cancer, lung cancer, brain cancer, melanoma, breast cancer, Non-Hodgkin lymphoma, cervical cancer, ovarian cancer, colorectal cancer, pancreatic cancer, esophageal cancer, prostate cancer, kidney cancer, skin cancer, leukemia, thyroid cancer, liver cancer, or uterine cancer.

Improperly spliced or partially spliced mRNA in some instances causes a neuromuscular disease or disorder. Exemplary neuromuscular diseases include muscular dystrophy such as Duchenne muscular dystrophy, Becker muscular dystrophy, facioscapulohumeral muscular dystrophy, congenital muscular dystrophy, or myotonic dystrophy. In some instances, muscular dystrophy is genetic. In some instances, muscular dystrophy is caused by a spontaneous mutation. Becker muscular dystrophy and Duchenne muscular dystrophy have been shown to involve mutations in the DMD gene, which encodes the protein dystrophin. Facioscapulohumeral muscular dystrophy has been shown to involve mutations in double homeobox, 4 (DUX4) gene.

In some instances, improperly spliced or partially spliced mRNA causes Duchenne muscular dystrophy. Duchenne muscular dystrophy results in severe muscle weakness and is caused by mutations in the DMD gene that abolishes the production of functional dystrophin. In some instances, Duchenne muscular dystrophy is a result of a mutation in an exon in the DMD gene. In some instances, Duchenne muscular dystrophy is a result of a mutation in at least one of exon 1, 2, 3, 4, 5, 6, 7, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78 and 79 in the DMD gene. In some instances, Duchenne muscular dystrophy is a result of a mutation in at least one of exon 3, 4, 5, 6, 7, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, and 63 in the DMD gene. In some instances, Duchenne muscular dystrophy is a result of a mutation in at least one of exon 8, 23, 35, 43, 44, 45, 50, 51, 52, 53, and 55 in the DMD gene. In some instances, multiple exons are mutated. For example, mutation of exons 48-50 is common in Duchenne muscular dystrophy patients. In some instances, Duchenne muscular dystrophy is a result of mutation of exon 51. In some instances, Duchenne muscular dystrophy is a result of mutation of exon 23. In some instances, a mutation involves a deletion of one or multiple exons. In some instances, a mutation involves a duplication of one or multiple exons. In some instances, a mutation involves a point mutation in an exon. For example, it has been shown that some patients have a nonsense point mutation in exon 51 of the DMD gene.

Pharmaceutical Formulation

In some embodiments, the pharmaceutical formulations described herein are administered to a subject by multiple administration routes, including but not limited to, parenteral (e.g., intravenous, subcutaneous, intramuscular), oral, intranasal, buccal, rectal, or transdermal administration routes. In some instances, the pharmaceutical composition describe herein is formulated for parenteral (e.g., intravenous, subcutaneous, intramuscular, intra-arterial, intraperitoneal, intrathecal, intracerebral, intracerebroventricular, or intracranial) administration. In other instances, the pharmaceutical composition describe herein is formulated for oral administration. In still other instances, the pharmaceutical composition describe herein is formulated for intranasal administration.

In some embodiments, the pharmaceutical formulations include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations (e.g., nanoparticle formulations), and mixed immediate and controlled release formulations.

In some instances, the pharmaceutical formulation includes multiparticulate formulations. In some instances, the pharmaceutical formulation includes nanoparticle formulations. In some instances, nanoparticles comprise cMAP, cyclodextrin, or lipids. In some cases, nanoparticles comprise solid lipid nanoparticles, polymeric nanoparticles, self-emulsifying nanoparticles, liposomes, microemulsions, or micellar solutions. Additional exemplary nanoparticles include, but are not limited to, paramagnetic nanoparticles, superparamagnetic nanoparticles, metal nanoparticles, fullerene-like materials, inorganic nanotubes, dendrimers (such as with covalently attached metal chelates), nanofibers, nanohorns, nano-onions, nanorods, nanoropes and quantum dots. In some instances, a nanoparticle is a metal nanoparticle, e.g., a nanoparticle of scandium, titanium, vanadium, chromium, manganese, iron, cobalt, nickel, copper, zinc, yttrium, zirconium, niobium, molybdenum, ruthenium, rhodium, palladium, silver, cadmium, hafnium, tantalum, tungsten, rhenium, osmium, iridium, platinum, gold, gadolinium, aluminum, gallium, indium, tin, thallium, lead, bismuth, magnesium, calcium, strontium, barium, lithium, sodium, potassium, boron, silicon, phosphorus, germanium, arsenic, antimony, and combinations, alloys or oxides thereof.

In some instances, a nanoparticle includes a core or a core and a shell, as in a core-shell nanoparticle.

In some instances, a nanoparticle is further coated with molecules for attachment of functional elements (e.g., with one or more of a polynucleic acid molecule or binding moiety described herein). In some instances, a coating comprises chondroitin sulfate, dextran sulfate, carboxymethyl dextran, alginic acid, pectin, carragheenan, fucoidan, agaropectin, porphyran, karaya gum, gellan gum, xanthan gum, hyaluronic acids, glucosamine, galactosamine, chitin (or chitosan), polyglutamic acid, polyaspartic acid, lysozyme, cytochrome C, ribonuclease, trypsinogen, chymotrypsinogen, α-chymotrypsin, polylysine, polyarginine, histone, protamine, ovalbumin or dextrin or cyclodextrin. In some instances, a nanoparticle comprises a graphene-coated nanoparticle.

In some cases, a nanoparticle has at least one dimension of less than about 500 nm, 400 nm, 300 nm, 200 nm, or 100 nm.

In some instances, the nanoparticle formulation comprises paramagnetic nanoparticles, superparamagnetic nanoparticles, metal nanoparticles, fullerene-like materials, inorganic nanotubes, dendrimers (such as with covalently attached metal chelates), nanofibers, nanohorns, nano-onions, nanorods, nanoropes or quantum dots. In some instances, a polynucleic acid molecule or a binding moiety described herein is conjugated either directly or indirectly to the nanoparticle. In some instances, at least 1, 5, 10, 15, 20, 30, 40, 50, 60, 70, 80, 90, 100 or more polynucleic acid molecules or binding moieties described herein are conjugated either directly or indirectly to a nanoparticle.

In some embodiments, the pharmaceutical formulation comprise a delivery vector, e.g., a recombinant vector, the delivery of the polynucleic acid molecule into cells. In some instances, the recombinant vector is DNA plasmid. In other instances, the recombinant vector is a viral vector. Exemplary viral vectors include vectors derived from adeno-associated virus, retrovirus, adenovirus, or alphavirus. In some instances, the recombinant vectors capable of expressing the polynucleic acid molecules provide stable expression in target cells. In additional instances, viral vectors are used that provide for transient expression of polynucleic acid molecules.

In some embodiments, the pharmaceutical formulations include a carrier or carrier materials selected on the basis of compatibility with the composition disclosed herein, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. Pharmaceutically compatible carrier materials include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

In some instances, the pharmaceutical formulations further include pH adjusting agents or buffering agents which include acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In some instances, the pharmaceutical formulation includes one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Therapeutic Regimens

In some embodiments, the pharmaceutical compositions described herein are administered for therapeutic applications. In some embodiments, the pharmaceutical composition is administered once per day, twice per day, three times per day or more. The pharmaceutical composition is administered daily, every day, every alternate day, five days a week, once a week, every other week, two weeks per month, three weeks per month, once a month, twice a month, three times per month, or more. The pharmaceutical composition is administered for at least 1 month, 2 months, 3 months, 4 months, 5 months, 6 months, 7 months, 8 months, 9 months, 10 months, 11 months, 12 months, 18 months, 2 years, 3 years, or more.

In some embodiments, one or more pharmaceutical compositions are administered simultaneously, sequentially, or at an interval period of time. In some embodiments, one or more pharmaceutical compositions are administered simultaneously. In some cases, one or more pharmaceutical compositions are administered sequentially. In additional cases, one or more pharmaceutical compositions are administered at an interval period of time (e.g., the first administration of a first pharmaceutical composition is on day one followed by an interval of at least 1, 2, 3, 4, 5, or more days prior to the administration of at least a second pharmaceutical composition).

In some embodiments, two or more different pharmaceutical compositions are coadministered. In some instances, the two or more different pharmaceutical compositions are coadministered simultaneously. In some cases, the two or more different pharmaceutical compositions are coadministered sequentially without a gap of time between administrations. In other cases, the two or more different pharmaceutical compositions are coadministered sequentially with a gap of about 0.5 hour, 1 hour, 2 hour, 3 hour, 12 hours, 1 day, 2 days, or more between administrations.

In the case wherein the patient's status does improve, upon the doctor's discretion the administration of the composition is given continuously; alternatively, the dose of the composition being administered is temporarily reduced or temporarily suspended for a certain length of time (i.e., a "drug holiday"). In some instances, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday is from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained.

In some embodiments, the amount of a given agent that correspond to such an amount varies depending upon factors such as the particular compound, the severity of the disease, the identity (e.g., weight) of the subject or host in need of treatment, but nevertheless is routinely determined in a manner known in the art according to the particular circumstances surrounding the case, including, e.g., the specific agent being administered, the route of administration, and the subject or host being treated. In some instances, the desired dose is conveniently presented in a single dose or as divided doses administered simultaneously (or over a short period of time) or at appropriate intervals, for example as two, three, four or more sub-doses per day.

The foregoing ranges are merely suggestive, as the number of variables in regard to an individual treatment regime is large, and considerable excursions from these recommended values are not uncommon. Such dosages is altered depending on a number of variables, not limited to the activity of the compound used, the disease or condition to be treated, the mode of administration, the requirements of the individual subject, the severity of the disease or condition being treated, and the judgment of the practitioner.

In some embodiments, toxicity and therapeutic efficacy of such therapeutic regimens are determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it is expressed as the ratio between LD50 and ED50. Compounds exhibiting high therapeutic indices are preferred. The data obtained from cell culture assays and animal studies are used in formulating a range of dosage for use in human. The dosage of such compounds lies preferably within a range of circulating concentrations that include the ED50 with minimal toxicity. The dosage varies within this range depending upon the dosage form employed and the route of administration utilized.

Kits/Article of Manufacture

Disclosed herein, in certain embodiments, are kits and articles of manufacture for use with one or more of the compositions and methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include anti-transferrin receptor receptor antibodies and optionally one or more target nucleic acid molecules described herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error.

The section headings used herein are for organizational purposes only and are not to be construed as limiting the subject matter described.

"Antibodies" and "immunoglobulins" (Igs) are glycoproteins having the same structural characteristics. The terms are used synonymously. In some instances, the antigen specificity of the immunoglobulin is known.

The term "antibody" is used in the broadest sense and covers fully assembled antibodies, antibody fragments that can bind antigen (e.g., Fab, F(ab')$_2$, Fv, single chain antibodies, diabodies, antibody chimeras, hybrid antibodies, bispecific antibodies, humanized antibodies, and the like), and recombinant peptides comprising the forgoing.

The terms "monoclonal antibody" and "mAb" as used herein refer to an antibody obtained from a substantially homogeneous population of antibodies, i.e., the individual antibodies comprising the population are identical except for possible naturally occurring mutations that may be present in minor amounts.

Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy-chain variable domains.

The term "variable" refers to the fact that certain portions of the variable domains differ extensively in sequence among antibodies. Variable regions confer antigen-binding specificity. However, the variability is not evenly distributed throughout the variable domains of antibodies. It is concentrated in three segments called complementarity determining regions (CDRs) or hypervariable regions, both in the light chain and the heavy-chain variable domains. The more highly conserved portions of variable domains are celled in the framework (FR) regions. The variable domains of native heavy and light chains each comprise four FR regions, largely adopting a β-pleated-sheet configuration, connected by three CDRs, which form loops connecting, and in some cases forming part of, the β-pleated-sheet structure. The CDRs in each chain are held together in close proximity by the FR regions and, with the CDRs from the other chain, contribute to the formation of the antigen-binding site of antibodies (see, Kabat et al. (1991) NIH PubL. No. 91-3242, Vol. I, pages 647-669). The constant domains are not involved directly in binding an antibody to an antigen, but exhibit various effector functions, such as Fc receptor (FcR) binding, participation of the antibody in antibody-dependent cellular toxicity, initiation of complement dependent cytotoxicity, and mast cell degranulation.

The term "hypervariable region," when used herein, refers to the amino acid residues of an antibody that are responsible for antigen-binding. The hypervariable region comprises amino acid residues from a "complementarily determining region" or "CDR" (i.e., residues 24-34 (L1), 50-56 (L2), and 89-97 (L3) in the light-chain variable domain and 31-35 (H1), 50-65 (H2), and 95-102 (H3) in the heavy-chain variable domain; Kabat et al. (1991) Sequences of Proteins of Immunological Interest, 5th Ed. Public Health Service, National Institute of Health, Bethesda, Md.) and/or those residues from a "hypervariable loop" (i.e., residues 26-32 (L1), 50-52 (L2), and 91-96 (L3) in the light-chain variable domain and (H1), 53-55 (H2), and 96-101 (13) in the heavy chain variable domain; Clothia and Lesk, (1987) J. Mol. Biol., 196:901-917). "Framework" or "FR" residues are those variable domain residues other than the hypervariable region residues, as herein deemed.

"Antibody fragments" comprise a portion of an intact antibody, preferably the antigen-binding or variable region of the intact antibody. Examples of antibody fragments include Fab, Fab, F(ab')2, and Fv fragments; diabodies; linear antibodies (Zapata et al. (1995) Protein Eng. 10:1057-1062); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment that contains a complete antigen recognition and binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain ($C_{H1}$) of the heavy chain. Fab fragments differ from Fab' fragments by the addition of a few residues at the carboxy terminus of the heavy chain $C_{H1}$ domain including one or more cysteines from the antibody hinge region. Fab'-SH is the designation herein for Fab' in which the cysteine residue(s) of the constant domains bear a free thiol group. Fab' fragments are produced by reducing the F(ab')2 fragment's heavy chain disulfide bridge. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of human immunoglobulins: IgA, IgD, IgE, IgG, IgM, and IgY, and several of these may be further divided into subclasses (isotypes), e.g., IgG1, IgG2, IgG3, IgG4, IgA1, and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known. Different isotypes have different effector functions. For example, human IgG1 and IgG3 isotypes have ADCC (antibody dependent cell-mediated cytotoxicity) activity.

In some instances, the CDRs of an antibody is determined according to (i) the Kabat numbering system (Kabat et al. (197) Ann. NY Acad. Sci. 190:382-391 and, Kabat et al. (1991) Sequences of Proteins of Immunological Interest Fifth Edition, U.S. Department of Health and Human Services, NIH Publication No. 91-3242); or (ii) the Chothia numbering scheme, which will be referred to herein as the "Chothia CDRs" (see, e.g., Chothia and Lesk, 1987, *J. Mol. Biol.*, 196:901-917; Al-Lazikani et al., 1997, *J Mol. Biol.*, 273:927-948; Chothia et al., 1992, *J. Mol. Biol.*, 227:799-817; Tramontano A et al., 1990, *J. Mol. Biol.* 215(1): 175-82; and U.S. Pat. No. 7,709,226); or (iii) the ImMunoGeneTics (IMGT) numbering system, for example, as described in Lefranc, M.-P., 1999, *The Immunologist*, 7: 132-136 and Lefranc, M.-P. et al, 1999, *Nucleic Acids Res.*, 27:209-212 ("IMGT CDRs"); or (iv) MacCallum et al, 1996, *J. Mol. Biol.*, 262:732-745. See also, e.g., Martin, A., "Protein Sequence and Structure Analysis of Antibody Variable Domains," in Antibody Engineering, Kontermann and Diibel, eds., Chapter 31, pp. 422-439, Springer-Verlag, Berlin (2001).

With respect to the Kabat numbering system, CDRs within an antibody heavy chain molecule are typically present at amino acid positions 31 to 35, which optionally can include one or two additional amino acids, following 35 (referred to in the Kabat numbering scheme as 35 A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). As is well known to those of skill in the art, using the Kabat numbering system, the actual linear amino acid sequence of the antibody variable domain can contain fewer or additional amino acids due to a shortening or lengthening of a FR and/or CDR and, as such, an amino acid's Kabat number is not necessarily the same as its linear amino acid number.

With respect to the Chothia numbering system, CDRs within an antibody heavy chain molecule are typically present at amino acid positions 26 to 31, which optionally can include one or two additional amino acids, following 31 (referred to in the Chotia numbering scheme as 31A and 31 B) (CDR1), amino acid positions 52 to 56 (CDR2), and amino acid positions 95 to 102 (CDR3). Using the Chotia numbering system, CDRs within an antibody light chain molecule are typically present at amino acid positions 24 to 34 (CDR1), amino acid positions 50 to 56 (CDR2), and amino acid positions 89 to 97 (CDR3). As is well known to those of skill in the art, using the Chotia numbering system, the actual linear amino acid sequence of the antibody variable domain can contain fewer or additional amino acids due to a shortening or lengthening of a FR and/or CDR and, as such, an amino acid's Chotia number is not necessarily the same as its linear amino acid number.

The term "chimeric" antibody refers to an antibody in which a portion of the heavy and/or light chain is derived from a particular source or species, while the remainder of the heavy and/or light chain is derived from a different source or species.

The term "humanized antibody" refers to antibodies in which the framework or the CDRs have been modified to comprise the CDR of an immunoglobulin of different specificity as compared to that of the parent immunoglobulin.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

EXAMPLES

These examples are provided for illustrative purposes only and not to limit the scope of the claims provided herein.

Example 1: Humanized Anti-TfR Antibody Production and Characterization

Nucleic acids encoding exemplary anti-TfR antibodies were stably transfected into CHOK1SV GSKO cells to create 3 stable pools per product. The stable pools were monitored for cell growth and Protein A titre from day 8 post transfection. Once cultures reached a threshold of $0.6 \times 10e^6$ cells/mL at 70% viability, the stable pools were passaged. When the viability of the cells was in excess of 97%, the highest producing pools among the tested pools were used to seed a 600 mL fed batch overgrow culture (FOG) per product, at $0.2 \times 10e^6$ cells/mL. The FOG cultures were fed on days 4 and 8 and harvested on day 11 by centrifugation and sterile filtration. Sterile cell culture supernatant was purified by Protein A purification using 3×5 ml MabSelect-SuRE columns in tandem on an AKTA purifier (run at 10 mL/min). Columns were equilibrated with 50 mM sodium phosphate; 250 mM sodium chloride, pH 7.0, washed with 50 mM sodium phosphate and 1 M sodium chloride, pH 7.0, and eluted with 10 mM sodium formate, pH 3.5. Eluted fractions were neutralized by diluting 1:2 with 2×PBS, then pH adjusted to 7.4 using diluted NaOH.

The antibodies were analyzed by SE-HPLC and SDS-PAGE. Duplicate samples were analyzed by SE-HPLC using a Zorbax GF-250 9.4 mm ID×25 cm column (Agilent). 80 μl aliquots of 1 mg/ml samples were injected and run in 50 mM sodium phosphate, 150 mM sodium chloride, 500 mM L-arginine, pH 6.0 at 1 ml/min for 15 minutes. All variants showed small peaks <16.89% with a retention time of ~7.66 min, consistent with soluble aggregates. Soluble aggregate levels were analyzed using Empower v3 software.

Table 9 illustrates the construct design and HPLC analysis of the tested anti-TfR antibodies.

TABLE 9

| Antibody Name | HC Name | LC Name | Retention Time (Min) | % Monomer |
|---|---|---|---|---|
| 13E4-Variant 2i | 13E_VH2_a | 13E4_VL1 | 8.315 | 95.44 |
| 13E4-Variant 2ii | 13E_VH2_b | 13E4_VL1 | 8.326 | 95.86 |
| 13E4-Variant 2iii | 13E_VH2_c | 13E4_VL1 | 8.324 | 95.85 |
| 13E4-Variant 9i | 13E_VH1_a | 13E4_VL3 | 8.337 | 94.40 |
| 13E4-Variant 9ii | 13E_VH1_b | 13E4_VL3 | 8.347 | 94.62 |
| 13E4-Variant 9iii | 13E_VH1_c | 13E4_VL3 | 8.324 | 96.28 |
| 13E4-Variant 15i | 13E_VH3_a | 13E4_VL4 | 8.311 | 83.11 |
| 13E4-Variant 15ii | 13E_VH3_b | 13E4_VL4 | 8.316 | 87.39 |
| 13E4-Variant 15iii | 13E_VH3_c | 13E4_VL4 | 8.311 | 88.50 |

The binding kinetics of nine exemplary humanized anti-TfR antibodies and the parent chimeric antibody were characterized. Studies were run on a BioRad ProteOn XPR36 optical biosensor using a GLM sensor chip coated with Protein A for mAb capture. Running buffer included 10 mM HEPES, 150 mM NaCl, pH 7.4 with 0.05% tween-20 with 0.2 mg/ml BSA. Data were collected at 25 degrees C. All mAbs were diluted into running buffer to 2 ug/ml based on the stock concentration provided. Each was then captured for 40 seconds over a Protein A surface.

hTfR (100 ug) was dissolved into 300 uL of water to yield a 4.3 uM stock concentration. hTfR was diluted to 43 nM as the highest concentration and tested in a 3 fold dilution series. hTfR was injected at 200 ul/min for 2 minutes followed by a one-hour dissociation phase.

Response data were processed by subtracting data from the inner-spot reference surfaces, as well as double referenced with a buffer injection.

Table 10 illustrates the binding constants determined at 25° C.

TABLE 10

| | $k_a$ (M$^{-1}$s$^{-1}$) | $k_d$ (s$^{-1}$) | $K_D$ (pM) |
|---|---|---|---|
| 13E4_WT 1st | 1.0608(2)*e6 | 3.7(2)e-7 | 0.35(1) |
| 13E4_WT 2nd | 9.03(1)e5 | 1.50(2)e-6 | 1.66(1) |
| 13E4_WT 3rd | 8.402(9)e5 | 1.18(2)e-6 | 1.40(1) |
| Average (n = 3) | 9[1]**e5 | 1.0[6]e-6 | 1.1[7] |
| 13E4_variant 2-i | 9.132(1)e5 | 3.9(2)e-7 | 0.43(1) |
| 13E4_variant 2-ii | 8.801(1)e5 | 4.3(2)e-7 | 0.49(1) |
| 13E4_variant 2-iii | 8.623(1)e5 | 8.2(2)e-7 | 0.95(1) |
| 13E4_variant 9-i | 8.427(2)e5 | 1.02(2)e-6 | 1.21(2) |
| 13E4_variant 9-ii | 7.843(2)e5 | 1.81(3)e-6 | 2.31(1) |
| 13E4_variant 9-iii | 7.913(8)e5 | 4.17(2)e-6 | 5.27(1) |
| 13E4_variant 15-i | 7.205(7)e5 | 6.13(2)e-6 | 8.51(1) |
| 13E4_variant 15-ii | 6.966(8)e5 | 9.14(3)e-6 | 13.1(1) |
| 13E4_variant 15-iii | 6.947(9)e5 | 6.94(3)e-6 | 9.99(1) |

*Number in parentheses represents the standard error in the last reported digit based on a fit of the data set.
**Number in brackets represent the experiment standard deviation based on replicate data sets.
For example, 9[1]e5 represents (9 ± 1)e5.

Example 2

In Vivo Gene Downregulation Using a hIgG2 TfR1 Chimeric Antibody siRNA (SSB) Conjugate The CDRs of a mouse IgG2 antibody against hTfR1 were subcloned into a human IgG2 background and transfected, see Example 4 for sequence, into CHO-K1 SP cells. Stable cell pools were selected, amplified and seeded in Dynamis medium (GIBCO) in cellbags (GE Healthcare) at 37° C. with 5% CO2 using a Wave Bioreactor (GE Healthcare). 8% of final culture volume (25 liters) was fed every two days stating at day 4 for a total of 14 days incubation. The culture supernatant was harvested, depth filtered, and purified using a Monofinity A Resin (GenScript) at a flow rate of 30 ml/min. The buffer of the eluted protein was changed to PBS, and the purified protein was analyzed by SDS-PAGE under reducing and non-reducing conditions and SEC-HPLC for molecular weight and purity. The final protein was >98% pure.

Conjugation of the TfR1-IgG2 mAb Chimera to SSB siRNA Using a Bis-Maleimide (BisMal) Linker For the conjugate used in this experiment a SSB siRNA duplex was used. The sequence of the 21 mer SSB guide/antisense strand was (5' to 3') UUACAUUAAAGUCU-GUUGUUU (SEQ ID NO: 81). Single strands were fully assembled on solid phase using standard phospharamidite chemistry and purified using HPLC. Base, sugar and phosphate modifications that are well described in the field of RNAi were used to optimize the potency of the duplex and reduce immunogenicity. The siRNA passenger strand contained a C6-NH$_2$ conjugation handle on the 5' end, see FIG. 1. The siRNA duplex was designed as a blunt ended duplex with 19 bases of complementarity and one 3' dinucleotide overhang. The conjugation handle was connected to siRNA passenger strand via a phosphodiester on the terminal base, see FIG. 2.

Step 1: Antibody Reduction with TCEP

Antibody was buffer exchanged with 25 mM borate buffer (pH 8) with 1 mM DTPA and made up to 10 mg/ml concentration. To this solution, 4 equivalents of TCEP in the same borate buffer were added and incubated for 2 hours at 37° C. The resultant reaction mixture was combined with a solution of BisMal-siRNA (1.25 equivalents) in pH 6.0 10 mM acetate buffer at room temperature (RT) and kept at 4° C. overnight. Analysis of the reaction mixture by analytical SAX column chromatography showed antibody siRNA conjugate along with unreacted antibody and siRNA. The reaction mixture was treated with 10 EQ of N-ethylmaleimide (in DMSO at 10 mg/mL) to cap any remaining free cysteine residues.

Step 2: Purification

The crude reaction mixture was purified by AKTA Pure FPLC using anion exchange chromatography (SAX) method-1. Fractions containing DAR1 antibody-siRNA conjugates were isolated, concentrated and buffer exchanged with pH 7.4 PBS.

Anion Exchange Chromatography Method (SAX)-1.

Column: Tosoh Bioscience, TSKGel SuperQ-SPW, 21.5 mm ID×15 cm, 13 μm

Solvent A: 20 mM TRIS buffer, pH 8.0; Solvent B: 20 mM TRIS, 1.5 M NaCl, pH 8.0; Flow Rate: 6.0 ml/min Gradient:

| a) | % A | % B | Column Volume |
|---|---|---|---|
| b) | 100 | 0 | 1 |
| c) | 81 | 19 | 0.5 |
| d) | 50 | 50 | 13 |
| e) | 40 | 60 | 0.5 |
| f) | 0 | 100 | 0.5 |
| g) | 100 | 0 | 2 |

Strong Anion Exchange Chromatography (SAX) Method-2

Column: Thermo Scientific, ProPac™ SAX-10, Bio LC™, 4×250 mm

Solvent A: 80% 10 mM TRIS pH 8, 20% ethanol; Solvent B: 80% 10 mM TRIS pH 8, 20% ethanol, 1.5 M NaCl; Flow Rate: 0.75 ml/min
Gradient:

| a) | Time | % A | % B |
|---|---|---|---|
| b) | .0 | 90 | 10 |
| c) | 3.00 | 90 | 10 |
| d) | 11.00 | 40 | 60 |
| e) | 14.00 | 40 | 60 |
| f) | 15.00 | 20 | 80 |
| g) | 16.00 | 90 | 10 |
| h) | 20.00 | 90 | 10 |

The purity of the conjugate was assessed by analytical HPLC using SAX method-2 (Table 11).

TABLE 11

| Conjugate | SAX retention time (min) | % purity (by peak area) |
|---|---|---|
| TfR-SSB DAR 1 | 9.41 | 99 |

Analytical data table of conjugates used in this example: HPLC retention time (RT) in minutes and % purity by chromatographic peak area.

In Vitro Activity of hTfR1-IgG2 mAb siRNA DAR1 Conjugates

The ability of the hTfR1-IgG2 mAb siRNA conjugates to bind human and cynoTfR1 was assessed using an ELISA assay. Half-well high-binding 96-well plates (Costar #3690) were coated with recombinant human transferrin receptor protein (Sino Biological 11020-H07H) or recombinant cyno transferrin receptor protein (Sino Biological 90253-C07H) at 1 ng/µL PBS (Gibco 14190) and incubated overnight at 4° C. Plates were washed four times with 100 µL of Tris buffered saline+Tween (20×TBST, Cell Signaling 9997S). 100 µL of Superblock (ThermoFisher PI-37535) was added to each well and incubated for 1 hour at room temperature. The wash step was repeated before the addition of the samples. Samples were added at concentrations up to 10 nM, 50 µL/well. Plates were incubated for another hour at room temp and wash step repeated. Secondary antibody (Peroxidase AffiniPure Goat Anti-Human IgG, Fcγ Fragment Specific, Jackson Immunoresearch, 109-035-098) was diluted 1:5000 in Superblock and 50 µL/well added. Plates were incubated for 1 hour at room temperature and washed one more time. Binding was measured by the addition of 50 µL of 1-Step™ Ultra TMB-ELISA (ThermoFisher, 34028), incubated for 5 minutes, and the reaction was stopped with the addition of 25 µL of Stop Solution 2N sulfuric Acid (R&D Systems DY994). Absorbance was measured at 450 nm, with reference wavelength 570 nm subtracted. Binding constants were determined using GraphPad Prism Specific Binding with Hill Slope.

Figure 3A:
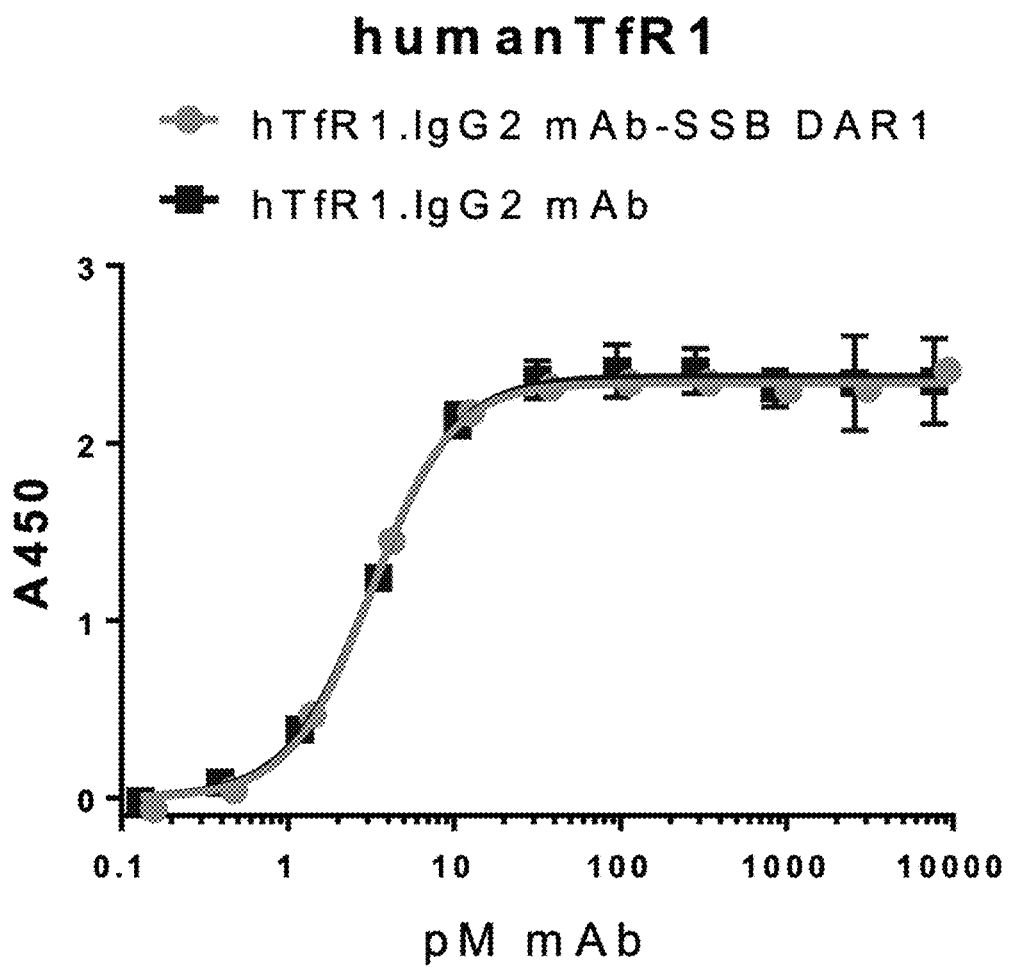
FIG. 3A illustrates in vitro binding of TfR1.IgG2 mAb and TfR1.IgG2 mAb-SSB to recombinant human TfR1.
Figure 3B:
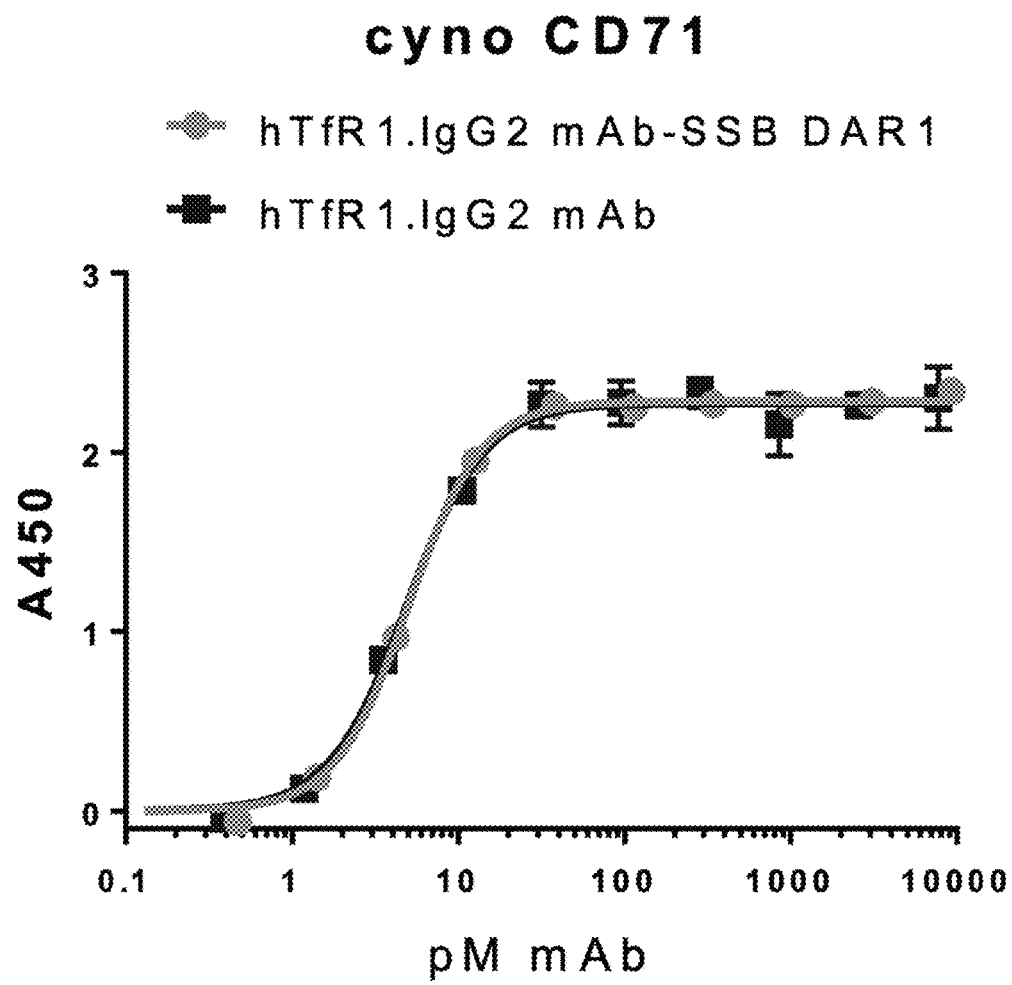
FIG. 3B illustrates in vitro binding of TfR1.IgG2 mAb and TfR1.IgG2 mAb-SSB to recombinant cyno TfR1.

The non-conjugated and conjugated hTfR1.IgG2 mAb antibody binds recombinant human and cyno TfR1 with similar affinity (FIG. 3A-FIG. 3B).

The ability of the TfR1.IgG2 mAb-SSB conjugate to downregulate SSB expression was monitored in HEL92.1.7 and human skeletal muscle cells. HEL92.1.7 cells (ATCC® TIB-180™) were cultured in RPMI 1640 containing 10% fetal bovine serum (Nucleus Biologics FBS1824). Cells were diluted to 100,000/mL and 100 µL was added to each well of the plate. Antibody conjugates were diluted for a maximum concentration of 100 nM. 20 µL of conjugates or PBS as negative control were added to wells of a 96-well plate, the treated cells were placed at 37° C. and 5% CO2 for 72 hours.

Figure 4A:
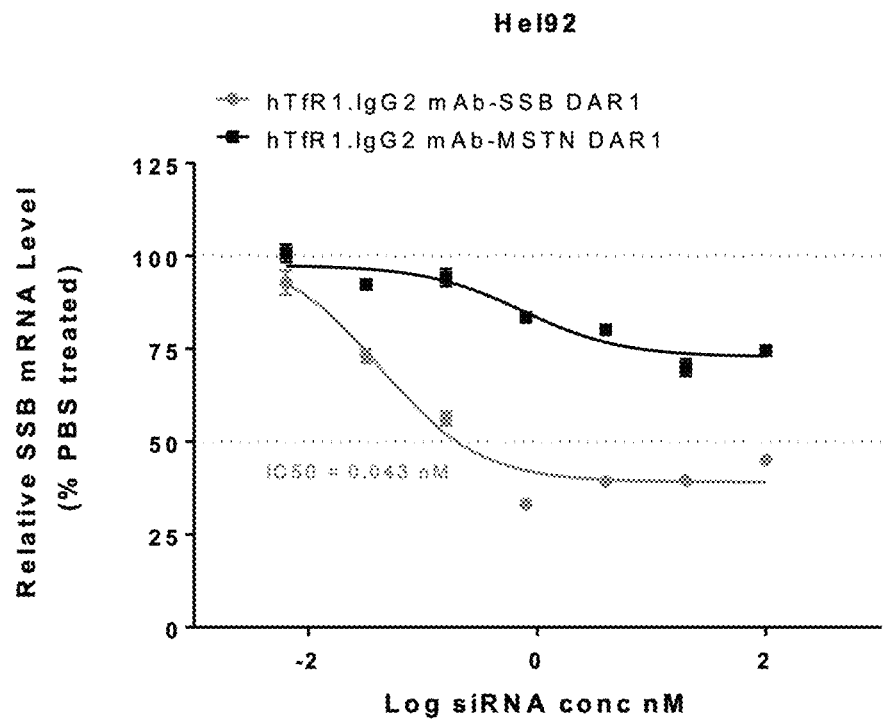
FIG. 4A illustrates SSB mRNA levels in siRNA delivery in He192.1.7 cells treated with hTfR1.IgG2 mAb SSB or hTfR1.IgG2 mAb MSTN (negative control) conjugates.
Figure 4B:
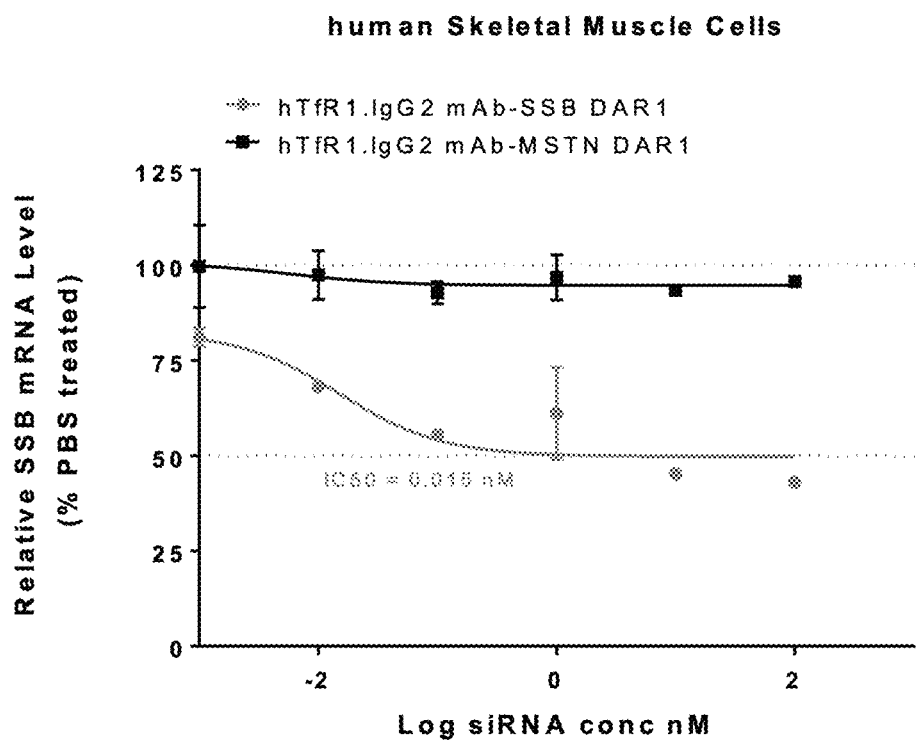
FIG. 4B illustrates SSB mRNA levels in siRNA delivery in immortalized human skeletal muscle cells treated with hTfR1.IgG2 mAb SSB or hTfR1.IgG2 mAb MSTN (negative control) conjugates.

Immortalized human skeletal muscle cells (Institute of Myology, Paris) were plated in 500 µl Skeletal Muscle Cell Growth Medium (PromoCell C-23260) on 24-well collagen plates (Thermo Fisher A1142802) and incubated at 37° C. in 5% CO2 until myoblasts became confluent. At this point differentiation to myotubes was induced by incubation in 500 µl differentiation medium (DMEM (Gibco 10566-016) supplemented with 10 ug/ml Insulin and 50 µg/ml gentamycin) for 4 days. The medium was refreshed and 50 µl TfR1.IgG2 mAb-SSB conjugates diluted in PBS were added. The treated cells were incubated for 72 hours. For harvesting and analysis of either cell type, media was removed from wells and 150 µl of Trizol (Ambion 15596018) was added. Plates were frozen at −80° C. for overnight or longer before analysis. RNA was isolated using a Direct-zol 96 RNA kit following manufacturer's instructions and quantified spectroscopically. RNA (100-200 ng) was reverse transcribed according to manufacturer's instructions using the High Capacity cDNA kit (Thermo Fisher #4368813). mRNA levels were quantified using TaqMan qPCR, using the appropriately designed primers and probes. PPIB (housekeeping gene) was used as an internal RNA loading control. % mRNA was calculated using the ΔΔCt method, with PBS treated cells set to 100% expression. In these experiments the TfR1.IgG2 mAb-SSB conjugate downregulated SSB by up to 60%, whereas SSB were maximally 25% downregulated in cells treated with an TfR1.IgG2 mAb-MSTN conjugate (negative control) (FIG. 4A-FIG. 4B).

Activity and Safety of the hTfR1-IgG2 mAb SSB siRNA Conjugate in Cynomolgus Monkeys The PK, PD, and safety features of the hIgG2 TfR1.mAb-siSSB conjugate were assessed in cynomolgus monkeys. Animals were male, 2-3 years old and weighed between 2-3 kg. Animals were dosed with the conjugate at 30 mg/kg or 60 mg/kg (mAb concentration), or PBS by 30 minutes (+/−3 minutes) intravenous (IV) infusion. Blood specimens and muscle biopsies were collected from peripheral veins of restrained, conscious animals or gastrocnemius and quadriceps of sedated animals, respectively, at different times as outlined in Table 12.

TABLE 12

Schedule of sampling cynomolgus monkeys treated with hTfR1.IgG2 mAb siRNA conjugates.

| Time Point (Study Week) | Hematology | Serum Chemistry | PK | Muscle Biopsy[c] |
|---|---|---|---|---|
| Acclimation (Week −2) | 1x | 1x | — | 1x (Gastroc) |
| Acclimation (Week −1) | 1x | 1x | — | 1x (Gastroc) |
| Dosing Day 1 | 1x | 1x | 3x (5', 4 h) | — |
| Day 2 | 1x | 1x | 1x | — |
| Day 3 | | | 1x | — |
| Day 4 | 1x | 1x | 1x | — |
| Day 8 | 1x | 1x | 1x | — |
| Day 15 | 1x | 1x | 1x | — |
| Day 22 | 1x | 1x | 1x | 1x (Gastroc) |
| Day 29 | 1x | 1x | 1x | 2x (Gastroc, Quad) |

The plasma concentration of hIgG2 TfR1.mAb-siSSB conjugate was determined using a stem-loop qPCR assay.

Briefly, plasma samples were directly diluted in TE buffer+ 0.1% v/v Triton X-100. Standard curves were generated by spiking siRNA into plasma from untreated animals and then serially diluting with TE buffer+0.1% v/v Triton X-100. The antisense strand of the siRNA was reverse transcribed using a TaqMan MicroRNA reverse transcription kit (Applied Biosystems) with 25 nM of a sequence-specific stem-loop RT primer. The cDNA from the RT step was utilized for real-time PCR using TaqMan Fast Advanced Master Mix (Applied Biosystems) with 1.5 µM of forward primer, 0.75 µM of reverse primer, and 0.2 µM of probe. The sequences of the SSB siRNA antisense strands and all primers and probes used to measure them are shown in Table 13. Quantitative PCR reactions were performed using standard cycling conditions in a QuantStudio 7 Flex Real-Time PCR System (Life Technologies). The Ct values were transformed into plasma or tissue concentrations using the linear equations derived from the standard curves.

TABLE 13

Sequences for all siRNA antisense strands, primers, and probes used in the stem-loop qPCR assay.

| Target | Name | Sequence (5'-3') | SEQ ID NO: |
|---|---|---|---|
| SSB | Antisense (guide) | UUACAUUAAAGUCUGUUGUUU | 81 |
| SSB | RT | GTCGTATCCAGTGCAGGGTCCGAGGTATTCGCACTGGATACGACAAACAAC | 82 |
| SSB | Forward | GGCGGCTTACATTAAAGTCTGT | 83 |
| SSB | Reverse | AGTGCAGGGTCCGAG | 84 |
| SSB | Probe | (6FAM)-TGGATACGACAAACAA-(NFQ-MGB) | 85 |

The clearance and half-life of the conjugates are shown in Table 14. The PK properties of these conjugates were similar to mouse anti-transferrin mAb conjugates tested in mice.
Table 14: PK parameter estimates for the hTfR1.IgG2 mAb-SSB conjugate following administration at 30 and 60 mg/kg by 30 min infusion in cynomolgus monkeys (n=3).

TABLE 14

| AOC | Dose (mg/kg) | $AUC_{0-29d}$ (mg/mL)*min | Dose mg/kg | CL mL/min/kg | CL uL/min/kg | alpha $t_{1/2}$ h | beta $t_{1/2}$ h |
|---|---|---|---|---|---|---|---|
| hTfR1.IgG2 mAb-SSB (DAR1) | 3 | 82.89 | 3 | 0.036 | 36 | 12.9 | 230 |
| hTfR1.IgG2 mAb-SSB (DAR1) | 6 | 155.2 | 6 | 0.039 | 39 | 13.8 | 269 |

To assess the siRNA concentration and the activity of the conjugate in muscle, muscle biopsies (gastrocnemius and quadriceps) were obtained according to the schedule shown in Table 12. Muscle biopsies were taken by 6 mm punches, weighed and snap-frozen in liquid nitrogen. Frozen tissue samples were homogenized in 1 ml cold TRIZO1 (vendor). To determine mRNA knockdown, total RNA was extracted from the tissue using a Direct-zol 96 RNA kit following manufacturer's instructions and quantified spectroscopically. RNA (100-200 ng) was reverse transcribed according to manufacturer's instructions using the High Capacity cDNA kit (Thermo Fisher #4368813). SSB mRNA levels were quantified using TaqMan qPCR, using the appropriately designed primers and probes. PPIB (housekeeping gene) was used as an internal RNA loading control. % mRNA was calculated using the ΔΔCt method, with either SSB mRNA levels in the same animal pre-treatment or SSB levels in animals treated with PBS set to 100% expression.

Quantitation of tissue siRNA concentrations was determined using a stem-loop qPCR assay. Briefly, 15-50 mg tissue pieces were homogenized in 500 uL of Trizol using a TissueLyser II plate-based homogenizer (Qiagen) and then diluted in TE buffer+0.1% v/v Triton X-100. Standard curves were generated by spiking siRNA into homogenized tissue from untreated animals and then serially diluting with TE buffer+0.1% v/v Triton X-100. The antisense strand of the siRNA was reverse transcribed using a TaqMan MicroRNA reverse transcription kit (Applied Biosystems) with 25 nM of a sequence-specific stem-loop RT primer. The cDNA from the RT step was utilized for real-time PCR using TaqMan Fast Advanced Master Mix (Applied Biosystems) with 1.5 µM of forward primer, 0.75 µM of reverse primer, and 0.2 µM of probe. The sequences of the SSB siRNA antisense strands and all primers and probes used to measure them are shown in Table 13. Quantitative PCR reactions were performed using standard cycling conditions in a QuantStudio 7 Flex Real-Time PCR System (Life Technologies). The Ct values were transformed into plasma or tissue concentrations using the linear equations derived from the standard curves.

Figure 5A:
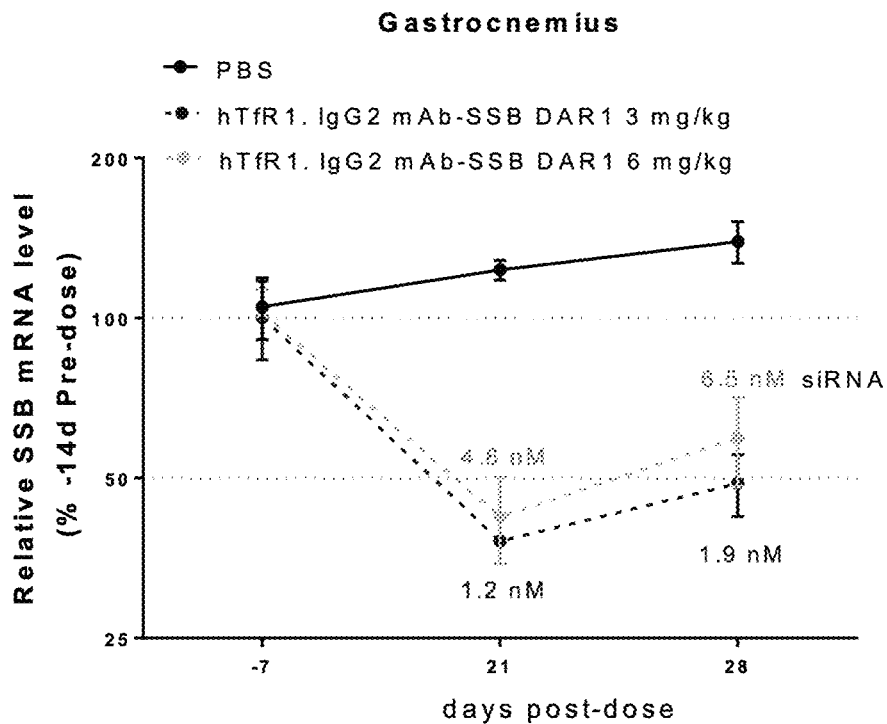
FIG. 5A illustrates SSB mRNA and SSB siRNA levels in gastrocnemius muscle of cynomolgus monkeys following administration of a hTfR1.IgG2 mAb-SSB conjugate at 30 and 60 mg/kg (n=3).
Figure 5B:
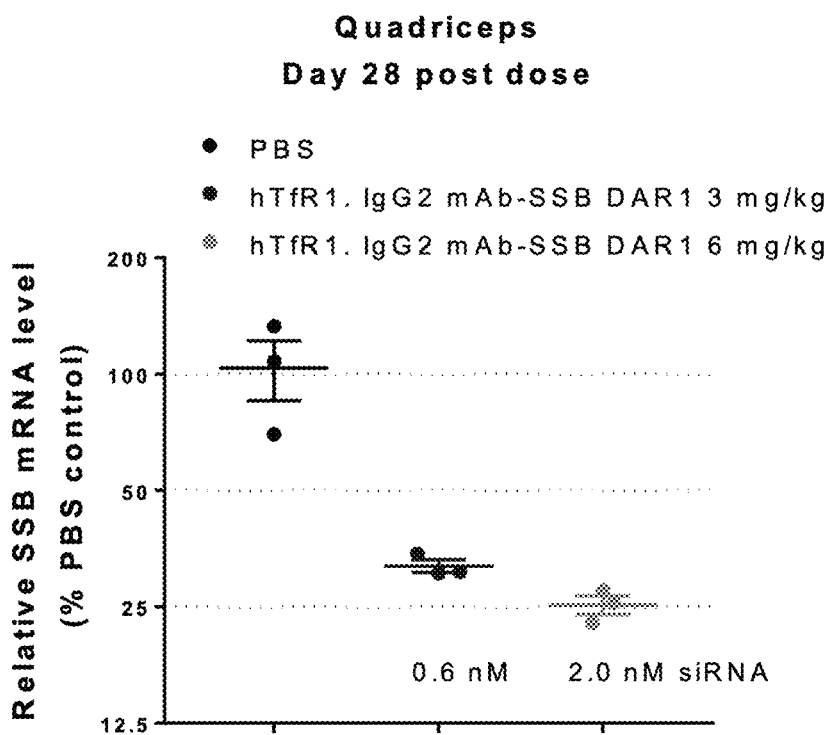
FIG. 5B illustrates SSB mRNA and SSB siRNA levels in quadriceps muscle of cynomolgus monkeys following administration of a hTfR1.IgG2 mAb-SSB conjugate at 30 and 60 mg/kg (n=3).

Treatment of cynomolgus monkeys with the conjugate resulted in downregulation of SSB mRNA in gastrocnemius up to 62% and in quadriceps up to 75% (FIG. 5A and FIG. 5B). The siRNA concentration in these tissues was dose-dependent and between 0.6-1.9 nM and 2.0-6.5 nM for the 30 mg/kg and 60 mg/kg dose, respectively. The activity of the conjugates and the siRNA concentration in the tissues were similar when probed at 21 or 28 days post-dose. These results demonstrate that the chosen TfR1 antibody can effectively deliver siRNAs into primate muscle tissues and that the activity of transferrin receptor-targeting AOCs translate between species.

Figure 6:
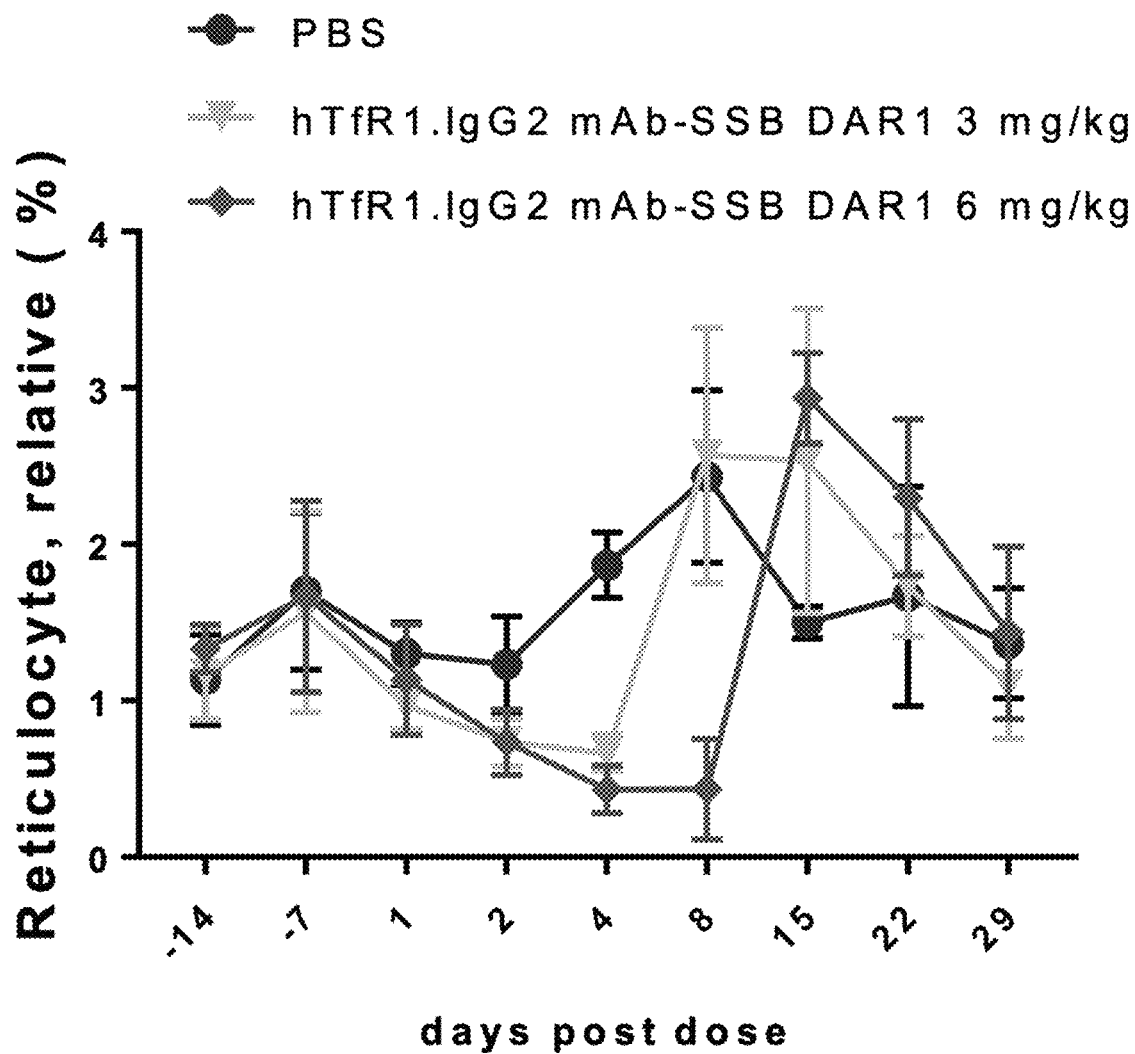
FIG. 6 illustrates relative reticulocyte levels in cynomolgus monkeys before and after dosing with hTfR1. IgG2 mAb-SSB conjugates at 30 and 60 mg/kg.

To monitor the safety of the chosen anti hTfR1 antibody in primates, hematology and clinical chemistry were analyzed according to the schedule shown in table x. With exception of a dose-dependent but transient depletion of reticulocytes (FIG. 6) no treatment-related effects were observed on any hematology or clinical chemistry parameters up to 28 days post dose. The observed transient downregulation of reticulocytes has been described as a side-effect of TfR1 antibodies. Murine TfR1 antibodies with intact effector function or complement binding capabilities have been shown to severely deplete TfR-expressing reticulocytes (Daniels-Wells, et al., "Transferrin receptor 1: a target for antibody-mediated cancer therapy," Immunotherapy 8(9): 991-994 (2016)). Since in primates the fraction of reticulocytes expressing high TfR1 levels is low, depletion of reticulocytes is only transient and less pronounced than in rodents. Importantly, studies by others have shown that this activity can be successfully suppressed by mutations that remove the ADCC/CDC activity of the antibody (WO 2014/189973 A2).

Example 3

Generation, Characterization and Humanization of Human/Cyno Cross-Reactive Anti-TfR1 Antibodies Using modern in silico antibody humanisation and deimmunisation programs that are well described in the art, 16 variants of the chimeric anti-transferrin 1 mAb tested in the NHP study in example 1 were designed, see table XYZ for the sequences of the variants. As part of the design, an assessment of manufacturability by identification of high risk post-translational modifications (PTMs) was undertaken, and where feasible their removal via amino acid substitution was performed as part of the humanisation activities. An assessment of Immunogenicity risk was also undertaken to identify and, where feasible, remove high risk epitopes. Introduction of mutations into the Fc domain of the variants were also undertaken to remove effector functions (ADCC and CDC). The 16 variants were then expressed in mammalian cell culture using techniques well described in the art and were purified using affinity chromatography based on Protein A resin. The mAb variants were then fully characterized and siRNA conjugates made as described below.

Human and Cyno TfR1 ELISA Assay

The goal of these assays was to verify that the 16 variant human anti-TfR1 antibodies bind to both human and cyno TfR1. The Human or Cyno Transferrin Receptor ELISA Assay Protocols are described below:

Half-well high-binding 96-well plates (Costar #3690) were coated with recombinant human transferrin receptor protein (Sino Biological 11020-H07H) or recombinant cyno transferrin receptor protein (Sino Biological 90253-C07H) at 1 ng/µL in PBS (Gibco 14190) and incubated overnight at 4° C. Plates were washed four times with 100 µL of Tris buffered saline+Tween (20×TBST, Cell Signaling 9997S). 100 µL of Superblock (ThermoFisher PI-37535) was added to each well and incubated for 1 hour at room temperature. The wash step was repeated before the addition of the samples. Samples were added at concentrations up to 10 nM, 50 µL/well. Plates were incubated for another hour at room temp and wash step repeated. Secondary antibody (Peroxidase AffiniPure Goat Anti-Human IgG, Fcγ Fragment Specific, Jackson Immunoresearch, 109-035-098) was diluted 1:5000 in Superblock and 50 µL/well added. Plates were incubated for 1 hour at room temperature and washed one more time. Binding was measured by the addition of 50 µL of 1-Step™ Ultra TMB-ELISA (ThermoFisher, 34028), incubated for 5 minutes, and the reaction was stopped with the addition of 25 µL of Stop Solution 2N sulfuric Acid (R&D Systems DY994). Absorbance was measured at 450 nm, with reference wavelength 570 nm subtracted. Binding constants were determined using GraphPad Prism Specific Binding with Hill Slope.

Figure 7:
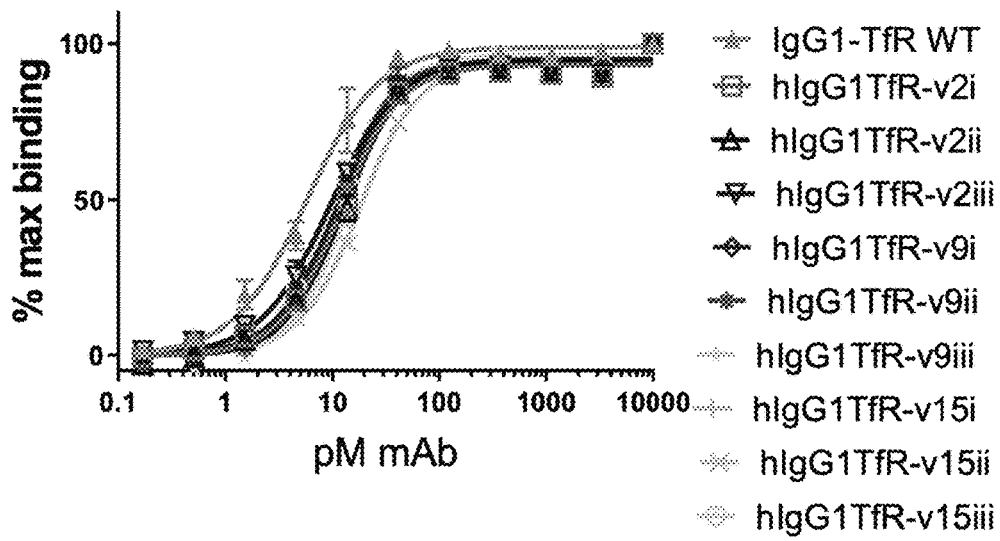
FIG. 7 illustrates the binding constants of exemplary anti-TfR antibodies to cyno CD71.
Figure 8:
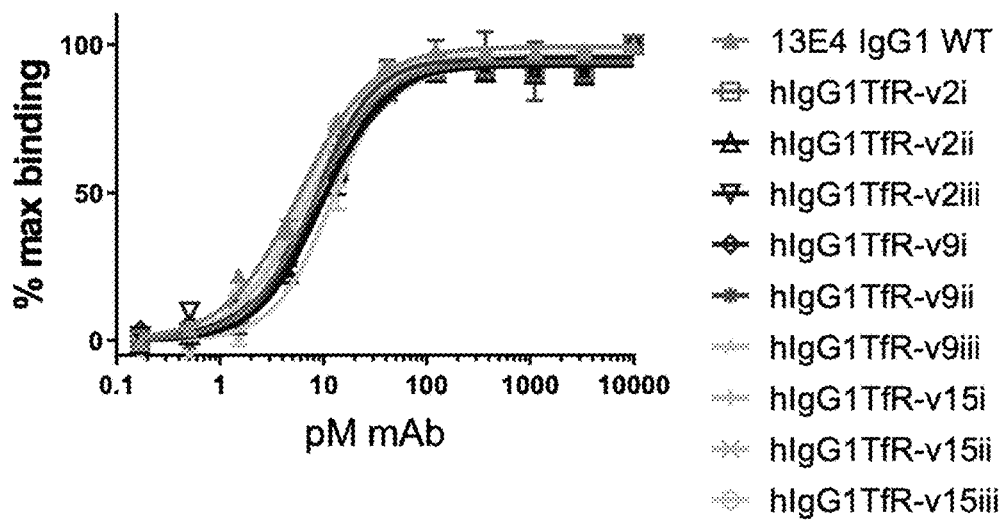
FIG. 8 illustrates the binding constants of exemplary anti-TfR antibodies to human CD71.

FIG. 7 and FIG. 8 illustrate the binding results to cyno CD71 and human CD71, respectively.

Tf-TfR Blocking ELISA Assay

The goal of this assay was to verify that the TfR antibodies bind to TfR in the presence of holo-transferrin.

Figures 9A, 9B:
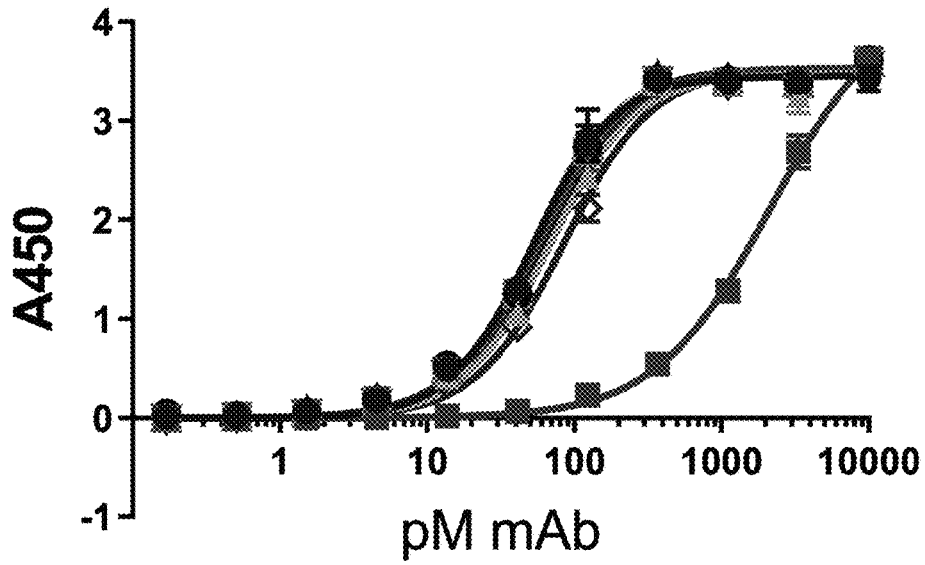
FIG. 9A illustrates binding of exemplary anti-TfR antibodies to TfR under a competitive setting.
FIG. 9B shows the binding constants of the tested anti-TfR antibodies of FIG. 9A.

Antibodies were biotinylated using 50 fold molar excess of EZ-Link No weigh NHS-Biotin (Thermo Scientific A39256) following manufacturer's instructions. Half-well high-bind plates (Costar #3690) were coated with 500 ng/mL purified human holo-transferrin (R&D Systems 2914-HT) in PBS at 4° C. overnight. For comparison, plates were coated directly with hTfR. Plates were washed four times with 100 µL of Tris buffered saline+Tween (20×TBST, Cell Signaling 9997S). 100 µL of Superblock (ThermoFisher PI-37535) was added to each well and incubated for 1 hour at room temperature. The wash step was repeated before the addition of the hTfR (200 ng/mL in 25 µl) to the transferrin plates, or Superblock to the hTfR plates, and incubated for 30 minutes. Biotinylated antibodies were diluted to 20 nM for the high concentration and added to the plates with 3-fold serial dilution. 25 µl/well was added to the 25 µl already in the plate. Plates were incubated for 1 hour, and wash step was repeated. Streptavidin-HRP (R&D Systems DY998) was added following recommended dilution on the package insert, and a final wash step was done. Binding was measured by the addition of 50 µL of 1-Step™ Ultra TMB-ELISA (ThermoFisher, 34028), incubated for 5 minutes, and the reaction was stopped with the addition of 25 µL of Stop Solution 2N sulfuric Acid (R&D Systems DY994). Absorbance was measured at 450 nm, with reference wavelength 570 nm subtracted. Binding constants were determined using GraphPad Prism Specific Binding with Hill Slope. Change in antibody binding constants in the presence versus absense of transferrin is considered relative to the commercially available antibody which is known to have an overlapping epitope with transferrin (AF2474, R&D Systems). See FIG. 9A-FIG. 9B.

HFE-TfR Binding ELISA Assay

The goal of this assay was to verify that the TfR antibodies maintain binding when TfR is bound to HFE.

Figures 10A, 10B:
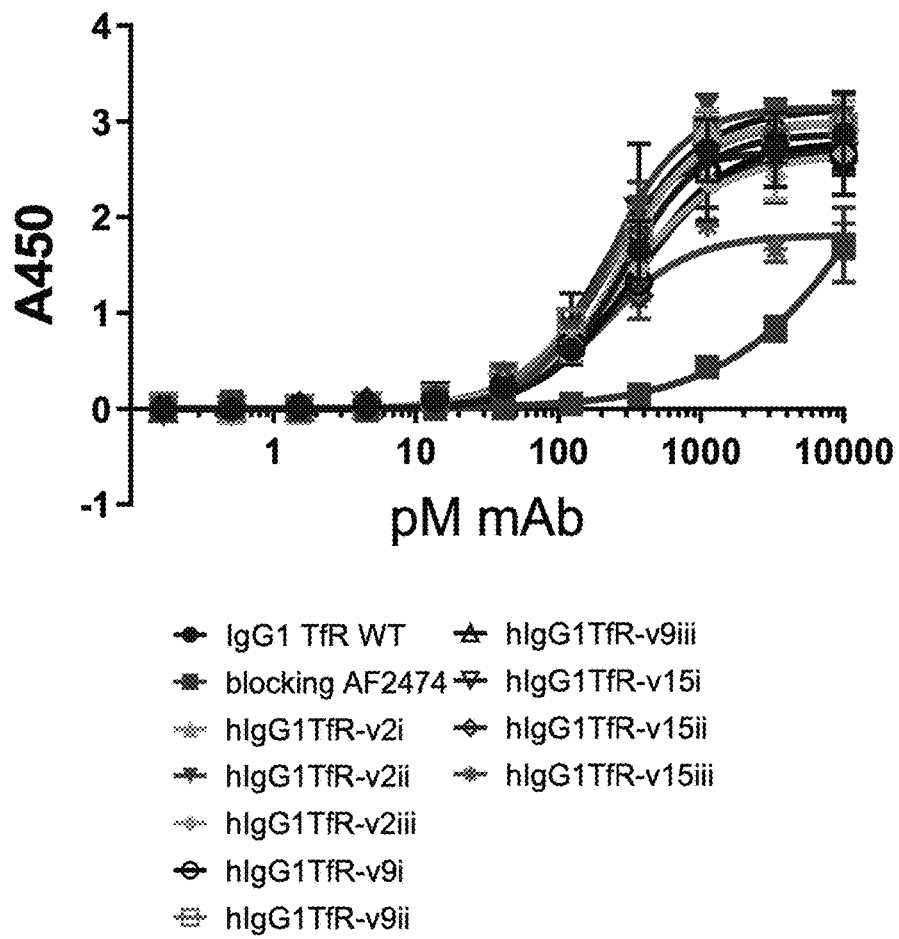
FIG. 10A shows that binding of exemplary anti-TfR antibodies to TfR is maintained.
FIG. 10B shows the binding constants of the tested anti-TfR antibodies of FIG. 10A.

This assay is run following the same method as the TfR binding in the presence of transferrin, with the transferrin replaced by the cofactor HFE (hereditary hemochromatosis protein, mybiosource.com, MBS953891). See FIG. 10A-FIG. 10B.

FcγRIIIA (CD16a) ELISA

Figure 11:
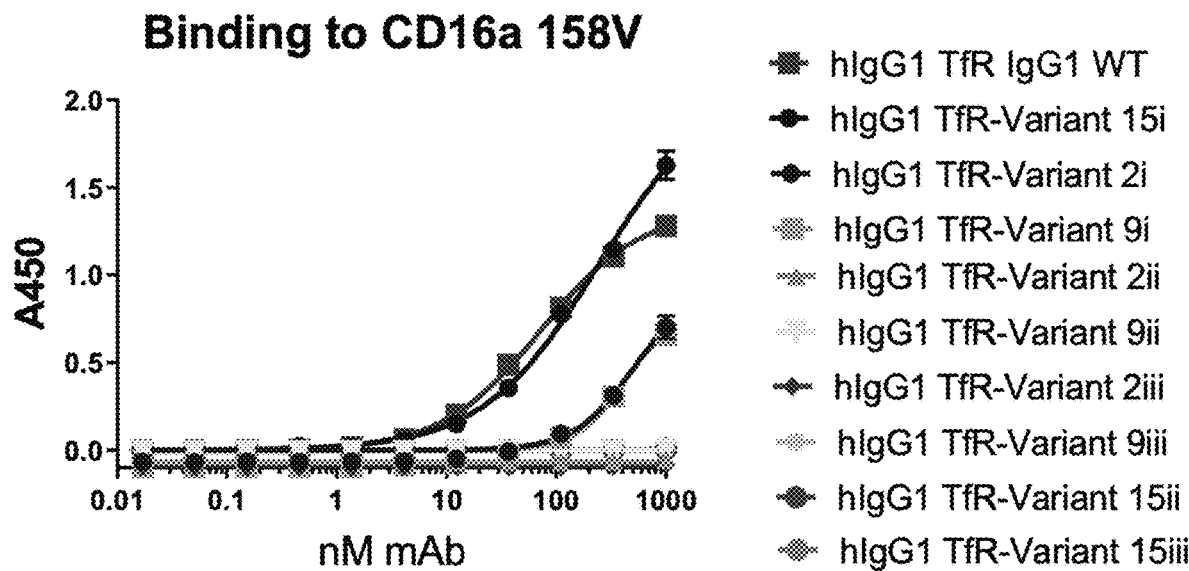
FIG. 11 shows the ADCC activities of exemplary anti-TfR antibodies.
Figure 12:
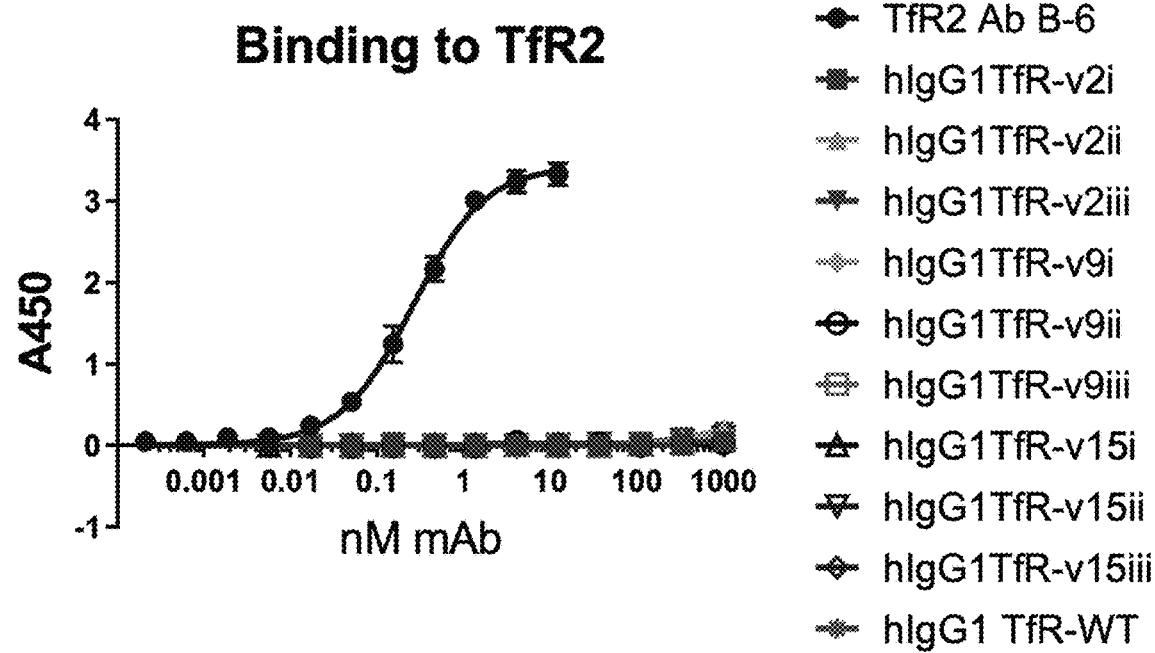
FIG. 12 shows that the anti-TfR antibodies do not bind to TfR2.

The goal of this assay was to determine the potential for ADCC activity of antibodies by measuring binding to FcγRIIIA (CD16a) genotype V158. Half-well high-binding 96-well plates (Costar #3690) were coated with recombinant CD16a protein (Sino Biological 10389-H27H1) at 2 ng/µL in PBS (Gibco 14190) and incubated overnight at 4° C. Plates were washed four times with 100 µL of Tris buffered saline+Tween (20×TBST, Cell Signaling 9997S). 100 µL of Superblock (ThermoFisher PI-37535) was added to each well and incubated for 1 hour at room temperature. The wash step was repeated before the addition of the samples. Samples were added at concentrations up to 1 µM, 50 µL/well. Plates were incubated for another hour at room temp and wash step repeated. Secondary antibody (Peroxidase AffiniPure Goat Anti-Human IgG, Fcγ Fragment Specific, Jackson Immunoresearch, 109-035-098) was diluted 1:5000 in Superblock and 50 µL/well added. Plates were incubated for 1 hour at room temperature and washed one more time. Binding was measured by the addition of 50 µL of 1-Step™ Ultra TMB-ELISA (ThermoFisher, 34028), incubated for 5 minutes, and the reaction was stopped with the addition of 25 µL of Stop Solution 2N sulfuric Acid (R&D Systems DY994). Absorbance was measured at 450 nm, with reference wavelength 570 nm subtracted. Binding constants were determined using GraphPad Prism Specific Binding with Hill Slope. See FIG. 11.

In Vitro Potency Assay in HEL92.1.7 Cells

The goal of this assay was to demonstrate that the TfR mAb conjugates are capable of delivery of siRNA and gene specific downregulation. The mAb variants were either conjugated to an active siRNA (SSB) or a scrambled control (Scr). The HEL92.1.7 cells line (ATCC® TIB-180™) were cultured in RPMI 1640 (Gibco A10491) containing 10% fetal bovine serum (Nucleus Biologics FBS1824). Antibody-siRNA conjugates were diluted for a maximum dose of 100 nM. 20 μl of conjugates were added to wells of a 96-well plate. 20 μl of PBS was added to some wells as an additional negative control. Cells were diluted to 100,000/mL and 100 μl was added to each well of the plate. Cells were placed at 37° C. and 5% $CO_2$ for 72 hours. Media was removed from wells and 150 μl of Trizol (Ambion 15596018) was added. Plates were frozen at −80° C. for overnight or longer before analysis. RNA was isolated using Direct-zol 96 RNA isolation kit (Zymo Research R2056) following manufacturer's instructions. RNA was reverse transcribed according to manufacturer's instructions using High Capacity cDNA kit (Applied biosystems 4368814) and qPCR was done with Taqman Fast Advanced Master Mix (Applied Biosystems 4444558) with SSB and PPIB Taqman probe sets (ThermoFisher Hs04187362_g1 and Hs00168719_m1). % mRNA was calculated using ΔΔCt method, with PBS treated cells set to 100% expression.

The DAR1 conjugates containing an active siRNA (SSB) or an inactive or scrambled siRNA (Scr) and were made and characterized as described in Example 2. For these conjugates, the SSB siRNA contained a Cy5 florescent tag conjugated on position 11 of the passenger strand on the ribose 2' hydroxyl. This was introduced during the solid phase synthesis and did not inhibit the activity of the guide strand but allowed uptake assay to be conducted. The purity of the conjugates was assessed by analytical HPLC using anion exchange chromatography method-2 and the chromatographic retention times and purity are described in the Table 15 below.

TABLE 15

| Conjugate | SAX retention time (min) | % purity (by peak area) |
|---|---|---|
| hIgG1 TfRVar2i-SSB DAR 1 | 9.106 | 98.2 |
| hIgG1 TfR-Var2i-Scr DAR 1 | 8.905 | 98.0 |
| hIgG1 TfR-Var2ii-SSB DAR 1 | 9.059 | 98.3 |
| hIgG1 TfR-Var2ii-Scr DAR 1 | 8.863 | 98.4 |
| hIgG1 TfR-Var2iii-SSB DAR 1 | 9.069 | 98.2 |
| hIgG1 TfR-Var2iii-Scr DAR 1 | 8.871 | 98.5 |
| hIgG1 TfR-Var9i-SSB DAR 1 | 9.066 | 98.4 |
| hIgG1 TfR-Var9i-Scr DAR 1 | 8.867 | 98.5 |
| hIgG1 TfR-Var9ii-SSB DAR 1 | 9.048 | 98.6 |
| hIgG1 TfR-Var9ii-Scr DAR 1 | 8.855 | 98.8 |
| hIgG1 TfR-Var9iii-SSB DAR 1 | 9.069 | 98.6 |
| hIgG1 TfR-Var9iii-Scr DAR 1 | 8.862 | 99.0 |
| hIgG1 TfR-Var15i-SSB DAR 1 | 9.097 | 98.8 |
| hIgG1 TfR-Var15i-Scr DAR 1 | 8.892 | 98.6 |
| hIgG1 TfR-Var15ii-SSB DAR 1 | 9.082 | 98.2 |
| hIgG1 TfR-Var15ii-Scr DAR 1 | 8.882 | 98.8 |
| hIgG1 TfR-Var15iii-SSB DAR 1 | 9.078 | 98.3 |
| hIgG1 TfR-Var15iii-Scr DAR 1 | 8.877 | 98.6 |
| hIgG1 TfR-WT-SSB DAR 1 | 9.045 | 98.6 |
| hIgG1 TfR-WT-Scr DAR 1 | 8.847 | 98.9 |

Analytical data table of conjugates used in this example: HPLC retention time (RT) in minutes and % purity by chromatographic peak area.

Antibody-Dependent Cellular Cytotoxicity (ADCC) Mediated by TfR1 Antibodies and Antibody siRNA Conjugates (ASCs) in PBMCs Studies in mice and nonhuman primates (NHPs) have demonstrated that antibodies binding murine/cyno TfR with effector function and/or complement binding capabilities selectively deplete TfR-expressing reticulocytes. To ascertain whether the variants had effector function, ADCC assays were carried out using peripheral blood mononuclear cells (PBMCs) from healthy human donors as effector cells.

Materials:
PBMC from BUYPBMC.COM, lot #2010113378 with STRONG ADCC activity.
Target cells: HEL-92.1.7 (ATCC, #TIB-180); HEL (#JCRB0062)
Cytotoxicity LDH kit, Pierce (ThermoFisher), #88953
Tissue culture medium with serum (complete medium) RPMI 1640 (Life Technologies) containing 10% heat-inactivated FBS (30 minutes at 56° C.) and 2% L-glutamine
hIgG1 mAb variants Procedure:
Thaw PBMC cells with gentle agitation in a 37° C. water bath. Once thawed, add 1 mL of warm culture media to the vial drop by drop over 30 seconds to allow the cells to adjust to the change in environment. Slowly add the cells to a 15- or 50-mL conical tube containing 9 mL of warm culture media. Rinse the original vial with 1 mL of the cell-containing media to recover cells that may have adhered to the sides; add the rinse media to the conical tube. Pellet the cells by centrifugation at 350×g for 8-12 minutes. Discard the supernatant. Re-suspend the cell pellet by gently tapping (avoid excessive shear forces). Rinse the cells again by adding 10 mL of warm culture media to the conical tube. Pellet the cells by centrifugation at 350×g for 8-12 minutes. Discard the supernatant from the second wash. Re-suspend the cell pellet by gently tapping (avoid excessive shear forces). Resuspend the cells in 10 mL of warm media as required. Incubate at 37° C. overnight in a T75 to acclimate the cells.

Harvest and wash target cell HEL-92 with cold assay media 2×; ensure high viability. Seed target cells in cold 50 μl ($8 \times 10^5$) assay medium (RPMI-1640 with 1% BSA and 100 units/mL penicillin and streptomycin) in a 96-well, round-bottom plate at $4 \times 10^4$/well on ice. Dilutions (6×, starting at 10 μg/ml) of test and control antibodies/ASCs (10 μl) will be added to the plates containing the target cells as in following table, followed by incubation on ice for 30 minutes to allow opsonization. 10 μl of media will be added to control wells to maintain volume.

Controls:
Background low control: Target Cell Spontaneous LDH Release Control corrects for spontaneous release from target cells (low control). Add the same number of target cells used in the experimental wells. Adjust the final volume to 100 μL/well with culture medium.
Positive high control: Target Cell Maximum LDH Release Control is required in calculations to determine 100% release of LDH. Add the same number of target cells used in experimental wells. The final volume must be 100 μL/well (Step 5 adds 10 μL of 10× Lysis Buffer).
Antibody-independent cellular cytotoxicity (AICC) will be measured in wells containing target and effector cells without the addition of antibody.

The following two controls are for monitoring assay conditions, not needed for ADCC calculations.
Effector Cell Spontaneous LDH Release Control corrects for spontaneous release of LDH from effector cells. Add effector cells at various numbers used in the experimental wells. Adjust the final volume to 100 μL/well with culture medium.
Culture Medium Background Control is required to correct for the contributions caused by LDH activity that may be present in serum containing culture medium. Add 100 μL of culture medium to a triplicate set of wells (without cells).

After the 30 min incubation on ice, 8×10⁵ PBMC effector cells in 50 µl warm assay medium (RPMI-1640 with 1% BSA and 100 units/mL penicillin and streptomycin) will be added to each well to give a ratio of 20:1 effector: target cells, incubate the plates for an additional 4 hours at 37° C.

Forty-five minutes before harvesting the supernatant, add 10 µL of Lysis Buffer (10×) to Target Cell Maximal LDH Release Control (positive control) and Volume Correction Control. Add 10 µL of PBS to Background low controls with cells, samples and other controls. Centrifuge the plates after incubation (350 g, 10 min). Transfer 50 ul supernatants to a 96-well clear flat-bottom plate and add 50 µL of Reaction Mixture to each sample well and mix by gentle tapping. Incubate the plate at room temperature for 30 minutes protected from light. Add 50 µL of Stop Solution to each sample well and mix by gentle tapping. Measure the absorbance at 490 nm and 680 nm. To determine LDH activity, subtract the 680 nm absorbance value (background signal from instrument) from the 490 nm absorbance value.

Specific ADCC activity was calculated as follows:

$$\% \text{ ADCC}=100\times((A_{490}(\text{sample})-A_{490}(\text{AICC}))/(A_{490}(\text{high control})-A_{490}(\text{low control}))$$

Figure 13A:
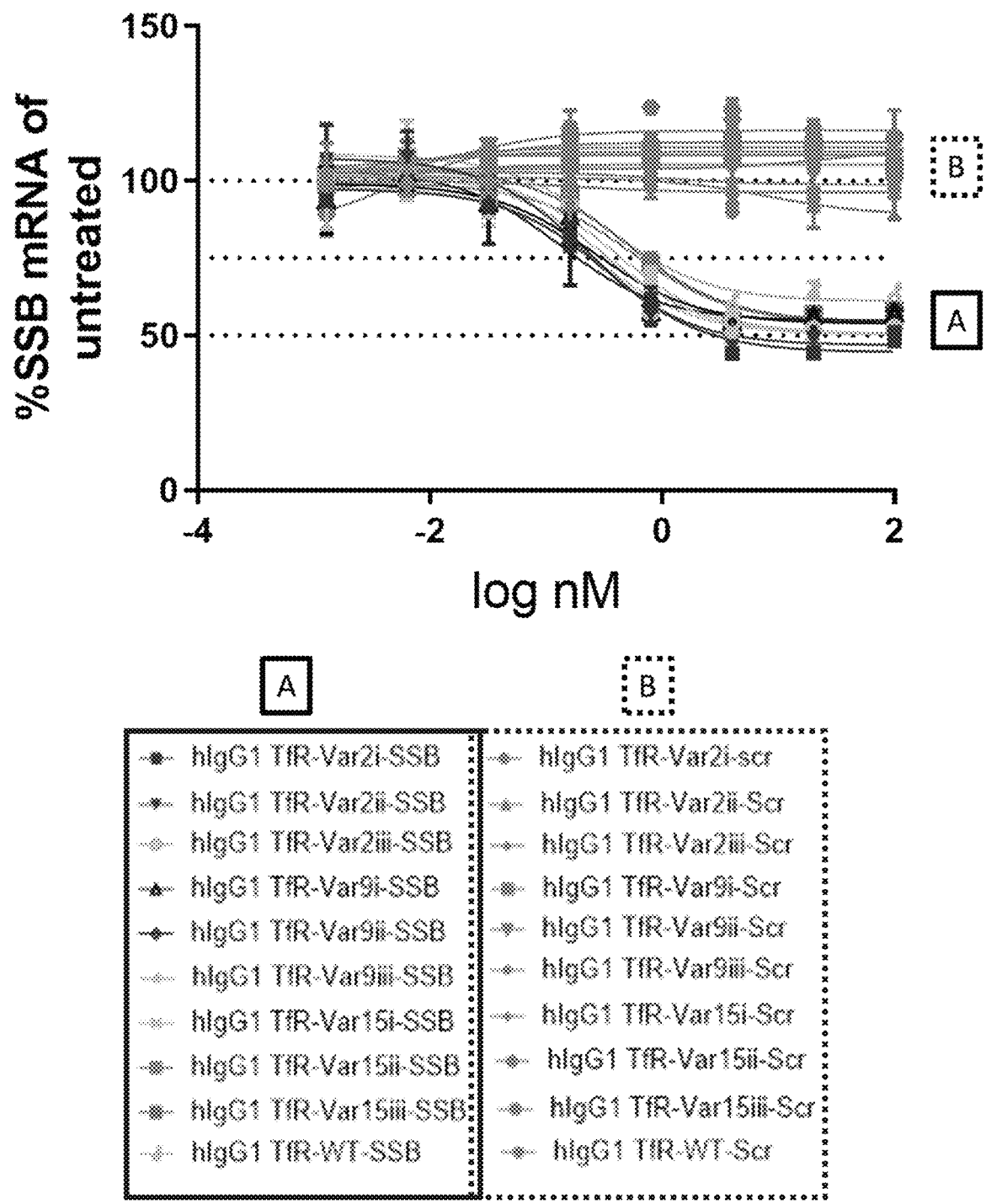
FIG. 13A shows the % SSB mRNA knockdown in HEL92 cells.
Figures 13B, 14:
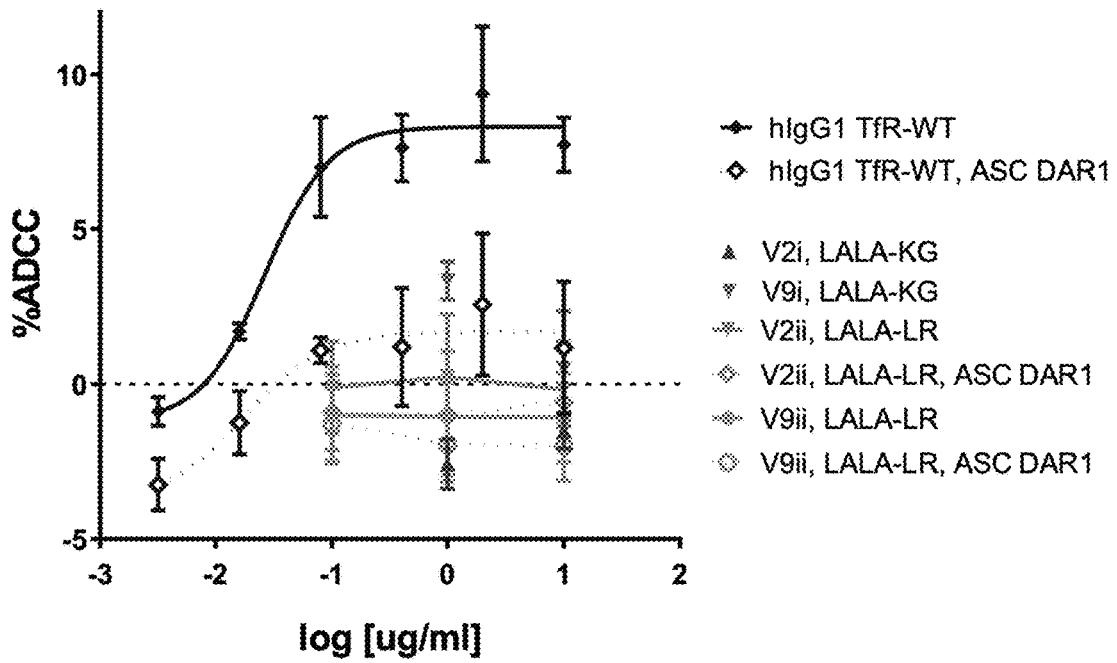
FIG. 13B shows the EC50s of the tested anti-TfR antibodies of FIG. 13A.
FIG. 14 illustrates ADCC activities of exemplary anti-TfR antibodies.

Result is illustrated in FIG. 14.

Complement-Dependent Cytotoxicity (ADCC) Mediated by TfR1 Antibodies and Antibody siRNA Conjugates (ASCs) in Rabbit Serum Materials:

Rabbit Complement, Lyophilized. Reconstitute with ice cold distilled water. Gently agitate to ensure that all lyophilized material is dissolved. Use within one hour of reconstitution. Keep reconstituted material on ice at all times. Discard aliquots if not fully active at ½ dilution.

Target cells: HEL-92.1.7 (ATCC, #TIB-180)

Viobility 405/452 fixable dye

Tissue culture medium with serum (complete medium) RPMI 1640 (Life Technologies) containing 10% heat-inactivated FBS (30 minutes at 56° C.) and 2% L-glutamine hIgG1 Variants Procedure:

HEL92.1.7 target cells were harvested and washed twice with cold assay media. Cells were seeded in cold 25 µl assay medium (RPMI-1640 with 1% BSA and 100 units/mL penicillin and streptomycin) in a 96-well, round-bottom plate at 5×10⁴/well. Dilutions (5×, starting at 100 ug/ml for final 50 ug/ml) of test and control antibodies (25 µl) were added to the plates containing the 25 µl target cells, followed by incubation on ice for 30 minutes to allow opsonization.

Controls:

Background low control: Target Cell Spontaneous LDH Release Control corrects for spontaneous release from target cells (low control). Add the same number of target cells used in the experimental wells. Adjust the final volume to 100 µL/well with culture medium.

Antibody-independent cellular cytotoxicity (AICC) will be measured in wells containing target and CDC without the addition of antibody.

After the 30 min incubation, 50 µL complement was added to each well, except media and low controls (with 50 µL media), and the plates were incubated for an additional 60 min at 37° C. The plates were centrifuged at the end of incubation (350 g, 10 min). Diluted Viobility 405/452 dye (0.5 µL dye in 100 µL staining buffer) was added. Plate was at room temperature for 15 minutes protected from light. Cells were washed and fixed. Flow analysis was done to measure dead cells Specific CDC activity will be calculated as follows:

$$\% \text{ CDC}=\% \text{ dead cells in samples}-\% \text{ dead cells in control}$$

Figure 15:
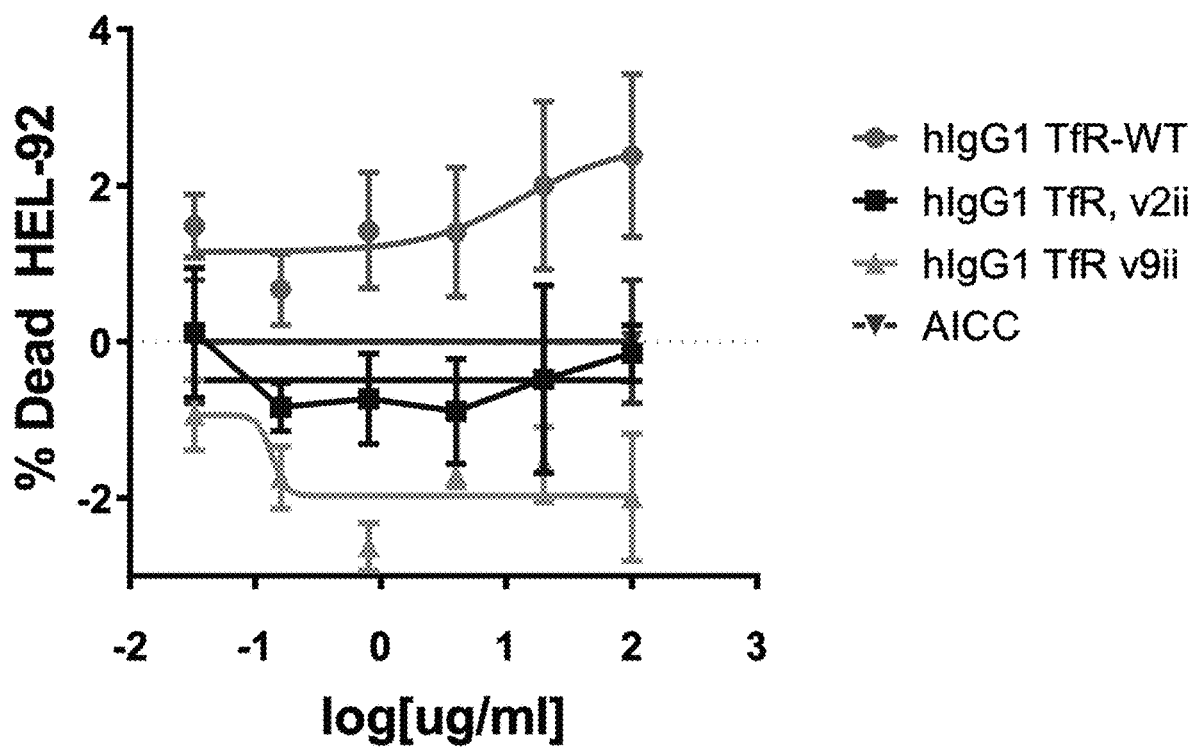
FIG. 15 illustrates CDC activities of exemplary anti-TfR antibodies.

Result is illustrated in FIG. 15.

Figure 16:
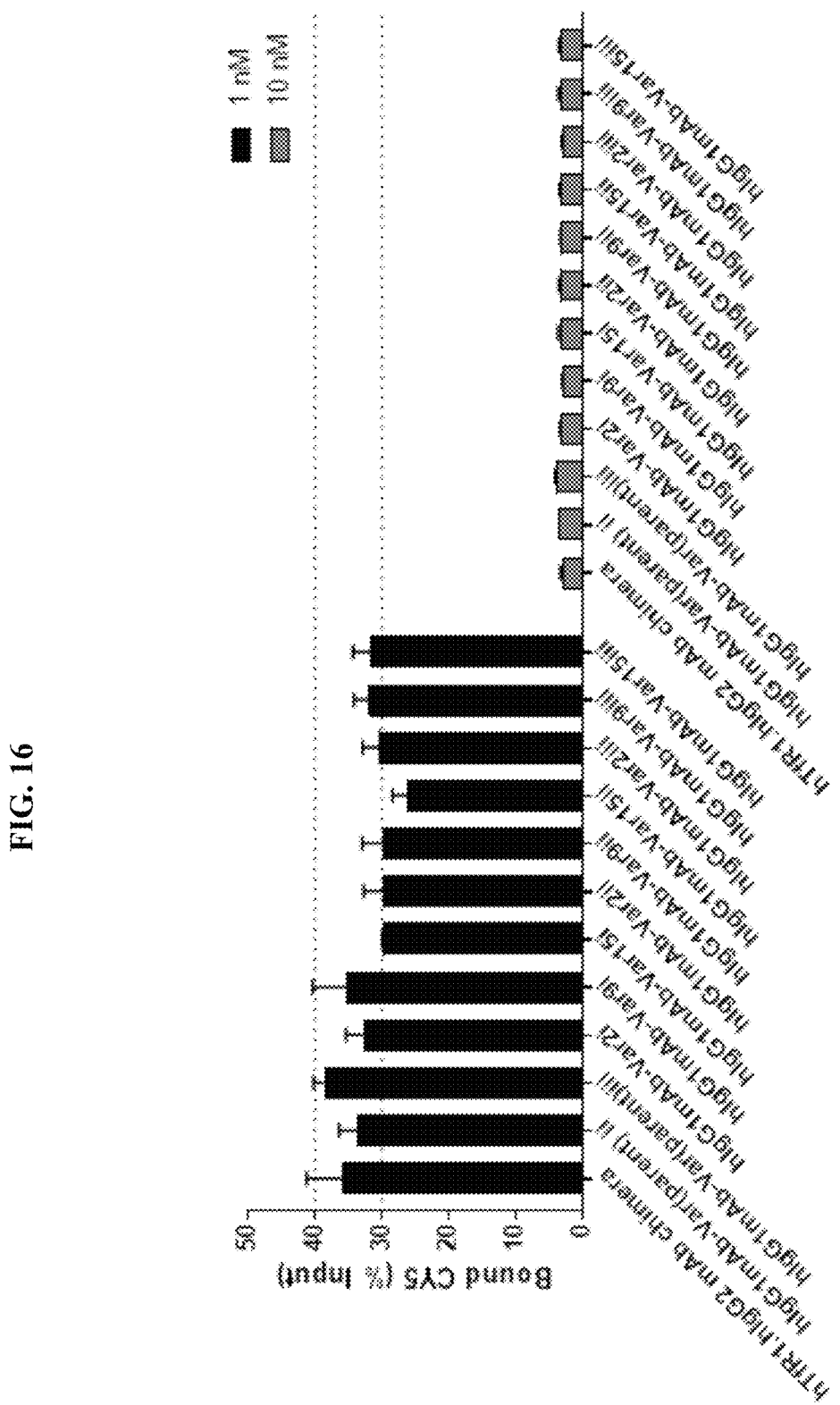
FIG. 16 shows uptake of TfR1.mAb conjugates in primary human skeletal muscle cells (myotubes).

In Vitro Uptake of Human Anti-TfR1 IgG1 siRNA Conjugates (ASCs) in to Human Skeletal Myotubes To monitor uptake of the ASCs into muscle cells, primary human skeletal myoblasts (Thermo Fisher Scientific A11440) were plated on 24-well collagen plates (Thermo Fisher A1142802) in 1 mL DMEM (ATCC 30-2002) supplemented with 10% FBS (Nucleus Biologics FBS1824) and 1×ITS (Thermo Fisher Scientific 41400045). Cells were incubated at 37° C. in 5% CO2 until myoblasts became confluent. At this point differentiation to myotubes was induced by incubation in 1000 µl 1 mL DMEM (ATCC 30-2002) supplemented with 2% horse serum (ATCC 30-2040) and 1×ITS (Thermo Fisher Scientific 41400045) for 2 days. The medium was replaced by 500 ul differentiation medium and 50 µl TfR1.IgG2 mAb-SSB(Cy5) conjugates diluted in PBS were added to a final concentration of 1 and 10 nM. Cells were incubated for 24 hours at 37° C. in 5% CO2, then washed 3× with 500 ul PBS and lysed in 150 ul T-PER lysis buffer (Thermo Fisher Scientific 78510) using a freeze-thaw cycle. 75 ul of the lysed cells were diluted with 75 µl nuclease free water and the fluorescence determined (Ex 635 nM-Em 675 nM) using a TECAN plate reader. The results are presented as the fluorescence in cells relative to input (FIG. 16).

Figure 17:
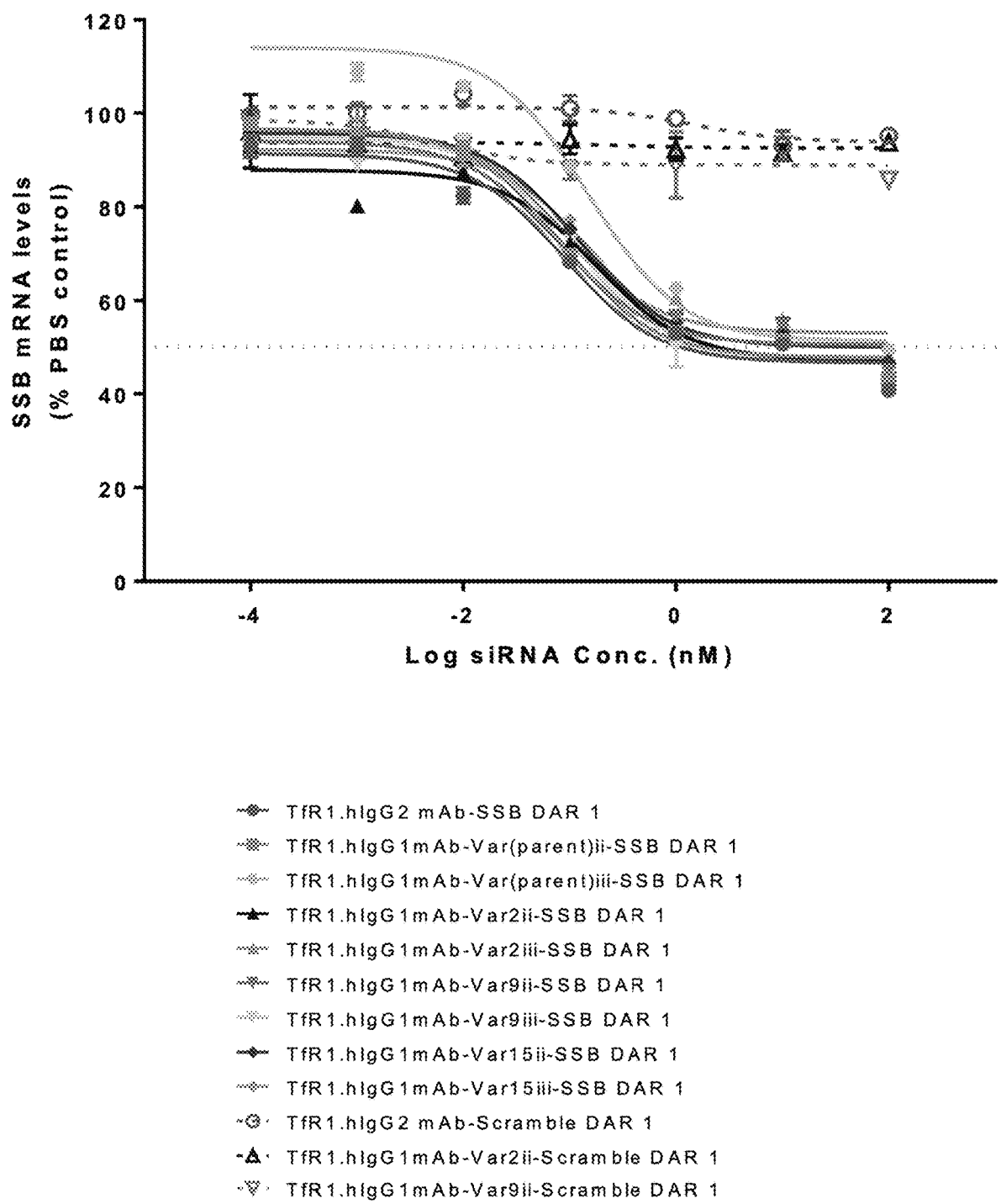
FIG. 17 shows SSB mRNA levels in primary human skeletal muscle cells treated with SSB or Scramble siRNA conjugates of TfR1.hIgG2 mAb or TfR1.hIgG1 mAb variants.
Figure 18:
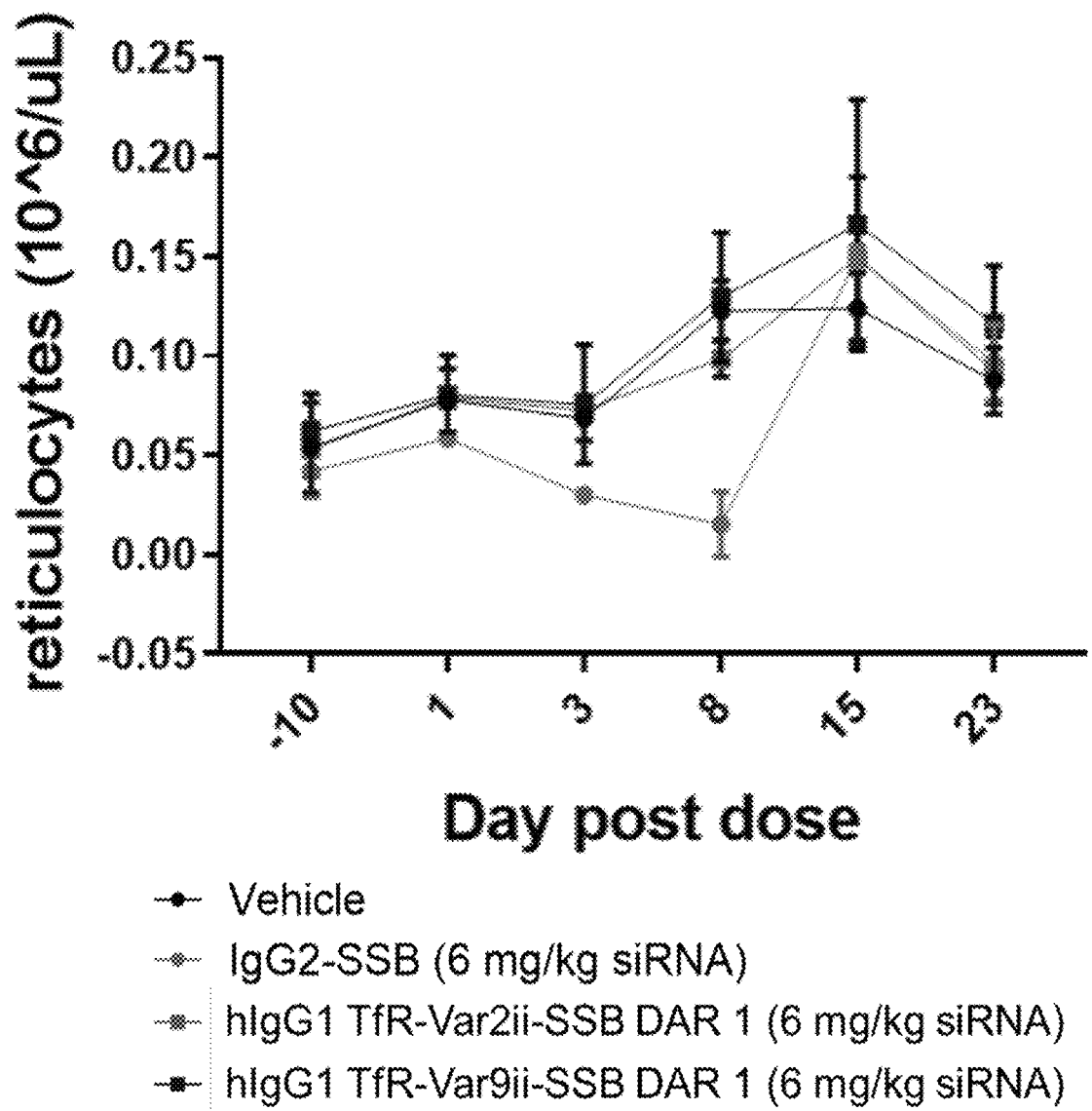
FIG. 18 shows absolute reticulocyte levels in cynomolgus monkeys pre/post dosing of TfR1 targeting AOCs (single dose at day 1).
Figure 19:
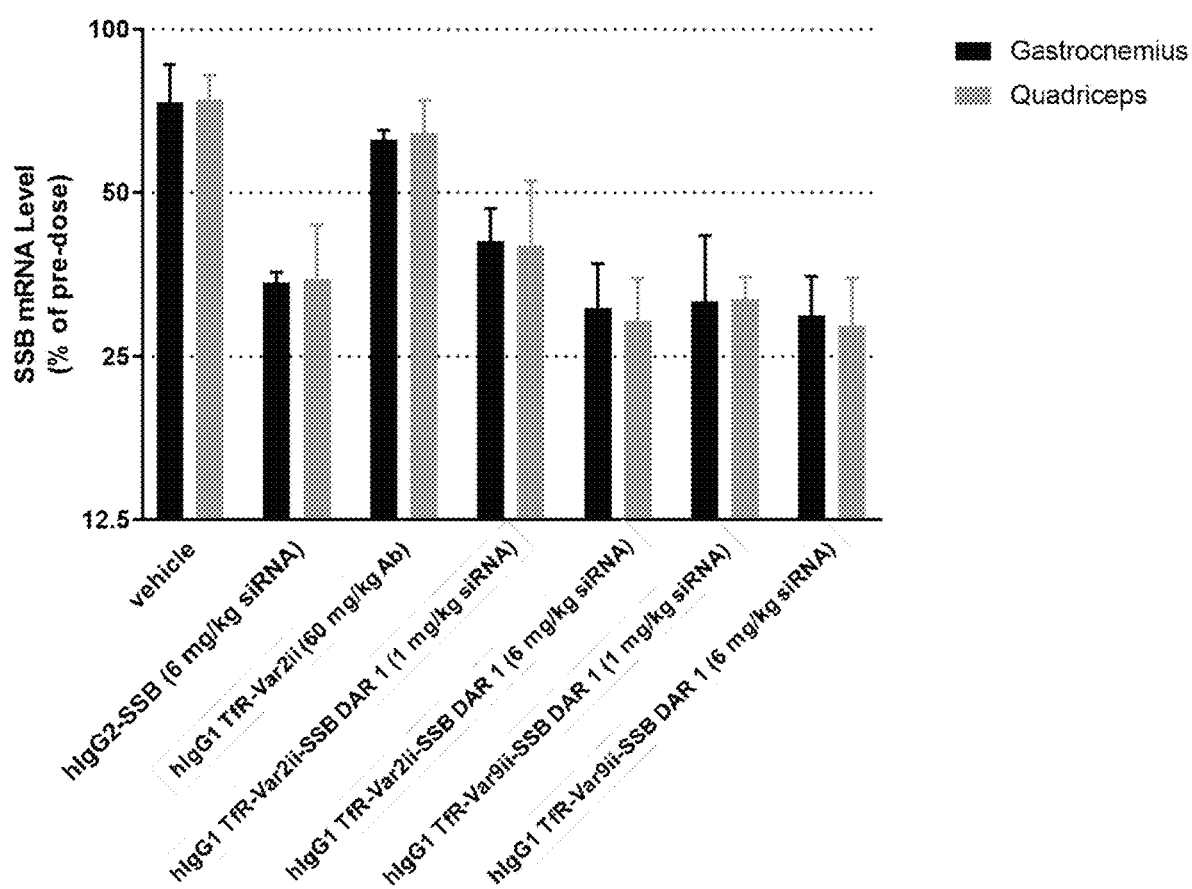
FIG. 19 shows SSB mRNA levels in muscles of cynomolgus monkeys 21 days post single doses of TfR1 mAb SSB conjugates (n=3).

In Vitro Gene Downregulation Mediated by Human Anti-TfR1 IgG1 siRNA Conjugates (ASCs) in Human Skeletal Myotubes To monitor the ability of TfR1.mAb-SSB conjugates to downregulate SSB mRNA levels, primary human skeletal myoblasts (Thermo Fisher Scientific A11440) were plated on 24-well collagen plates (Thermo Fisher A1142802) in 1 mL DMEM (ATCC 30-2002) supplemented with 10% FBS (Nucleus Biologics FBS1824) and 1×ITS (Thermo Fisher Scientific 41400045). Cells were incubated at 37° C. in 5% CO2 until myoblasts became confluent. At this point differentiation to myotubes was induced by incubation in 1000 ul 1 mL DMEM (ATCC 30-2002) supplemented with 2% horse serum (ATCC 30-2040) and 1×ITS (Thermo Fisher Scientific 41400045) for 2 days. The medium was refreshed and 100 ul TfR1.IgG2 mAb-SSB conjugates diluted in PBS were added. The treated cells were incubated for 72 hours. For harvesting, media was removed from wells and 150 uL of Trizol (Ambion 15596018) was added. Plates were frozen at −80° C. for overnight or longer before analysis. RNA was isolated using a Direct-zol 96 RNA kit following manufacturer's instructions and quantified spectroscopically. RNA (100-200 ng) was reverse transcribed according to manufacturer's instructions using the High Capacity cDNA kit (Thermo Fisher #4368813). mRNA levels were quantified using TaqMan qPCR, using the appropriately designed primers and probes. PPIB (housekeeping gene) was used as an internal RNA loading control. % mRNA was calculated using the ΔΔCt method, with PBS treated cells set to 100% expression. All tested SSB siRNA conjugates downregulated SSB by 50% with similar potency (FIG. 17).

Example 4

```
hTfR1 Heavy Chain: 461 aa
NruI -Kozak sequence-- Artificial signal
peptide -hTfR1 mAb HC variable region-
Human IgG2 constant region (P01859)-- stop
codon-PmlI
MGWSCIILFLVATAGVHSQVQLQQPGAELVKPGASVKLSCKASGYTFTNYWM

HWVKQRPGQGLEWIGEINPINGRSNYGERFKTKATLTVDKSSSTAYMQLSSLTSEDSAV

YYCARGTRAMHYWGQGTSVTVSSASTKGPSVFPLAPCSRST

SESTAALGCLVKDYFPEPVTVSWNSGALTSGVHTFPAVLQSS

GLYSLSSVVTVPSSNFGTQTYTCNVDHKPSNTKVDKTVERKC

CVECPPCPAPPVAGPSVFLFPPKPKDTLMISRTPEVTCVVVD

VSHEDPEVQFNWYVDGVEVHNAKTKPREEQFNSTFRVVSVLT

VVHQDWLNGKEYKCKVSNKGLPAPIEKTISKTKGQPREPQVY

TLPPSREEMTKNQVSLTCLVKGFYPSDISVEWESNGQPENNY

KTTPPMLDSDGSFFLYSKLTVDKSRWQQGNVFSCSVMHEALH

NHYTQKSLSLSPGK (SEQ ID NO: 86)

hTfR1 Light Chain: 233 aa
AscI -Kozak sequence-- Artificial signal
peptide - hTfR1 mAb LC variable region-
Human Ig kappa constant region (P01834)--
stop codon-FseI
MGWSCIILFLVATATGVHSDIQMTQSPASLSVSVGETVTITC

RTSENIYNNLAWYQQKQGKSPQLLVYAATNLADGVPSRFSGS

GSGTQYSLKINSLQSEDFGNYYCQHFWGTPLTFGAGTKLELK

RTVAAPSVFIFPPSDEQLKSGTASVVCLLNNFYPREAKVQWK

VDNALQSGNSQESVTEQDSKDSTYSLSSTLTLSKADYEKHKV

YACEVTHQGLSSPVTKSFNRGEC (SEQ ID NO: 87)
```

Example 5: SSB siRNA Knockdown of Exemplary Anti-TfR Antibodies in a Cyno Study Treatment of cynomolgus monkeys with exemplary anti-TfR antibodies will be tested to determine the percentage of SSB mRNA downregulation in gastrocnemius. Doses of 30 mg/kg, 10 mg/kg, and 3 mg/kg will be tested. The activity of the antibody conjugates will be probed at 21 and/or 28 days post-dose. The safety of the primates will also be monitored via hematology and clinical chemistry analysis.

Example 6: SSB Conjugates of hIgG1 TfR-Var2ii and hIgG1 TfR-Var9ii do not Affect Absolute Reticulocyte Levels in Cynomolgus Monkeys hIgG1 TfR-Var2ii and hIgG1 TfR-Var9ii are humanized IgG1 antibodies targeting hTfR1 that contain mutations in the hinge region of the IgG1 heavy chain, designed to remove the effector function (LALA+L328R). Contrary to the chimeric hIgG2 TfR1 antibody, SSB conjugates of hIgG1 TfR-Var2ii and hIgG1 TfR-Var9ii do not reduce reticulocyte levels after dosing in cynomolgus monkeys. This result is consistent with studies by others demonstrating that the depletion of immature reticulocytes by TfR1 targeting antibodies can be successfully suppressed by mutations that remove the ADCC/CDC activity of the antibody (WO 2014/189973 A2).

Method:

Cynomolgus monkeys (male; 2-3 years old; BW 2-3 kg) were dosed by 30 minutes (+/−3 minutes) intravenous (IV) infusion at day one. Blood specimens were collected from peripheral veins of restrained, conscious animals at different timepoints post dosing as indicated in FIG. 18.

Example 7: SSB Conjugates of hIgG1 TfR-Var2ii Ab and hIgG1 TfR-Var9ii Ab Downregulate SSB RNA Levels in Muscles of Cynomolgus Monkeys Compared to pre-dose SSB mRNA levels, single doses of 1 or 6 mg/kg (siRNA) of the hIgG1 TfR-Var2ii or hIgG1 TfR-Var9ii SSB conjugates downregulated SSB mRNA levels in gastrocnemius and quadriceps by up to 72% at 21 days post dose (FIG. 19). The activity of the humanized antibodies is similar to that of the parental chimeric IgG2 TfR1 antibody. An unconjugated TfR-Var2ii Ab dosed at 60 mg/kg (this equals a 6 mg/kg AOC dose) showed no significant downregulation of SSB.

Method:

Cynomolgus monkeys (male; 2-3 years old; BW 2-3 kg) were dosed by 30 minutes (+/−3 minutes) intravenous (IV) infusion at day one. Muscle biopsies (gastrocnemius and quadriceps) were taken by 6 mm punches from sedated animals at day −10 and +21 post dose, weighed and snap-frozen in liquid nitrogen. Frozen tissue samples were homogenized in 1 ml cold TRIzol (Thermo Fisher

15596026). To determine mRNA knockdown, total RNA was extracted from the tissue using a Direct-zol 96 RNA kit following manufacturer's instructions and quantified spectroscopically. RNA (100-200 ng) was reverse transcribed according to manufacturer's instructions using the High Capacity cDNA kit (Thermo Fisher #4368813). SSB mRNA levels were quantified using TaqMan qPCR, using the appropriately designed primers and probes. PPIB (housekeeping gene) was used as an internal RNA loading control. % mRNA was calculated using the ΔΔCt method, with either SSB mRNA levels in the same animal pre-treatment or SSB levels in animals treated with PBS set to 100% expression.

Example 8: AOC Mediated SSB Knockdown but not siRNA Delivery is Muscle-Specific

At 21 days post a single 6 mg/kg dose of hIgG1 TfR-Var2ii-SSB most tissues displayed SSB siRNA concentrations between 10-100 nM. The highest siRNA levels were in the liver and adrenal gland (≥1000 nM); the lowest in brain (2 nM). siRNA concentrations in skeletal muscles were 3-20 nM. Despite relatively low siRNA exposure, only skeletal muscles and heart displayed >50% reduction in SSB mRNA levels. This result demonstrates that the delivery of oligonucleotide payloads by TfR1 targeting antibodies is muscle-specific and driven by cell-specific trafficking pathways rather than siRNA exposure.

Figure 20A:
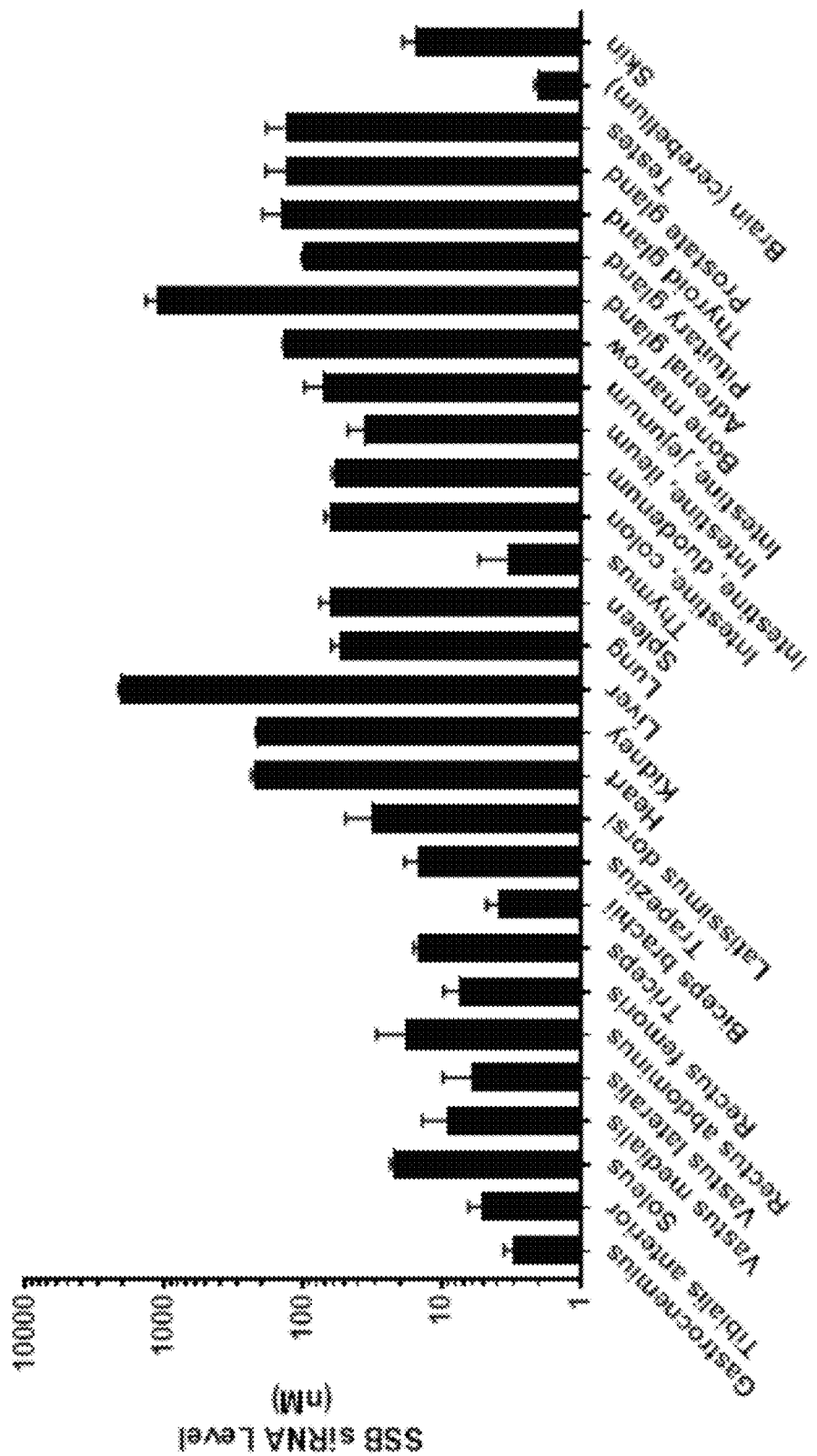
FIG. 20A shows SSB siRNA levels in tissues of cynomolgus monkeys 21 days post a single 6 mg/kg dose of hIgG1 TfR-Var2ii-SSB conjugate (n=2).
Figure 20B:
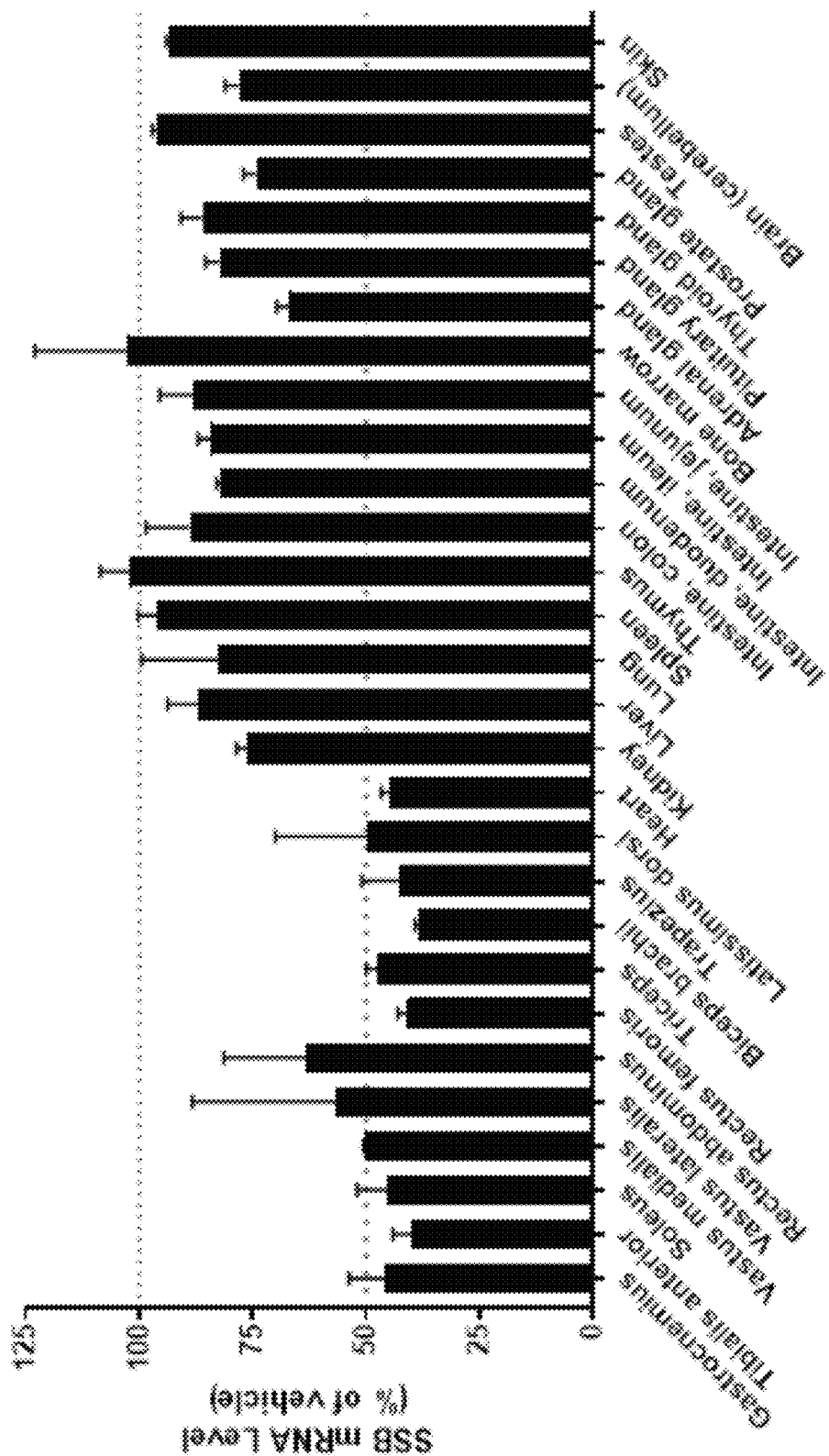
FIG. 20B shows SSB mRNA levels in tissues of cynomolgus monkeys 21 days post a single 6 mg/kg dose of hIgG1 TfR-Var2ii-SSB conjugate (n=2).

Method:

Cynomolgus monkeys (male; 2-3 years old; BW 2-3 kg) were dosed by 30 minutes (+/−3 minutes) intravenous (IV) infusion at day one. At day 21 post dose, muscle biopsies were taken by 6 mm punches from sedated animals. All other tissue samples were collected within 30 min post-mortem. Tissue samples were processed and SSB mRNA levels determined as described above (FIG. 20B). Tissue SSB siRNA concentrations were determined using a stem-loop qPCR assay as described in the methods section (FIG. 20A). The antisense strand of the siRNA was reverse transcribed using a TaqMan MicroRNA reverse transcription kit using a sequence-specific stem-loop RT primer. The cDNA from the RT step was then utilized for real-time PCR and Ct values were transformed into plasma or tissue concentrations using the linear equations derived from the standard curves.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. An anti-transferrin receptor antibody comprising a variable heavy chain (VH) region and a variable light chain (VL) region, wherein the VH region comprises HCDR1 sequence comprising SEQ ID NO: 1; HCDR2 sequence comprising EINPIX$_1$GRSNYAX$_2$KFQG (SEQ ID NO: 88), wherein X$_1$ is selected from N or Q and X$_2$ is selected from Q or E; and HCDR3 sequence comprising SEQ ID NO: 3, and wherein the VL region comprises LCDR1 sequence comprising RTSENIYX$_3$NLA (SEQ ID NO: 89), LCDR2 sequence comprising AX$_4$TNLAX$_5$ (SEQ ID NO: 90), and LCDR3 sequence comprising QHFWGTPLTX$_6$ (SEQ ID NO: 91), wherein X$_3$ is selected from N or S, X$_4$ is selected from A or G, X$_5$ is selected from D or E, and X$_6$ is present or absent, and if present, is F.

2. The anti-transferrin receptor antibody of claim 1, wherein the VH region comprises HCDR1 sequence comprising SEQ ID NO: 1, HCDR2 sequence comprising SEQ ID NO: 4, and HCDR3 sequence comprising SEQ ID NO: 3.

3. The anti-transferrin receptor antibody of claim 1, wherein the V$_L$ region comprises LCDR1 sequence comprising SEQ ID NO: 6, LCDR2 sequence comprising AATNLAX$_5$ (SEQ ID NO: 92), and LCDR3 sequence comprising QHFWGTPLTX$_6$ (SEQ ID NO: 91), wherein X$_5$ is selected from D or E and X$_6$ is present or absent, and if present, is F.

4. The anti-transferrin receptor antibody of claim 1, wherein the VL region comprises LCDR1 sequence comprising SEQ ID NO: 6, LCDR2 sequence comprising SEQ ID NO: 7, and LCDR3 sequence comprising SEQ ID NO: 8.

5. The anti-transferrin receptor antibody of claim 1, wherein the VH region comprises HCDR1 sequence comprising SEQ ID NO: 1, HCDR2 sequence comprising SEQ ID NO: 4, and HCDR3 sequence comprising SEQ ID NO: 3; and the VL region comprises LCDR1 sequence comprising SEQ ID NO: 6, LCDR2 sequence comprising SEQ ID NO: 7, and LCDR3 sequence comprising SEQ ID NO: 8.

6. The anti-transferrin receptor antibody of claim 1, wherein the VH region comprises at least 80%, 85%, 90%, 95%, 99%, or 100% sequence identity to a sequence selected from SEQ ID NOs: 13-16, and wherein the VL region comprises at least 80%, 85%, 90%, 95%, 99%, or 100% sequence identity to a sequence selected from SEQ ID NOs: 18-21.

7. The anti-transferrin receptor antibody of claim 1, wherein the anti-transferrin receptor antibody comprises a humanized antibody or binding fragment thereof or a chimeric antibody or binding fragment thereof.

8. The anti-transferrin receptor antibody of claim 1, wherein the anti-transferrin receptor antibody comprises a multi-specific antibody or a binding fragment thereof.

9. The anti-transferrin receptor antibody of claim 1, wherein the anti-transferrin receptor antibody comprises an IgG-scFv, nanobody, BiTE, diabody, DART, TandAb, scDiabody, scDiabody-CH3, triple body, mini-antibody, minibody, TriBi minibody, scFv-CH3 KIH, Fab-scFv-Fc KIH, Fab-scFv, scFv-CH-CL-scFv, Fab', F(ab')2, F(ab')3, F(ab')2-scFv2, scFv, scFv-KIH, Fab-scFv-Fc, tetravalent HCAb, scDiabody-Fc, diabody-Fc, tandem scFv-Fc, or intrabody.

10. The anti-transferrin receptor antibody of claim 1, wherein the anti-transferrin receptor antibody comprises at least one of an IgG1 framework, an IgG2 framework, an IgG2b framework, or an IgG4 framework.

11. The anti-transferrin receptor antibody of claim 1, wherein the anti-transferrin receptor antibody further comprises at least one mutation in the Fc region, and the at least one mutation modulates effector function.

12. The anti-transferrin receptor antibody of claim 11, wherein the effector function comprises attenuation or elimination of Fc-γ receptor binding.

13. The anti-transferrin receptor antibody of claim 11, wherein the at least one mutation is at residue position D265, N297, K322, L328, or P329, wherein the residue position is in reference to IgG1.

14. The anti-transferrin receptor antibody of claim 11, wherein the Fc region comprises mutations at L233 and L234, wherein the residues correspond to position 233 and 234 of SEQ ID NO: 23.

15. The anti-transferrin receptor antibody of claim 11, wherein the Fc region comprises mutations at D265 and N297.

16. The anti-transferrin receptor antibody of claim 1, wherein the anti-transferrin receptor antibody comprises a heavy chain (HC) sequence selected from SEQ ID NOs: 23-46 and a light chain (LC) sequence selected from SEQ ID NOs: 47-50.

17. The anti-transferrin receptor antibody of claim 1, wherein the anti-transferrin receptor antibody specifically binds to human transferrin receptor (TfR).

18. An anti-transferrin receptor antibody conjugate, comprising Formula (I):

$$A\text{-}(X^1\text{-}B)_n \quad \text{Formula (I)}$$

wherein,
A comprises the anti-transferrin receptor antibody, wherein the anti-transferrin receptor antibody comprises a variable heavy chain (VH) region and a variable light chain (VL) region, wherein the VH region comprises HCDR1 sequence comprising SEQ ID NO: 1; HCDR2 sequence comprising EINPIX$_1$GRSNYAX$_2$KFQG (SEQ ID NO: 88), wherein X$_1$ is selected from N or Q and X$_2$ is selected from Q or E; and HCDR3 sequence comprising SEQ ID NO: 3, and wherein the VL region comprises LCDR1 sequence comprising RTSENIYX$_3$NLA (SEQ ID NO: 89), LCDR2 sequence comprising AX$_4$TNLAX$_5$ (SEQ ID NO: 90), and LCDR3 sequence comprising QHFWGTPLTX$_6$ (SEQ ID NO: 91), wherein X$_3$ is selected from N or S, X$_4$ is selected from A or G, X$_5$ is selected from D or E, and X$_6$ is present or absence, and if present, is F;
B comprises a polynucleic acid molecule;
X$^1$ consists of a bond or linker; and
n is an averaged value selected from 1-12.

19. The anti-transferrin receptor antibody conjugate of claim 18, wherein the polynucleic acid molecule comprises a passenger strand and a guide strand.

20. The anti-transferrin receptor antibody conjugate of claim 19, wherein the guide strand comprises at least one modified internucleotide linkage, at least one inverted abasic moiety, at least one 5'-vinylphosphonate modified non-natural nucleotide, or a combination thereof.

21. The anti-transferrin receptor antibody conjugate of claim 18, wherein the polynucleic acid molecule further comprises a modification of a sugar moiety at the 2' position, and wherein the modification at the 2'-position is selected from 2'-O-methyl, 2'-O-methoxyethyl (2'-O-MOE), 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified nucleotide.

22. The anti-transferrin receptor antibody conjugate of claim 19, wherein the passenger strand comprises at least 6, 7, 8, 9, 10, 11, 12, 13, 14, 15, 16, 17, 18, 19, 20, or more phosphorodiamidate morpholino oligomer-modified non-natural nucleotides.

23. The anti-transferrin receptor antibody conjugate of claim 19, wherein A-X$^1$ is conjugated to the 5' end of the passenger strand or 3' end of the passenger strand.

24. The anti-transferrin receptor antibody conjugate of claim 18, wherein the polynucleic acid molecule hybridizes to a target sequence of a gene, and wherein the polynucleic acid molecule mediates RNA interference against the gene.

25. The anti-transferrin receptor antibody conjugate of claim 24, the gene comprises an upregulated gene within the IGF1-Akt-FoxO pathway, the glucocorticoids-GR pathway, the PGC1α-FoxO pathway, the TNFα-NF$_\kappa$B pathway, or the myostatin-ActRIIb-Smad2/3 pathway, E3 ligase, Forkhead box transcription factor, atrogin-1 gene (FBXO32), MuRF1 gene (TRIM63), FOXO1, FOXO3, MSTN, DMD, or DMPK.

26. The anti-transferrin receptor antibody conjugate of claim 24, wherein the RNA interference is preferentially mediated in a muscle when the anti-transferrin receptor antibody conjugate is administered to a subject.

27. A pharmaceutical composition comprising:
an anti-transferrin receptor antibody of claim 1; and
a pharmaceutically acceptable excipient.

* * * * *

SEQUENCE LISTING

```
<160> NUMBER OF SEQ ID NOS: 92

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Tyr Thr Phe Thr Asn Tyr Trp Met His
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Ile Asn Pro Ile Asn Gly Arg Ser Asn Tyr Ala Gln Lys Phe Gln
1               5                   10                  15

Gly

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3
```

```
Gly Thr Arg Ala Met His Tyr
1               5

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Glu Ile Asn Pro Ile Asn Gly Arg Ser Asn Tyr Ala Glu Lys Phe Gln
1               5                   10                  15

Gly

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Glu Ile Asn Pro Ile Gln Gly Arg Ser Asn Tyr Ala Glu Lys Phe Gln
1               5                   10                  15

Gly

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Thr Ser Glu Asn Ile Tyr Asn Asn Leu Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Ala Thr Asn Leu Ala Asp
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln His Phe Trp Gly Thr Pro Leu Thr
1               5

<210> SEQ ID NO 9
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Ala Thr Asn Leu Ala Glu
1               5

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln His Phe Trp Gly Thr Pro Leu Thr Phe
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Thr Ser Glu Asn Ile Tyr Ser Asn Leu Ala
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Gly Thr Asn Leu Ala Asp
1               5

<210> SEQ ID NO 13
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Glu Ile Asn Pro Ile Asn Gly Arg Ser Asn Tyr Ala Gln Lys Phe
    50                  55                  60

Gln Gly Arg Val Thr Leu Thr Val Asp Thr Ser Ile Ser Thr Ala Tyr
65                  70                  75                  80
```

```
Met Glu Leu Ser Arg Leu Arg Ser Asp Asp Thr Ala Val Tyr Tyr Cys
            85                  90                  95

Ala Arg Gly Thr Arg Ala Met His Tyr Trp Gly Gln Gly Thr Leu Val
        100                 105                 110

Thr Val Ser Ser
        115

<210> SEQ ID NO 14
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Ile
        35                  40                  45

Gly Glu Ile Asn Pro Ile Asn Gly Arg Ser Asn Tyr Ala Glu Lys Phe
    50                  55                  60

Gln Gly Arg Val Thr Leu Thr Val Asp Thr Ser Ser Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Gly Thr Arg Ala Met His Tyr Trp Gly Gln Gly Thr Leu Val
        100                 105                 110

Thr Val Ser Ser
        115

<210> SEQ ID NO 15
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Glu Ile Asn Pro Ile Gln Gly Arg Ser Asn Tyr Ala Glu Lys Phe
    50                  55                  60

Gln Gly Arg Val Thr Leu Thr Val Asp Thr Ser Ser Ser Thr Ala Tyr
65                  70                  75                  80

Met Glu Leu Ser Ser Leu Arg Ser Glu Asp Thr Ala Thr Tyr Tyr Cys
            85                  90                  95

Ala Arg Gly Thr Arg Ala Met His Tyr Trp Gly Gln Gly Thr Leu Val
        100                 105                 110

Thr Val Ser Ser
        115
```

<210> SEQ ID NO 16
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Glu Ile Asn Pro Ile Asn Gly Arg Ser Asn Tyr Ala Glu Lys Phe
    50                  55                  60

Gln Gly Arg Val Thr Leu Thr Val Asp Thr Ser Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Gly Thr Arg Ala Met His Tyr Trp Gly Gln Gly Thr Leu Val
            100                 105                 110

Thr Val Ser Ser
        115

<210> SEQ ID NO 17
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Trp Met His Trp Val Lys Gln Arg Pro Gly Gln Gly Leu Glu Trp Ile
        35                  40                  45

Gly Glu Ile Asn Pro Ile Asn Gly Arg Ser Asn Tyr Gly Glu Arg Phe
    50                  55                  60

Lys Thr Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Thr Arg Ala Met His Tyr Trp Gly Gln Gly Thr Ser Val
            100                 105                 110

Thr Val Ser Ser
        115

<210> SEQ ID NO 18
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Asn Asn
            20                  25                  30

Leu Ala Trp Tyr Gln Gln Lys Pro Gly Lys Ser Pro Lys Leu Leu Ile
        35                  40                  45

Tyr Ala Ala Thr Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Gly Thr Pro Leu
                85                  90                  95

Thr Phe Gly Gly Gly Thr Lys Val Glu Ile Lys
            100                 105

<210> SEQ ID NO 19
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Asn Asn
            20                  25                  30

Leu Ala Trp Tyr Gln Gln Lys Pro Gly Lys Ala Pro Lys Leu Leu Ile
        35                  40                  45

Tyr Ala Ala Thr Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Gly Thr Pro Leu
                85                  90                  95

Thr Phe Gly Gly Gly Thr Lys Val Glu Ile Lys
            100                 105

<210> SEQ ID NO 20
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Asn Asn
            20                  25                  30

Leu Ala Trp Tyr Gln Gln Lys Pro Gly Lys Ala Pro Lys Leu Leu Ile
        35                  40                  45

Tyr Ala Ala Thr Asn Leu Ala Glu Gly Val Pro Ser Arg Phe Ser Gly
    50                  55                  60

```
Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln His Phe Trp Gly Thr Pro Leu
                 85                  90                  95

Thr Phe Gly Gly Gly Thr Lys Val Glu Ile Lys
                100                 105
```

<210> SEQ ID NO 21
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Asp Ile Gln Met Thr Gln Ser Pro Ser Ser Leu Ser Ala Ser Val Gly
 1               5                  10                  15

Asp Arg Val Thr Ile Thr Cys Arg Thr Ser Glu Asn Ile Tyr Ser Asn
                 20                  25                  30

Leu Ala Trp Tyr Gln Gln Lys Pro Gly Lys Ala Pro Lys Leu Leu Ile
             35                  40                  45

Tyr Ala Gly Thr Asn Leu Ala Asp Gly Val Pro Ser Arg Phe Ser Gly
         50                  55                  60

Ser Gly Ser Gly Thr Asp Tyr Thr Leu Thr Ile Ser Ser Leu Gln Pro
 65                  70                  75                  80

Glu Asp Phe Ala Asn Tyr Tyr Cys Gln His Phe Trp Gly Thr Pro Leu
                 85                  90                  95

Thr Phe Gly Gly Gly Thr Lys Val Glu Ile Lys
                100                 105
```

<210> SEQ ID NO 22
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Asp Ile Gln Met Thr Gln Ser Pro Ala Ser Leu Ser Val Ser Val Gly
 1               5                  10                  15

Glu Thr Val Thr Ile Thr Cys Arg Thr Ser Glu Asn Ile Tyr Asn Asn
                 20                  25                  30

Leu Ala Trp Tyr Gln Gln Lys Gln Gly Lys Ser Pro Gln Leu Leu Val
             35                  40                  45

Tyr Ala Ala Thr Asn Leu Ala Asp Gly Val Pro Ser Arg Phe Ser Gly
         50                  55                  60

Ser Gly Ser Gly Thr Gln Tyr Ser Leu Lys Ile Asn Ser Leu Gln Ser
 65                  70                  75                  80

Glu Asp Phe Gly Asn Tyr Tyr Cys Gln His Phe Trp Gly Thr Pro Leu
                 85                  90                  95

Thr Phe Gly Ala Gly Thr Lys Leu Glu Leu Lys
                100                 105
```

<210> SEQ ID NO 23
<211> LENGTH: 445
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 23

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Glu Ile Asn Pro Ile Asn Gly Arg Ser Asn Tyr Ala Gln Lys Phe
    50                  55                  60

Gln Gly Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Arg Ala Met His Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400
```

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 24
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Glu Ile Asn Pro Ile Asn Gly Arg Ser Asn Tyr Ala Gln Lys Phe
    50                  55                  60

Gln Gly Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Arg Ala Met His Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys

```
                305                 310                 315                 320
Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly
                435                 440                 445

<210> SEQ ID NO 25
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Met His Trp Val Arg Gln Ala Pro Gly Gln Gly Leu Glu Trp Met
                35                  40                  45

Gly Glu Ile Asn Pro Ile Asn Gly Arg Ser Asn Tyr Ala Gln Lys Phe
    50                  55                  60

Gln Gly Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Arg Ala Met His Tyr Trp Gly Gln Gly Thr Leu Val
                100                 105                 110

Thr Val Ser Ser Ala Ser Thr Lys Gly Pro Ser Val Phe Pro Leu Ala
                115                 120                 125

Pro Ser Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Arg Val Glu Pro Lys Ser Cys Asp Lys Thr His Thr
            210                 215                 220
```

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
        260                 265                 270

Lys Phe Asn Trp Tyr Val Asp Gly Val Glu Val His Asn Ala Lys Thr
    275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Gly Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Glu Glu Met Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly
    435                 440                 445

<210> SEQ ID NO 26
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Glu Ile Asn Pro Ile Asn Gly Arg Ser Asn Tyr Ala Gln Lys Phe
    50                  55                  60

Gln Gly Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Arg Ala Met His Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
    195                 200                 205

Lys Val Asp Lys Arg Val Glu Pro Lys Ser Cys Asp Lys Thr His Thr
210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Arg Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 27
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Glu Ile Asn Pro Ile Asn Gly Arg Ser Asn Tyr Ala Gln Lys Phe

```
                    50                  55                  60
Gln Gly Arg Val Thr Leu Thr Val Asp Thr Ser Ile Ser Thr Ala Tyr
 65                  70                  75                  80

Met Glu Leu Ser Arg Leu Arg Ser Asp Asp Thr Ala Val Tyr Tyr Cys
                     85                  90                  95

Ala Arg Gly Thr Arg Ala Met His Tyr Trp Gly Gln Gly Thr Leu Val
                100                 105                 110

Thr Val Ser Ser Ala Ser Thr Lys Gly Pro Ser Val Phe Pro Leu Ala
                115                 120                 125

Pro Ser Ser Lys Ser Thr Ser Gly Gly Thr Ala Ala Leu Gly Cys Leu
                130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Arg Val Glu Pro Lys Ser Cys Asp Lys Thr His Thr
                210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
                275                 280                 285

Lys Pro Arg Glu Glu Gln Tyr Asn Ser Thr Tyr Arg Val Val Ser Val
                290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly
                435                 440                 445

<210> SEQ ID NO 28
<211> LENGTH: 445
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Glu Ile Asn Pro Ile Asn Gly Arg Ser Asn Tyr Ala Gln Lys Phe
    50                  55                  60

Gln Gly Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Arg Ala Met His Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Ala Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Gly Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp

-continued

```
                385                 390                 395                 400
Gly Ser Phe Phe Leu Tyr Ser Lys Leu Thr Val Asp Lys Ser Arg Trp
                    405                 410                 415
Gln Gln Gly Asn Val Phe Ser Cys Ser Val Met His Glu Ala Leu His
                420                 425                 430
Asn His Tyr Thr Gln Lys Ser Leu Ser Leu Ser Pro Gly
                435                 440                 445

<210> SEQ ID NO 29
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asn Tyr
                20                  25                  30
Trp Met His Trp Val Arg Gln Ala Pro Gly Gln Gly Leu Glu Trp Ile
            35                  40                  45
Gly Glu Ile Asn Pro Ile Asn Gly Arg Ser Asn Tyr Ala Glu Lys Phe
        50                  55                  60
Gln Gly Arg Val Thr Leu Thr Val Asp Thr Ser Ser Ser Thr Ala Tyr
65                  70                  75                  80
Met Glu Leu Ser Arg Leu Arg Ser Asp Asp Thr Ala Val Tyr Tyr Cys
                85                  90                  95
Ala Arg Gly Thr Arg Ala Met His Tyr Trp Gly Gln Gly Thr Leu Val
            100                 105                 110
Thr Val Ser Ser Ala Ser Thr Lys Gly Pro Ser Val Phe Pro Leu Ala
        115                 120                 125
Pro Ser Ser Lys Ser Thr Ser Gly Gly Thr Ala Ala Leu Gly Cys Leu
    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
        195                 200                 205
Lys Val Asp Lys Arg Val Glu Pro Lys Ser Cys Asp Lys Thr His Thr
    210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
        275                 280                 285
Lys Pro Arg Glu Glu Gln Tyr Asn Ser Thr Tyr Arg Val Val Ser Val
    290                 295                 300
```

```
Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Glu Glu Met Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
            435                 440                 445

<210> SEQ ID NO 30
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Ile
        35                  40                  45

Gly Glu Ile Asn Pro Ile Asn Gly Arg Ser Asn Tyr Ala Glu Lys Phe
    50                  55                  60

Gln Gly Arg Val Thr Leu Thr Val Asp Thr Ser Ser Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Arg Ala Met His Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220
```

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 31
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Ile
        35                  40                  45

Gly Glu Ile Asn Pro Ile Asn Gly Arg Ser Asn Tyr Ala Glu Lys Phe
    50                  55                  60

Gln Gly Arg Val Thr Leu Thr Val Asp Thr Ser Ser Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Arg Ala Met His Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu

```
                130                 135                 140
Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Arg Val Glu Pro Lys Ser Cys Asp Lys Thr His Thr
                210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
                275                 280                 285

Lys Pro Arg Glu Glu Gln Tyr Asn Ser Thr Tyr Arg Val Val Ser Val
                290                 295                 300

Leu Thr Val Leu His Gln Asp Trp Leu Asn Gly Lys Glu Tyr Lys Cys
305                 310                 315                 320

Gly Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly
                435                 440                 445

<210> SEQ ID NO 32
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Met His Trp Val Arg Gln Ala Pro Gly Gln Gly Leu Glu Trp Ile
                35                  40                  45
```

Gly Glu Ile Asn Pro Ile Asn Gly Arg Ser Asn Tyr Ala Glu Lys Phe
 50                  55                  60

Gln Gly Arg Val Thr Leu Thr Val Asp Thr Ser Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Gly Thr Arg Ala Met His Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Arg Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 33
<211> LENGTH: 445
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 33

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Ile
        35                  40                  45

Gly Glu Ile Asn Pro Ile Asn Gly Arg Ser Asn Tyr Ala Glu Lys Phe
    50                  55                  60

Gln Gly Arg Val Thr Leu Thr Val Asp Thr Ser Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Arg Ala Met His Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380
```

```
Gln Pro Glu Asn Asn Tyr Lys Thr Thr Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
            435                 440                 445

<210> SEQ ID NO 34
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Met His Trp Val Arg Gln Ala Pro Gly Gln Gly Leu Glu Trp Ile
            35                  40                  45

Gly Glu Ile Asn Pro Ile Asn Gly Arg Ser Asn Tyr Ala Glu Lys Phe
        50                  55                  60

Gln Gly Arg Val Thr Leu Thr Val Asp Thr Ser Ser Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Arg Ala Met His Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Ala Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Gly Ser Thr Tyr Arg Val Val Ser Val
290                 295                 300
```

```
Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 35
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Glu Ile Asn Pro Ile Gln Gly Arg Ser Asn Tyr Ala Glu Lys Phe
    50                  55                  60

Gln Gly Arg Val Thr Leu Thr Val Asp Thr Ser Ser Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Gly Thr Arg Ala Met His Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
```

```
                210                 215                 220
Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
                275                 280                 285

Lys Pro Arg Glu Glu Gln Tyr Asn Ser Thr Tyr Arg Val Val Ser Val
                290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly
                435                 440                 445

<210> SEQ ID NO 36
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Met His Trp Val Arg Gln Ala Pro Gly Gln Gly Leu Glu Trp Met
            35                  40                  45

Gly Glu Ile Asn Pro Ile Gln Gly Arg Ser Asn Tyr Ala Glu Lys Phe
        50                  55                  60

Gln Gly Arg Val Thr Leu Thr Val Asp Thr Ser Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Gly Thr Arg Ala Met His Tyr Trp Gly Gln Gly Thr Leu Val
                100                 105                 110

Thr Val Ser Ser Ala Ser Thr Lys Gly Pro Ser Val Phe Pro Leu Ala
                115                 120                 125
```

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 37
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Glu Ile Asn Pro Ile Gln Gly Arg Ser Asn Tyr Ala Glu Lys Phe
    50                  55                  60

Gln Gly Arg Val Thr Leu Thr Val Asp Thr Ser Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Gly Thr Arg Ala Met His Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Gly Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 38
<211> LENGTH: 445

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Glu Ile Asn Pro Ile Gln Gly Arg Ser Asn Tyr Ala Glu Lys Phe
    50                  55                  60

Gln Gly Arg Val Thr Leu Thr Val Asp Thr Ser Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Gly Thr Arg Ala Met His Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Arg Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

```
Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
            435                 440                 445

<210> SEQ ID NO 39
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Glu Ile Asn Pro Ile Gln Gly Arg Ser Asn Tyr Ala Glu Lys Phe
    50                  55                  60

Gln Gly Arg Val Thr Leu Thr Val Asp Thr Ser Ser Thr Ala Tyr
65                  70                  75                  80

Met Glu Leu Ser Ser Leu Arg Ser Glu Asp Thr Ala Thr Tyr Tyr Cys
            85                  90                  95

Ala Arg Gly Thr Arg Ala Met His Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Arg Val Glu Pro Lys Ser Cys Asp Lys Thr His Thr
            210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
```

```
                     290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 40
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Glu Ile Asn Pro Ile Gln Gly Arg Ser Asn Tyr Ala Glu Lys Phe
    50                  55                  60

Gln Gly Arg Val Thr Leu Thr Val Asp Thr Ser Ser Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Gly Thr Arg Ala Met His Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205
```

```
Lys Val Asp Lys Arg Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Ala Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Gly Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 41
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Glu Ile Asn Pro Ile Asn Gly Arg Ser Asn Tyr Ala Glu Lys Phe
    50                  55                  60

Gln Gly Arg Val Thr Leu Thr Val Asp Thr Ser Ser Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Gly Thr Arg Ala Met His Tyr Trp Gly Gln Gly Thr Leu Val
            100                 105                 110

Thr Val Ser Ser Ala Ser Thr Lys Gly Pro Ser Val Phe Pro Leu Ala
        115                 120                 125
```

```
Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 42
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
```

```
            35                  40                  45
Gly Glu Ile Asn Pro Ile Asn Gly Arg Ser Asn Tyr Ala Glu Lys Phe
 50                  55                  60

Gln Gly Arg Val Thr Leu Thr Val Asp Thr Ser Ser Thr Ala Tyr
 65                  70                  75                  80

Met Glu Leu Ser Ser Leu Arg Ser Glu Asp Thr Ala Thr Tyr Tyr Cys
                 85                  90                  95

Ala Arg Gly Thr Arg Ala Met His Tyr Trp Gly Gln Gly Thr Leu Val
                100                 105                 110

Thr Val Ser Ser Ala Ser Thr Lys Gly Pro Ser Val Phe Pro Leu Ala
                115                 120                 125

Pro Ser Ser Lys Ser Thr Ser Gly Gly Thr Ala Ala Leu Gly Cys Leu
                130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Arg Val Glu Pro Lys Ser Cys Asp Lys Thr His Thr
210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
                275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly
                435                 440                 445

<210> SEQ ID NO 43
```

<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Glu Ile Asn Pro Ile Asn Gly Arg Ser Asn Tyr Ala Glu Lys Phe
    50                  55                  60

Gln Gly Arg Val Thr Leu Thr Val Asp Thr Ser Ser Thr Ala Tyr
65                  70                  75                  80

Met Glu Leu Ser Ser Leu Arg Ser Glu Asp Thr Ala Tyr Tyr Cys
                85                  90                  95

Ala Arg Gly Thr Arg Ala Met His Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Gly Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
```

-continued

```
                370                 375                 380
Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
            435                 440                 445

<210> SEQ ID NO 44
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Met His Trp Val Arg Gln Ala Pro Gly Gln Gly Leu Glu Trp Met
            35                  40                  45

Gly Glu Ile Asn Pro Ile Asn Gly Arg Ser Asn Tyr Ala Glu Lys Phe
    50                  55                  60

Gln Gly Arg Val Thr Leu Thr Val Asp Thr Ser Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Gly Thr Arg Ala Met His Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285
```

```
Lys Pro Arg Glu Glu Gln Tyr Asn Ser Thr Tyr Arg Val Val Ser Val
    290                 295                 300
Leu Thr Val Leu His Gln Asp Trp Leu Asn Gly Lys Glu Tyr Lys Cys
305                 310                 315                 320
Lys Val Ser Asn Lys Ala Arg Pro Ala Pro Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly
        435                 440                 445

<210> SEQ ID NO 45
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asn Tyr
            20                  25                  30
Trp Met His Trp Val Arg Gln Ala Pro Gly Gln Gly Leu Glu Trp Met
        35                  40                  45
Gly Glu Ile Asn Pro Ile Asn Gly Arg Ser Asn Tyr Ala Glu Lys Phe
50                  55                  60
Gln Gly Arg Val Thr Leu Thr Val Asp Thr Ser Ser Ser Thr Ala Tyr
65                  70                  75                  80
Met Glu Leu Ser Ser Leu Arg Ser Glu Asp Thr Ala Thr Tyr Tyr Cys
                85                  90                  95
Ala Arg Gly Thr Arg Ala Met His Tyr Trp Gly Gln Gly Thr Leu Val
            100                 105                 110
Thr Val Ser Ser Ala Ser Thr Lys Gly Pro Ser Val Phe Pro Leu Ala
        115                 120                 125
Pro Ser Ser Lys Ser Thr Ser Gly Gly Thr Ala Ala Leu Gly Cys Leu
    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
        195                 200                 205
```

```
Lys Val Asp Lys Arg Val Glu Pro Lys Ser Cys Asp Lys Thr His Thr
            210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
            325                 330                 335

Lys Ala Lys Gly Gln Pro Arg Glu Pro Gln Val Tyr Thr Leu Pro Pro
                340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 46
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Glu Ile Asn Pro Ile Asn Gly Arg Ser Asn Tyr Ala Glu Lys Phe
    50                  55                  60

Gln Gly Arg Val Thr Leu Thr Val Asp Thr Ser Ser Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Gly Thr Arg Ala Met His Tyr Trp Gly Gln Gly Thr Leu Val
            100                 105                 110

Thr Val Ser Ser Ala Ser Thr Lys Gly Pro Ser Val Phe Pro Leu Ala
```

```
            115                 120                 125
Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Ala Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Gly Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 47
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Asn Asn
            20                  25                  30
```

```
Leu Ala Trp Tyr Gln Gln Lys Pro Gly Lys Ser Pro Lys Leu Leu Ile
         35                  40                  45

Tyr Ala Ala Thr Asn Leu Ala Asp Gly Val Pro Ser Arg Phe Ser Gly
 50                      55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln His Phe Trp Gly Thr Pro Leu
                 85                  90                  95

Thr Phe Gly Gly Gly Thr Lys Val Glu Ile Lys Arg Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
 130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 48
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Asp Ile Gln Met Thr Gln Ser Pro Ser Ser Leu Ser Ala Ser Val Gly
1               5                  10                  15

Asp Arg Val Thr Ile Thr Cys Arg Thr Ser Glu Asn Ile Tyr Asn Asn
            20                  25                  30

Leu Ala Trp Tyr Gln Gln Lys Pro Gly Lys Ala Pro Lys Leu Leu Ile
         35                  40                  45

Tyr Ala Ala Thr Asn Leu Ala Asp Gly Val Pro Ser Arg Phe Ser Gly
 50                      55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln His Phe Trp Gly Thr Pro Leu
                 85                  90                  95

Thr Phe Gly Gly Gly Thr Lys Val Glu Ile Lys Arg Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
 130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 49
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Asn Asn
            20                  25                  30

Leu Ala Trp Tyr Gln Gln Lys Pro Gly Lys Ala Pro Lys Leu Leu Ile
        35                  40                  45

Tyr Ala Ala Thr Asn Leu Ala Glu Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Gly Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 50
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Ser Asn
            20                  25                  30
```

```
Leu Ala Trp Tyr Gln Gln Lys Pro Gly Lys Ala Pro Lys Leu Leu Ile
         35                  40                  45

Tyr Ala Gly Thr Asn Leu Ala Asp Gly Val Pro Ser Arg Phe Ser Gly
         50                  55                  60

Ser Gly Ser Gly Thr Asp Tyr Thr Leu Thr Ile Ser Ser Leu Gln Pro
 65                  70                  75                  80

Glu Asp Phe Ala Asn Tyr Tyr Cys Gln His Phe Trp Gly Thr Pro Leu
                 85                  90                  95

Thr Phe Gly Gly Gly Thr Lys Val Glu Ile Lys Arg Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
     130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 51
<211> LENGTH: 24
<212> TYPE: PRT
<213> ORGANISM: Unknown
<220> FEATURE:
<223> OTHER INFORMATION: Description of Unknown:
      INF7 sequence

<400> SEQUENCE: 51

Cys Gly Ile Phe Gly Glu Ile Glu Glu Leu Ile Glu Glu Gly Leu Glu
 1               5                  10                  15

Asn Leu Ile Asp Trp Gly Asn Ala
            20

<210> SEQ ID NO 52
<211> LENGTH: 24
<212> TYPE: PRT
<213> ORGANISM: Unknown
<220> FEATURE:
<223> OTHER INFORMATION: Description of Unknown:
      INF7 sequence

<400> SEQUENCE: 52

Gly Leu Phe Glu Ala Ile Glu Gly Phe Ile Glu Asn Gly Trp Glu Gly
 1               5                  10                  15

Met Ile Asp Gly Trp Tyr Gly Cys
            20

<210> SEQ ID NO 53
<211> LENGTH: 27
<212> TYPE: PRT
<213> ORGANISM: Unknown
<220> FEATURE:
<223> OTHER INFORMATION: Description of Unknown:
      INF7 sequence
```

```
<400> SEQUENCE: 53

Gly Leu Phe Glu Ala Ile Glu Gly Phe Ile Glu Asn Gly Trp Glu Gly
1               5                   10                  15

Met Ile Trp Asp Tyr Gly Ser Gly Ser Cys Gly
            20                  25

<210> SEQ ID NO 54
<211> LENGTH: 23
<212> TYPE: PRT
<213> ORGANISM: Unknown
<220> FEATURE:
<223> OTHER INFORMATION: Description of Unknown:
      INF7 sequence

<400> SEQUENCE: 54

Gly Leu Phe Glu Ala Ile Glu Gly Phe Ile Glu Asn Gly Trp Glu Gly
1               5                   10                  15

Met Ile Asp Gly Trp Tyr Gly
            20

<210> SEQ ID NO 55
<211> LENGTH: 27
<212> TYPE: PRT
<213> ORGANISM: Unknown
<220> FEATURE:
<223> OTHER INFORMATION: Description of Unknown:
      INF7 sequence

<400> SEQUENCE: 55

Gly Leu Phe Glu Ala Ile Glu Gly Phe Ile Glu Asn Gly Trp Glu Gly
1               5                   10                  15

Met Ile Trp Asp Tyr Gly Ser Gly Ser Cys Lys
            20                  25

<210> SEQ ID NO 56
<211> LENGTH: 27
<212> TYPE: PRT
<213> ORGANISM: Unknown
<220> FEATURE:
<223> OTHER INFORMATION: Description of Unknown:
      melittin sequence

<400> SEQUENCE: 56

Cys Leu Ile Gly Ala Ile Leu Lys Val Leu Ala Thr Gly Leu Pro Thr
1               5                   10                  15

Leu Ile Ser Trp Ile Lys Asn Lys Arg Lys Gln
            20                  25

<210> SEQ ID NO 57
<211> LENGTH: 26
<212> TYPE: PRT
<213> ORGANISM: Unknown
<220> FEATURE:
<223> OTHER INFORMATION: Description of Unknown:
      melittin sequence

<400> SEQUENCE: 57

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 58
```

```
<211> LENGTH: 13
<212> TYPE: PRT
<213> ORGANISM: Unknown
<220> FEATURE:
<223> OTHER INFORMATION: Description of Unknown:
      meucin sequence

<400> SEQUENCE: 58

Ile Phe Gly Ala Ile Ala Gly Leu Leu Lys Asn Ile Phe
1               5                   10

<210> SEQ ID NO 59
<211> LENGTH: 18
<212> TYPE: PRT
<213> ORGANISM: Unknown
<220> FEATURE:
<223> OTHER INFORMATION: Description of Unknown:
      meucin sequence

<400> SEQUENCE: 59

Phe Phe Gly His Leu Phe Lys Leu Ala Thr Lys Ile Ile Pro Ser Leu
1               5                   10                  15

Phe Gln

<210> SEQ ID NO 60
<211> LENGTH: 21
<212> TYPE: PRT
<213> ORGANISM: Simian virus 40

<400> SEQUENCE: 60

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 61
<211> LENGTH: 19
<212> TYPE: PRT
<213> ORGANISM: Unknown
<220> FEATURE:
<223> OTHER INFORMATION: Description of Unknown:
      pVEC sequence

<400> SEQUENCE: 61

Leu Leu Ile Ile Leu Arg Arg Arg Ile Arg Lys Gln Ala His Ala
1               5                   10                  15

His Ser Lys

<210> SEQ ID NO 62
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Asp Pro Lys Gly Asp Pro Lys Gly Val Thr Val Thr Val Thr
1               5                   10                  15

Val Thr Gly Lys Gly Asp Pro Lys Pro Asp
            20                  25

<210> SEQ ID NO 63
<211> LENGTH: 17
<212> TYPE: PRT
```

```
<213> ORGANISM: Unknown
<220> FEATURE:
<223> OTHER INFORMATION: Description of Unknown:
      C105Y sequence

<400> SEQUENCE: 63

Cys Ser Ile Pro Pro Glu Val Lys Phe Asn Lys Pro Phe Val Tyr Leu
1               5                   10                  15

Ile

<210> SEQ ID NO 64
<211> LENGTH: 27
<212> TYPE: PRT
<213> ORGANISM: Unknown
<220> FEATURE:
<223> OTHER INFORMATION: Description of Unknown:
      Transportan sequence

<400> SEQUENCE: 64

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 65
<211> LENGTH: 21
<212> TYPE: PRT
<213> ORGANISM: Unknown
<220> FEATURE:
<223> OTHER INFORMATION: Description of Unknown:
      TP10 sequence

<400> SEQUENCE: 65

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Ala Leu Phe Leu Gly Phe Leu Gly Ala Ala Gly Ser Thr Met Gly
1               5                   10                  15

Ala

<210> SEQ ID NO 67
<211> LENGTH: 20
<212> TYPE: PRT
<213> ORGANISM: Herpes simplex virus

<400> SEQUENCE: 67

His Gly Leu Ala Ser Thr Leu Thr Arg Trp Ala His Tyr Asn Ala Leu
1               5                   10                  15

Ile Arg Ala Phe
            20

<210> SEQ ID NO 68
<211> LENGTH: 20
```

```
<212> TYPE: PRT
<213> ORGANISM: Unknown
<220> FEATURE:
<223> OTHER INFORMATION: Description of Unknown:
      CADY sequence

<400> SEQUENCE: 68

Gly Leu Trp Arg Ala Leu Trp Arg Leu Leu Arg Ser Leu Trp Arg Leu
1               5                   10                  15

Leu Trp Arg Ala
            20

<210> SEQ ID NO 69
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
            20                  25                  30

<210> SEQ ID NO 70
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Leu Phe Glu Ala Ile Glu Gly Phe Ile Glu Asn Gly Trp Glu Gly
1               5                   10                  15

Met Ile Asp Gly Trp Tyr Gly Cys
            20

<210> SEQ ID NO 71
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Leu Phe Gly Ala Ile Ala Gly Phe Ile Glu Asn Gly Trp Glu Gly
1               5                   10                  15

Met Ile Asp Gly Trp Tyr Gly
            20

<210> SEQ ID NO 72
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gly Leu Phe Gly Ala Ile Ala Gly Phe Ile Glu Asn Gly Trp Glu Gly
1               5                   10                  15
```

```
Met Ile Asp Gly Arg Gln Ile Lys Ile Trp Phe Gln Asn Arg Arg Met
            20                  25                  30

Lys Trp Lys Lys
        35

<210> SEQ ID NO 73
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Leu Phe Gly Ala Ile Ala Gly Phe Ile Glu Asn Gly Trp Glu Gly
1               5                   10                  15

Met Ile Asp Gly Ser Ser Lys Lys Lys Lys
            20                  25

<210> SEQ ID NO 74
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Leu Phe Glu Ala Ile Ala Gly Phe Ile Glu Asn Gly Trp Glu Gly
1               5                   10                  15

Met Ile Asp Gly Gly Gly Tyr Cys
            20

<210> SEQ ID NO 75
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Leu Phe His Ala Ile Ala His Phe Ile His Gly Gly Trp His Gly
1               5                   10                  15

Leu Ile His Gly Trp Tyr Gly
            20

<210> SEQ ID NO 76
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Gly Leu Phe Glu Ala Ile Glu Gly Phe Ile Glu Asn Gly Trp Glu Gly
1               5                   10                  15

Leu Ala Glu Ala Leu Ala Glu Ala Leu Glu Ala Leu Ala Ala
            20                  25                  30

<210> SEQ ID NO 77
<211> LENGTH: 29
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 77

Lys Trp Lys Leu Phe Lys Lys Ile Gly Ala Val Leu Lys Val Leu Thr
1               5                   10                  15

Thr Gly Tyr Gly Arg Lys Lys Arg Gln Arg Arg Arg
            20                  25

<210> SEQ ID NO 78
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Gly Phe Gly
1

<210> SEQ ID NO 79
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ala Leu Ala Leu
1

<210> SEQ ID NO 80
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Phe Leu Gly
1

<210> SEQ ID NO 81
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
uuacauuaaa gucuguuguu u                                            21

<210> SEQ ID NO 82
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
gtcgtatcca gtgcagggtc cgaggtattc gcactggata cgacaaacaa c           51
```

-continued

```
<210> SEQ ID NO 83
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
ggcggcttac attaaagtct gt                                              22

<210> SEQ ID NO 84
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
agtgcagggt ccgag                                                      15

<210> SEQ ID NO 85
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 85
tggatacgac aaacaa                                                     16

<210> SEQ ID NO 86
<211> LENGTH: 461
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Met Gly Trp Ser Cys Ile Ile Leu Phe Leu Val Ala Thr Ala Thr Gly
1               5                   10                  15

Val His Ser Gln Val Gln Leu Gln Gln Pro Gly Ala Glu Leu Val Lys
                20                  25                  30

Pro Gly Ala Ser Val Lys Leu Ser Cys Lys Ala Ser Gly Tyr Thr Phe
            35                  40                  45

Thr Asn Tyr Trp Met His Trp Val Lys Gln Arg Pro Gly Gln Gly Leu
        50                  55                  60

Glu Trp Ile Gly Glu Ile Asn Pro Ile Asn Gly Arg Ser Asn Tyr Gly
65                  70                  75                  80

Glu Arg Phe Lys Thr Lys Ala Thr Leu Thr Val Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Gly Thr Arg Ala Met His Tyr Trp Gly Gln Gly
        115                 120                 125

Thr Ser Val Thr Val Ser Ser Ala Ser Thr Lys Gly Pro Ser Val Phe
    130                 135                 140

Pro Leu Ala Pro Cys Ser Arg Ser Thr Ser Glu Ser Thr Ala Ala Leu
```

145                 150                 155                 160
Gly Cys Leu Val Lys Asp Tyr Phe Pro Glu Pro Val Thr Val Ser Trp
                    165                 170                 175

Asn Ser Gly Ala Leu Thr Ser Gly Val His Thr Phe Pro Ala Val Leu
                180                 185                 190

Gln Ser Ser Gly Leu Tyr Ser Leu Ser Ser Val Val Thr Val Pro Ser
            195                 200                 205

Ser Asn Phe Gly Thr Gln Thr Tyr Thr Cys Asn Val Asp His Lys Pro
        210                 215                 220

Ser Asn Thr Lys Val Asp Lys Thr Val Glu Arg Lys Cys Cys Val Glu
225                 230                 235                 240

Cys Pro Pro Cys Pro Ala Pro Pro Val Ala Gly Pro Ser Val Phe Leu
                245                 250                 255

Phe Pro Pro Lys Pro Lys Asp Thr Leu Met Ile Ser Arg Thr Pro Glu
                260                 265                 270

Val Thr Cys Val Val Val Asp Val Ser His Glu Asp Pro Glu Val Gln
            275                 280                 285

Phe Asn Trp Tyr Val Asp Gly Val Glu Val His Asn Ala Lys Thr Lys
        290                 295                 300

Pro Arg Glu Glu Gln Phe Asn Ser Thr Phe Arg Val Val Ser Val Leu
305                 310                 315                 320

Thr Val Val His Gln Asp Trp Leu Asn Gly Lys Glu Tyr Lys Cys Lys
                325                 330                 335

Val Ser Asn Lys Gly Leu Pro Ala Pro Ile Glu Lys Thr Ile Ser Lys
                340                 345                 350

Thr Lys Gly Gln Pro Arg Glu Pro Gln Val Tyr Thr Leu Pro Pro Ser
            355                 360                 365

Arg Glu Glu Met Thr Lys Asn Gln Val Ser Leu Thr Cys Leu Val Lys
        370                 375                 380

Gly Phe Tyr Pro Ser Asp Ile Ser Val Glu Trp Glu Ser Asn Gly Gln
385                 390                 395                 400

Pro Glu Asn Asn Tyr Lys Thr Thr Pro Pro Met Leu Asp Ser Asp Gly
                405                 410                 415

Ser Phe Phe Leu Tyr Ser Lys Leu Thr Val Asp Lys Ser Arg Trp Gln
                420                 425                 430

Gln Gly Asn Val Phe Ser Cys Ser Val Met His Glu Ala Leu His Asn
            435                 440                 445

His Tyr Thr Gln Lys Ser Leu Ser Leu Ser Pro Gly Lys
        450                 455                 460

<210> SEQ ID NO 87
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Met Gly Trp Ser Cys Ile Ile Leu Phe Leu Val Ala Thr Ala Thr Gly
1               5                   10                  15

Val His Ser Asp Ile Gln Met Thr Gln Ser Pro Ala Ser Leu Ser Val
            20                  25                  30

Ser Val Gly Glu Thr Val Thr Ile Thr Cys Arg Thr Ser Glu Asn Ile
        35                  40                  45

```
Tyr Asn Asn Leu Ala Trp Tyr Gln Gln Lys Gln Gly Lys Ser Pro Gln
 50                  55                  60

Leu Leu Val Tyr Ala Ala Thr Asn Leu Ala Asp Gly Val Pro Ser Arg
 65                  70                  75                  80

Phe Ser Gly Ser Gly Ser Gly Thr Gln Tyr Ser Leu Lys Ile Asn Ser
             85                  90                  95

Leu Gln Ser Glu Asp Phe Gly Asn Tyr Tyr Cys Gln His Phe Trp Gly
            100                 105                 110

Thr Pro Leu Thr Phe Gly Ala Gly Thr Lys Leu Glu Leu Lys Arg Thr
            115                 120                 125

Val Ala Ala Pro Ser Val Phe Ile Phe Pro Pro Ser Asp Glu Gln Leu
130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
            195                 200                 205

Lys Val Tyr Ala Cys Glu Val Thr His Gln Gly Leu Ser Ser Pro Val
210                 215                 220

Thr Lys Ser Phe Asn Arg Gly Glu Cys
225                 230
```

<210> SEQ ID NO 88
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Asn or Gln
<220> FEATURE:
<221> NAME/KEY: MOD_RES
<222> LOCATION: (13)..(13)
<223> OTHER INFORMATION: Gln or Glu

<400> SEQUENCE: 88

```
Glu Ile Asn Pro Ile Xaa Gly Arg Ser Asn Tyr Ala Xaa Lys Phe Gln
 1               5                  10                  15

Gly
```

<210> SEQ ID NO 89
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Asn or Ser

<400> SEQUENCE: 89

```
Arg Thr Ser Glu Asn Ile Tyr Xaa Asn Leu Ala
 1               5                  10
```

```
<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ala or Gly
<220> FEATURE:
<221> NAME/KEY: MOD_RES
<222> LOCATION: (7)..(7)
<223> OTHER INFORMATION: Asp or Glu

<400> SEQUENCE: 90

Ala Xaa Thr Asn Leu Ala Xaa
1               5

<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (10)..(10)
<223> OTHER INFORMATION: This residue may or may not be present

<400> SEQUENCE: 91

Gln His Phe Trp Gly Thr Pro Leu Thr Phe
1               5                   10

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Asp or Glu

<400> SEQUENCE: 92

Ala Ala Thr Asn Leu Ala Xaa
1               5
```